(12) United States Patent
Williams et al.

(10) Patent No.: US 11,388,799 B2
(45) Date of Patent: Jul. 12, 2022

(54) DISTRIBUTED PHOTOBIOMODULATION THERAPY SYSTEM AND METHOD

(71) Applicant: Applied BioPhotonics Ltd., Hong Kong (CN)

(72) Inventors: Richard K. Williams, Cupertino, CA (US); Keng-Hung Lin, Chupei (TW); Laura E. Williams, Cupertino, CA (US)

(73) Assignee: Applied BioPhotonics Ltd., Hong Kong (CN)

( * ) Notice: Subject to any disclaimer, the term of this patent is extended or adjusted under 35 U.S.C. 154(b) by 260 days.

(21) Appl. No.: 16/377,181

(22) Filed: Apr. 6, 2019

(65) Prior Publication Data
US 2019/0246463 A1    Aug. 8, 2019

Related U.S. Application Data

(60) Continuation-in-part of application No. 15/857,002, filed on Dec. 28, 2017, now Pat. No. 11,006,488, which is a division of application No. 14/073,371, filed on Nov. 6, 2013, now Pat. No. 9,877,361.

(60) Provisional application No. 62/653,846, filed on Apr. 6, 2018, provisional application No. 61/723,950, filed on Nov. 8, 2012.

(51) Int. Cl.
| *H05B 45/00* | (2022.01) |
| *H05B 45/325* | (2020.01) |
| *A61N 5/06* | (2006.01) |
| *H05B 45/24* | (2020.01) |
| *H05B 45/46* | (2020.01) |
| *H05B 45/3725* | (2020.01) |
| *H05B 45/397* | (2020.01) |
| *H05B 45/36* | (2020.01) |
| *H05B 45/375* | (2020.01) |
| *H05B 45/38* | (2020.01) |
| *H05B 45/39* | (2020.01) |

(52) U.S. Cl.
CPC .............. *H05B 45/325* (2020.01); *A61N 5/06* (2013.01); *H05B 45/24* (2020.01); *H05B 45/3725* (2020.01); *H05B 45/397* (2020.01); *H05B 45/46* (2020.01); *A61N 2005/0626* (2013.01); *A61N 2005/0651* (2013.01); *H05B 45/36* (2020.01); *H05B 45/375* (2020.01); *H05B 45/38* (2020.01); *H05B 45/39* (2020.01)

(58) Field of Classification Search
CPC .. A61N 2005/0652; A61N 5/06; H05B 33/08; H05B 33/50
See application file for complete search history.

(56) References Cited

U.S. PATENT DOCUMENTS 5,103,395 A * 4/1992 Spako .................. A61N 5/1007
 600/3
2001/0028227 A1* 10/2001 Lys ........................ H05B 47/18
 315/317

(Continued)

*Primary Examiner* — Rex R Holmes
*Assistant Examiner* — Sana Sahand
(74) *Attorney, Agent, or Firm* — Patentability Associates

(57) ABSTRACT

A phototherapy system includes a channel driver, a first microcontroller and a pad comprising a string of light-emitting diodes (LEDs). The pad also comprises a second microcontroller that autonomously controls the string of LEDs such that the LEDs are controlled even if communication between the first microcontroller and the pad is interrupted.

16 Claims, 134 Drawing Sheets

(56) References Cited

U.S. PATENT DOCUMENTS

| | | | |
|---|---|---|---|
| 2004/0044384 A1* | 3/2004 | Leber | A61N 5/0622 607/88 |
| 2009/0062682 A1* | 3/2009 | Bland | A61B 5/0031 600/545 |
| 2010/0286673 A1* | 11/2010 | Altshuler | A61N 5/0616 606/9 |
| 2011/0109228 A1* | 5/2011 | Shimomura | H05B 47/175 315/113 |
| 2012/0165716 A1* | 6/2012 | Reuben | A61N 5/0616 602/56 |

* cited by examiner

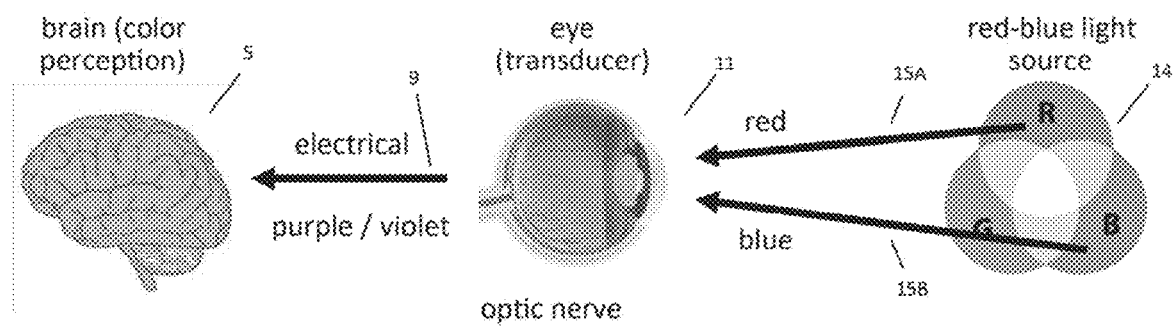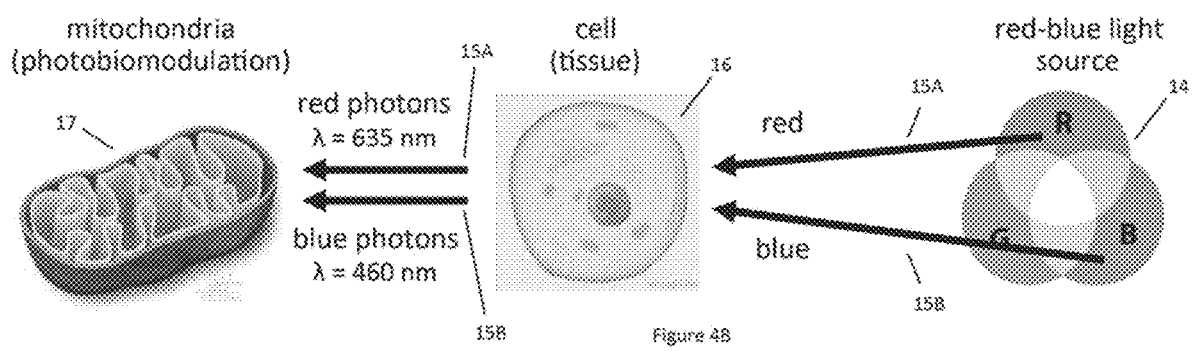
Figure 4B

Function

Block Diagram

Circuit Schematic

| Function | Block Diagram | Circuit Schematic |
|---|---|---|
| 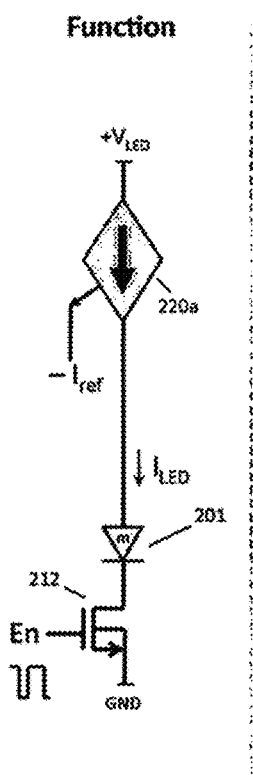 | 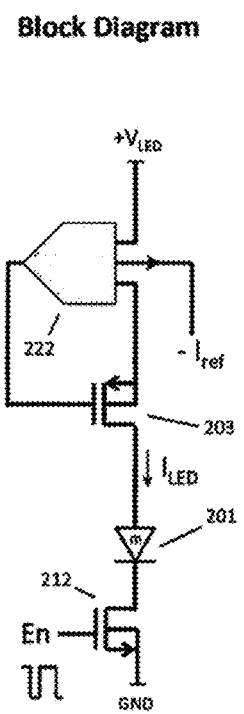 | 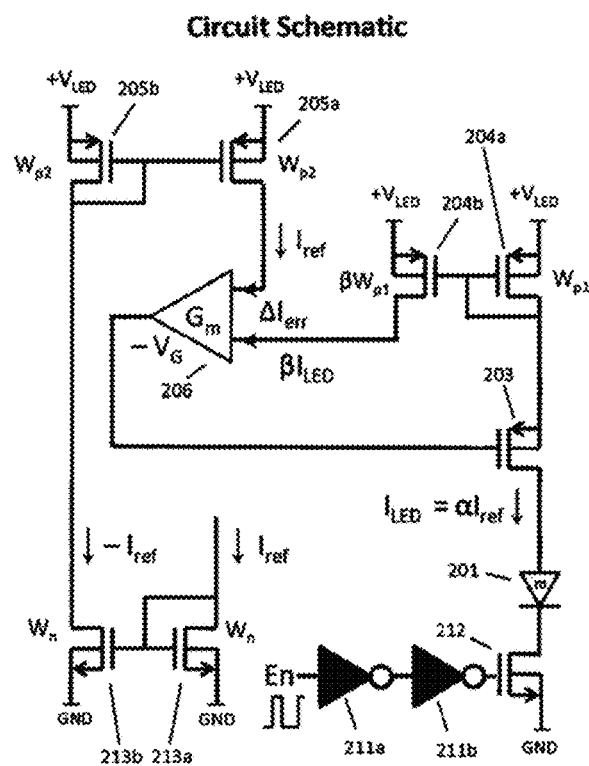 |
| Figure 23A | Figure 23B | Figure 23C |

Figure 39  Download LED Player into LED Pad

Figure 44 — Synthesizer Block Diagram

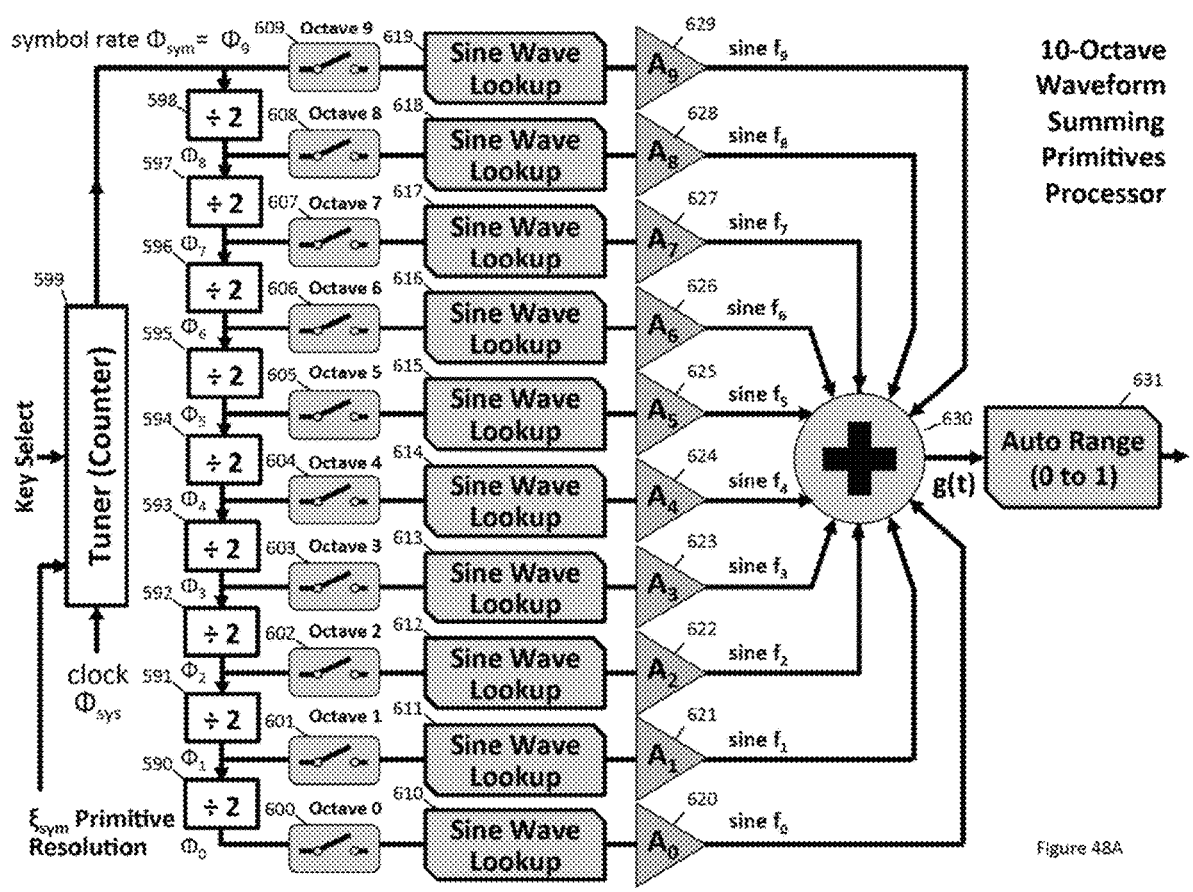

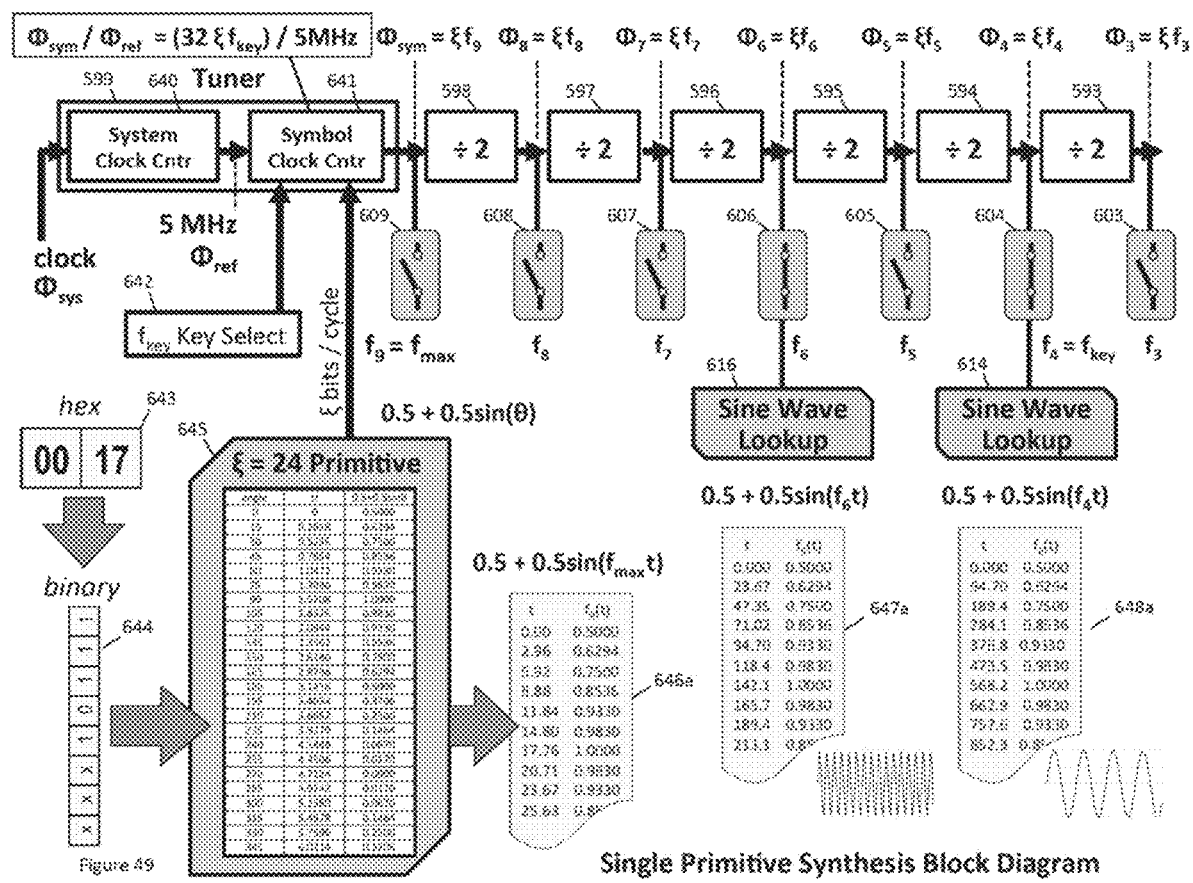

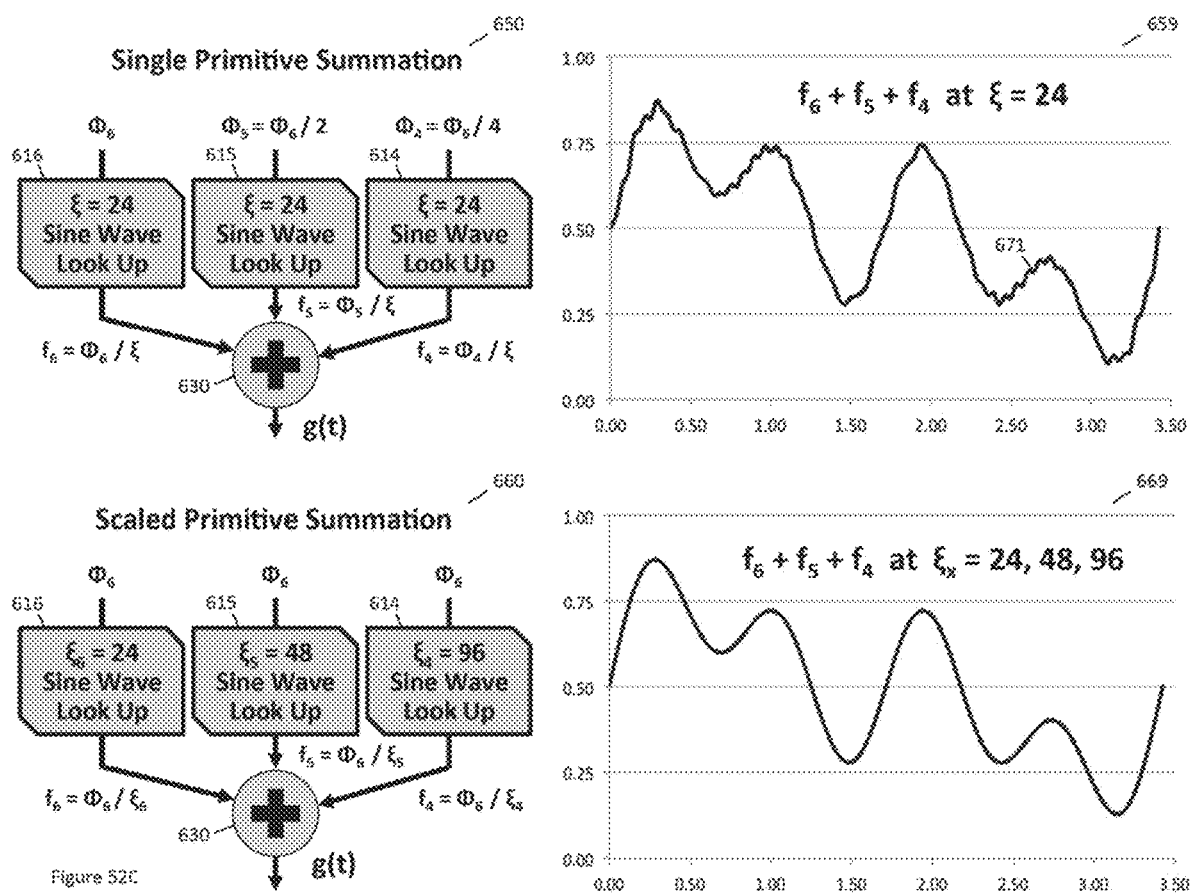

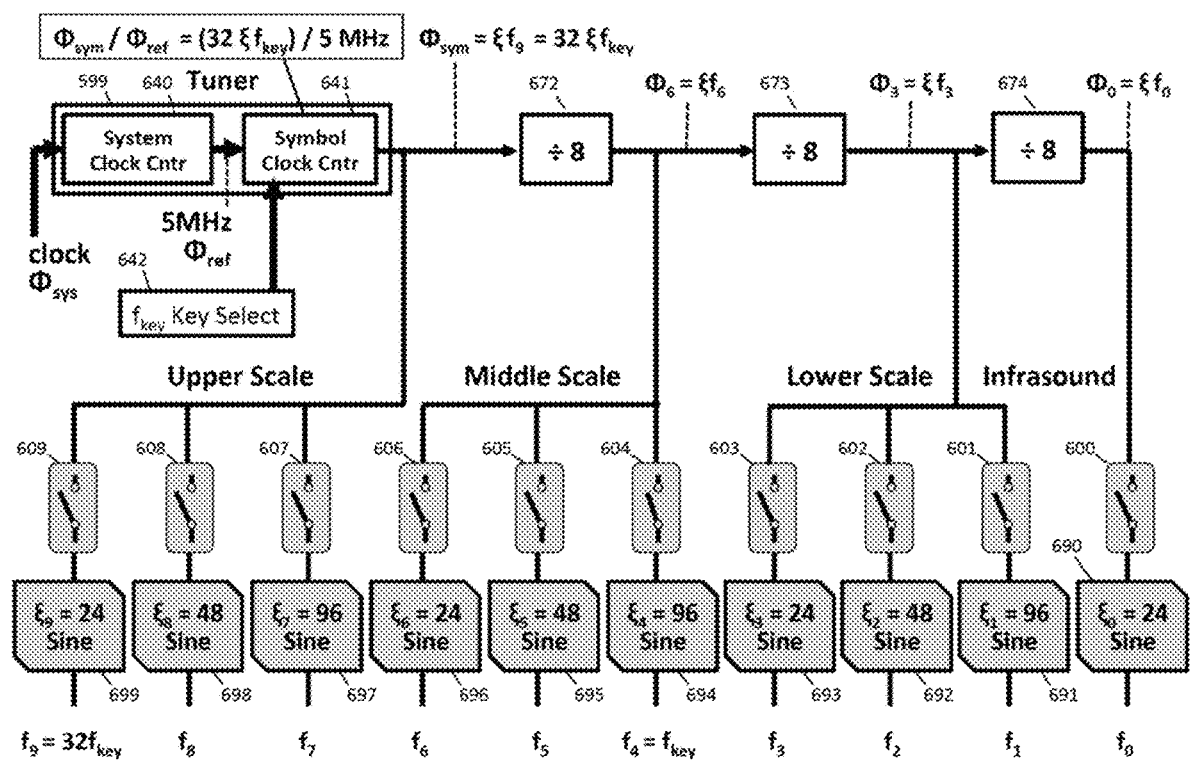
Figure 53  Quad-Range Scaled-Primitive Synthesis Block Diagram

Set Global Key (Musical)
1. User selects scale type (UI top menu)
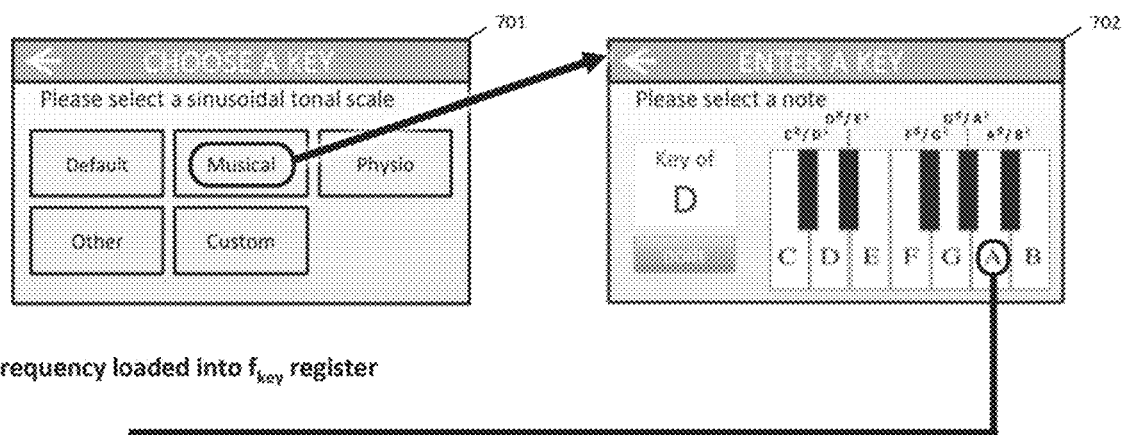
2. Frequency loaded into $f_{key}$ register
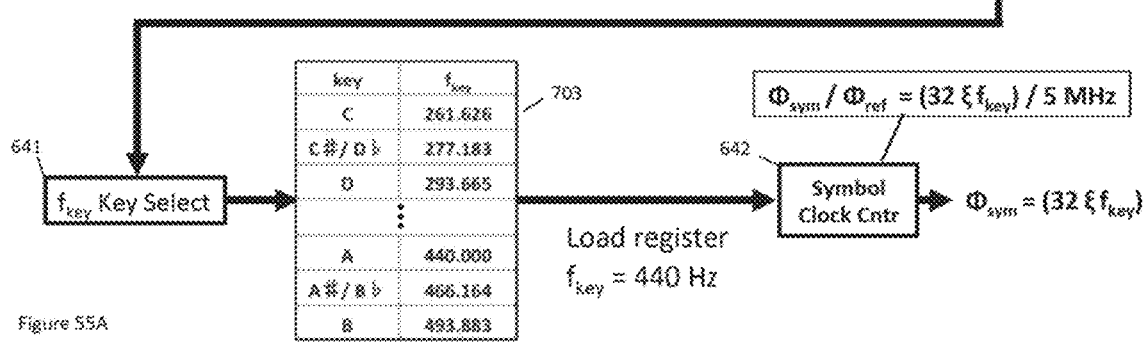
Figure 55A

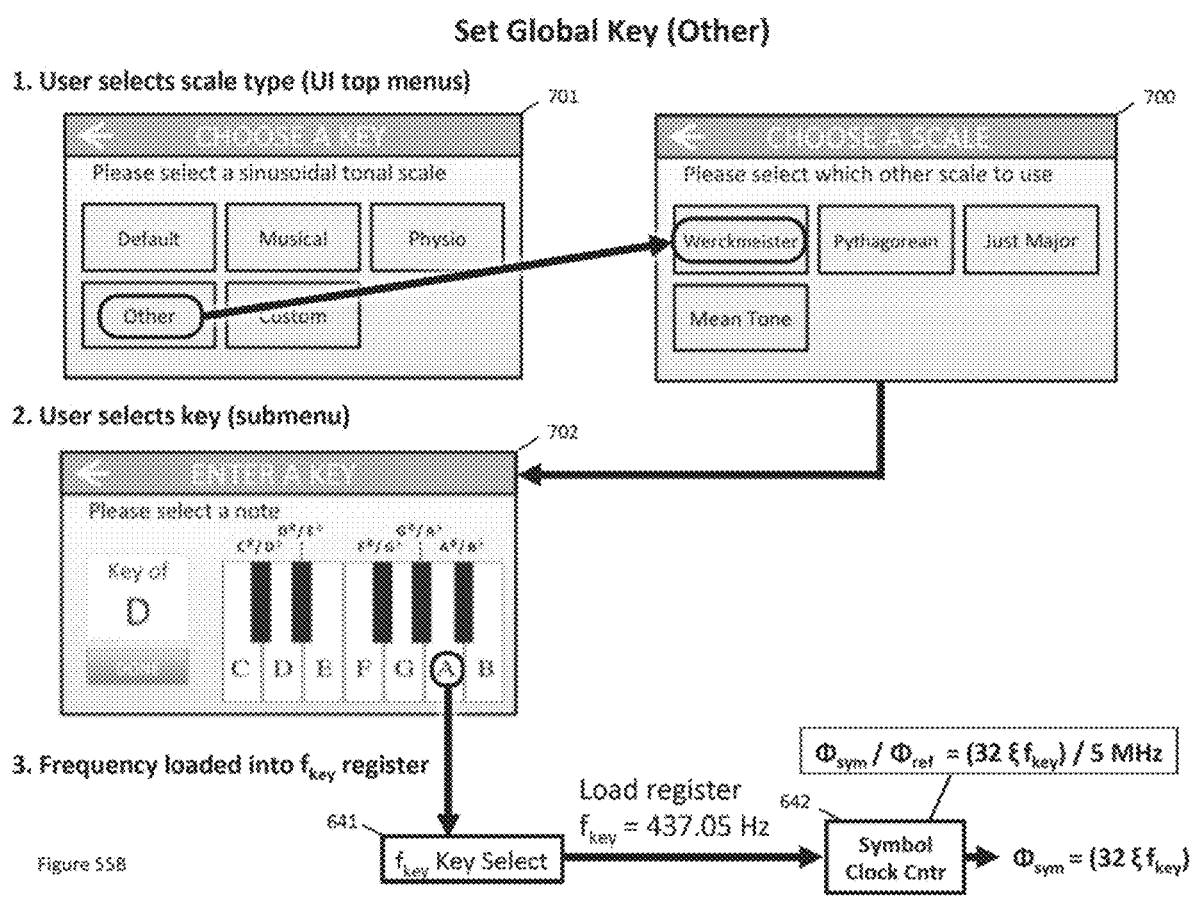

Set Global Key (Custom)
1. User selects scale type and key (UI top menu)
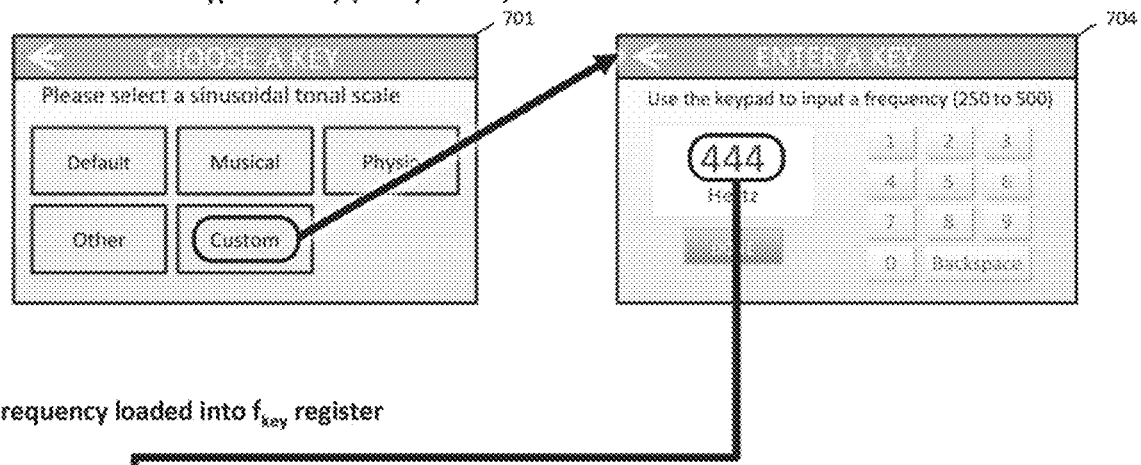
2. Frequency loaded into $f_{key}$ register
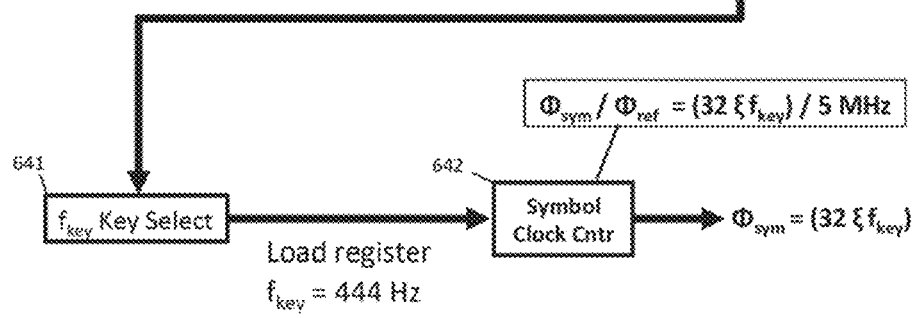
Figure 56

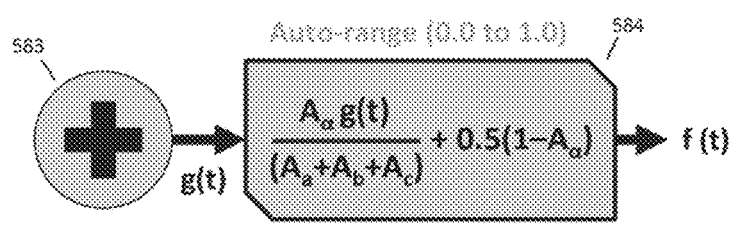
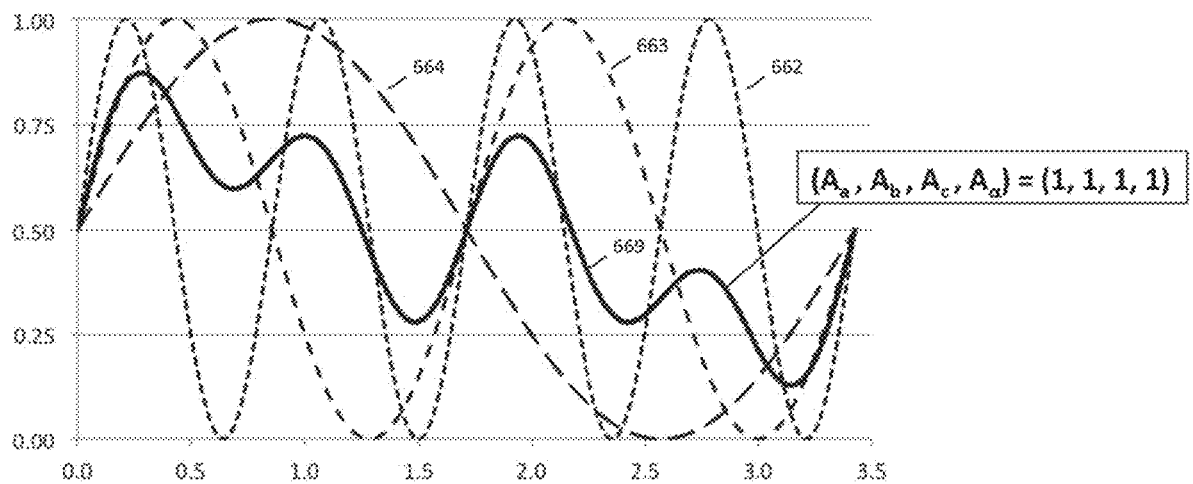
Figure 58A

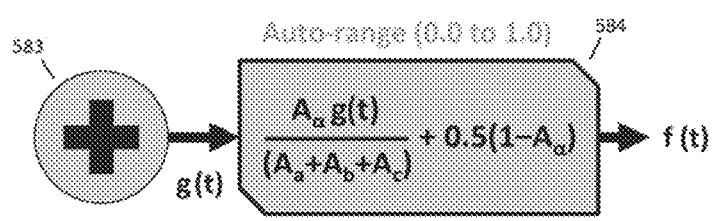
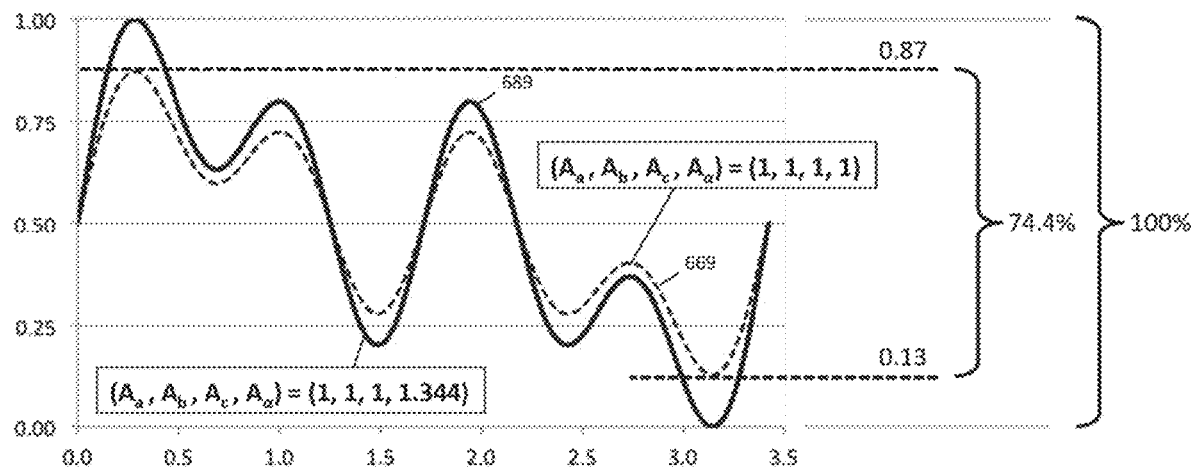
Figure 58B

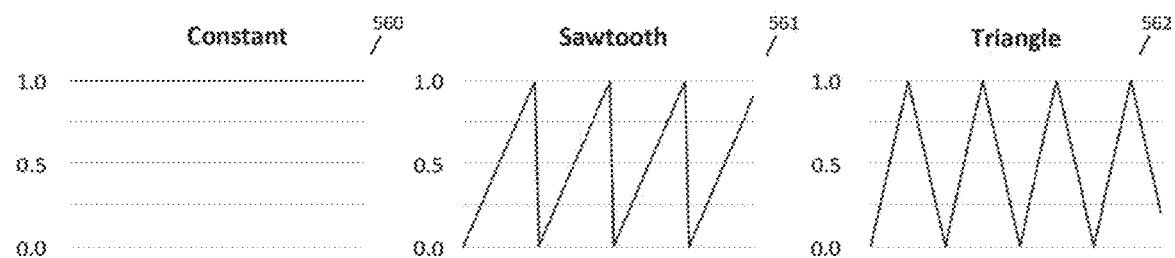
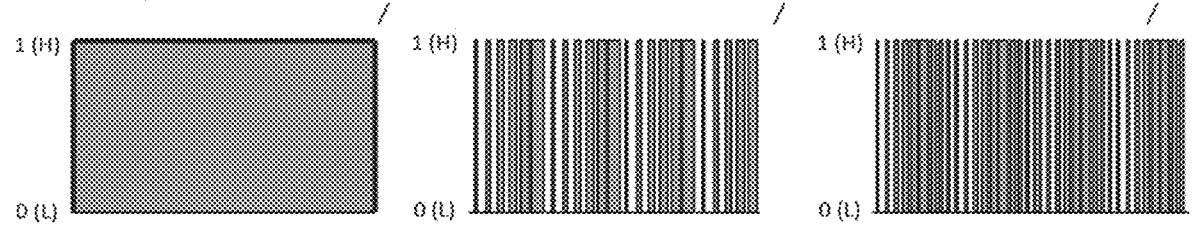
Figure 60

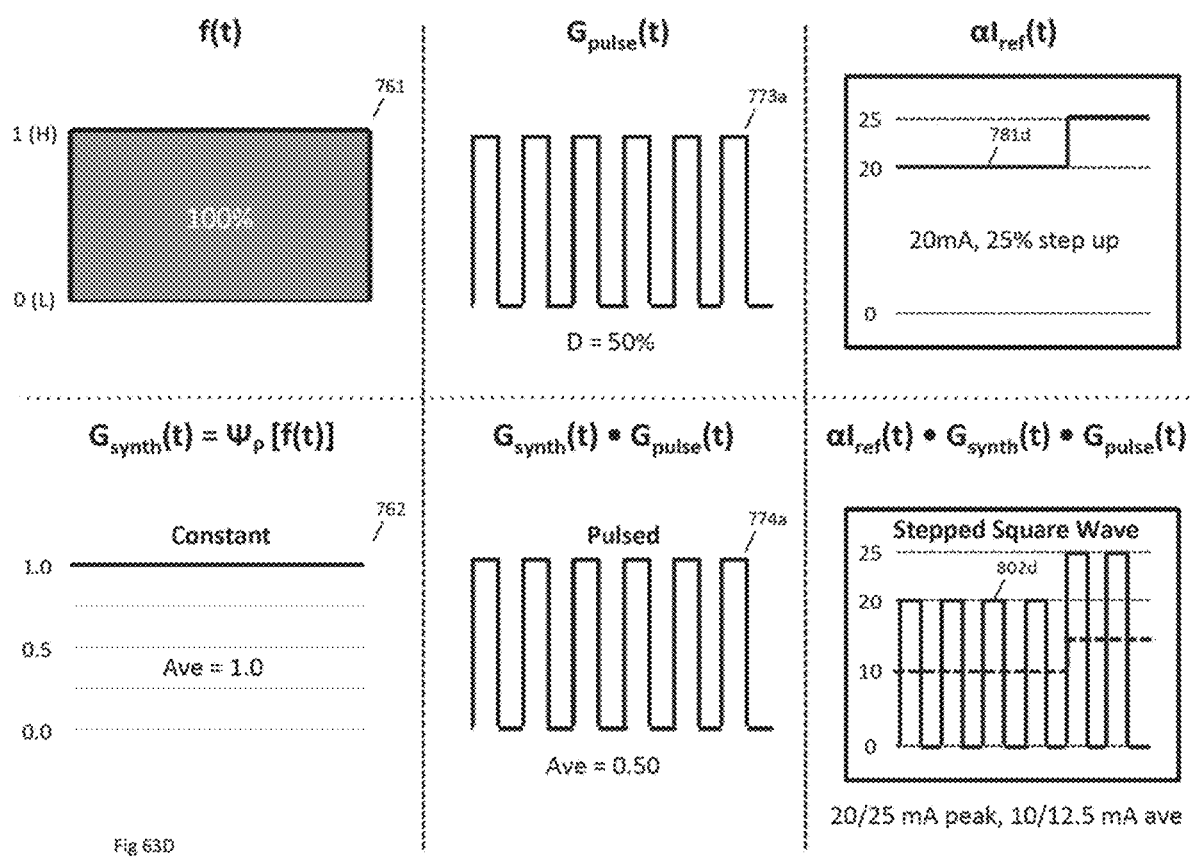

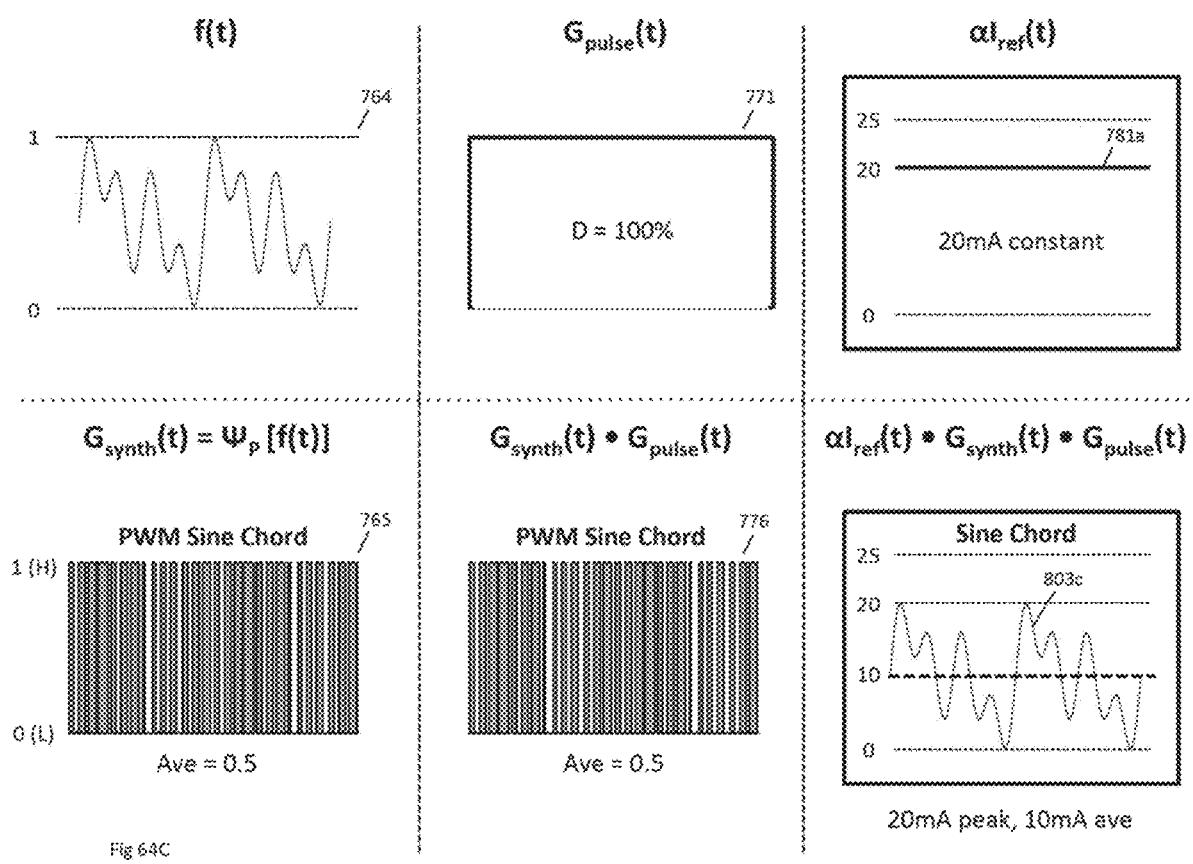

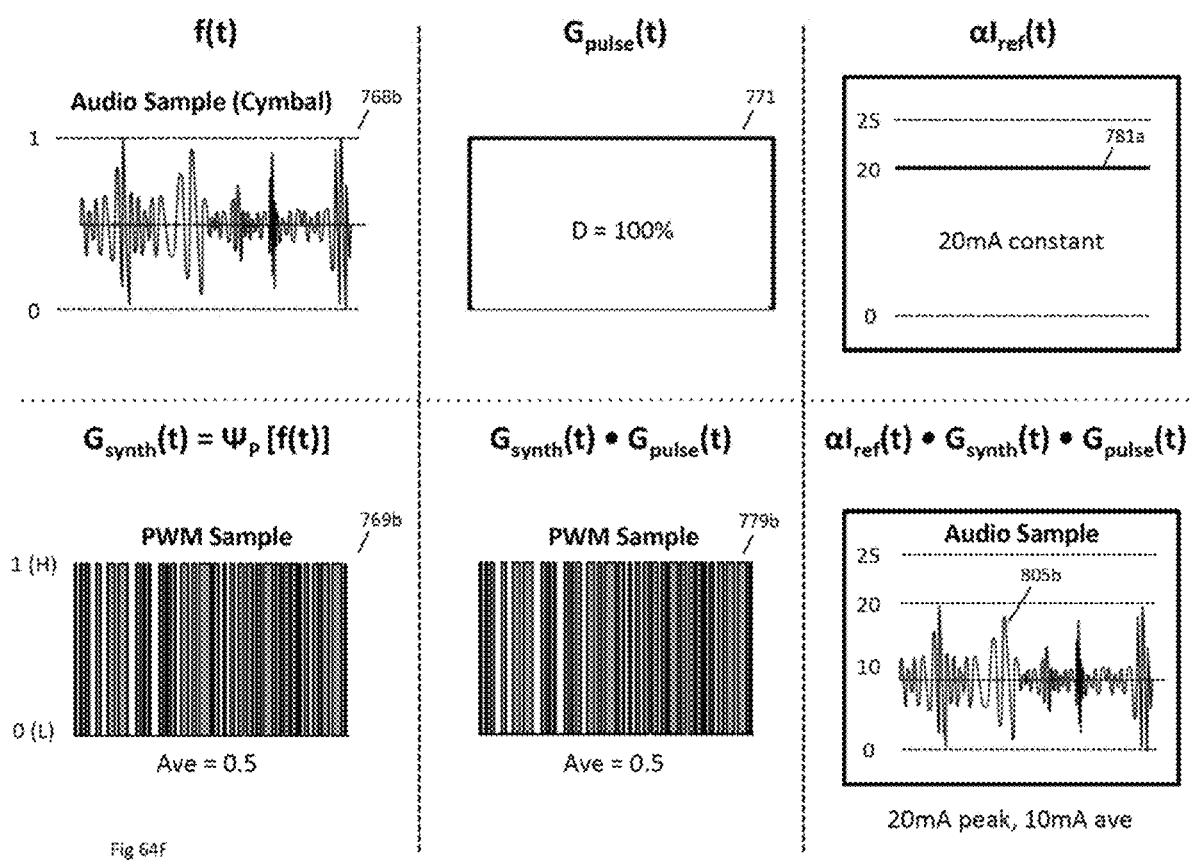

DISTRIBUTED PHOTOBIOMODULATION THERAPY SYSTEM AND METHOD

CROSS-REFERENCE TO RELATED APPLICATIONS

This application claims the priority of Provisional Application No. 62/653,846, titled "Distributed Photobiomodulation Therapy System And Method," filed Apr. 6, 2018. This application is a continuation-in-part of application Ser. No. 15/857,002, titled "Phototherapy Process Including Dynamic LED Driver with Programmable Waveform," filed Dec. 28, 2017, which in turn is a divisional of application Ser. No. 14/073,371, filed Nov. 6, 2013, now U.S. Pat. No. 9,877,361, issued Jan. 23, 2018, which claimed the priority of Provisional Application No. 61/723,950, filed Nov. 8, 2012.

This application is related to the following applications: application Ser. No. 14/461,147, titled "Sinusoidal Drive System And Method for Phototherapy," filed Aug. 15, 2014; Application Ser. No. 14/919,594, titled "3D Bendable Printed Circuit Board With Redundant Interconnections," filed Oct. 21, 2015, now U.S. Pat. No. 10,064,276, issued Aug. 28, 2018; and application Ser. No. 16/377,192, titled "Distributed Photobiomodulation Therapy Devices And Methods, Biofeedback, And Communication Protocols Therefor," filed concurrently herewith.

Each of the foregoing applications and patents is incorporated herein by reference in its entirety.

BACKGROUND

Field of Invention

This invention relates to biotechnology for medical and health applications, including photobiomodulation, phototherapy, and photobiomodulation therapy (PBT).

Discussion of Related Art

Biophotonics is the biomedical field relating to the electronic control of photons, i.e. light, and its interaction with living cells and tissue. Biophotonics includes surgery, imaging, biometrics, disease detection, and photobiomodulation (PBM). Photobiomodulation therapy (PBT), also referred to as phototherapy, is the controlled application of light photons, typically infrared, visible and ultraviolet light to invoke photobiomodulation for medically therapeutic purposes including combating injury, disease, pain and immune system distress. More specifically, PBT involves subjecting cells and tissue undergoing treatment to a stream of photons of specific wavelengths of light either continuously or in repeated discontinuous pulses to control the energy transfer and absorption behavior of living cells and tissue.

FIG. 1 illustrates elements of a PBT system capable of continuous or pulsed light operation including an LED driver 1 controlling and driving LEDs as a source of photons 3 emanating from an LED pad 2 on tissue 5 for the patient. Although a human brain is shown as tissue 5, any organ, tissue or physiological system may be treated using PBT. Before and after, or during treatment, a doctor or clinician 7 may adjust the treatment by controlling the settings of LED driver 1 in accordance with observations on LED driver 1.

While there are many potential mechanisms, as shown in FIG. 2, it is generally agreed that the dominant photobiological process 22 responsible for photobiomodulation during PBT treatment using red and infrared light occurs within mitochondria 21, an organelle present in every eukaryotic cell 20 comprising both plants and animals including birds, mammals, horses, and humans. To the present understanding, photobiological process 22 involves a photon 23 impinging on a cytochrome-c oxidase (CCO) molecule 24, which acts as a battery charger increasing the cellular energy content by transforming adenosine monophosphate (AMP) into a higher energy adenosine diphosphate (ADP) molecule, and converting the ADP molecule into an even higher energy adenosine triphosphate (ATP) molecule. In the process of increasing stored energy in an AMP-to-ADP-to-ATP charging sequence 25, the cytochrome-c oxidase molecule 24 acts as a battery charger with the ATP molecule 26 acting as a cellular battery storing energy, a process which could be considered animal "photosynthesis". The cytochrome-c oxidase molecule 24 is also capable of converting energy from glucose resulting from digestion of food to fuel in the ATP charging sequence 25, or through a combination of digestion and photosynthesis. To power cellular metabolism, the ATP 26 molecule is able to release energy 29 through an ATP-to-ADP-to-AMP discharging process 28. Energy 29 is then used to drive protein synthesis including the formation of catalysts, enzymes, DNA polymerase, and other biomolecules.

Another aspect of photobiological process 22 is that the cytochrome-c oxidase molecule 24 is a scavenger for a nitric oxide (NO) molecule 27, an important signaling molecule in neuron communication and angiogenesis, the growth of new arteries and capillaries. Illumination of cytochrome-c oxidase molecule 24 in cells treated during PBT releases NO molecule 27 in the vicinity of injured or infected tissue, increasing blood flow and oxygen delivery to the treated tissue, accelerating healing, tissue repair, and immune response.

To perform PBT and stimulate the cytochrome-c oxidase molecule 24 to absorb energy from photon 23, the intervening tissue between the light source and the tissue absorbing light cannot block or absorb the light. As illustrated in FIG. 3, the electromagnetic radiation (EMR) molecular absorption spectrum of human tissue is illustrated in a graph 40 of absorption coefficient versus the wavelength of electromagnetic radiation $\lambda$, (measured in nm). Shown in FIG. 3 are the relative absorption coefficients of oxygenated hemoglobin (curve 44a), deoxygenated hemoglobin (curve 44b), cytochrome c (curves 41a, 41b), water (curve 42) and fats and lipids (curve 43) as a function of the wavelength of the light. As illustrated, deoxygenated hemoglobin (curve 44b) and also oxygenated hemoglobin, i.e. blood, (curve 44a) strongly absorb light in the red portion of the visible spectrum, especially for wavelengths shorter than 650 nm. At longer wavelengths in the infrared portion of the spectrum, i.e. above 950 nm, EMR is absorbed by water ($H_2O$) shown as curve 42. At wavelengths between 650 nm to 950 nm, human tissue is essentially transparent, as illustrated by transparent optical window 45.

Aside from absorption by fats and lipids (curve 43), EMR comprising photons 23 of wavelengths $\lambda$ within in transparent optical window 45, is directly absorbed by cytochrome-c oxidase (curves 41aa, 41b). Specifically, cytochrome-c oxidase molecule 24 absorbs the infrared portion of the spectrum represented by curve 41b unimpeded by water or blood. A secondary absorption tail for cytochrome-c oxidase (curve 41a), illuminated by light in the red portion of the visible spectrum, is partially blocked by the absorption properties of deoxygenated hemoglobin (curve 44b), limiting any photobiological response for deep tissue but still activated in epithelial tissue and cells. FIG. 3 thus shows that PBT for skin and internal organs and tissue requires different treatments and light wavelengths, red for skin and infrared for internal tissue and organs.

Present Photonic Delivery Systems

In order to achieve maximum energy coupling into tissue during PBT, it is important to devise a consistent delivery system for illuminating tissue with photons consistently and uniformly. While early attempts used filtered lamps, lamps are extremely hot and uncomfortable for patients, potentially can burn patients and doctors, and are extremely difficult in maintaining uniform illumination during a treatment of extended durations. Lamps also suffer short lifetimes, and if constructed using rarified gasses, can also be expensive to replace regularly. Because of the filters, the lamps must be run very hot to achieve the required photon flux to achieve an efficient therapy in reasonable treatment durations. Unfiltered lamps, like the sun, actually deliver too broad of a spectrum and limit the efficacy of the photons by simultaneously stimulating both beneficial and unwanted chemical reactions, some involving harmful rays, especially in the ultraviolet portion of the electromagnetic spectrum. Extended periods of exposure to ultraviolet light are also known to increase the risk for contracting cancer because UV light damages DNA. In the infrared spectrum, expended exposure to far infrared electromagnetic radiation and heat can cause drying of skin and cause premature aging by destroying elastin and collagen.

As an alternative, lasers have been and continue to be employed to perform PBT, generally referred to by the term LLLT an acronym for low-level laser therapy. Unlike lamps, lasers risk burning a patient, not through heat, but rather by exposing tissue to intense concentrated optical power, also known as ablation. To prevent that problem, special care must be taken that the laser light is limited in its power output and that unduly high current producing dangerous light levels cannot accidentally occur. A second, more practical problem arises from a laser's small "spot size", the illuminated area. Because a laser illuminates a small focused area, it is difficult to treat large organs, muscles, or tissue and it is much easier for an overpower condition to arise.

Another problem with laser light is that its "coherence," which prevents a laser beam from spreading out, makes it more difficult to cover large areas during treatment. Studies reveal there is no inherent extra benefit from PBT using coherent light. For one thing, bacterial, plant and animal life evolved on and naturally absorbs scattered, not coherent light because coherent light does not occur naturally from any known light sources. Secondly, the first two layers of epithelial tissue already destroy any optical coherence, so the coherent character of an incident laser beam is quickly lost as it is absorbed in human or animal tissue. Laser manufacturers have promoted the premise that optical interference patterns of laser light called 'speckles' arising from backscattering enhance therapeutic efficacy, but no scientific evidence has been provided to support such marketing-motivated assertions.

Moreover, the optical spectrum of a laser is too narrow to fully excite all the beneficial chemical and molecular transitions needed for to achieve high efficacy PBT. The limited spectrum of a laser, typically a range of ±1 nm around the laser's center wavelength value, makes it difficult to properly excite all the beneficial chemical reactions needed in PBT. It is difficult to cover a range of frequencies with a narrow bandwidth optical source. For example, referring again to FIG. 3, the chemical reactions of chromophores (light absorbing molecules) involved in making the CCO absorption spectrum (curve 41b) are clearly different than the reactions giving rise to absorption tail (curve 41a). Assuming the absorption spectra of both regions are shown to be beneficial it is difficult to cover this wide range with an optical source having a wavelength spectrum only 2 nm wide.

So just as sunlight has an excessively broad spectrum of wavelengths, photobiologically exciting many competing chemical reactions with many EMR wavelengths, some even harmful, the wavelength spectrum of laser light is too narrow and does not stimulate enough chemical reactions to reach full efficacy in phototherapeutic treatment. This subject is discussed in greater detail in a related application entitled "Phototherapy System And Process Including Dynamic LED Driver With Programmable Waveform", by Williams et al. (U.S. application Ser. No. 14/073,371), now U.S. Pat. No. 9,877,361, issued Jan. 23, 2018, which is incorporated herein by reference.

To deliver PBT by exciting the entire range of wavelengths in the transparent optical window 45, i.e. the full width from approximately 650 nm to 950 nm, even if four different wavelength light sources are employed to span the range, each light source would require a bandwidth almost 80 nm wide. This is more than an order of magnitude wider than the bandwidth of a laser light source. This range is simply too wide for lasers to cover in a practical manner. Today, LEDs are commercially available for emitting a wide range of light spectra from the deep infrared through the ultraviolet portion of the electromagnetic spectrum. With bandwidths of ±30 nm to ±40 nm, it is much easier to cover the desired spectrum with center frequencies located in the red, the long red, the short near infrared (NIR) and the mid NIR portions of the spectrum, e.g. 670 nm, 750 nm, 810 nm, and 880 nm.

Photobiomodulation therapy (PBT) is sharply distinguishable from photo-optical therapy. As shown in FIG. 4A, PBT involves direct stimulation of tissue 5 with photons 3 emitted from LED pad 2. Tissue 5 may be unrelated to the eyes and may comprise organs associated with the endocrine and immune systems, such as kidneys, liver, glands, lymph nodes, etc. or the musculoskeletal system, such as muscles, tendons, ligaments, and even bone. PBT also directly treats and repairs neurons including peripheral nerves, the spinal cord, as well (as shown) brain 5 and the brain stem. PBT transcranial treatment penetrates the skull and exhibits significant and rapid therapeutic benefits in concussion recovery and repairing damage from mild traumatic brain injury (mTBI). In other words, PBT energy is absorbed by chromophores in cells not associated with the optic nerve. Photo-optical therapy in contrast is based on exciting the retina with colored light or images to invoke a cognitive or an emotional response or to help synchronize the body's circadian rhythms to its surroundings. In such cases, image 12 from light source 12 stimulates the optic nerve in eye 11 to send electrical signals, i.e. neural impulses, to the brain 5.

Several rudimentary tests highlight the many and vast differences between PBT and photo-optical therapy. For one, photo-optical therapy only works on the eyes, whereas PBT affects any cell including internal organs and brain cells. In photo-optical therapy, light is directed to light perceiving cells (photo-transduction), which in turn results in the generation of electrical signals that are carried to the brain, whereas PBT stimulates chemical transformations, ionic, electron and thermal transport within treated cells and tissue, with no need for signal transduction to the brain. The effect is local and systemic without the assistance of the brain. For example, blind patients respond to PBT but not to photo-optical therapy. Another distinction between photo-optical therapy and PBT is illustrated in FIG. 4B. In the case of sight, i.e. photo-optical stimulation or vision, the combination of red light 15A and blue light 15B emanating from light source 14 once received by eye 11 sends an electrical signal 9 to brain 5, which perceives the color of the impinging light as purple. In reality, violet/purple light has a much shorter wavelength than blue or red light, and as such comprises photons with higher energy than red light 15A or blue light 15B. In the case of PBT, cell 16 and the mitochondria 17 contained therein will respond photo-chemically to light source 14 as though it is emitting red light 15A and blue light 15B (which it truly is), and not respond as though purple light is present. Only true short wavelength purple light emitted from a violet or ultraviolet light source can produce a photobiomodulation response to purple light. In other words, mitochondria and cells are not "fooled" by the blending of different colored light the way the eye and the brain are. In conclusion, photo-optical stimulation is very different from photobiomodulation, As such, techniques and developments in the art of photo-optical therapy cannot be considered as applicable in or relevant to PBT.

As an etymological side note, ambiguity in nomenclature prompted researchers to change original references using the catholic term 'phototherapy' or PT into the more modern currently accepted term 'photobiomodulation therapy' or PBT. The term phototherapy was used generically to mean any therapeutic application of light including (i) photo-optical therapy involving visual stimulation, (ii) photobiomodulation therapy or PBT involving cellular modulation, and (iii) photodynamic therapy or PDT activating an injected chemical or applied ointment with light to encourage a chemical reaction. A similarly broad term 'photochemistry', chemical reactions stimulated by light, also ambiguously refers to any and all of the foregoing treatments. So, while photochemistry and phototherapy have broad meaning today, PBT, PDT, and photo-optical therapy have specific non-overlapping interpretations.

As another source of confusion, the term LLLT was originally intended to mean 'low level laser therapy' to distinguish lasers operated at low power levels (sometimes called 'cold' lasers in the popular press) from lasers operating at high power for tissue ablation and surgery. With the advent of LED based therapies, some authors conflated the nomenclature for laser- and LED-based therapies into 'low-level light therapy', having the same acronym LLLT. This unfortunate action caused much confusion in the published art and indiscriminately blurred the distinction of two very different photonic delivery systems. A 'low level' laser is eye safe and burn-safe only because it is operated at low levels. If a cold laser is powered up to a higher level either intentionally or accidentally so that it is no longer 'cold', it can cause severe burns or blindness in milliseconds. In contrast, LEDs always operate at low levels and cannot be operated at high optical power densities. At no power level can LEDs cause blindness. And although LEDs can overheat by running too much current through them for extended durations, they cannot cause an instantaneous burns or tissue ablation the way a last can. As such, the term low-level light is meaningless in reference to a LED. Accordingly, throughout this application the acronym LLLT shall refer only to laser PBT meaning low-level laser therapy and will not be used to refer to LED PBT.

Present Day Photobiomodulation Therapy Systems

Today's state-of-the-art photobiomodulation therapy systems, shown by example system 50 in FIG. 5, comprises controller 51, electrically connected to two sets of LED pads.

Specifically, output A of controller 51 is connected by cable 53a to a first LED pad set comprising electrically interconnected LED pad 52b. LED pads 52a and 52c are optionally connected to LED pad 52b by electrical jumpers 54a and 54b to create a first LED pad set operating as a single LED pad comprising over 600 LEDs and covering a treatment area exceeding 600 $cm^2$. In a similar manner, output B of controller 51 is connected by cable 53b to a second LED pad set comprising electrically interconnected LED pad 52e. LED pads 52d and 52f are optionally connected to LED pad 52d by electrical jumpers 54c and 54d to create a second LED pad set operating as a single LED pad comprising over 600 LEDs and covering a treatment area exceeding 600 $cm^2$.

In the system shown, controller 51 not only generates the signals to control the LEDs within the pads but also provides a source of power to drive the LEDs. The electrical power delivered from controller 51 to the LED pads is substantial, typically 12 W for two sets of three pads each. An exemplary electrical schematic of the system is shown in FIG. 6A, where controller 61 includes switch-mode power supply SMPS 65 used to convert power from the 120 V to 220 V AC mains 64 into at least two regulated DC voltage supplies, namely 5 V for control and logic, and a higher voltage supply+$V_{LED}$ used for powering the strings of LEDs in the LED pads. Typical voltages for +$V_{LED}$ range from 24 V to 40 V depending on the number of LEDs connected in series. To facilitate algorithmic control, microcontroller (μC) 67 executes dedicated software in response to user commands input on touchscreen LCD panel 66. The result is a series of a pulses output in some alternating pattern on outputs A from logic buffers 68a and 68b used to independently control red and near infrared (NIR) LEDs in the LED pads connected to output A. A similar arrangement is included for output B using its own dedicated logic buffers but where μC 67 is able to manage and control both A and B outputs concurrently.

The signal on output A is then routed to one or more LED pads 62 through shielded-cable 63 comprising high current power lines ground GND 69a, 5V supply line 69b, and +$V_{LED}$ supply line 69c, as well as LED control signal line 70a for controlling conduction in NIR LEDs 71a through 71m, and LED control signal line 70b for controlling conduction in red LEDs 72a through 72m. Control signal lines 70a and 70b in turn drive the base terminals of bipolar junction transistors 73a and 73b, respectively, the transistors operating as switches to pulse the corresponding strings of LEDs on and off. When the input to either bipolar transistor is low, i.e. biased to ground, no base current and no collector current flow and the LED string remains dark. When the input to either bipolar transistor is high, i.e. biased to 5V, base current flows and in a corresponding manner collector current flows, illuminating the LEDs in the corresponding LED string. LED current flow is set by the LED turn-on voltages and by current limiting resistors 74a or 74b. Using resistors to set LED brightness is not preferred because any variation in the LED voltage either from manufacturing stochastic variability or from variations in temperature during operation will result in a change in LED brightness. The result is poor uniformity in LED brightness across an LED pad, from LED pad to LED pad, and from one manufacturing batch to the next. An improvement in maintaining LED brightness uniformity can be gained by replacing resistors 74a and 74b with fixed value constant current sources or sinks 75a and 75b, as shown in FIG. 6B.

The physical connection between PBT-controller 61 and LED pads 62, over shielded cable 63 can also be described as two interacting communication stacks in the parlance of the 7-layer open source initiative or 7-layer OSI model. As shown in FIG. 7, PBT controller 61 can be represented as stack 80 comprising application Layer-7, the PBT controller's operating system referred to LightOS v1. In operation the application layer transfers data to the Layer-1 physical or PHY layer comprising logic buffers. Stack 80 unidirectionally sends electrical signals 82 to the PHY Layer-1, i.e. the LED string drivers, in communication stack 81 of passive LED pad 62.

Because the electrical signals comprise simple digital pulses, parasitic impedances in cable 63 can affect communication signal integrity and LED pad operation. As shown in FIG. 8, as sent square wave electrical signal 82 may be significantly distorted into received waveform 83 including reduced magnitude and duration 84a, slow rise times 84b, voltage spikes 84c, oscillations 84d, and ground loops 89 affecting the signal ground bounce 84e. The cable parasitics responsible for these distortions include power line series resistances 87a to 87c and inductances 86a to 86c, and inter-conductor capacitances 85a to 85e. Other effects can include ground loop conduction 89 and antenna effects 88.

Another disadvantage of using simple electrical signal connections between PBT controller 61 and the LED pads is the PBT system cannot confirm if the peripheral attached to cable 63 is in fact a qualified LED pad or an invalid load. For example, improper LED configurations not matched to the PBT controller, as shown in FIG. 9, will result in either inadequate or excessive LED current. Specifically, as shown by icon 91, too many series LEDs will result in a high voltage-drop with low or no LED illumination. In contrast, shown in icon 92, too few series connected LED can result in excessive current, overheating, and possible patient burn risks.

Powering non-LED loads from PBT controller 61 can damage the invalid peripheral, the controller, or both. This is particularly problematic because one pin on the PBT controller's output supplies high voltage of 20V or greater, exceeding the 5V rating of most semiconductors and causing permanent damage to ICs. Inductive loads as represented by icon 94 can cause overvoltage voltage spikes that may damage the controller. Loads containing motors such as disk drives or fans can lead to excessive damaging inrush currents. Shorted-cables or shorted electrical loads, as depicted by icon 93, can cause fires. Connecting a battery to the PBT controller 61, as shown by icon 96, can result to excessive current and fire risk. Overcharging or subjecting a chemical cell to an overvoltage also has the potential to cause intense fire or even an explosion. Unknown electrical loads, shown by icon 95, represent unspecified risks. Especially problematic is any connection between PBT controller 61 and an electrical power source such as a generator, car battery, or UPS, the result of which may include complete destruction of the system and an extreme fire hazard. In FIG. 9 the icons are intended to represent a class of electrical loads but should not be considered as a specific circuit.

Other problems arise when mismatched LED pads are connected to the same output. For example, in FIG. 10 two different LED pads 62 and 79, powered by a common cable 63, share connections to ground 69a, 5V supply 69b, high voltage $+V_{LED}$ supply 69c, visible light $LED_v$ control signal 70a and near infrared $LED_{nir}$ control signal 70b. As shown, LED pad 62 includes current sinks 75a and 75b and switches 73a and 73b driving corresponding LEDs 71a through 71m having a visible light wavelength $\lambda_v$ and LEDs 72a through 72m having a near infrared wavelength $\lambda_{nir2}$. Alternatively, LED pad 79 includes the same current sinks 75a and 75b and switches 73a and 73b but drives different wavelength LEDs, specifically LEDs 76a through 76m having a visible light wavelength $\lambda_{v2}$ and LEDs 77a through 77m having a near infrared wavelength $\lambda_{nir2}$. None of the LED strings has the same wavelength light as the other LED strings. For example, $\lambda_v$ may comprise red light while $\lambda_{v2}$ may comprise blue light. Similarly, $\lambda_{nir}$ may comprise 810 nm radiation while $\lambda_{v2}$ may comprise 880 nm. In operation, the parallel connection of the red and blue LEDs driven by the $LED_v$ signal 70a means that a treatment for red light could inadvertently be driving blue light. Similarly, the parallel connection of the 810 nm and 880 nm LEDs driven by the $LED_{nir}$ signal 70a means that a treatment for one wavelength NIR LED could inadvertently be driving a different wavelength.

Another issue arises when two or more LED pads are connected to both LED outputs at the same time, as shown in FIG. 11A. As shown PBT controller 51 has two outputs, output A and output B. These outputs are intended to drive separate sets of LED pads. As shown, Output A connects to LED pad 52d through cable 53a. Output B connects to LED pad 52e through cable 53b and also connects through jumper 54d to LED pad 52f. Accidentally, however, jumper 54c connects LED pad 52e to LED 52d and thereby shorts output A to output B. The electrical impact of shorting outputs A and B together depends on the treatment program being executed. FIG. 11B illustrates the case where both outputs A and B of buffer 100 are driving the red/visible light output, specifically buffers 101a and 101c are active at the same time. As shown, the outputs are shorted through electrical conductors 102a to LED pad 105a, through connector 104a to LED pad 105b, and ultimately through connector 103a. In operation, the frequency and pulse patterns of the two outputs are asynchronous meaning any combination of high and low output biases can occur. If the pull-up transistors are too strong, the output buffers can destroy on another; if not, the alternating on-signals can cause the LEDs to stay on with a high duty factor causing overheating and presenting a possible patient burn risk.

In FIG. 11C, buffer 101a in output A is powering the red LEDs in LED pads 105a and 105b while buffer 101d in output B is powering the NIR LEDs also in LED pads 105a and 105b. Although the independent operation of both red and NIR LEDs does not represent an electrical problem, the simultaneous conduction of both red and NIR LEDs will result in overheating of the LED pad, potentially damaging the pad and possibly burning a patient. This overpower condition is illustrated by the waveforms shown in FIG. 11D where the power $P_v$ of the conducting visible LEDs shown by waveform 110 has an average power $P_{ave}$ 113, and the power $P_{nir}$ of NIR LEDs shown by waveform 111 has an average power $P_{ave}$ 114. Together the aggregate power waveform 112 has an average power 115 of magnitude $2P_{ave}$.

In today's LED pads, overheating for any reason is problematic because there is no temperature protection. As shown in FIG. 12, even if LED pad 109 does have temperature sensing, with unidirectional data flow 82 in cable 63 there is no way for LED pad 109 to inform PBT controller 61 of an over temperature condition or to suspend operation.

As described in the foregoing, the limitations of today's PBT systems above are numerous, impacting PBT system utility, functionality, safety, and expandability. These limitations include the following issues:

Electrical "signal" communication to LED pad—Signals from the PBT controller to LED pads are simple digital pulses, not differential communication between a bus transceiver pair. These signals are sensitive to common mode noise and ground loops affecting the magnitude and duration of the pulses controlling LED operation. As simple electrical pulses, the system also lacks any error checking capability so malfunctions cannot be corrected or even detected.

Unidirectional signal flow from PBT controller to LED pad—With unidirectional data flow, PBT controllers cannot authenticate any LED pad connected to its output, nor once connected can they monitor a pad's operating condition. Unidirectional data also prevents feedback of a LED pad's status or reporting of other pad information to the host PBT controller.

Inability to detect a multi pad misconnection short—Through user error, the misconnection of two outputs of a PBT controller to the same LED pad or pads, i.e. inadvertently shorting two outputs together, means both outputs are driving the same LED strings. This misconnection error can damage the LED driver circuitry, cause LED overheating, patient burn risk, and potentially fire.

Inability to identify approved LED pads or certified manufacturers—Lacking any ability to identify an LED pad's pedigree a PBT system will unknowingly drive any LED connected to it including illegal, counterfeit, or knock-off LED pads. Driving pads not made or certified by the system specifier or manufacturer has unknown consequences ranging from loss of functionality and reduced efficacy to safety risks. Commercially, the merchandizing and sale of counterfeit and copycat LED pads also robs IP licensed PBT device merchants of legal income.

Inability to identify a connected device as an LED pad—Without the ability to confirm if a device connected to a PBT controller output is an LED pad (rather than a completely unrelated peripheral such as a speaker, battery, motor, etc.), connection of an unauthorized electrical load to a PBT system's output will invariably damage either the accessory, the PBT controller, or both. When driving an unknown electrical load, high voltage present on the controller's output pins during operation also presents a fire hazard.

Inability to identify power sources—The inability of a PBT controller to identify connection of its output to a power source (such as AC power adapters, batteries, car electrical power, or generators) represents a real safety risk, whereby the power supply contained within the PBT controller competes with the external power source. The interconnection of two dissimilar power supplies may result in excessive currents, voltages, power dissipation, or uncontrolled oscillations leading to damage of the external power source, the PBT controller, or both.

Inability to control or limit driver output current—Connection of a shorted load such as a damaged pad, a wire short, or any load that exhibits a high inrush current (such as a motor) represents a high current risk and possibly a fire hazard. Inductive loads such as solenoids also can momentarily create excessive voltages damaging low-voltage components.

Inability to detect batteries connected to a PBT system's output—Connecting a battery pack to a PBT system's output has the potential for damaging the battery pack, accidentally charging the battery with the wrong charging conditions and giving rise to over-voltage, over-current, or over-temperature conditions in the electrochemical cells. Improper charging of wet-chemistry or acid batteries has the potential for acid or electrolyte leaks. The improper charging of lithium ion batteries can cause overheating, fire, and even explosions.

Inability to detect over-temperature conditions in LED pads—Overheating of a LED pad risks patient discomfort and burns, pad damage, and in extreme cases the possibility of fire.

Inability to identify the LED configuration within a LED pad—Unable to identify the series-parallel array configuration of LEDs in a LED pad, the PBT controller is unable to determine if the pad is compatible with the PBT system or even if LED operation is possible. For example, too few series connected LEDs can damage the LEDs with too much voltage. Too many series connected LEDs will result in dim or no illumination. Too many parallel strings of LEDs can result in excessive total pad current and consequentially overheating, as well as large voltage drops across interconnections, poor light uniformity across a LED pad, and possible damage to PCB's conductive traces.

Inability to identify the types of LEDs contained within a LED pad—Unable to detect what wavelength LEDs are in a pad, a PBT system has no means by which to match its treatment programs to the LED array or to select the right wavelength LEDs for each specific waveform in the treatment protocol.

PBT controller outputs are each limited to a fixed number of control signals—With only one or two control signals per output, today's PBT controllers are incapable of driving three, four, or more different wavelengths of LEDs within the same pad with different excitation patterns.

Limited mobility—In present day medical grade PBT systems, the connection of a central PBT controller to LED pads requires cable connections. While such tethered PBT systems are generally acceptable in hospital applications (and possibly in clinical settings), in consumer, paramedic, and military applications limiting mobility with cables or wires is not useful.

Incapable of waveform synthesis—PBT systems lack the technology to drive LEDs with any waveforms other than square wave pulses. Square wave pulsed operation limits LED illumination patterns to one-frequency-at-a-time operation. Since pulse frequency affects the energy coupling to specific tissue types, a single frequency PBT system can only optimally treat one tissue type at a time, extending the required therapy time and patient/insurance cost. Analysis also reveals square wave pulses waste energy, producing off harmonics not necessarily beneficial to a therapy. LED drive using sinusoids, chords, triangle waves, sawtooth waveforms, noise bursts, or audio samples requires complex waveform synthesis within the LED pad. Although host PBT controllers should have sufficient compute capability to synthesize such waveforms, the capability is not beneficial because the signal cannot be delivered over long cables without suffering significant waveform distortion. Unfortunately, LED pads cannot perform the task. Using cheap discrete components, present day LED pads are incapable of performing any waveform synthesis whatsoever, not to mention that the communication protocols needed to remotely select or change the synthesized waveform do not exist.

Distribution of new LED driver algorithms—Present PBT systems lack the ability to download software updates from a database or server to correct software bugs or to install new treatment algorithms.

Inability to capture and record real time patient biometric data—Present PBT systems lack the ability to collect biometric data such as brain waves, blood pressure, blood sugar, blood oxygen, and other biometrics during a treatment or the ability to embed this collected data into the treatment file record.

Inability to gather real time images of treatment area—Present PBT systems lack any means by which to measure or create images of tissue during treatment. The systems also lack the ability to store still and video images or to match the images to a PBT session's treatment time.

Inability for users (doctors) to create new treatment algorithms—Present PBT systems lack any capability for users such as physicians or researchers to create new algorithms or to string existing treatments together to form complex therapy specific treatments, e.g. optimizing an excitation sequence for activating injected stem cells (useful in accelerating stem cell differentiation while reducing rejection risks.)

Electronic distribution of documentation—Present PBT systems are unable to distribute and update any documentation electronically. It would be beneficial if the distribution of FDA advisories or rulings, as well as errata and updates to PBT operating and therapy manuals, treatment guides, and other documentation can be provided electronically to all PBT system users. Such capability is not available in any medical devices today.

Treatment tracking—Present PBT systems are unable to track the treatment use history, capture the system's use in a treatment log, and upload the treatment log to a server. Lacking real time treatment logs via network connectivity, the widespread commercial adoption of PBT systems by physicians, hospitals, clinics, and spas is problematic. Without uploaded use logs, present day PBT systems cannot support revenue-sharing lease business models because the lessor is unable to verify the lessee's system use. Similarly, hospitals and clinics cannot confirm PBT systems use for insurance audits and for fraud prevention. In pay-to-use SaaS (software as a service) payment models, the PBT service agent is unable to confirm a client's use history.

Electronic prescriptions—No physical medicine devices today including PBT systems are capable of securely transferring and distributing doctor prescriptions into a medical device.

Remote disable—No PBT system today is capable of disabling device operation in the case of non-payment or in the case of theft to stop black market trade.

Location tracking—No PBT system today is capable of tracing the location of a stolen PBT system to track the thieves.

Secure communication—Since PBT systems today use electrical signals rather than packet-based communication to control LED pads, then hacking and direct measurement of communication between a host PBT system and an LED pad is trivial, lacking any security whatsoever. Moreover, PBT systems today lack any provision for Internet communication and the security methods needed to prevent content hacking and to thwart identity theft in compliance with HEPA regulations. In the future, encryption alone is expected to be inadequate in securing data communication across the Internet. In such cases connectivity to private hypersecure networks will also be required.

In summary, the architecture of present day PBT systems is completely outmoded, and requires an entirely new system architecture, new control methods, and new communication protocols to facilitate an efficacious, flexible, versatile, and secure solution to providing photobiomodulation therapy.

SUMMARY OF THE INVENTION

In the photobiomodulation therapy (PBT) process of this invention, defined patterns (e.g., sequences of square-wave pulses, sine waves, or combinations thereof) of electromagnetic radiation (EMR) having one or more wavelengths, or spectral bands of wavelengths, are introduced into a living organism (e.g. a human being or animal) using a distributed system comprising two or more distributed components or "nodes" communicating using a bus or transceiver to send instructions or files between or among the constituent components. The radiation is normally within the infrared or visible parts of the EMR spectrum, although ultraviolet light may sometimes be included.

EMR of a single wavelength may be used, or the pattern may include EMR having two, three or more wavelengths. Rather than consisting of radiation of a single wavelength, the EMR may include spectral bands of radiation, often represented as a range of wavelengths centered on a central wavelength, e.g., $\lambda \pm \Delta\lambda$. The pulses or waveforms may be separated by gaps, during which no radiation is generated, the trailing edge of one pulse or waveform may coincide temporally with the leading edge of the following pulse, or the pulses may overlap such that radiation of two or more wavelengths (or spectral bands of wavelengths) may be generated simultaneously.

In one embodiment, the distributed PBT system's components comprise a PBT controller and one or more intelligent LED pads communicating using a unidirectional serial data bus sending data, files, instructions, or executable code from the PBT controller to the intelligent LED pads. In a second embodiment, the distributed PBT system's components comprise a PBT controller and one or more intelligent LED pads communicating using a bidirectional data bus or transceiver whereby the PBT controller is able to send data, files, instructions, or executable code to the intelligent LED pad and conversely the intelligent LED pad is able to return data to the PBT controller regarding the pad's operating status or patient condition, including LED pad configuration data, program status, fault conditions, skin temperature or other sensor data. The other sensor data may include two-dimensional temperature maps, two- or three-dimensional ultrasound images, or may comprise biometric data such as pH, humidity, blood oxygen, blood sugar, or skin impedance etc., which in turn may optionally be used to change the treatment conditions, i.e. operating in a closed biofeedback loop.

In one embodiment, the EMR is generated by light-emitting diodes (LEDs) arranged in serial "strings" connected to a common power supply. Each LED string may comprise LEDs designed to generate radiation of a single wavelength or band of wavelengths in response to a defined constant or time varying current. The LEDs may be embedded in a flexible pad designed to fit snuggly against a skin surface of a human body, allowing the target tissue or organ to be exposed to a uniform pattern of radiation. Power may be delivered to each intelligent pad from a cable connecting the LED pad to the PBT controller or alternatively may be provided to the LED pad from a separate power source. In an alternative embodiment, semiconductor laser diodes may be used in place of LEDs configured in an array to create a uniform pattern of radiation or alternatively mounted in a handheld wand to create a spot or small area of concentrated radiation.

In the distributed PBT system disclosed herein, each of the LED strings is controlled by an LED driver, which in turn is controlled by a microcontroller contained within the intelligent LED pad. The LED pad's microcontroller communicates with another microcontroller or computer in the PBT controller via a communication bus, which may include wired connectivity such as USB, RS232, HDMI, I$^2$C, SMB, Ethernet, or proprietary formats and communication protocols, or which may alternatively comprise wireless media and protocols including Bluetooth, WiFi, WiMax, cellular radio using 2G, 3G, 4G/LTE, or 5G protocols, or other proprietary communication methods.

Using a display, keyboard or other input device connected to the PBT controller, a doctor or clinician can select the particular algorithm (process sequence) that is suited to the condition or disease being treated. The instructions are then communicated from the PBT controller over the wired or wireless data bus to one or more intelligent LED pads, instructing the pad's microcontroller when to commence or suspend a PBT treatment and specifying what treatment is to be performed.

In one embodiment, referred to as data streaming, the PBT controller sends a stream of data packets specifying the LED driving waveforms including the timing of when an LED is instructed to conduct current and the magnitude of the current to be conducted. The streaming instructions sent by the controller are selected from a "pattern library" of algorithms, each of which defines a particular process sequence of pulses or waveforms of the EMR generated by the LED strings. Upon receiving the data packets over the data bus, the intelligent LED pad stores the instruction in memory, then commences "playback" of the streaming data file, i.e. driving the LEDs in accordance with the instructions received. During the playback of the streaming data file, communication from the PBT controller to the intelligent LED pad over the data bus may be interrupted to accommodate system safety checks or to allow the intelligent LED pad to report its status or to upload sensor data to the PBT controller.

Unlike prior art PBT systems, in the disclosed distributed PBT system the PBT controller is not constantly sending instructions to the intelligent LED pads. During intervals when the PBT controller is silent, either listening to the data bus, or receiving data from the intelligent LED pads over the data bus, each intelligent LED pad must operate autonomously and independently from the PBT controller and the other LED pads connected on the same data bus or communication network. This means the PBT controller must send sufficient data to the intelligent LED pad to be stored in the pad's memory to support uninterrupted LED playback operation until the next data file can be delivered.

In another embodiment, the PBT controller delivers a complete playback file to the intelligent LED pad, defining the entire execution sequence of a PBT treatment or session. In this method the file is delivered prior to commencing playback, i.e. before executing treatment. As soon as the file is loaded into the memory of the intelligent LED pad, the in-pad local microcontroller can execute playback in accordance with instructions contained in the playback file. The transferred playback file may comprise either (i) an executable code file including the totality of all LED driving waveform instructions, (ii) a passive playback file defining the treatment durations and settings that is interpreted by executable code comprising a LED player software, or (iii) data files comprising waveform primitives that are subsequently combined in a prescribed manner by the LED pad's microcontroller to control the LED illumination pattern and execute a PBT treatment or session.

In the latter two examples, the executable code needed to interpret the playback file, referred to as the "LED player", must be loaded into the intelligent LED pad prior to commencing playback. This LED player can be loaded into the intelligent LED pad at the time a user instructs the PBT controller to commence therapy, or can be loaded into the intelligent pad at a previous date, e.g. when the LED pad is programmed during manufacturing or at the time the PBT controller is turned on and establishes that the intelligent LED pad is connected to the PBT controller's local area network. In cases where the LED player file is previously loaded into an intelligent LED pad and stored in non-volatile memory for extended durations, the distributed PBT system must include provisions to determine whether the LED player file previously loaded into the LED pad is still current or has become obsolete. If the PBT controller determines that the LED player file stored in the LED pad is up-to-date, LED playback can commence immediately. Alternatively, if the PBT controller determines that the LED player file stored in the LED pad is obsolete, expired, or just not up-to-date, the PBT controller can download the current LED player file to the LED pad either immediately or after first obtaining the user's approval. In some instances, performing treatments using an obsolete LED player file may result in improper playback or a system malfunction. In such cases, the operation of the intelligent pad may be mandatorily suspended by the PBT controller until the current LED player file is downloaded and stored in the LED pad.

The ability of an LED pad to function independently and autonomously for a defined duration distinguishes the LED pad as "intelligent" as compared to a passive LED pad. Passive LED pads, in contrast, are limited to responding to real time signals sent from the PBT controller, where any interruption in communication will immediately result in disruption of the LED pad's operation, affecting the pulse train or waveform of the EMR emitted by the LEDs in the pad. In other words, bus communication between the PBT controller and one or more intelligent LED pads can be considered as a packet-switched local area network (LAN).

Another key feature of the disclosed distributed PBT system is its autonomous safety systems—protection and safety functions operating in each intelligent LED pad independent of the PBT controller. Specifically, in network connected professional medical devices, safety systems must continue to operate without fail even when network connectivity is lost. As a key feature of this invention, during operation each intelligent LED pad regularly executes a safety related subroutine to ensure that its software is operating normally and that no dangerous conditions exist. These intelligent LED pad embedded protective features include a software related "blink timer" subroutine, a watchdog timer, overvoltage protection, LED current balancing, and over-temperature protection. The autonomous safety functions are included in firmware comprising the intelligent LED pad's local operating system (referred to herein as "LightPadOS," which is stored in non-volatile memory in the intelligent LED pad and executed by the microcontroller included within each intelligent LED pad.

Upon receiving an instruction to commence therapy, an intelligent LED pad's LightPadOS starts a software timer and concurrently resets and starts a hardware counter in the pad's microcontroller. The LightPadOS then launches the executable code to perform a PBT treatment, executed as a streaming data file or as a LED player (playing a specific playback file) in synchrony with an advancing program counter. The program counter advances at a frequency defined by either a shared system clock or a precision time reference specific to one or several intelligent LED pads. Such time references can be established using a RC relaxation oscillator, a RLC resonant tank oscillator, a crystal oscillator, or a micromechanical machine based oscillator. In this manner, pulses with nanosecond precision can be used to synthesize square wave pulses, sine waves, and other waveforms varying in frequency and in duration. The synthesized waveforms are then used to drive strings of varying waveform LEDs in the selected patterns according to defined algorithms.

During program execution (playback), both the software blink timer and the hardware-based watchdog timer continue to count in synchrony with the program counter time base. When the software blink timer reaches a certain predefined time (referred to herein as the blink interval), e.g. 30 seconds, the blink timer generates an interrupt signal which is sent to the pad's operating system LightPadOS and which suspends the treatment's program counter and commences an 'interrupt service routine" or ISR. The ISR then performs housekeeping functions, which may include reading the temperature of one or more sensors in the intelligent LED pad, sending the temperature data to the PBT controller, and concurrently comparing the highest measured temperature to a defined range. If the temperature exceeds the defined range a warning flag is also generated and sent to the PBT controller as a request for the system to take some action, e.g. to reduce the LED duty factor (on time per cycle) to lower the pad's temperature, or to suspend treatment.

If, however, the highest measured temperature exceeds a predetermined safety threshold, the intelligent LED pad immediately suspends execution of the treatment program and simultaneously sends a message to the PBT controller. Unless the PBT controller restarts the program, the overheating intelligent LED pad will remain off indefinitely. In this manner, if an over-temperature condition occurs while the PBT controller is unavailable or malfunctioning, or if the network or communication bus is busy or unavailable, the default condition is to stop the treatment.

During an ISR the intelligent LED pad can perform other safety tests, for example checking for excessive input voltages resulting from a power supply failure, excessive currents resulting from an internal pad short circuit, or detecting excessive moisture resulting from sweat or water contacting the intelligent LED pad, possibly resulting a missing or improperly applied sanitary barrier between the patient and the LED pad. In any case, the malfunctioning intelligent LED pad firsts suspends operation and then sends a message to the PBT controller, informing the PBT controller of the fault. The other LED pads may also be informed of the fault. In such a case the other LED pads may continue to operate independently (even though one pad has discontinued operation) or, alternatively, all the intelligent LED pads may be shut down concurrently (either by the PBT controller or via direct pad-to-pad communications). After the ISR is complete, control is returned to the LED pad performing the PBT treatment by restarting the program counter, restarting the software blink timer, and restarting the watchdog timer.

In the event that a software execution failure occurs either in the LED playback file or in the ISR subroutine, the program counter will not resume operation and the blink timer will not be reset and restarted. If the watchdog timer reaches its full count without being reset (e.g. at 31 seconds), it means software execution has failed. A watchdog timer time-out instantly generates an interrupt flag suspending program execution in the offending LED pad and sending a fault message to the PBT controller and optionally to the other LED pads. As a result, a software failure always defaults to a non-operational state for the malfunctioning LED pad to ensure patient safety even in the absence of network connectivity.

Aside from autonomous safety features, in another embodiment the disclosed distributed PBT system includes centralized protection of the networked components administered by the PBT controller. Specifically, the PBT operating system operating with the PBT controller, referred to herein as "LightOS," includes a number of protective provisions, including the ability to detect if a component attached to the network or communication bus is an authorized component or a fraud. If a user attempts to connect a light pad or other component to the PBT controller's network that cannot pass a prescribed authentication process, then the component will be denied access to the network. The PBT controller's LightOS operating system can prohibit unauthorized access in any number of ways including shutting down the entire distributed system until the offending device is removed, not sending any data packets to the fraudulent device's IP address, or encrypting the commands so as to make them unrecognizable by the unauthorized component.

To effectuate multi-layer secure communication in the disclosed distributed PBT system, the operating system of the PBT controller (LightOS) and the operating system of the intelligent LED pads (LightPadOS) comprise parallel communication stacks using consistent protocols and shared secrets not discernable to a device operator, hackers, or unauthorized developers. As such the distributed PBT system operates as a protected communication network with the ability to execute security on any number of communication layers including data link Layer-2, network Layer-3, transport Layer-4, session Layer-5, presentation Layer-6, or application Layer-7.

For example, a numeric code installed and cryptographically hidden in both a PBT controller and an intelligent LED pad, i.e. a shared secret, can be used to confirm the authenticity of a network connected intelligent LED pad without ever divulging the key itself. In one method of LED pad validation executed on data link Layer-2, the PBT controller passes a random number to the intelligent LED pad over the network or communication bus. In response, the microcontroller in the LED pad decrypts its copy of the shared secret (numeric code), merges it with the received random number then performs a cryptographic hash operation on the concatenated number. The intelligent LED pad then openly returns the cryptographic hash value across the same transceiver link.

Concurrently, the PBT controller performs an identical operation decrypting its own copy of the shared secret (numeric code), merging it with the generated random number it sent to the LED pad then performing a cryptographic hash operation on the concatenated number. The PBT controller next compares the received and locally generated hash values. If the two numbers match the pad is authentic, i.e. it is 'authorized' to connect to the network. The aforementioned authentication algorithm may be executed on any PHY Layer-1 and/or data-link Layer-2 connection over any data bus or packet switched network including USB, Ethernet, WiFi or cellular radio connections. In the event of a WiFi connection, the data link may also be established using WiFi protected access protocol WPA2.

For 'administrative' purposes and security tracking, the authorization time and date (and as available the GPS location) of the authenticated component is stored in non-volatile memory and optionally uploaded to a server. The benefit of employing secure communication and AAA (authentication, authorization, administration) validation of all connected components in the distributed PBT system is crucial to ensure safety and protection from the intentional connection of uncertified and potentially unsafe imposter devices. In this way, imposter devices cannot be driven by the distributed PBT system. AAA validation also protects against the accidental connection of devices not intended for operation as part of the PBT system such as lithium ion battery packs, unapproved power supplies, speakers, disk drives, motor drivers, high power Class III and Class IV lasers, and other potential hazards unrelated to the PBT system.

The security of a distributed PBT system using a packet switched network (such as Ethernet or WiFi) may also be enhanced by using dynamic addressing on network Layer-3 and dynamic port assignment on data transport Layer-4. In the operation of a PBT controller not connected to the Internet or any other local area network, the PBT controller generates a dynamic IP address and a dynamic port address, and then broadcasts the address to the other network connected devices to which the intelligent LED pads respond with their own dynamic IP addresses and their own dynamic port addresses. In the event that the distributed PBT system is in contact with a router or the Internet, a dynamic host configuration processor (DHCP) is used to assign dynamic IP addresses. Similarly, a remote procedure call (RPC) is used to perform a dynamic port number assignment. Since dynamic IP addresses and dynamic ports change whenever a device is connected to a network, the risk of a cyber attack surface is reduced. Additional Layer-4 security can be added using TLS 'transport layer security', IPSec security protocol, or other protocols.

Once the components of a distributed PBT system are established through Layer-2 authentication, and Layer-3 and Layer-4 network and port address assignments, the distributed PBT system is ready to execute treatments. Upon the PBT controller receiving a user 'start' command, PBT treatment commences with an exchange of encryption keys or digital certificates between the PBT controller and the network-connected intelligent LED pads to establish a Layer-5 session. Once the session is opened, the PBT controller and each intelligent LED pad maintain their secure link during the exchange of files and commands until the treatment is completed or is terminated. Additional network security can be performed using encryption on presentation Layer-6 or at the application Layer-7.

As disclosed, the network-connected distributed PBT system functions as a single unified virtual machine (VM) able to reliably and safely perform photobiomodulation therapy using multiple intelligent LED pads offering No waveform distortion resulting from cable parasitics Bidirectional communication between PBT controller and intelligent LED pad Ability to detect a multi-pad misconnection short Ability to identify approved LED pads or certified manufacturers Ability to identify a connected device as an intelligent LED pad Ability to identify power sources and to control their operating voltage Ability to control and limit driver LED current Ability to detect batteries and prevent their connection to a PBT system's output Ability to detect over-temperature conditions in LED pads Ability to identify the LED configuration within a LED pad Ability to identify the types and configuration of LEDs contained within an intelligent LED pad Ability to independently control multiple outputs Ability to perform distortion-free waveform synthesis within an intelligent LED pad Ability to distribute new LED driver algorithms to intelligent LED pads Ability to capture and record real time patient biometric data Ability to gather real time images of a treatment area Support for the ability for users (doctors) to create new treatment algorithms Ability to support the electronic distribution of documentation Ability to perform treatment tracking Ability to manage the distribution of electronic prescriptions Ability to support a network connected remote control Ability to perform location tracking of PBT systems Ability to perform secure communication among components In another embodiment, the disclosed distributed PBT system comprises three stage waveform generation involving digital waveform synthesis, PWM pulse generation, and a dynamic multiplexed multichannel LED driver able to produce square wave, triangle wave, sawtooth, and sine wave waveforms. Waveforms may comprise a single periodic function or a chord of multiple frequency components.

In another embodiment, the disclosed waveform generator can generate chords based on a prescribed key and frequency scale, e.g. a chord comprising two, three, or four different frequencies including noise filtering. LED driving waveforms can also be produced from audio samples or by combining chords of scalable audio primitive waveforms of varying resolution and frequency. Waveforms may be stored in libraries based on waveform synthesizer parametrics, PWM waveforms, and PWM chords, including major, minor, diminished, augmented chords, octaves, and inversions. The software-controlled LED driver includes I/O mapping (multiplexing), dynamic current control, and various dynamic programmable current references.

In another embodiment, a distributed PBT system comprises multiple sets of intelligent LED pads controlled from a centralized multichannel PBT control station. An optional WiFi PBT remote is included to facilitate local start-start and pause control. In yet another embodiment, the PBT controller comprises an application running on a mobile device or smartphone controlling intelligent LED pads. The mobile application includes intuitive UI/UX control and biofeedback display. The app may also connect to the Internet or to a PBT server as a therapy database. In another embodiment, the PBT system comprises a fully autonomous LED pad set programmed over the network.

The distributed PBT system may also be used to control LEDs mounted in a mouthpiece to combat gum inflammation and periodontal disease or to drive individual LEDs mounted in ear buds inserted into a nose or ear to kill bacterial inflections in the sinus cavities. A variation of the individual LED buds may be used as "spots" placed on acupuncture points.

The aforementioned distributed PBT system is not limited to driving LEDs but may be used to drive any energy emitter positioned adjacent to a patient in order to inject energy into living tissue, including coherent light from a laser, or time-varying magnetic fields (magneto-therapy), micro-electric currents (electrotherapy), ultrasonic energy, infrasound, far infrared electromagnetic radiation, or any combination thereof.

In one such embodiment, a LED or laser handheld wand comprises a large area head unit and a pivoting handle, an integral temperature sensor, a battery charger, a step-up (boost) voltage regulator, and integral safety system as a proximity detector. In yet another embodiment, a magneto therapy device comprises a coil implemented as a multilayer printed circuit board and used to generate time-varying magnetic fields. The magneto therapy device may be implemented in a pad or in a wand. Magnetotherapy, used to reduce inflammation and joint pain may be operated independently or in combination with PBT.

Another handheld wand version includes a modulated voice coil operated as a vibrator applying pressure to muscles and tissue at infrasound frequencies, i.e. below 10 Hz, similar to massage therapy but with deeper penetration. Infrasound therapy, used to reduce relax muscles and improve flexibility and range of motion, may be operated independently or in combination with PBT.

In another embodiment an ultrasound therapy device comprises a bendable PCB with one or more piezoelectric transducers modulated in the ultrasound band from 20 kHz to 4 MHz. The pad with piezoelectric transducers may also include LEDs modulated by pulses in the audio spectrum. In one application of a combination ultrasound-LED device, the ultrasound produced by the piezoelectric transducers is employed to break up scar tissue and the light emitted by the LEDs is used to improve circulation and remove the dead cells thereafter.

BRIEF DESCRIPTION OF THE DRAWINGS

FIG. 4B illustrates the photochemical stimulation of intracellular organelle mitochondria by light of blended wavelengths.

FIG. 23A is a schematic representation of a high-side current-control element or "current source" driving a series string of LEDs comprising "m" LEDs with a low-side N-channel MOSFET digital enable.

FIG. 23B is a schematic representation of a current-source type high-side LED driver comprising a P-channel MOS- FET and a current-sensing gate bias circuit with reference current input ($-I_{ref}$) driving a string of LEDs in series with a low-side N-channel MOSFET digital enable.

FIG. 23C is a schematic representation of an exemplary current-source type high-side LED driver implementation comprising a current mirror sensor, a transconductance amplifier bias circuit with reference current input ($-T_{ref}$) driving a string of series connected LEDs with a low-side N-channel MOSFET digital enablement.

FIG. 48A illustrates a counter-based sinusoidal synthesis system capable of blending chords over ten octaves with independent weighting and auto-range functionality.

FIG. 49 is a block diagram of a counter-based sinusoidal chord synthesizer using a single sine primitive with 24-point angle resolution.

FIG. 52C is a comparison between fixed resolution and scaled resolution sine wave synthesis of a three-sine-wave blended chord FIG. 53 is a block diagram of a counter-based sinusoidal chord synthesizer using scaled-resolution sine primitives and four clock scale ranges.

FIG. 55A illustrates the UI/UX interface for setting a global key for sine and chord synthesis based on even-tempered musical scales and a fourth octave note-based key.

FIG. 55B illustrates the UI/UX interface for setting a global key for sine and chord synthesis based on other scales and a fourth octave note-based key.

FIG. 56 illustrates the UI/UX interface for setting a global key for sine and chord synthesis based on a customized frequency.

FIG. 58A illustrates signal compression in three-sine summation synthesis without auto-range function.

FIG. 58B compares three-sine summation synthesized waveforms with and without auto-range amplification.

FIG. 60 illustrates examples of non-sinusoidal generated waveforms and their corresponding PWM representations.

FIG. 63D illustrates the constituent waveforms for a PWM player generated square wave with 50% duty factor and a 10 mA average LED current subsequently stepped up to 13 mA.

FIG. 64C illustrates the constituent waveforms for a PWM synthesized audio sample comprising a chord of sine waves with a 10 mA average LED current.

FIG. 64F illustrates the constituent waveforms for a PWM synthesized audio sample comprising a cymbal crash with a 10 mA average LED current.

FIG. 81A is a cross section, top view, and side view of an autonomous intelligent LED pad with an integrated switch.

FIG. 81B is a flow chart describing the program switch sequence of an autonomous intelligent LED pad.

FIG. 83 is an exploded diagram of planar magnetics used in a magnetotherapy pad.

FIG. 84 is a side view of a magnetotherapy pad with planar magnetics.

FIG. 85 is a top view of a magnetotherapy pad with planar magnetics.

FIG. 86 is a schematic of a distributed-system magnetotherapy drive circuit.

FIG. 87 is a cross section of a magnetotherapy pad using discrete magnetics.

FIG. 88A is a magnetotherapy pad comprising an array of electromagnets.

FIG. 88B is a magnetotherapy pad comprising an array of electromagnets and permanent magnets.

FIG. 88C is a magnetotherapy pad comprising an array of electromagnets and stacked hybrid electromagnet permanent magnets.

FIG. 88D is a magnetotherapy pad comprising an array of electromagnets and stacked hybrid permanent-magnet electromagnets.

FIG. 89 is a distributed system compatible handheld magnetotherapy device.

FIG. 90 is a plan view and cross-sectional view of a U-shaped PBT periodontal mouthpiece.

FIG. 91 is a side view of the manufacturing steps in fabricating a U-shaped PBT periodontal mouthpiece.

Figure 92A:
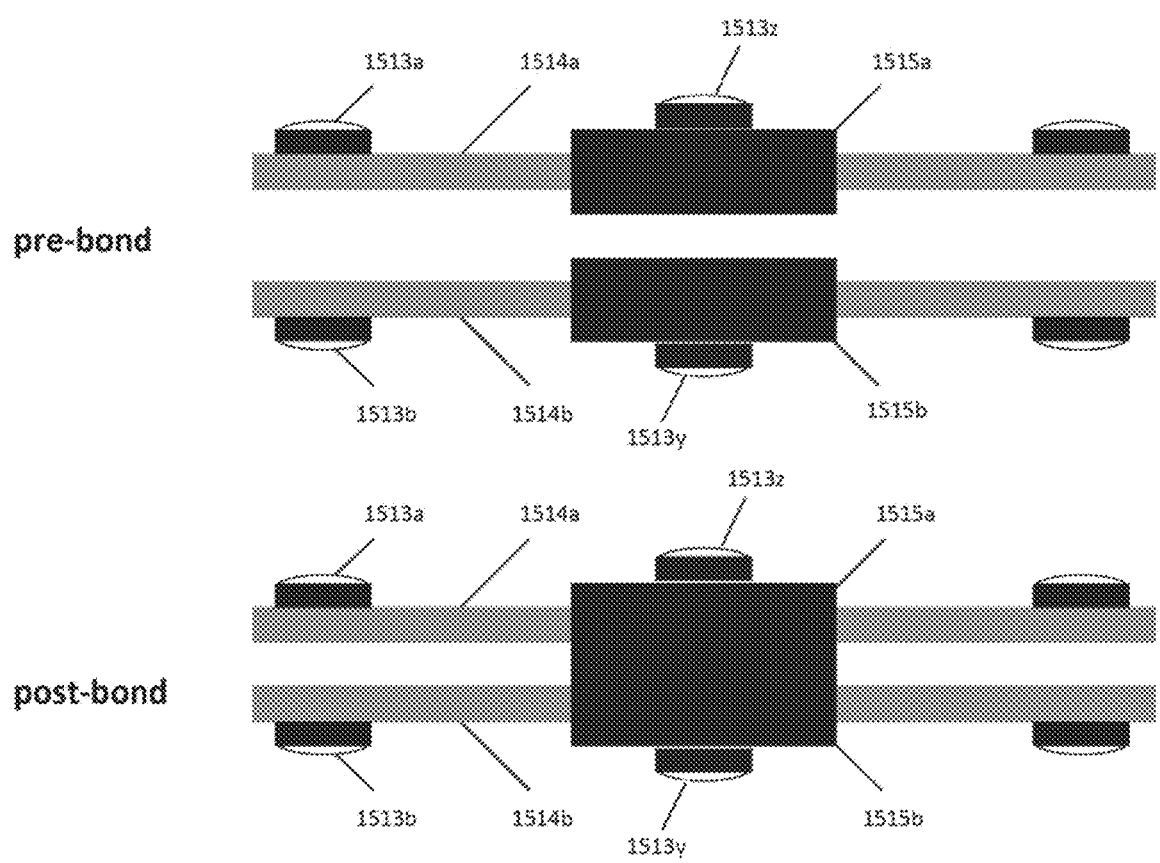

FIG. 92A is a side view of the manufacturing steps in fabricating an H-shaped PBT periodontal mouthpiece.

Figure 92B:
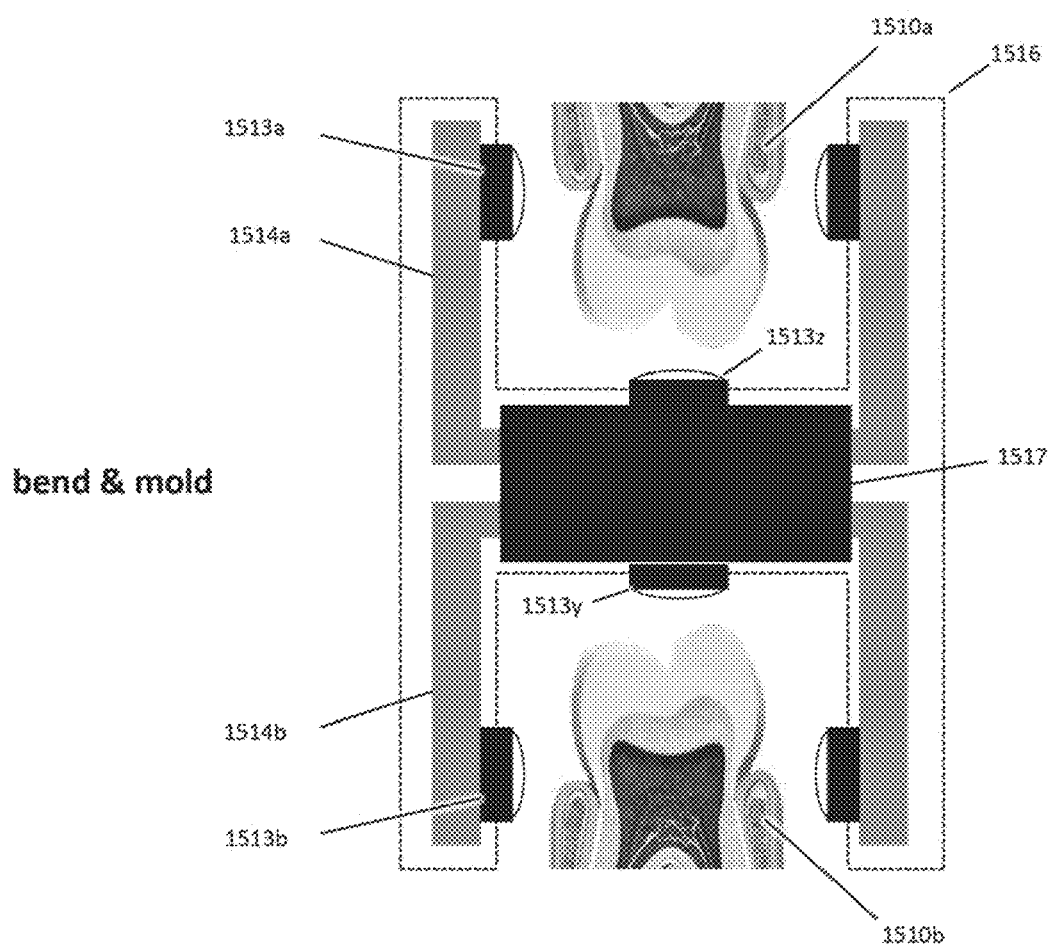

FIG. 92B is a side view of a fabricated H-shaped periodontal PBT mouthpiece.

Figure 93:
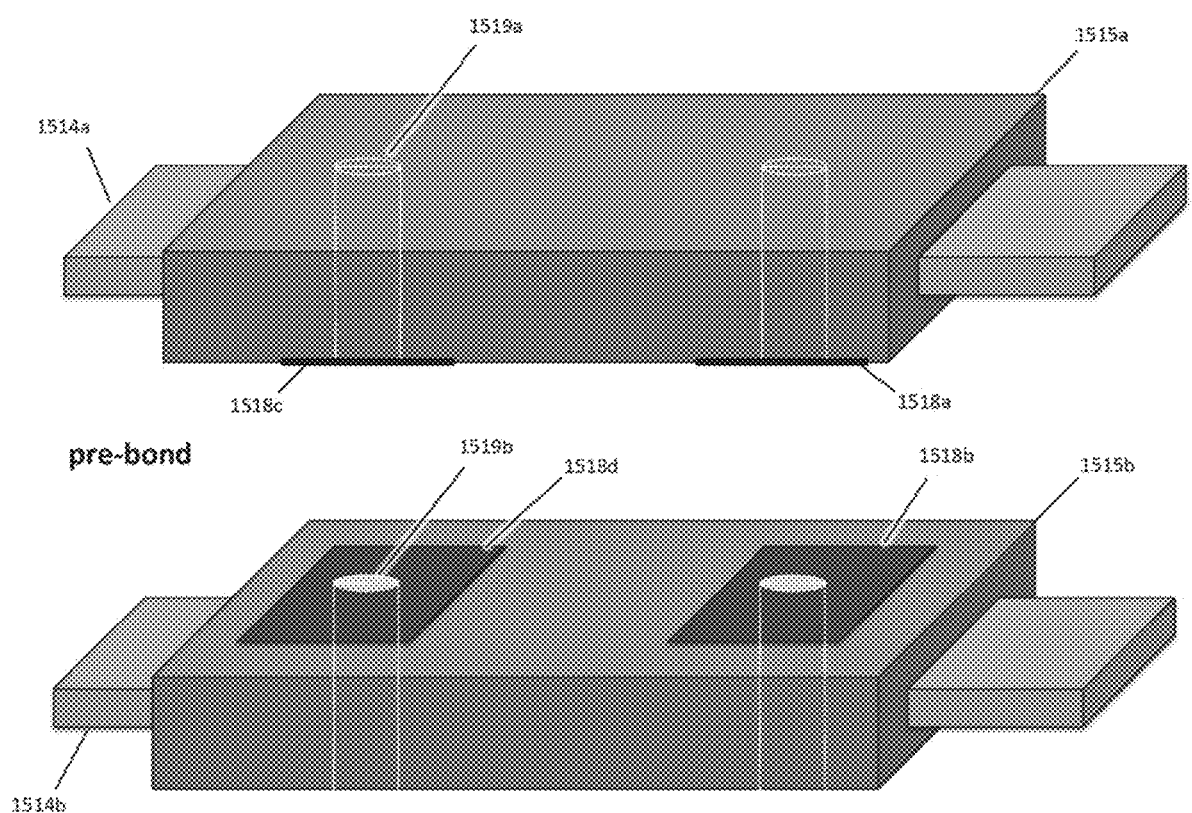
Figure 94:
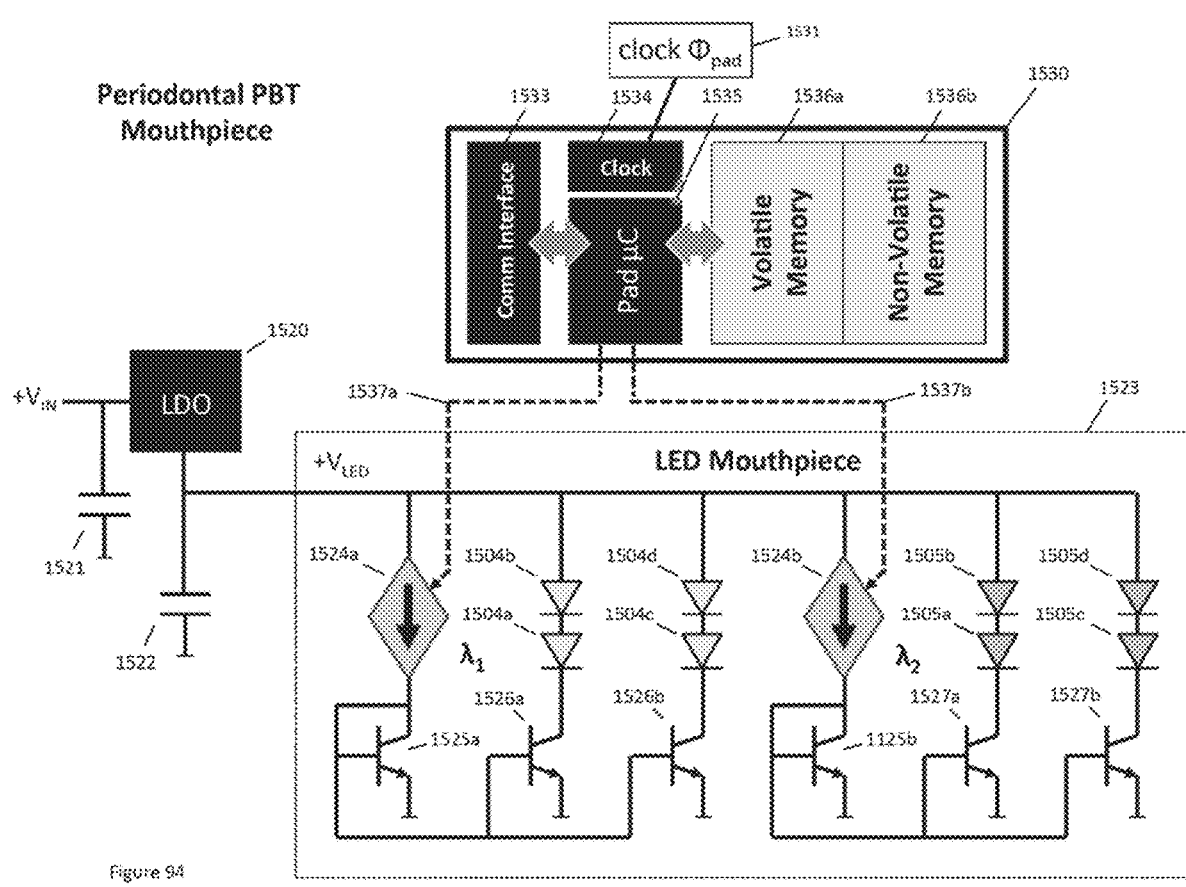

FIG. 93 shows the bonding process in the fabrication of an H-shaped PBT periodontal mouthpiece FIG. 94 illustrates the circuit diagram of a periodontal PBT mouthpiece.

Figure 95:
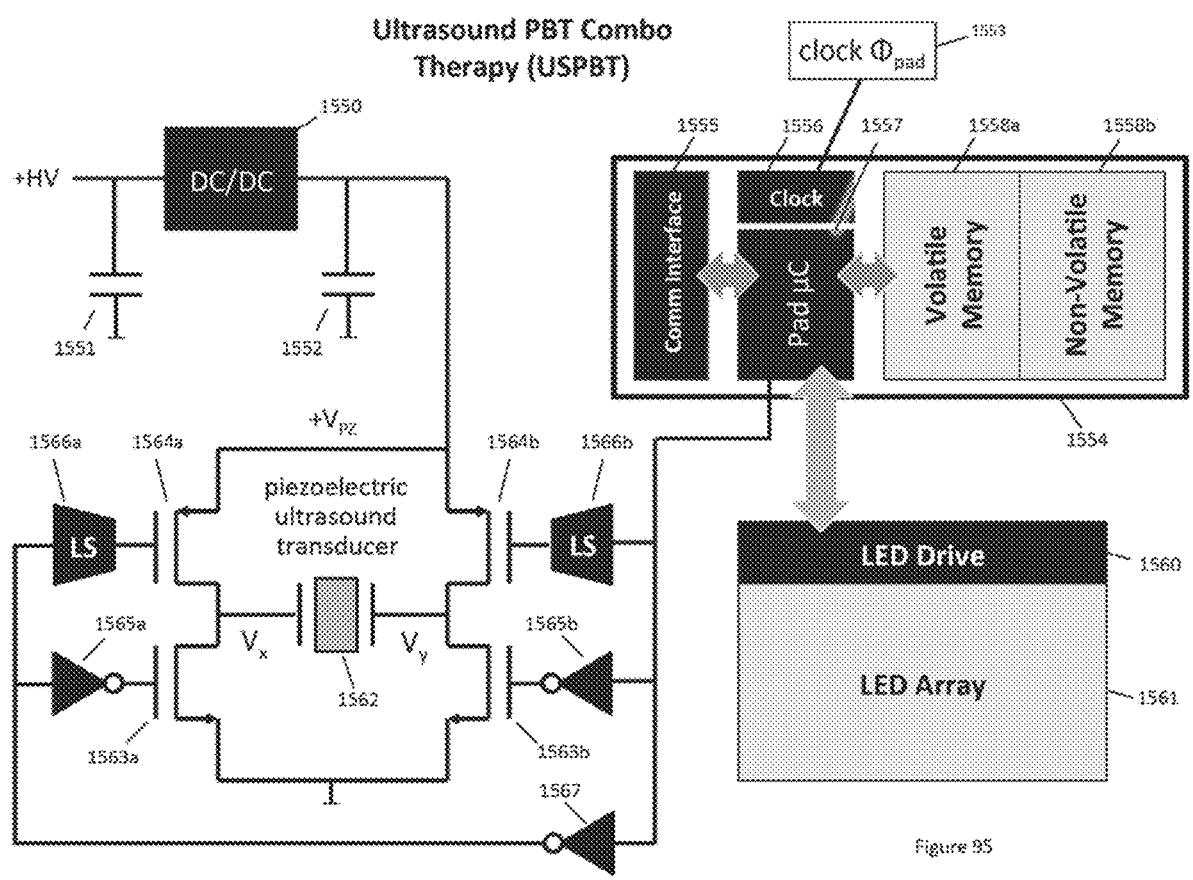

FIG. 95 illustrates the circuit diagram of a combination ultrasound PBT pad with H-bridge drive.

Figure 96:
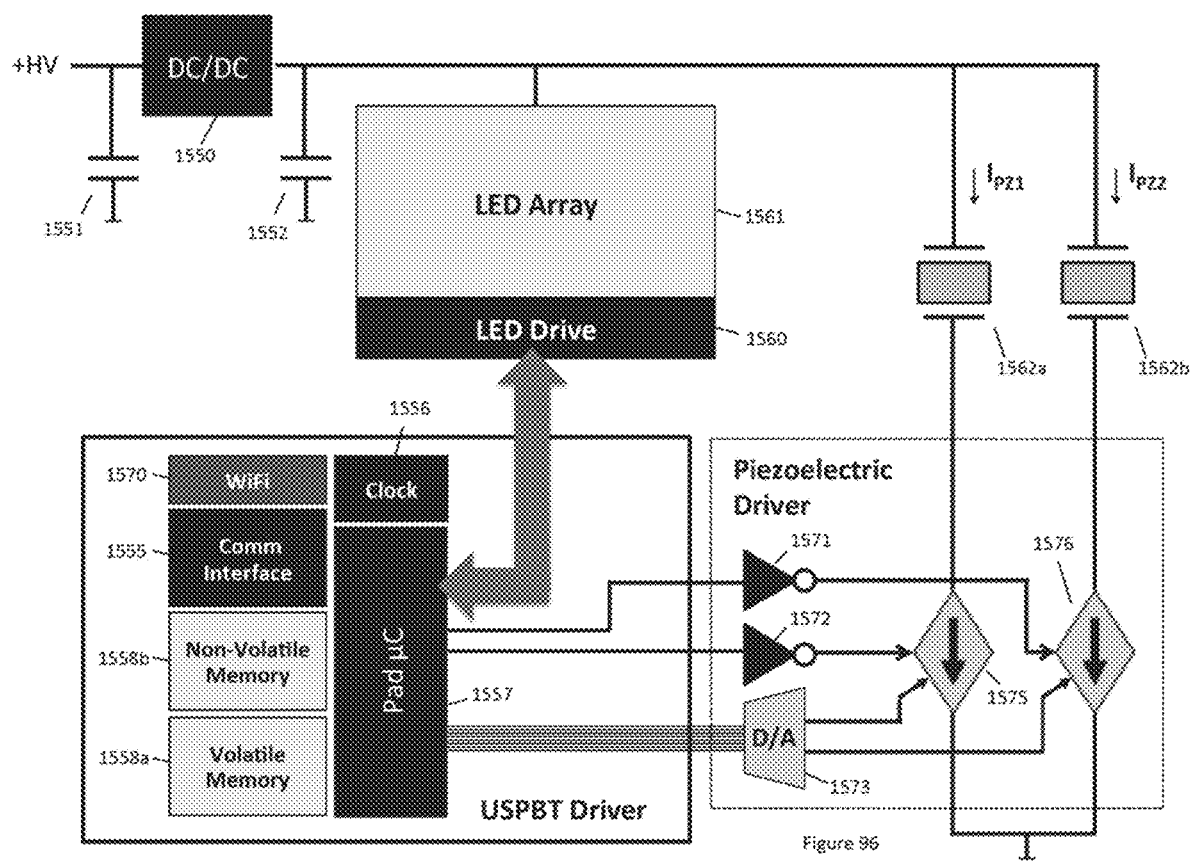

FIG. 96 illustrates the circuit diagram of a combination ultrasound PBT pad with current sink drive.

Figure 97:
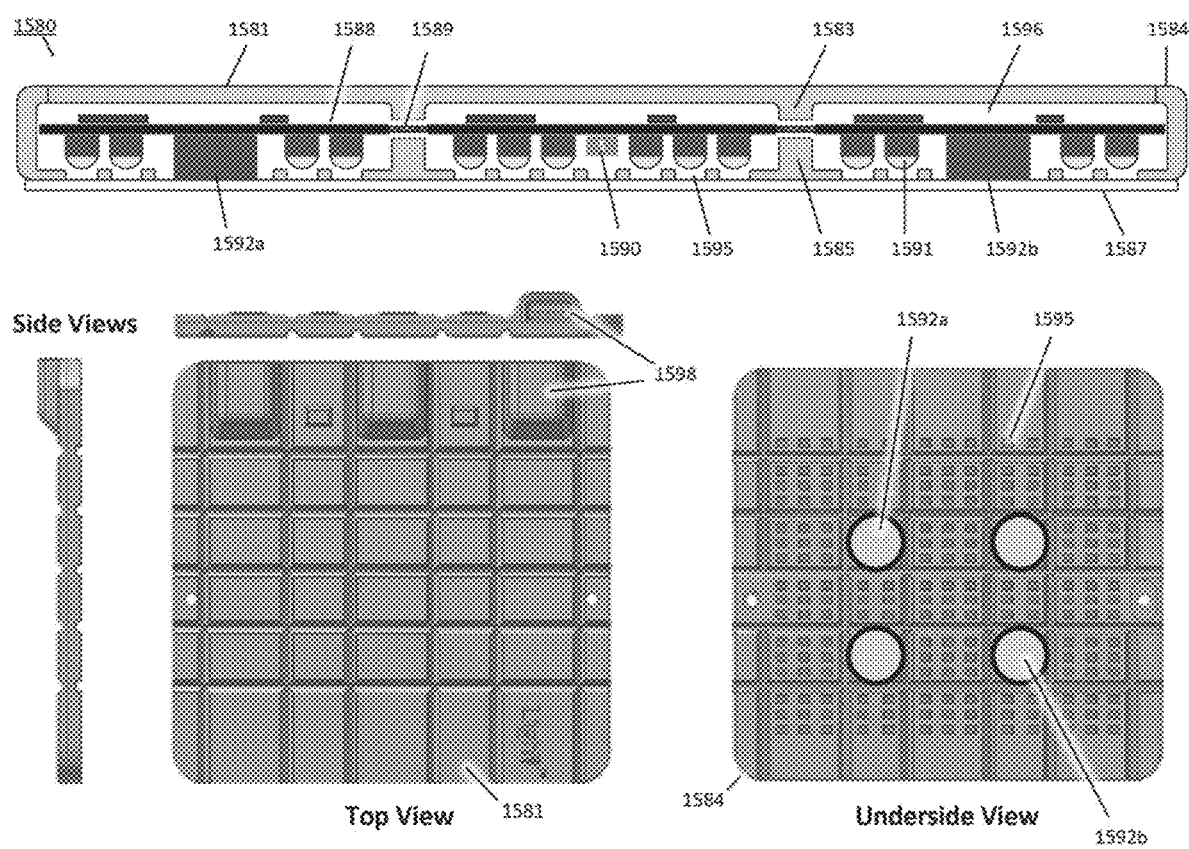

FIG. 97 comprises perspective views of a combination ultrasound PBT pad

DESCRIPTION OF THE INVENTION

In order to overcome the aforementioned limitations facing existing generation PBT systems, a completely new system architecture in required. Specifically, the generation of sinusoidal waveforms and chords combining sine waves must occur within close proximity of the LEDs being driven to avoid significant waveform distortion from cabling. Such a design criterion mandates relocating waveform synthesis, moving it out of the PBT controller and into the LED pad. To accomplish this seemingly minor re-partitioning of functions is in fact a significant design change, and requires converting the LED pad from a passive component into an active system or "intelligent" LED pad. While a passive LED pad contains only an array of LEDs, current sources, and switches, an intelligent LED pad must integrate a microcontroller, volatile and non-volatile memory, a communication transceiver or bus interface, LED drive electronics, and the LED array. Because of the need for long cabling or wireless operation the time reference for the microcontroller must also be relocated into the LED pad. Essentially each intelligent LED pad becomes a small computer, which once instructed, is able to independently produce LED excitation patterns.

So rather than using a centralized PBT controller producing and distributing electrical signals to passive LED pads, the new architecture is "distributed", comprising a network of autonomously operating electronic components lacking centralized real time control. This distributed PBT system, the first of its kind, requires the invention of intelligent LED pads—a therapeutic light delivery system whereby the LED pads perform all calculations needed to generate dynamic LED excitation patterns and safely execute LED drive accordingly. In distributed PBT operation, the role of the PBT controller is dramatically diminished to that of a UI/UX interface, allowing a user to select therapy treatments or sessions from available protocol libraries, and to start, pause, or terminate treatments. This lack of central hardware control is virtually unheard of in medical devices because ISO13485, IEC, and FDA regulations demand, for reasons of safety, hardware controllability at all times. As such, the implementation of effective safety systems in distributed hardware medical devices requires a new and innovative approach where safety functions must be performed locally and communicated system-wide. Such a safety protocol must be specified, designed, verified, validated and documented in accordance with FDA design regulations and international safety standards.

Another implication of a distributed PBT system with intelligent LED pads is the replacement of electrical signal communication with command-based instructions comprising data packets. Such command-based communication involves the design and development of a packet switched private communication network among the distributed system's components, adapting digital communication to meet the unique and stringent requirements of medical device control. Packet routing, security, and data payloads must be designed to prevent hacking or system malfunction, and must carry all requisite information to perform all necessary PBT operations.

Implementing a distributed PBT system with intelligent LED pads involves two sets of interrelated innovations. In this application, the intelligent LED pad's operation is disclosed including time-based LED excitation patterns delivered by streaming or by file transfer. This disclosure also considers the in-pad generation of waveforms using a three-step process of waveform synthesis, PWM player operation, and dynamic LED drive as well as requisite safety functions. In a related application filed by R.K. Williams et al., U.S. application Ser. No. 16/377,192, titled "Distributed Photobiomodulation Therapy Devices, Methods, and Communication Protocols Therefor," filed concurrently with this application, the data communication hierarchical stack and control protocol are disclosed.

In the distributed PBT systems disclosed herein, LED playback can be controlled using either a time-based instruction sequence (referred to as streaming) or through command-based waveform generation and synthesis. In either event, data packets carry the LED excitation pattern digitally in their payload. In operation, through a graphical interface a user or therapist selects a PBT treatment or therapy session, and agrees to commence treatment. The command is then packetized, i.e. prepared, formatted, compressed, and stuffed into a communication packet, and delivered over a serial peripheral communication bus, LAN, broadband connection, WiFi, fiber or other media to one or more intelligent LED pads. Although the payload data being carried in each data packet is digital comprising bits organized as octets or hexadecimal words, the actual communication medium is analog, comprising differential analog signals, radio waves, or modulated light.

In wired communication, the communication bus typically uses electrical signals comprising analog differential waveforms modulated at a specified rate known as the symbol rate or baud rate (https://en.wikipedia.org/wiki/Symbol_rate). Each symbol may comprise a frequency or code for a defined duration. The detection of each sequential symbol is immune to distortions caused by reactive parasitics in a cable or by noise sources and therefore overcomes all the issues associated with digital pulse signal transmission in prior art PBT implementations. In WiFi communication, incoming serial data is split and transmitted in small packets across multiple frequency sub-bands, known as OFDM, i.e. orthogonal frequency division multiplexing to achieve a high-symbol rate and low bit-error rate. Similar frequency splitting methods are used in fiber channel and DOCSIS communication to achieve high symbol rates. Since each transmitted symbol is capable of representing multiple digital states, the serial bus bit data rate is therefore higher than the media's symbol rate. The effective bit data rate (https://en.wikipedia.org/wiki/List_of_device_bit_rates) of several of the most common serial and wireless communication protocols above 50 MB/s are summarized here below for reference:

| Standard | Year | Media (PHY) | Bit Data Rate |
| --- | --- | --- | --- |
| Bluetooth 5.0 personal area network (PAN) | 2016 | Wireless PAN | 50 Mb/s |
| IEEE 802.11a | 1999 | WiFi | 54 Mb/s |
| IEEE 802.11g | 2003 | WiFi | 54 Mb/s |
| Fast Ethernet (100BASE-X) | 1995 | LAN | 100 Mb/s |
| Firewire 400 (IEEE 1394) | 1995 | Peripheral | 393 Mb/s |
| USB 2.0 | 2000 | Peripheral | 480 Mb/s |
| IEEE 802.11n | 2009 | WiFi | 600 Mb/s |
| Gigabit Ethernet (1000BASE-X) | 1998 | LAN | 1 Gb/s |
| Firewire 3200 (IEEE 1394b) | 2007 | Peripheral | 3.1457 Gb/s |
| USB 3.0 Superspeed | 2010 | Peripheral | 5 Gb/s |
| IEEE 802.11ac (max theoretical) | 2012 | WiFi | 6.8-6.93 Gb/s |
| IEEE 802.11ad (max theoretical) | 2011 | WiFi | 7.14-7.2 Gb/s |
| 10 Gigabit Ethernet (10GBASE-X) | 2002-2006 | LAN | 10 Gb/s |
| DOCSIS v3.1 | 2015 | Broadband | 10 GB/s |
| USB 3.1 Superspeed | 2013 | Peripheral | 10 Gb/s |
| Thunderbolt 2 | 2013 | Peripheral | 20 Gb/s |
| USB 3.2 Superspeed | 2017 | Peripheral | 20 Gb/s |
| Thunderbolt 3 | 2015 | Peripheral | 40 Gb/s |
| 100 Gigabit Ethernet (100GBASE-X) | 2010-2018 | LAN | 100 Gb/s |

In response to a user's commands, the PBT controller converts instructions into communication data packets, which are subsequently sent to all connected and qualified LED pads. The LED pads receive the instructions and respond accordingly, commencing a therapy session or performing other tasks. Because of high-bandwidth communication, the PBT system's user experience is that the treatment was instantaneous, i.e. users perceive a real time UI/UX response even though the system's operation was in fact performed as a sequence of inter-device communication and autonomous tasks.

The disclosed distributed PBT system involves multiple interacting components, each of which performs a dedicated function or functions within the de-centralized system. The number of unique components integrated into the system affects the system's overall complexity and impacts the sophistication of the communication protocol, i.e. the "language" used in inter-device communication. Various components of the disclosed distributed PBT system may include:

- A user interface comprising a central PBT controller or mobile application used for performing UI/UX based commands and dispatching instructions over the communication network.
- Intelligent LED pads performing dynamic photobiomodulation therapy treatments with local in-pad excitation pattern generation and waveform synthesis, and optionally with integrated sensors or imaging capability.
- Computer servers accessible over the Internet or private communication networks used for retaining and distributing PBT treatments, sessions, and protocols, or for uploading patient response, case study, or clinical trial data and associated files (e.g. MRIs, X-rays, blood tests).
- Optional therapeutic accessories such as laser wands or ultrasound therapy pads.
- Optional biometric sensors (e.g. EEG sensors, ECG monitors, blood oxygen, blood pressure, blood sugar, etc.) used for capturing and uploading patient sample or real-time data.
- Computer peripherals including high-definition displays and touchscreens, keyboards, mice, speakers, headphones, etc.

By combining or excluding various components in the PBT system, a variety of performance and system costs can be tailored for a wide range of users covering hospitals and clinics, and extending to individual users and consumers, spas, estheticians, sports trainers and athletes, as well as professional mobile applications for paramedics, police, or for military field doctors. Since the PBT components use a voltage higher than 5V, care in the disclosed design is exercised to prevent a user for accidentally connecting a USB peripheral into a high-voltage (12V to 42V) connection or bus.

LED Control in Distributed PBT Systems

Figure 1:
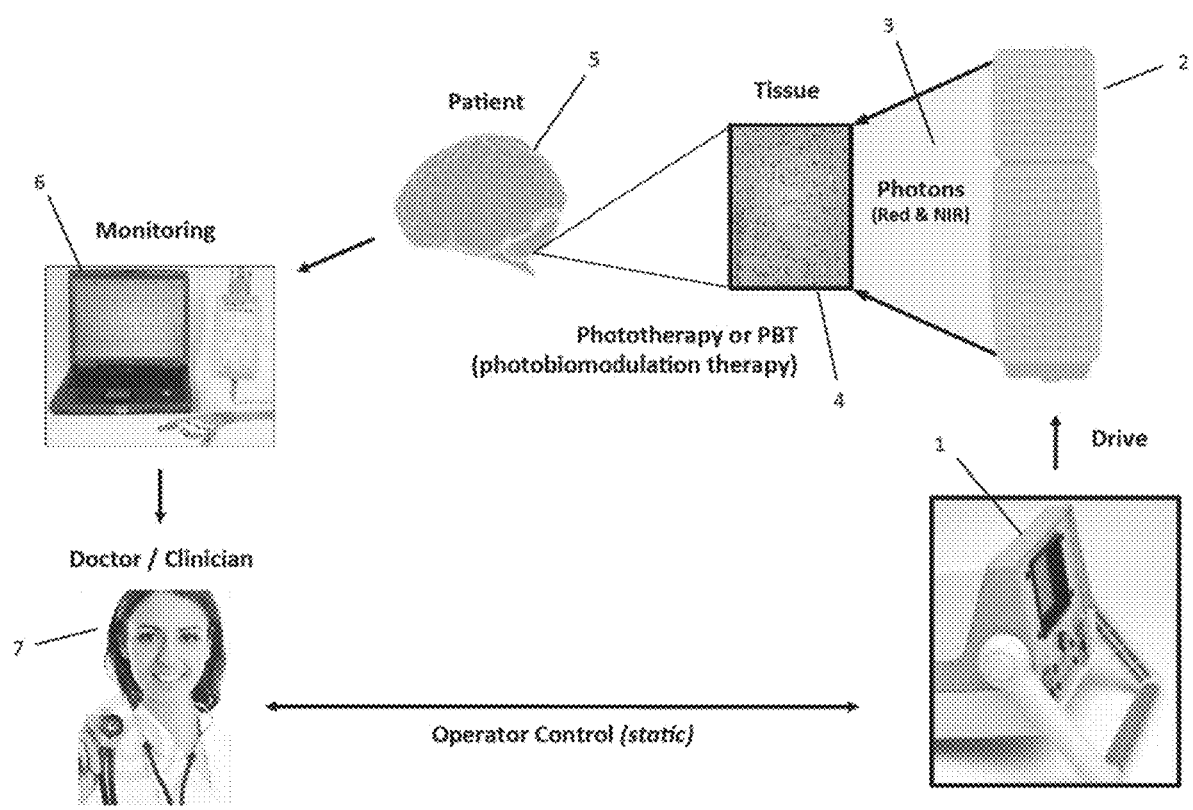
FIG. 1 illustrates a PBT system operating under therapist control.
Figure 2:
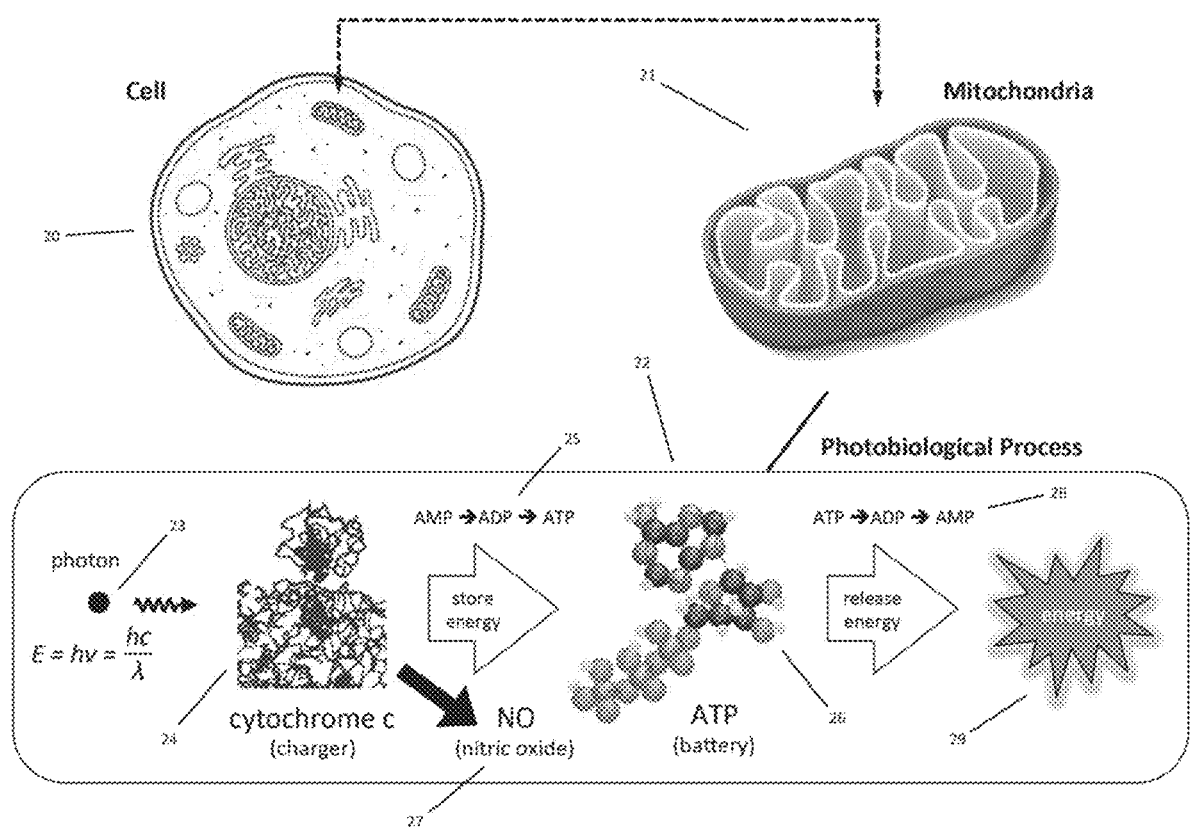
FIG. 2 illustrates photobiomodulation of mitochondria.
Figure 3:
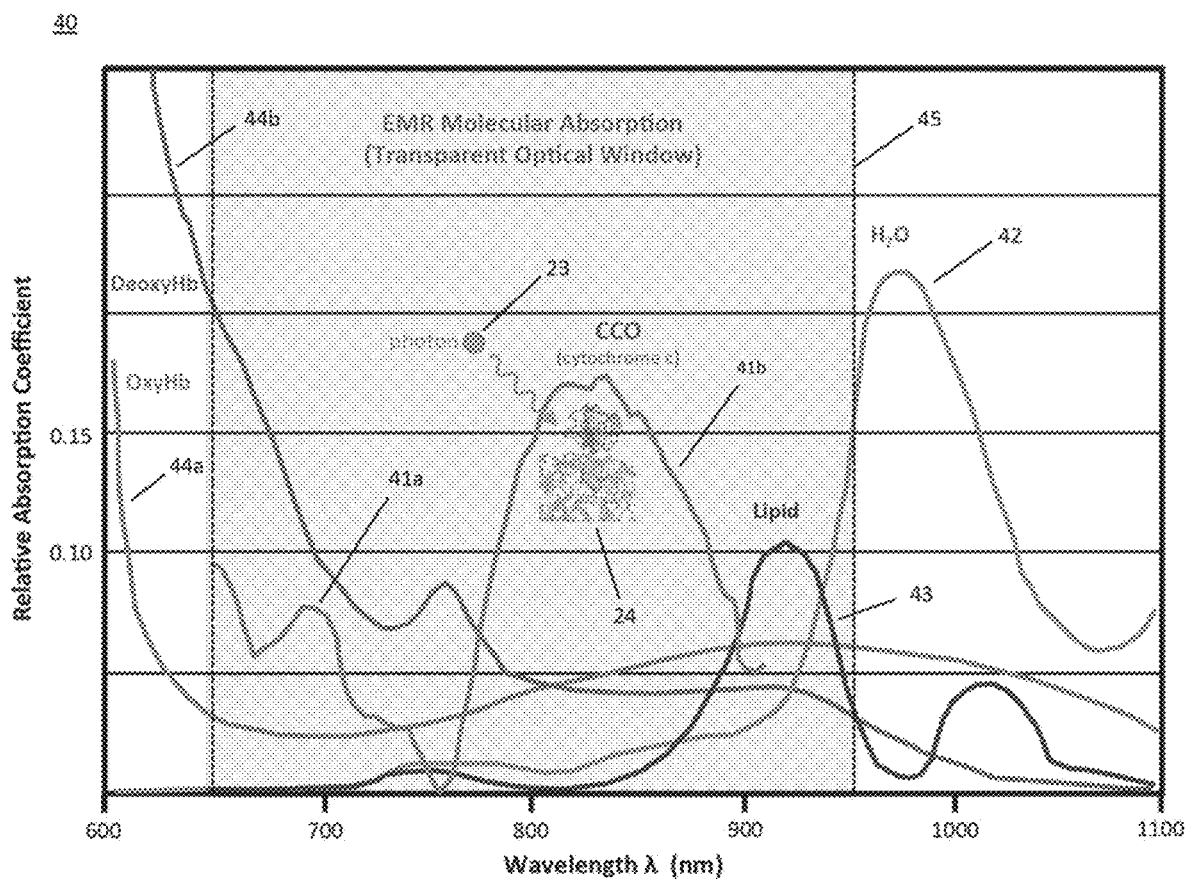
FIG. 3 illustrates the optical absorption spectra of various biomaterials.
Figure 4A:
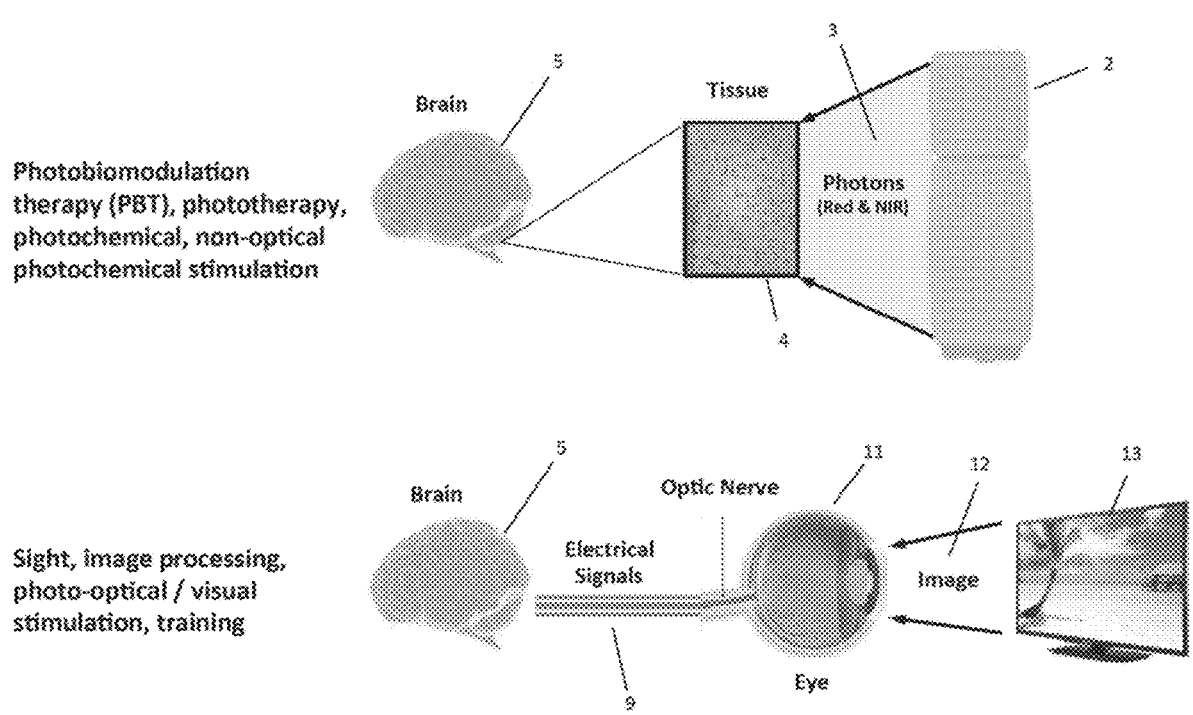
FIG. 4A contrasts differences between photo-optical therapy and photobiomodulation therapy.
Figure 5:
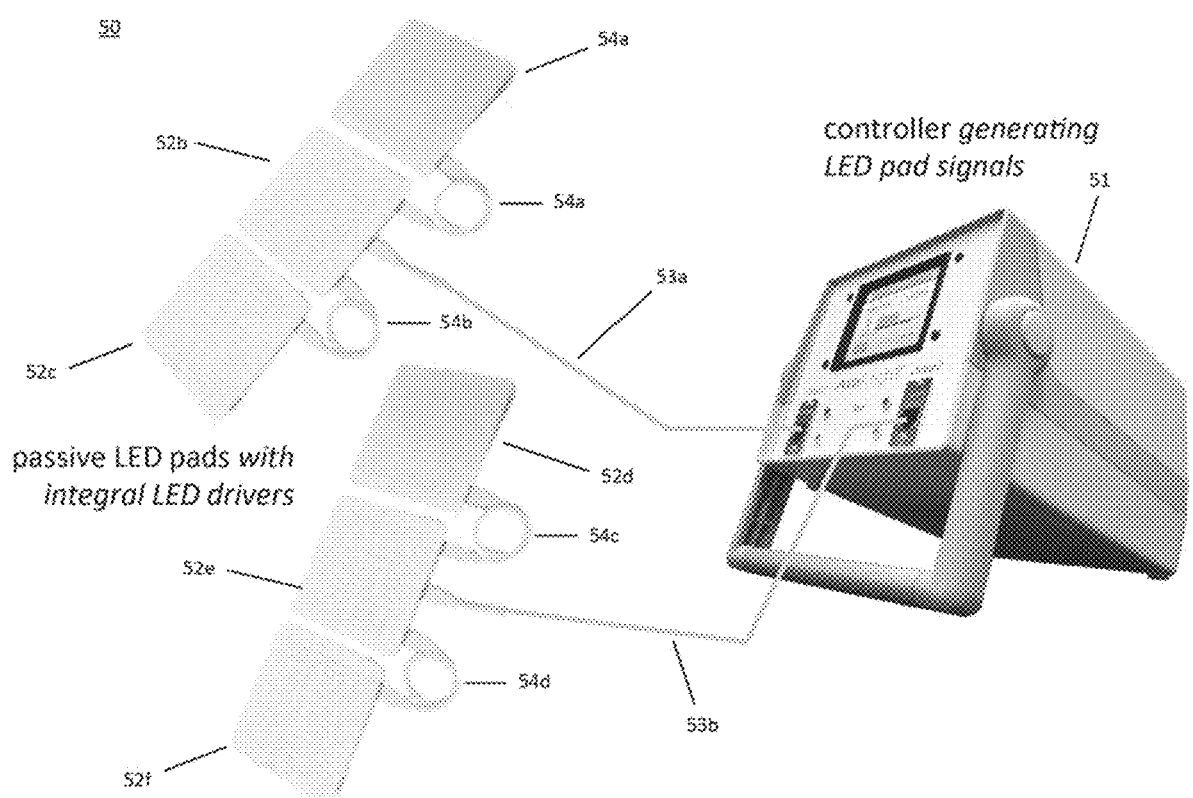
FIG. 5 represents a distributed PBT system with an active LED pad.
Figure 6A:
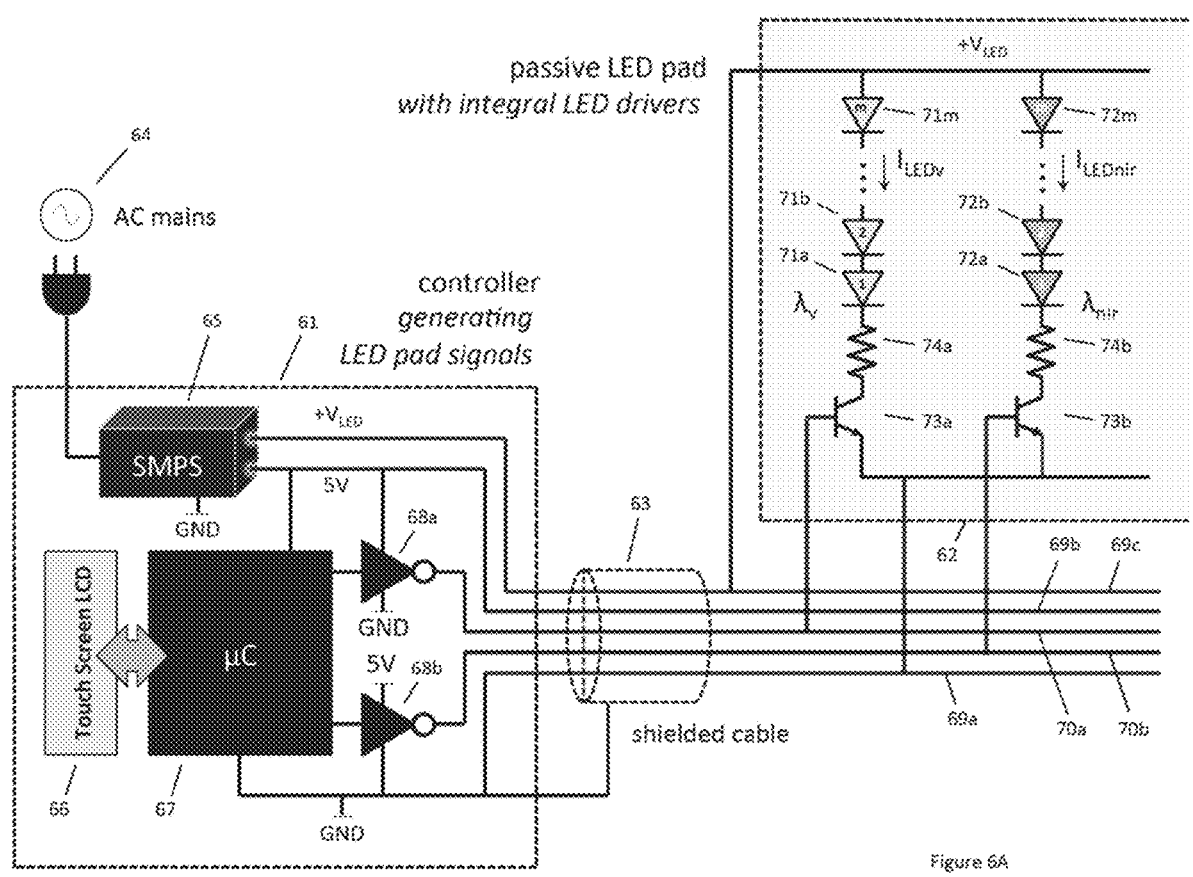
FIG. 6A is a schematic representation of a PBT system with passive LED pads using current limiting resistors.
Figure 6B:
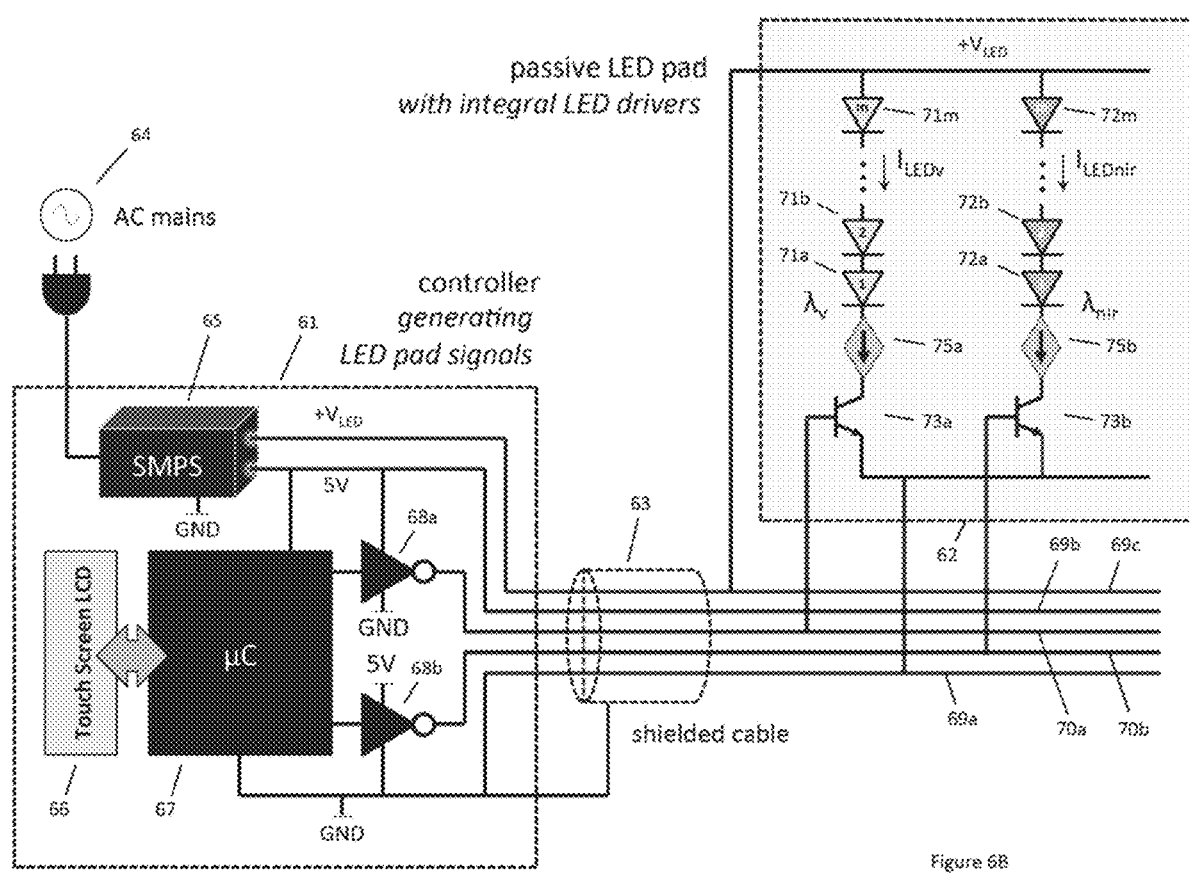
FIG. 6B is a schematic representation of a PBT system with passive LED pads using current control.
Figure 7:
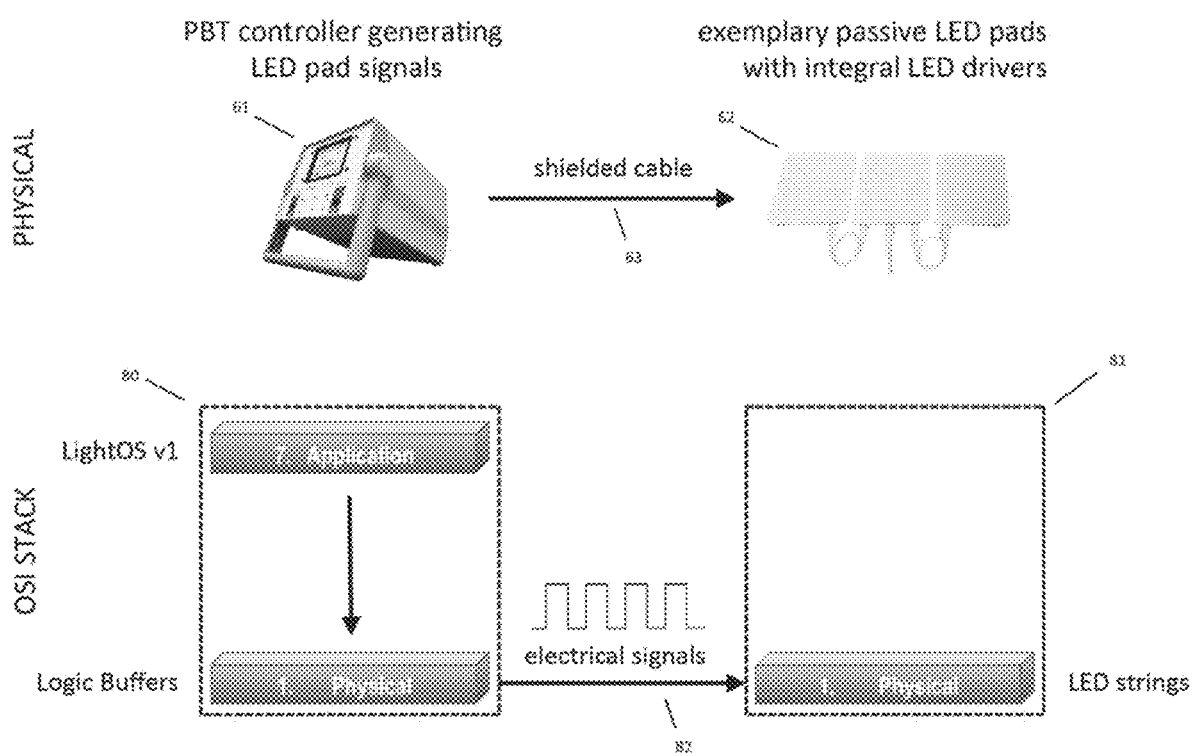
FIG. 7 is a network description of a PBT system with active LED pads using only physical (PHY) Layer-1 communication.
Figure 8:
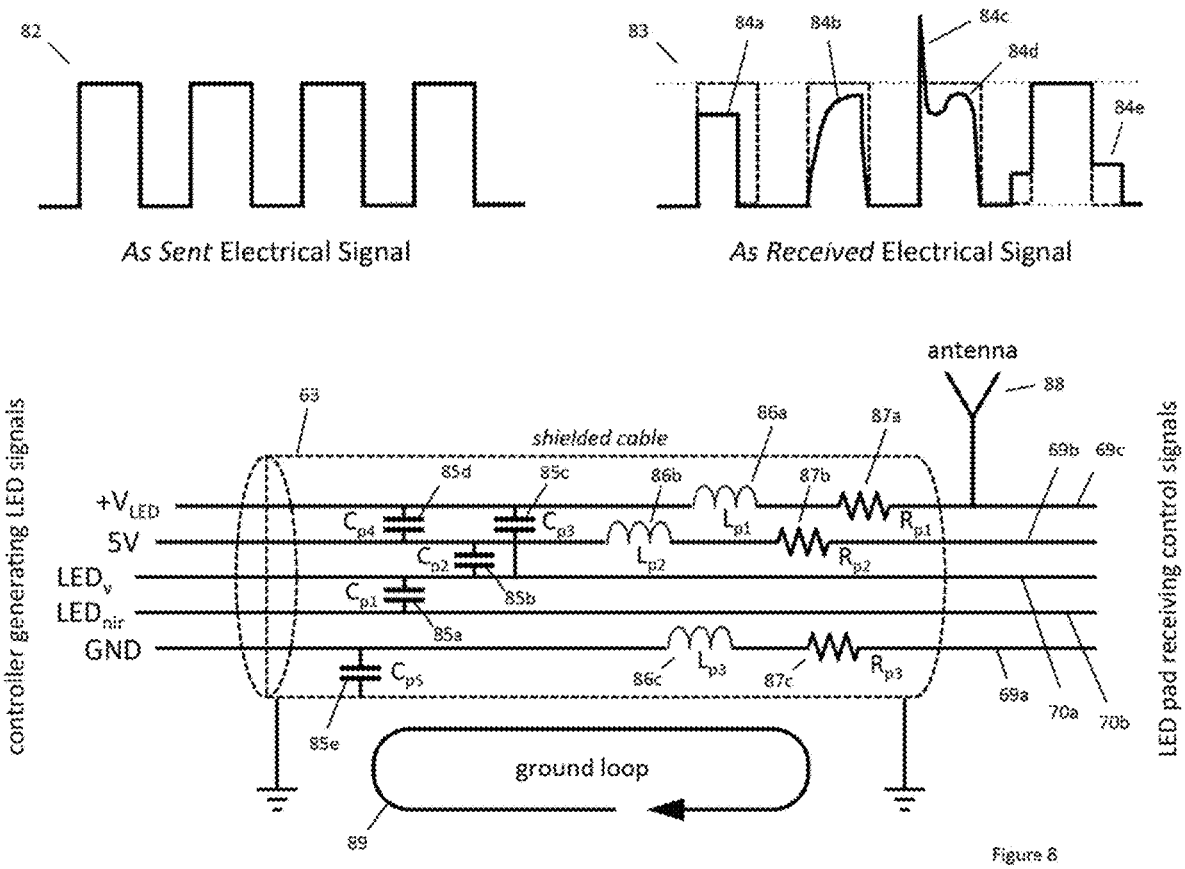
FIG. 8 is an equivalent circuit of a communication cable and its impact on electrical signals.
Figure 9:
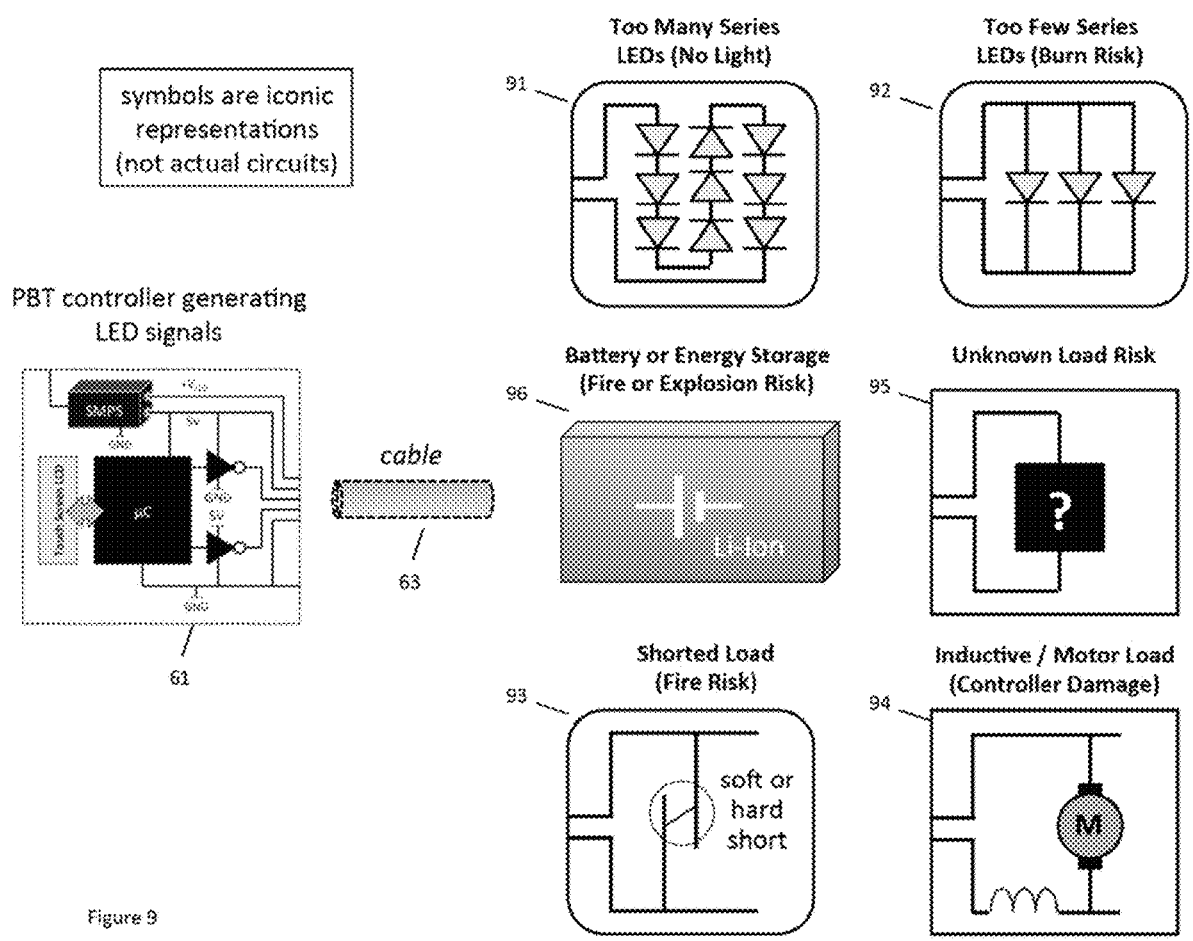
FIG. 9 is an iconic representation of the interconnection of a photobiomodulation therapy system to unqualified or improper electrical accessories or LED pads.
Figure 10:
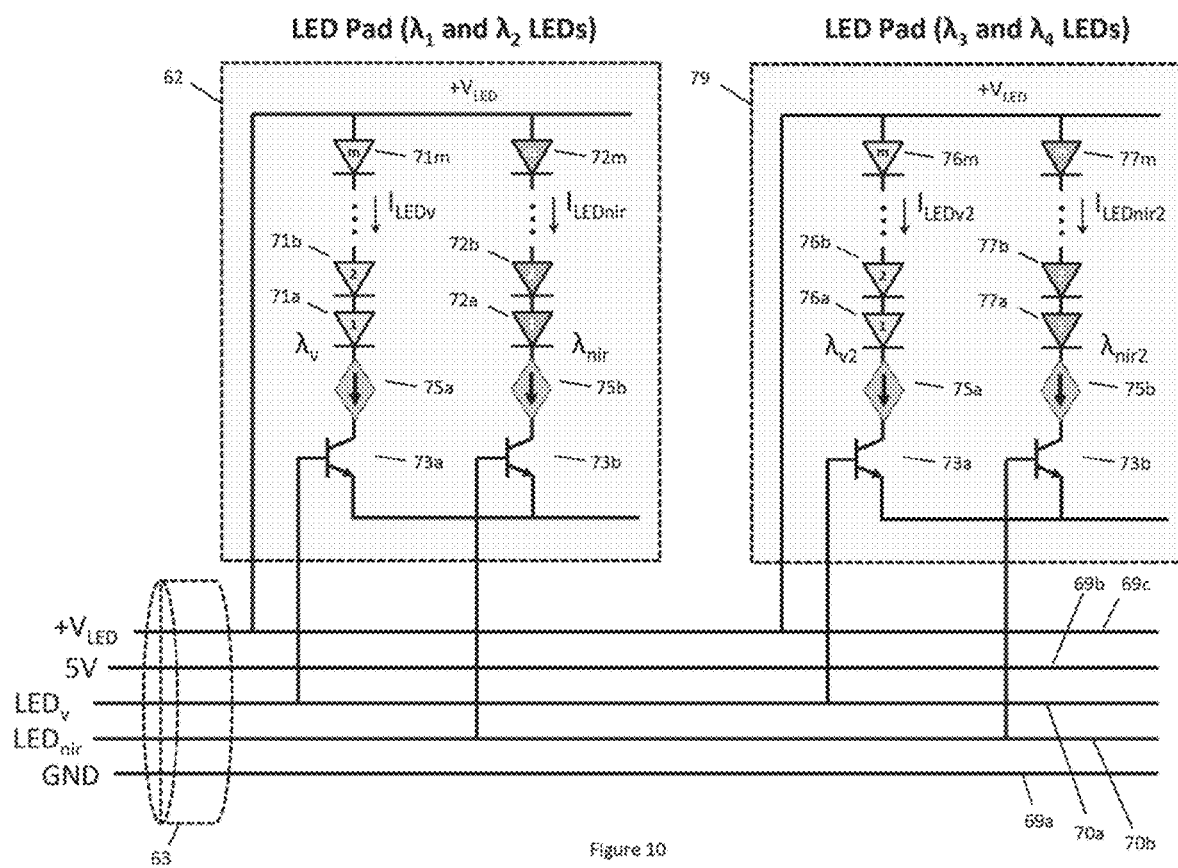
FIG. 10 depicts a photobiomodulation therapy system driving dissimilar LED pads with a common set of electrical signals.
Figure 11A:
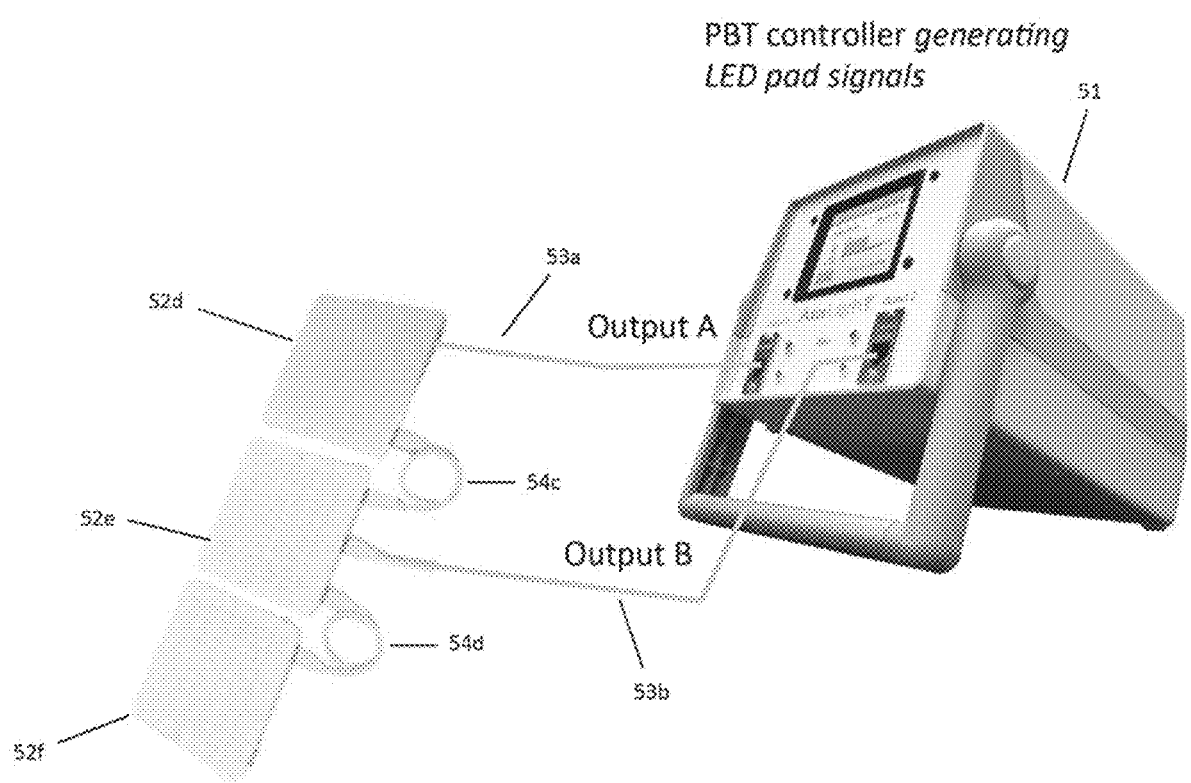
FIG. 11A illustrates an improper "shorted output" connection of two LED PBT system outputs to one common LED pad.
Figure 11B:
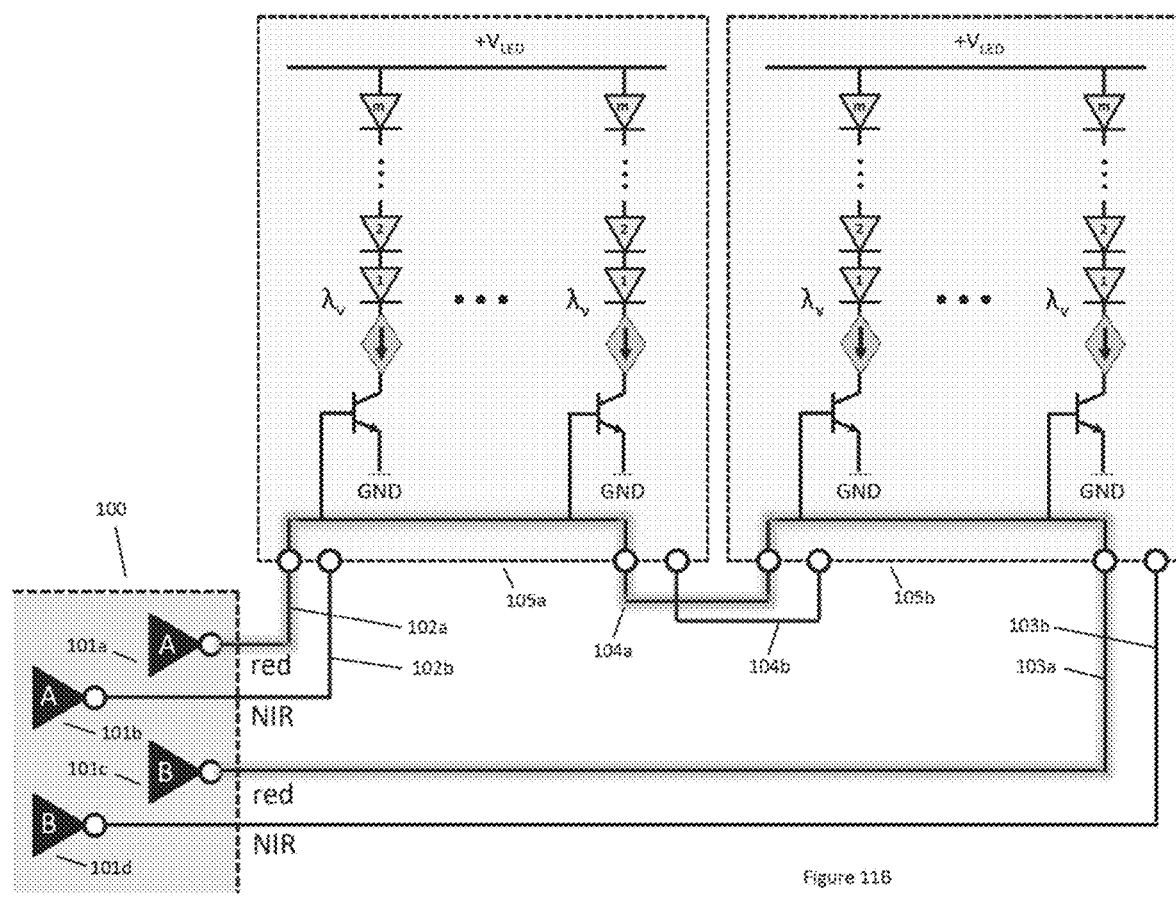
FIG. 11B illustrates a shorted output connection driving red LEDs strings with more than one competing control signal.
Figure 11C:
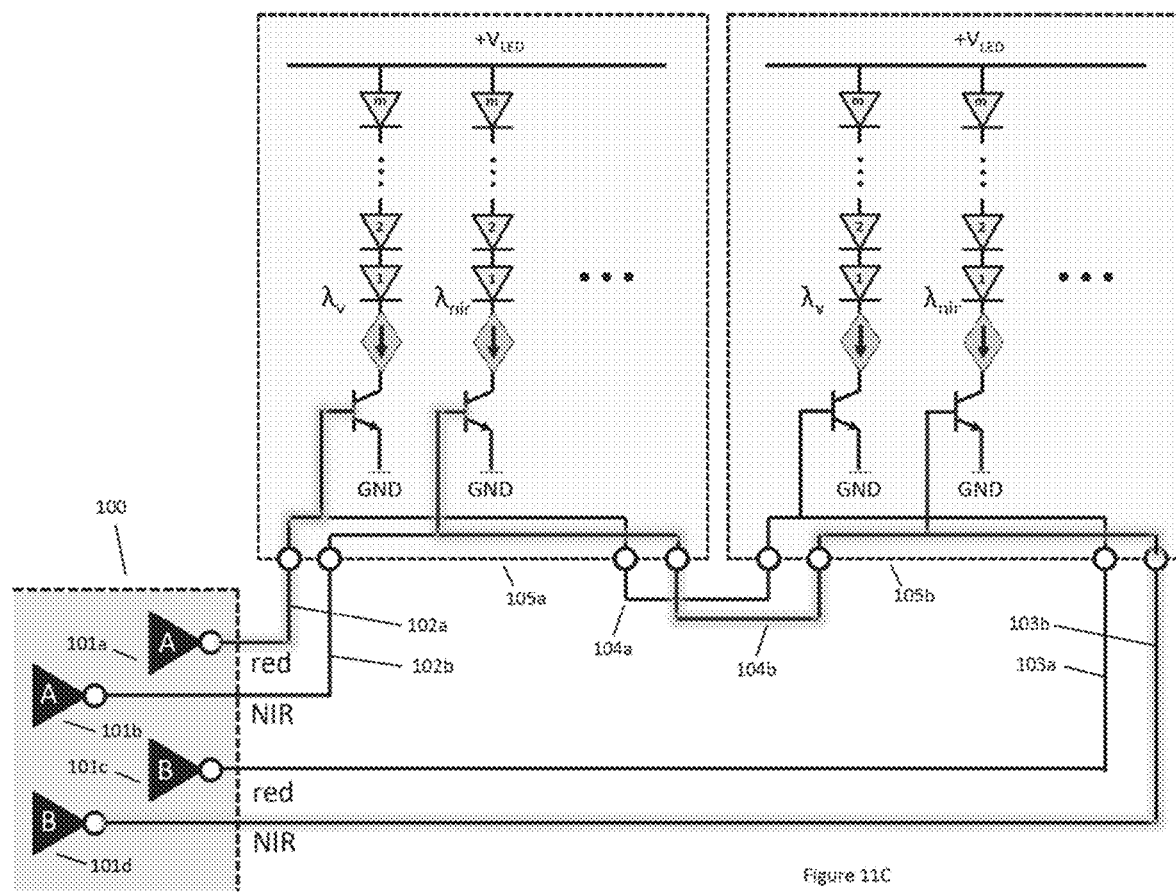
FIG. 11C illustrates a shorted output connection concurrently driving both NIR and red LEDs in the same LED pad with overlapping or concurrent control signals.
Figure 11D:
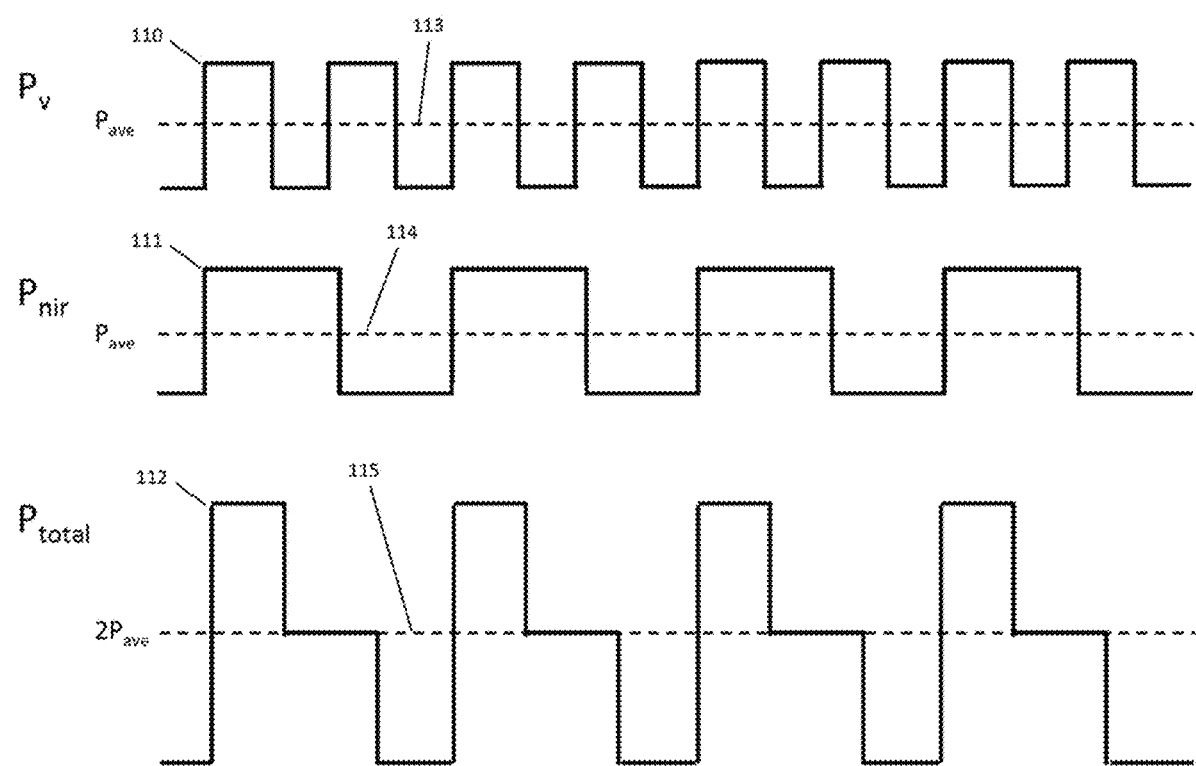
FIG. 11D illustrates the power output waveforms for a shorted output connection concurrently driving both NIR and red LEDs in the same LED pad with overlapping or concurrent control signals.
Figure 12:
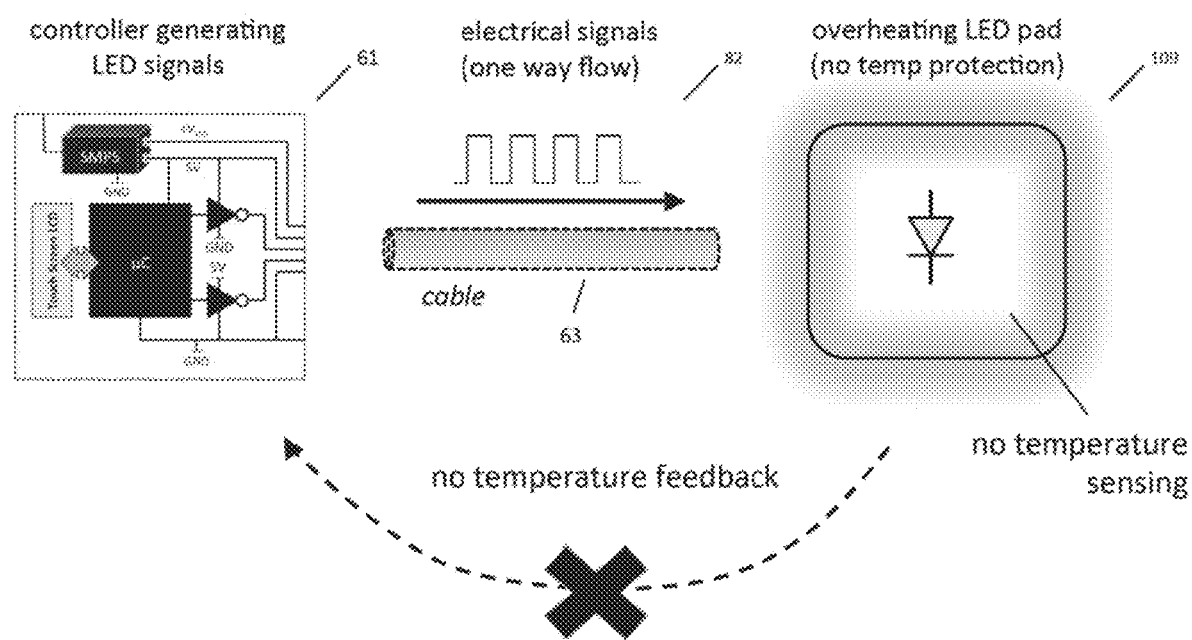
FIG. 12 is a PBT system lacking temperature sensing, protection, or feedback.
Figure 13:
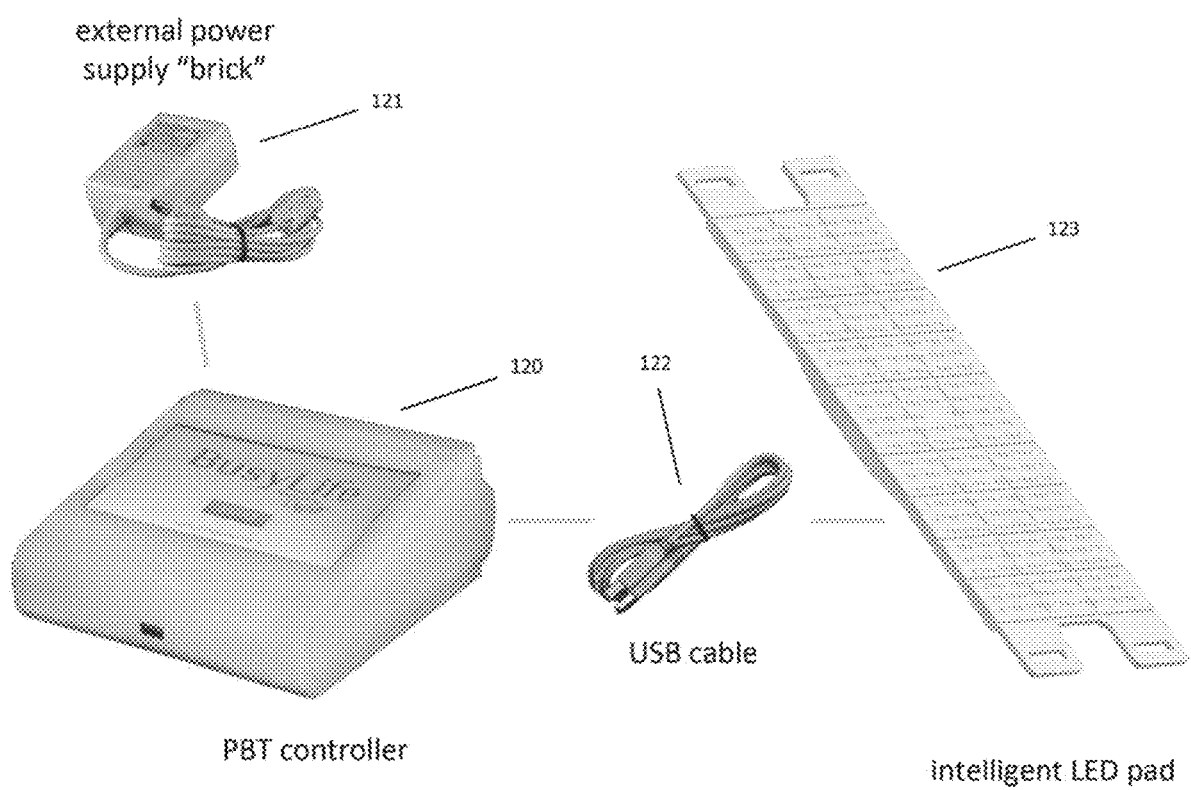
FIG. 13 represents a distributed PBT system with an active LED pad.
Figure 14:
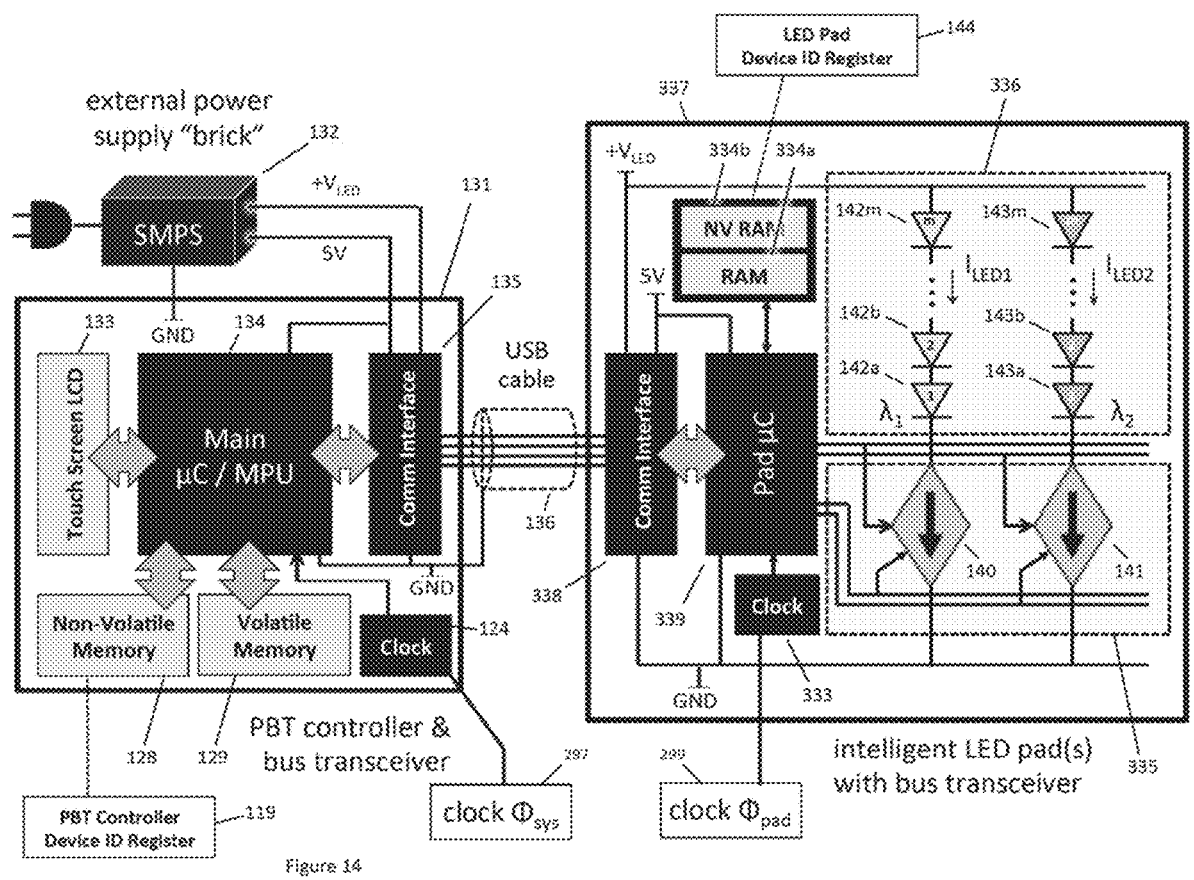
FIG. 14 is a schematic illustration of a distributed PBT system with an intelligent (active) LED pad.

One basic implementation of a distributed PBT system, shown in FIG. 13, involves three components—a PBT controller 120, a power supply 121, and a single intelligent LED pad 123 with an intervening USB cable 122. FIG. 14 illustrates a block diagram of an exemplary distributed PBT system's implementation, including a PBT controller and bus transceiver 131, one or more intelligent LED pads 337, a USB cable 136, and an external power supply "brick" 132. Although power supply brick 132 is shown as a discrete component in the illustration, in systems where PBT controller and bus transceiver 131 use a wired connection to an intelligent LED pad 337 the power supply may be included inside the PBT controller and transceiver rather than using a separate component. As shown, PBT controller and bus transceiver 131 includes a main microcontroller μC or MPU 134, a touchscreen LCD 133, a non-volatile memory 128, a volatile memory 129, a bus interface 135, and a clock 124, which produces clock pulses 297 at a frequency $\Phi_{sys}$. The clock and memory elements are shown separately from main MPU 134, to represent their function and are not intended to describe a specific realization or component partitioning. A RTC real time clock (not shown) may also included with PBT controller 131. A RTC is an extremely low power consumption clock that runs continuously and synchronizes to international time standards or network time whenever possible.

Construction of main MPU 134 may comprise a fully integrated single-chip microcontroller or a microprocessor-based module, optionally containing main system clock 124, bus interface 135, and portions of non-volatile memory 128 and volatile memory 129. Any number of partitions is possible including using multiple silicon integrated circuits (ICs), system on chip (SOC) integration, system in package (SIP), or as modules. For example, volatile memory 129 may comprise dynamic random access memory (DRAM), or static random access memory (SRAM). This memory may be integrated all, or in part, within main MPU 134 or may be realized by separate integrated circuits. Similarly, non-volatile memory 128 may comprise electrically erasable programmable random access memory (EPROM) or "flash" memory, which may be integrated all, or in part, within MPU 134. Within PBT controller 131 high-capacity non-volatile data storage may also be realized using moving media storage such as optical disks (CDs/DVDs), by magnetic hard disk drives (HDDs), and even through network connections to cloud storage.

The role of non-volatile data storage 128 within PBT controller 131 is multipurpose including storage of the main operating system, referred herein as LightOS, as well as to retain program libraries of PBT treatments and sessions, generally stored in encrypted form for security reasons. Non-volatile memory 128 may also be used to capture treatment logs, upload sensor data, and possibly retain treatment metadata. In contrast to non-volatile memory 128, the role of volatile memory 129 in PBT controller 131 is primarily that of scratchpad memory, holding data temporarily while calculations are performed. For example, in preparing a PBT session comprising a sequence of separate PBT treatments, the encrypted treatment algorithms must first be decrypted, assembled into a PBT session, re-encrypted, then assembled into a communication packet ready for network transport. Volatile memory 129 holds the data content during the communication packet assembly process.

Another consideration in a distributed PBT system is power distribution needed to power the PBT controller and the LED pads. Options include the following:

- Power the PBT controller using an internal power supply, then deliver power to the LED pads over the communication bus,
- Power the PBT controller using an external power supply (brick), then deliver power to the LED pads over the communication bus,
- Power the PBT controller using an internal power supply, and powering the LED pads using their own dedicated external power supply or supplies (bricks),
- Power the PBT controller using an external power supply (brick), and powering the LED pads using their own dedicated external power supply or supplies (bricks).

In the example shown, external power-supply brick 132 powers the entire PBT system, providing 5 V to integrated circuits and $+V_{LED}$ to the strings of LEDs. USB cable 136 carries transceiver symbol data from the bus interface 135 of PBT controller and bus transceiver 131 to a bus interface 338 of LED pad 337. USB cable 136 also supplies power; specifically ground (GND), 5V, and $+V_{LED}$ to intelligent LED pad 337, generally carried on copper conductors that are thicker and have a lower resistance than the cable's signal lines. Each LED pad 337 comprises a pad μC 339, the bus interface 338, a RAM volatile memory (e.g. SRAM or DRAM) 334a, a NV-RAM non-volatile memory (e.g. EEPROM or flash) 334b, a time reference clock 333, an LED driver 335, and an LED array 336. Time reference clock 333 produces clock pulses 299 at a frequency $\Phi_{pad}$. The LED driver 335 includes switched current sinks 140 and 141, a string of series connected LEDs 142a through 142m for generating a light of a wavelength $\lambda_1$, and a string of series connected LEDs 143a through 143m for generating light of a wavelength $\lambda_2$. Typically, an LED pad 337 would include more than two strings of LEDs and current sinks, with one current sink for each string of LEDS.

Memory within LED pad 337, including both volatile memory 334a and non-volatile memory 334b, is similar to that of the semiconductor memory employed in PBT controller 131 except that the total capacity can be smaller, and preferably consumes lower power. Memory in LED pad 337 must comprise semiconductor solutions because the risk of mechanical shock and breakage of moving media storage makes it inadvisable to integrate fragile data storage into LED pad 337. Specifically, volatile memory 334a in LED pad 337 may comprise dynamic random access memory (DRAM), or static random access memory (SRAM) and may be integrated all, or in part, within μC 339. In the LED pad 337, volatile memory 334a is useful to hold data that need not be retained except during use such as LED streaming files, LED player files and LED playback files. The advantage of only temporarily retaining executable code needed to perform the current PBT treatment (and not the entire library of treatments), is that in this way the capacity and cost of memory required within LED pad 337 can be greatly reduced as compared to the memory required in the PBT controller 131. It also has the advantage that it renders reverse engineering and copying of the treatment programs more difficult because any time power is removed from LED pad 337, all the data is lost.

Non-volatile memory 334b may comprise electrically erasable programmable random access memory (EPROM) or "flash" memory, which may be integrated all, or in part, within 339. Non-volatile memory 334b is preferably employed to hold firmware that does not need to be changed often, such as the operating system for the LED pad 337, herein referred to as LightPadOS, along with manufacturing data including pad identification data, i.e. the LED pad ID register, and manufacturing related LED configuration data. Non-volatile memory 334b may also be used to retain user logs of what treatments have been performed. Low-cost design for LED pads is another important economic consideration because one PBT controller is often sold with multiple LED pads, up to 6 or 8 per system. To lower the overall memory cost it is beneficial to concentrate memory, especially non-volatile memory, into the PBT controller where there is only a single device, and to minimize the memory contained within each LED pad, which occurs in multiple instances per system.

In operation, user commands input on touchscreen LCD 133 of PBT controller 131 are interpreted by main MPU 134, which in response retrieves treatment files stored in non-volatile memory 128 and transfers these files through USB bus interface 135, over USB cable 136 to bus interface 338 within intelligent LED pad 337. The treatment files, once transferred, are temporarily stored in volatile memory 334a. The μC 339 within pad 337, operating in accordance with the LightPadOS operating systems stored in non-volatile memory 334b, then interprets the treatments stored in RAM volatile memory 334a and controls the LED driver 335 in accordance with the LED excitation patterns of the selected treatment, whereby n strings of LEDs in LED array 336, a given string containing m LEDs, are illuminated and generate light of various wavelengths in a desired manner. Because PBT controller 131 and LED pad 337 operate using their own dedicated clocks 124 and 333, the distributed PBT system is asynchronous, being driven by clock pulses 297 and 299 at two different frequencies, specifically $\Phi_{sys}$ and $\Phi_{pad}$ respectively.

Since the two systems operate with different clock rates, communications between PBT controller 131 and LED pad 337 occur asynchronously, i.e. without a common synchronized clock. Asynchronous communication is compatible with a wide range of serial bus communication protocols including USB 136 as shown, or Ethernet, WiFi, 3G/LTE, 4G, and DOCSIS-3. Although a synchronous clock version of a distributed PBT system, i.e. one with a shared clock is technically possible, synchronous operation offers no performance or efficacy advantage over its asynchronous counterpart. Moreover, high frequency clock distribution over long cables is problematic suffering from clock skew, phase delays, pulse distortions and more.

The architecture of FIG. 14 comprising a distributed PBT system having two or more microcontroller or computer "brains" represents a fundamental architecture change in PBT systems which otherwise generally comprise either an all-in-one pad with integral controller or an active PBT controller driving passive LED pads. It should be known to those skilled in the art that instead of being a separate hardware device, a PBT controller may alternatively comprise a notebook or desktop personal computer, a computer server, an application program running on a mobile device such as a tablet or smartphone, or any other host device capable of executing computer software such as a video game console, and IoT device or more. Examples of such alternative embodiments are shown throughout the application.

Figure 15:
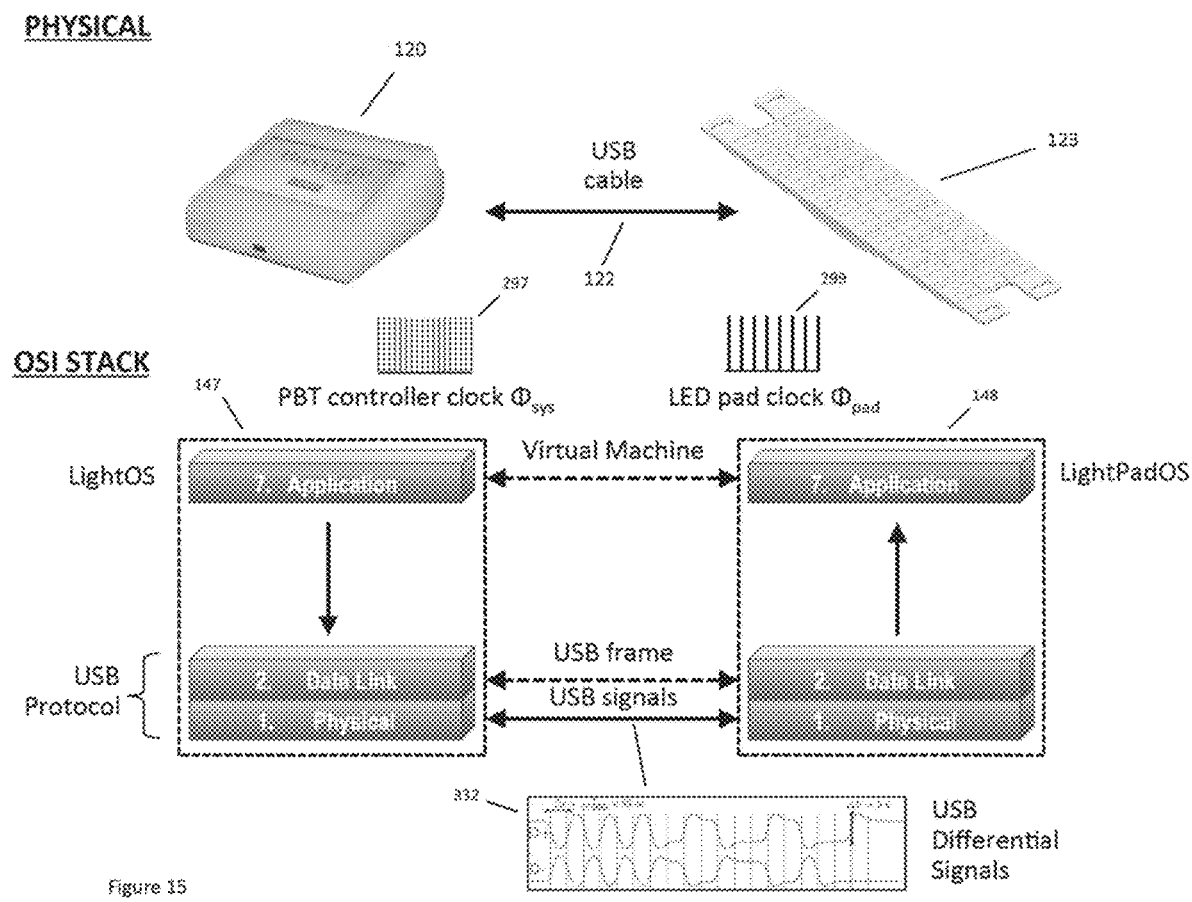
FIG. 15 is a network illustration of a PBT system with intelligent (active) LED pads using a 3-layer OSI stack.

As shown in FIG. 15, PBT operation can be interpreted as a sequence of communications used to control hardware operations. Using an open system implementation or OSI representation, PBT controller 120 contains communication stack 147 comprising an application Layer 7, a data link Layer-2 and a physical Layer-1. Within PBT controller 120, application Layer-7 is implemented using a customized operating system for photobiomodulation referred to herein as LightOS. Instructions received by LightOS user commends are passed down to the Layer-2 data link layer and together with the PHY Layer-1 communicate using the USB protocol using USB differential signals 332 to the corresponding PHY Layer-1 of communication stack 148 resident within intelligent LED pad 123. So although electrical signals comprise Layer-1 communications, the data constructs of USB behave as though the PBT controller and intelligent LED pad are communicating on Layer-2 with the packets arranged in time as USB data "frames". Once communication stack 148 receives a USB packet, the information is transferred up to the application Layer-7 executed by a LED pad resident operating system referred to herein as LightPadOS. Provided that the PBT controller's LightOS and the intelligent LED pad's operating system LightPadOS are designed to communicate and execute instructions in a self-consistent manner, the bidirectional link between communication stacks 147 and 148 functions as a virtual machine at the application layer, meaning the distributed device behaves the same as if it were a single piece of hardware.

To ensure components are able to exchange information and execute instructions at a high abstraction level, i.e. at the application layer and above, it is important that the two operating systems LightOS and LightPadOS are developed with parallel structure using the same encryption and security methods and protocols on any given layer. This criterion includes adopting common shared secrets, executing pre-defined validation sequences (needed for components to join the system's private network), executing common encryption algorithms, and more.

Figure 16:
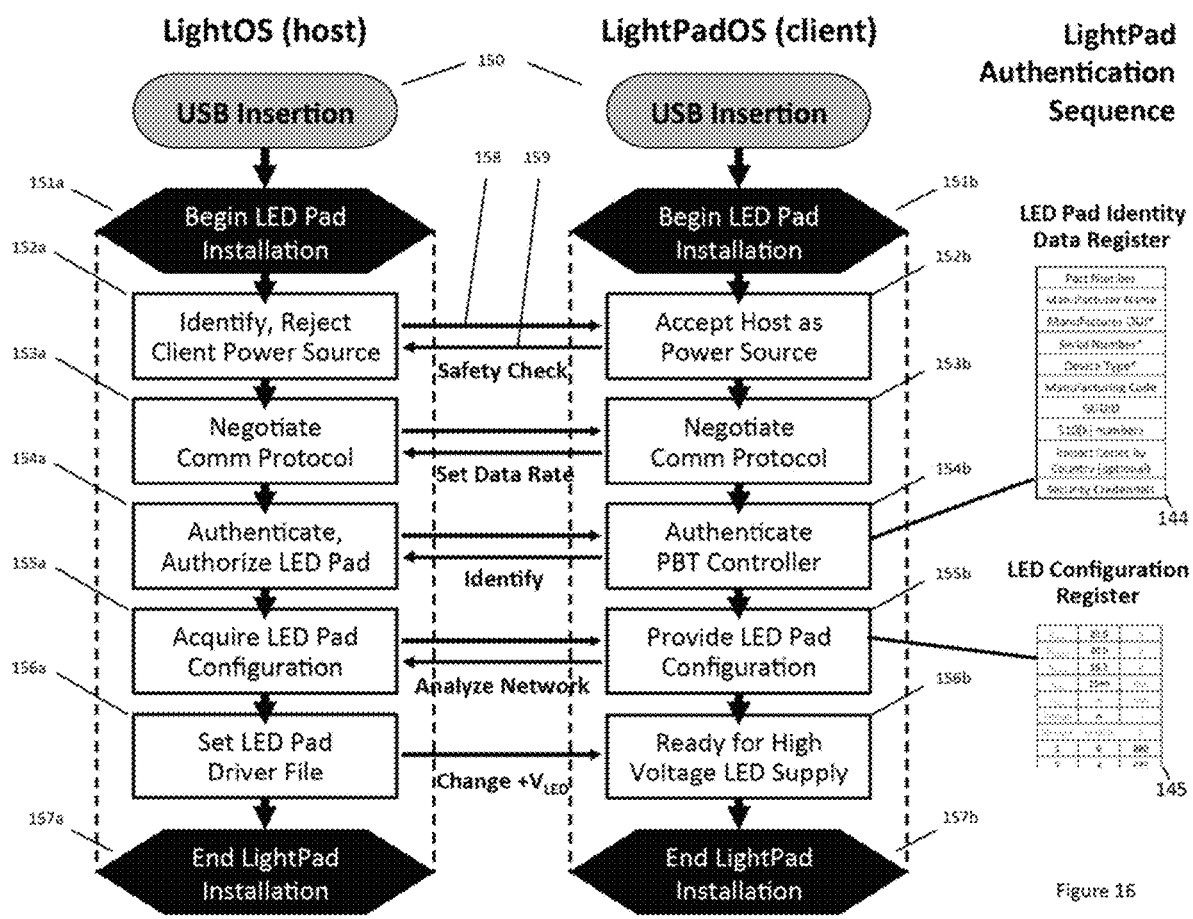
FIG. 16 is a flow chart of a LED pad authentication sequence.

To ensure that the two components can commence communication and perform tasks, the PBT controller must first establish whether the LED pad is indeed a manufacturer approved, system-validated component. This test, referred to as "authentication" is shown in the flow chart of FIG. 16 in two parallel sequences one occurring within LightOS operating as the "host", the other occurring within LightPadOS operating as the "client". As shown, upon completion of establishing a physical USB connection, i.e. insertion 150, the controller's LightOS operating system commences a subroutine 151a called "LightPad Installation" while concurrently the LED pad's LightPadOS operating system commences a subroutine 15 lb. In the first step 152a, used to determine whether the client is a power source (and reject it if it is), the PBT controller performs check 158 checking if the USB D+ and D− pins are shorted. If these data pins are shorted, according to the USB standard, the peripheral is a power source and not a LED pad, whereby the system rejects the connection, terminates the authentication, and LightOS informs the user the peripheral is not a valid component and to unplug it immediately. If the pins are not shorted, then the LightPadOS then the installation approval process may proceed.

In steps 153a and 153b, the two devices negotiate what is the maximum data rate they can each understand and reliably communicate. Once the communication data rate is established, the symmetric authentication processes 154a and 154b commence. During symmetric authentication, in step 154a the LightOS first queries the LightPadOS to determine if the LED pad 123 is a valid manufacturer-approved device by checking data stored in the LED pad identity data register 144. In the mirrored authentication process of step 154b, the LED pad 123 confirms that the PBT controller 120 is a valid device with a valid manufacturing ID approved for use with the LED pad 123. In this exchange certain encrypted security credentials and manufacturer's identification data including serial number, manufacturing code, and GUD ID number change hands to insure that both PBT controller 120 and the intelligent LED pad 123 are from the same manufacturer (or are otherwise licensed as an approved device). In the authorization fails, the host LightOS informs the user the LED pad is not approved for use in the system and instructs them to remove it. If LightOS is unable to authenticate LED pad 123 then PBT controller 120 will discontinue communication with the LED pad 123. Conversely, if the LED pad's LightPadOS is unable to determine the authenticity of PBT controller 120, then LED pad 123 will ignore the instructions of PBT controller 120. Only if symmetric authentication is confirmed can operation proceed.

Any number of authentication methods can be performed to establish a private network including PBT controller 120 and LED pad 123 and approve LED pad 123's connection to the private network. These methods may involve symmetric or asymmetric encryption and key exchange, employing 'certificate authority' based identity confirmation through the exchange of digital CA-certificates, or exchanging cryptographic hash data to confirm that LED pad 123 holds the same shared secrets as PBT controller 120, meaning that LED pad 123 was produced by a qualified manufacturer. For example, a numeric code installed and cryptographically hidden in both & PBT controller 120 and intelligent LED pad 123, i.e. a shared secret, can be used to confirm the authenticity of intelligent LED pad 123 without ever divulging the key itself. In one such method of LED pad validation executed on data link layer 2, the PBT controller 120 passes a random number to the intelligent LED pad 123 over the network or communication bus. In response, the microcontroller in the LED pad 123 decrypts its copy of the shared secret (numeric code), merges it with the received random number then performs a cryptographic hash operation on the concatenated number. The intelligent LED pad 123 then openly returns the cryptographic hash value across the same transceiver link.

Concurrently the PBT controller 120 performs an identical operation decrypting its own copy of the shared secret (numeric code), merging it with the generated random number it sent to the LED pad 123 then performing a cryptographic hash operation on the concatenated number. The PBT controller 120 next compares the received and locally generated hash values. If the two numbers match, the LED pad 123 is confirmed as authentic, i.e. LED pad 123 is 'authorized' to connect to the network. The aforementioned authentication algorithm may be executed on any PHY layer 1 and/or data-link 2 connection over any data bus or packet switched network including USB, Ethernet, WiFi or cellular radio connections. In the event of a WiFi connection, the data link may also be established using WiFi protected access protocol WPA2.

For 'administrative' purposes and security tracking, the authorization time and date (and as available the GPS location) of the authenticated component is stored in a non-volatile memory such as non-volatile memory 128 and optionally uploaded to a server. The benefit of employing secure communication and AAA (authentication, authorization, administration) validation of all connected components in the distributed PBT system is crucial to ensure safety and protection from the intentional connection of uncertified and potentially unsafe imposter devices. In this way, imposter devices cannot be driven by the distributed PBT system. AAA validation also protects against the accidental connection of devices not intended for operation as part of the PBT system such as lithium ion battery packs, unapproved power supplies, speakers, disk drives, motor drivers, high power Class III and Class IV lasers, and other potential hazards unrelated to the PBT system.

The security of a distributed PBT system using a packet switched network (such as Ethernet or WiFi) may also be enhanced using dynamic addressing on network layer 3 and dynamic port assignment on data transport layer 4 of communication stacks 147 and 148. In operation of a PBT controller not connected to the Internet or a local area network, the PBT controller generates a dynamic IP address and a dynamic port address, and then broadcasts the addresses to the other network connected devices, to which the intelligent LED pads respond with their own dynamic IP addresses and their own dynamic port addresses. In the event that the distributed PBT system is in contact with a router or the Internet, a dynamic host configuration processor (DHCP) is used to assign dynamic IP addresses. Similarly, a remote procedure call (RPC) is used to perform a dynamic port number assignment. Since dynamic IP addresses and dynamic ports change whenever a device is connected to a network, the cyber attack surface is reduced. Additional layer-4 security can be added using TLS transport layer security, IPSec security protocol, or other protocols. Once the intelligent LED pad is connected to the network, additional information such as LED configuration data can be exchanged to authorize the component to operate as part of the distributed PBT system.

In step 155a, the LightOS in the PBT controller 120 requests information regarding the LED configuration of the LED pad 123. In step 155b, the LightPadOS in the LED pad 123 responds by relaying the information within the configuration register 145 of the LED pad 123 to the PBT controller 120. In addition to containing a detailed description of the LED array 336 the configuration file also specifies the manufacturer's specification for the maximum, minimum and target voltage need to power the LED strings 142a-142m and 143a-143m in the array 336. The configuration file also specifies the minimum required current needed to drive the LEDs. If more than one LED pads are connected to the PBT controller 120, the LightOS in PBT controller 120 solicits and receives the same information from every attached LED pad, i.e. analyzing the entire network of connected devices.

In step 156a, the LightOS in PBT controller 120 inspects the voltage requirements of LED pad 123 and compares that value to the output voltage range of the high voltage power supply, e.g., the external power supply brick 132 shown in FIG. 14. In PBT controllers using a high voltage power supply capable of a fixed output voltage $+V_{LED}$, the LightOS operating system will confirm than this voltage falls within each LED pad's specified voltage range from $V_{min}$ to $V_{max}$. The system will also check to confirm that the required total current for all of the "n" LED strings in the LED pads connected to the PBT controller does not exceed the current rating of the supply (although this is generally not a concern, the current check is included to support low cost consumer PBT device designs with limited power).

If in step 156a, the power supply's output voltage meets the operating range of every connected LED pad, i.e. $V_{min} \leq +V_{LED} \leq V_{max}$, then the PBT controller 120 will enable the high supply voltage $+V_{LED}$. Optionally in step 156b the PBT controller 120 may inform the LED pad 123 of the supply voltage chosen which is stored in non-volatile memory 334b, documenting the last supply voltage delivered to the LED pad (useful when inspecting quality matters and field failures). In the event that the PBT controller 120 employs a programmable voltage power supply, the LightOS operating system will select the best voltage based on the operating $V_{target}$ of LED pad 123, as stored in the pad's LED configuration register 145. If the target voltages are mismatched, the LightOS operating system in PBT controller 120 will choose a voltage $+V_{LED}$ as some compromise of the various reported target voltages. The term "high supply voltage" in this context means a voltage between 19.5 V minimum and 42 V maximum. Common supply voltages include 20V, 24V, or 36V. Even after $+V_{LED}$ is enabled, this high voltage is not connected to the output socket or supplied to the LED pads until a treatment is selected and therapy initiated.

Figure 17:
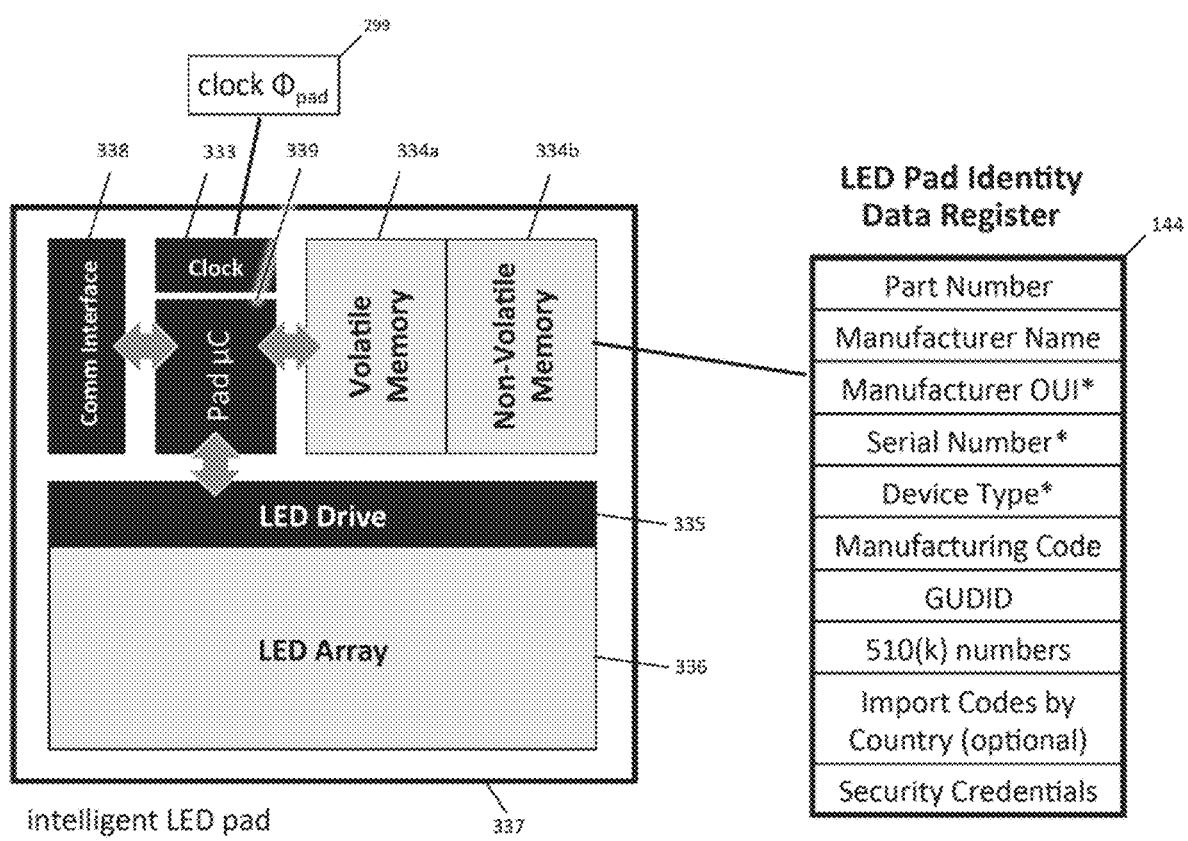
FIG. 17 illustrates a block diagram of an active LED pad with an identity data register.

During the authentication process and in the case of user inquiries, the PBT controller 120 must solicit information regarding the manufacturing of the LED pad 123. This data is beneficial for complying with medical device regulations of traceability, and for debugging quality or field failures or for processing return merchandise authorizations (RMAs). FIG. 17 illustrates an example of the type of product manufacturing information included in "LED pad identity data register" 144 stored in the LED pad 337's non-volatile memory 334b. This data may include the manufacturer's part number, the name of the manufacturer, the unit's serial number, a manufacturing code linked to a description of the specific unit's manufacturing history or pedigree, the USFDA specified global unique device identification database (GUDID) number [https://accessgudid.nlm.nih.gov/about-gudid], and as applicable a related 510(k) number. The register may also optionally include country specific codes for importing the device and other customs related information e.g. export license numbers or free-trade certificates. The information in identity data register 144 is stored in non-volatile memory 334b during manufacturing. The LED pad identity data register 144 also includes security credentials (such as encryption keys) used in the authentication process. The security credentials may be static as installed during manufacturing, or may be dynamically rewritten each time the LED pad 337 is authenticated, or alternatively rewritten after a prescribed number of valid authentications.

Figure 18:
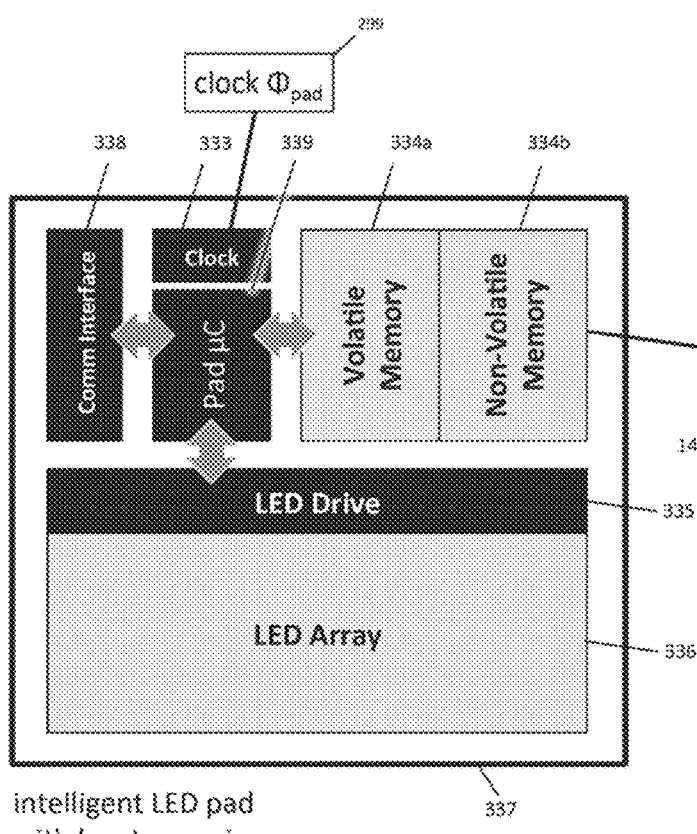
FIG. 18 illustrates a block diagram of an active LED pad with an LED configuration register.

As described, during the authentication process the PBT controller 120 gathers information regarding the LED configuration of every connected LED pad. As shown in FIG. 18, the LED configuration information of LED pad 337 is stored in the non-volatile memory 334b in "LED configuration register" 145, written during the manufacture of LED pad 337. The configuration register 145 stores the number n of LED strings in the LED array 336 and the specific information description of the LEDs in each string, including the wavelength λ of the light emitted by the LEDs and the number "m" of LEDs connected in series in each string. In operation, this LED string information is used for matching a LED treatment to a specific type of LED pad. For example, treatments designed exclusively for driving red LEDs will not function if an LED pad containing blue or green LEDs is attached. A user's IU/UX, i.e. menu choices on the touchscreen of PCB controller 120 are adjusted in accordance with the LED pads connected to PCB controller 120. If an LED pad containing LEDs designed to emit light of the wavelength required for a particular type of treatment is not attached to PCB controller 120, the menu selection for that type of treatment is hidden or grayed out.

Figure 19:
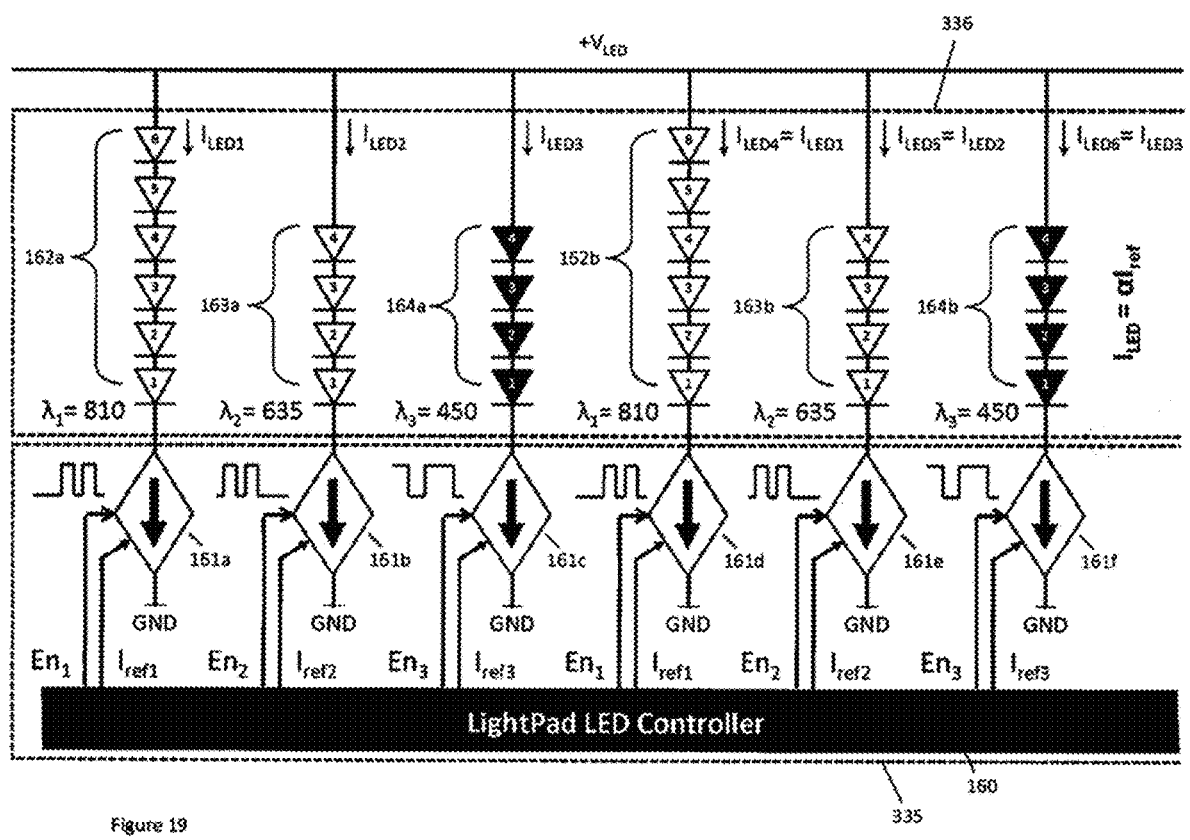
FIG. 19 is a schematic representation of an exemplary LED array and drive electronics comprising three wavelength LEDs.

The LED configuration register 145 is essentially a tabular description of LED pad 337's circuit. The schematic circuit diagram of FIG. 19 depicts a portion of LED pad 337 comprising LED driver 335 with a LED controller circuit 160 and current sinks 161a through 161f, and LED array 336, whereby String #1 in LED configuration register 145 describes string 162a comprising six series-connected near infrared LEDs of wavelength $\lambda_1$=810 nm driven by current sink 161a carrying current $I_{LED1}$.

String #2 in LED configuration register 145 describes string 163a comprising four series-connected red LEDs of wavelength $\lambda_2$=635 nm driven by current sink 161b carrying current $I_{LED2}$.

String #3 in LED configuration register 145 describes string 164a comprising four series-connected blue LEDs of wavelength $\lambda_3$=450 nm driven by current sink 161c carrying current $I_{LED3}$.

String #4 in LED configuration register 145 describes string 162b comprising six series-connected near infrared LEDs of wavelength $\lambda_1$=810 nm driven by current sink 161d carrying current $I_{LED4}=I_{LED1}$.

String #5 in LED configuration register 145 describes string 163b comprising four series-connected red LEDs of wavelength $\lambda_{2=635}$ nm driven by current sink 161e carrying current $I_{LED5}=I_{LED2}$.

String #6 in LED configuration register 145 describes string 164b comprising four series-connected blue LEDs of wavelength $\lambda_{3=450}$ nm driven by current sink 161f carrying current $I_{LED6}=I_{LED3}$.

The foregoing is intended to exemplify without limitation, the data formatting of LED configuration register 145 and its corresponding schematic equivalent, not to represent a specific design. In particular, the number of LED strings "n" and the number of LEDs connected in series in a given string "m" contained within the LED pad are likely to exceed the numbers shown in this example. In practice, the number of LEDs in the various strings may be identical or may differ from string to string. For example, an LED pad may include 15 strings comprising fourteen LEDs in series, or 210 LEDs. These LEDs may be arranged in three groups of five LED strings each; one-third near infrared (NIR), one-third red, and one-third blue. Each LED type may be configured with 5 parallel strings and 14 series connected LEDs, i.e. three 14s5p arrays.

LED configuration register 145 also includes the minimum and maximum operating voltages for the LED pad. For proper LED operation, the power supply voltage $+V_{LED}$ must exceed the minimum voltage specification $V_{min}$ of the LED pad to ensure uniform illumination, but to avoid damage from excessive voltage or heat the power supply voltage should not exceed the specified maximum voltage $V_{max}$. In other words, the value of the supply voltage acceptable for powering the LED pad must meet the criteria $V_{min} < +V_{LED} < V_{max}$. The manufacturer's specified value of $V_{min}$, stored in LED configuration register 145, must on a statistical basis exceed the highest voltage string of LEDs in the LED pad to insure that so long that the criteria $V_{min} < +V_{LED}$ are maintained, the pad's highest voltage strings will still be fully illuminated in operation. If the $V_{min}$ voltage is specified too low, in some LED pads individual LED strings may be dimmer than others during treatment. Poor brightness uniformity adversely impacts treatment efficacy by limiting a PBT treatment's peak and average power and reducing a treatment's total energy (dose).

The highest voltage string in a LED pad is determined by both design and stochastic voltage variability in LED manufacturing. Each LED string comprises m series-connected LEDs, where each LED has its own unique forward conducting voltage $V_{fx}$, where x varies from 1 to m, and where the total string voltage is the summation of these individual LED voltages $\Sigma V_{fx}$. The highest voltage could occur in a string comprising fewer series-connected LEDs with higher-voltage, or it could occur in a string comprising a larger number of lower forward voltage LEDs. A LED pad manufacturer must employ statistical sampling data of LED forward voltages on a lot-to-lot basis to ensure that no LED pad is manufactured with an LED string voltage exceeding the specified value of $V_{min}$.

Albeit less precise, the power supply must be capable of supplying a minimum required average current $I_{min}$ to illuminate all the LEDs of a particular color (wavelength) at once. Generally, in a two wavelength LED pad, 50% of the n strings of LEDs may be conducting at the same time. While in a three-color LED pad, it is likely that only one of the three LED wavelengths will be illuminated at a time to avoid overheating, a worst case assumption of $\frac{2}{3}^{rd}$ or 67% of the n-strings can be used to calculate the maximum current. The peak current in LED conducting in continuous operation will in the worse case not exceed 30 mA per string, i.e. $I_{LED} \leq 30$ mA. Using this worst case assumption, a pad with n=30, $\frac{2}{3}^{rd}$ of the strings illuminated at one time, and with $I_{LED} \leq 30$ mA will require a value of $I_{min}=30(\frac{2}{3})(30$ mA$)=600$ mA.

The value of $I_{max}$ specified in LED configuration register 145 is not a description of the maximum current flowing in the LEDs, but a description of maximum safe current at 50% duty factor in the pad's conductive traces. This current includes the current flowing in the LED pad's own LED strings plus any current bussed through the LED pad to another LED pad. The specification is included to prevent operating the pad where significant voltage drops occur in the LED pad's power lines resulting in heating, malfunction, electromigration, or metal fusing. One possible design guideline for an LED pad's printed circuit board (PCB) is to utilize copper conductors capable of carrying more than twice its rated current, meaning the pad can safely carry its own current and the current of another LED concurrently. An added design guard band of $\delta=25\%$ is included as a safety margin. For example, if $I_{min}=600$ mA then using a 25% guard band, $I_{max}=2I_{min}(1+\delta)=1500$ mA. Configuration register 145 also includes the mirror ratio $\alpha$ used to convert the reference current $I_{ref}$ into the LED string current $I_{LED}$ (or vice versa) in accordance with the relation $I_{LED}=\alpha I_{ref}$. If different ratios are used for each channel, the table can be modified accordingly to include $\alpha_1, \alpha_2, \alpha_3 \ldots$ whereby $I_{LED1}=\alpha_1 I^{ref1}$, $I_{LED2}=\alpha_2 I_{ref2}$, and so on.

Referring again FIG. 19, the current $I_{LED1}$ in NIR LED strings 162a, 162b is controlled by dedicated series-connected current sinks 161a, 161d, respectively, conducting on-state currents in proportion to $I_{ref1}$. The current $I_{LED2}$ in red LED strings 163a, 163b is controlled by dedicated series-connected current sinks 161b, 161e, respectively, conducting on-state currents in proportion to $I_{ref2}$. The current $I_{LED3}$ in blue LED strings 164a, 164b is controlled by dedicated series-connected current sinks 161c, 161f, respectively, conducting on-state currents in proportion to Imo. The current control device connected in series with each LED string may be either connected to the cathode side as a current "sink" as shown by current sink 161a in FIG. 20A, or connected to the anode side of the LED string as a current "source" as shown by current source 200a in FIG. 22A. In both current sink (FIG. 20A) and current source (FIG. 22A) implementations, the current $I_{LED}$ flowing in the current control device 161a, 200a, respectively, and in the LED string 165, 201, respectively is controlled by an analog reference current $I_{ref}$ and a digital enable pulse En. The origin of the signals $I_{ref}$ and En in a distributed PBT system is discussed later in this application. (Note: The terms "current source" and "current sink" are well-known in the art as referring to a component that provides or receives ("sinks") a current whose magnitude is relatively unaffected by the magnitude of the voltage across the component.)

Figures 20A, 20B, 20C:
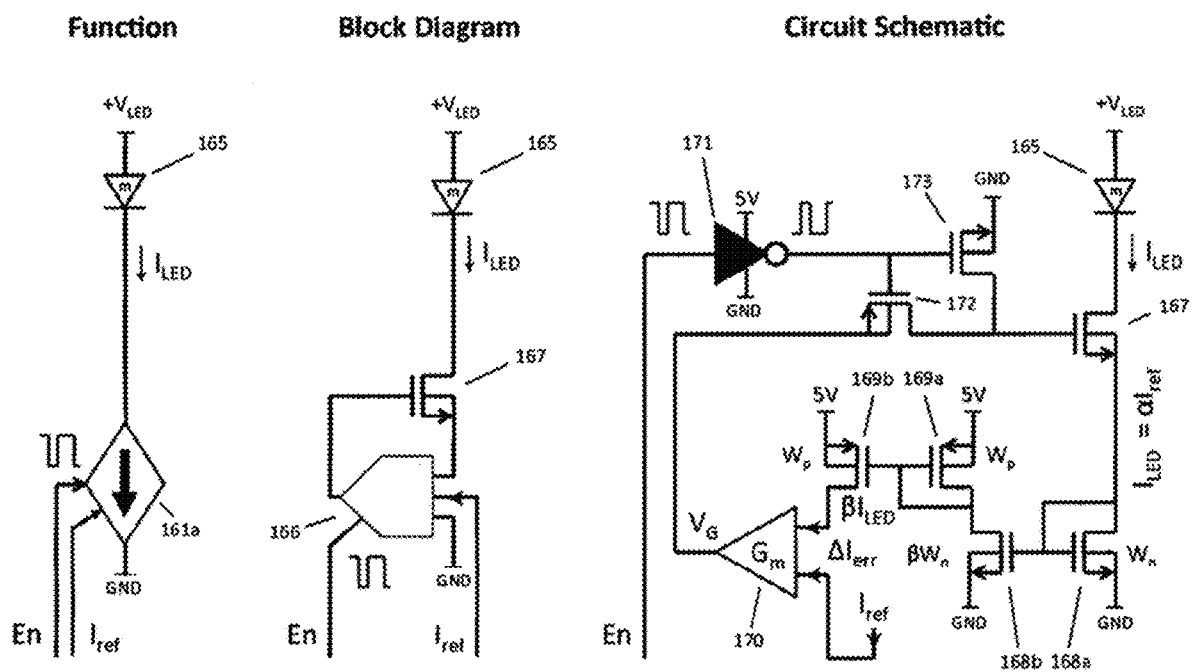
FIG. 20A is a schematic representation of a low-side switched current-control element or "current sink" driving a series string of LEDs comprising "m" LEDs
FIG. 20B is a schematic representation of a current-sink type switched low-side LED driver comprising a N-channel MOSFET and a current-sensing gate bias circuit with a reference current input $I_{ref}$.
FIG. 20C is a schematic representation of an exemplary current-sink type low-side switched LED driver implementation comprising a current mirror sensor, a transconductance amplifier bias circuit with reference current input $I_{ref}$ and a transmission gate with digital input.

FIG. 20B illustrates a block diagram representation of idealized current sink 161a showing a current sense and control element 166 driving the gate of an N-channel MOSFET 167. The MOSFET 167 (or alternatively a bipolar junction transistor) maintains the controlled current while sustaining the voltage across its drain-to-source terminals. Gate bias is provided by current sense and control element 166 to maintain a constant current despite variations in the drain-to-source voltage across MOSFET 167. FIG. 20C illustrates one implementation of the constant current sink 161a, wherein N-channel current mirror MOSFETs 168a and 168b provide a current reflecting the magnitude of the current $I_{LED}$. The ratio $\beta$ of the gate width of MOSFET 168b to the gate width of MOSFET 168a is less than one, meaning that the current in current mirror MOSFET 168b is a fraction of, but in a precise ratio to, the load current in current mirror MOSFET 168a ($I_{LED}$). The current in MOSFET 168B is transformed by a unity current mirror comprising P-channel MOSFET 169a and 169b having matched gate widths $W_p$ from a ground-referenced current to a 5V-supply-referenced current of magnitude $\beta I_{LED}$. The differential "error" signal $\Delta I_{err}$ representing the difference between $I_{ref}$ and $\beta I_{LED}$ is then amplified and converted proportionally into a voltage $V_G$ by transconductance amplifier 170 and fed to the gate of the current controlling element, i.e. MOSFET 167, forming a closed loop feedback path. In operation the gain $G_m$ of transconductance amplifier 170 results in a gate bias voltage $V_G$ that drives its error signal $\Delta I_{err}$ to zero, thereby forcing $I_{ref}=\beta I_{LED}$. For convenience's sake we redefine $\beta=1/\alpha$ whereby we can express the current source transfer function as $I_{LED}=\alpha I_{ref}$. The reference current $I_{ref}$ is distributed to all the LED strings within the same LED pad to insure uniform brightness across all LEDs.

In the switched current sink 161a, a digital inverter 171 and an analog transmission gate comprising a P-channel MOSFET 172 and a ground connected N-channel MOSFET 173 perform the digital enable function of the En input, controlling the gate of N-channel current sink MOSFET 167. Specifically, when the enable signal En is high, the output of inverter 171 is at ground, turning on P-channel transmission gate MOSFET 172 and turning off N-channel MOSFET 173. Because the P-channel MOSFET 172 has a grounded gate, it is biased in a fully on condition, i.e. its linear region, and behaves like a resistor, passing the analog voltage $V_G$ from the output of transconductance amplifier 170 to the gate of N-channel current sink MOSFET 167. Conversely, when the enable signal En is low (digital 0), the output of inverter 171 connected to P-channel transmission gate MOSFET 172 is biased to 5 V, and the P-channel MOSFET 172 is turned off, disconnecting the gate of N-channel current sink MOSFET 167 from the output of transconductance amplifier 170. Concurrently, N-channel MOSFET 172 is turned on, pulling the gate of current sink MOSFET 167 to ground and turning off the current sink MOSFET 167, i.e. $I_{LED}=0$. In conclusion, the circuit of FIG. 20C represents one circuit to implement the switched controlled current sink 161a. When the current sink 161a is enabled (En=digital 1), the current sink MOSFET 167 conducts and carries a controlled current $I_{LED}=\alpha I_{ref}$. When the current sink 161a is disabled (En=digital 0), the current sink MOSFET 167 is turned off and $I_{LED}=0$.

Figure 22A:
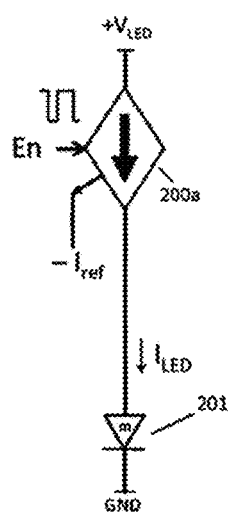
FIG. 22A is a schematic representation of a high-side switched current-control element or "current source" driving a series string of LEDs comprising "m" LEDs.
Figure 22B:
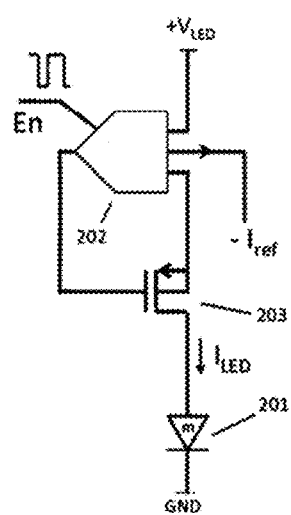
FIG. 22B is a schematic representation of a current-source type switched high-side LED driver comprising a P-channel MOSFET and a current-sensing gate bias circuit with a reference current input $(-I_{ref})$.

In a similar manner, the current source 200a of FIG. 22A can be realized using P-channel current mirror MOSFETs to source a controlled current from the +5V supply voltage $+V_{LED}$ into the anode of LED string 201. FIG. 22B illustrates a block diagram representation of this idealized current source 200a showing a current sense and control element 202 driving the gate of a P-channel MOSFET 203. The MOSFET 203 (or alternatively a bipolar junction transistor) maintains the controlled current $I_{LED}$ while sustaining the voltage across its drain-to-source terminals. Gate bias is provided by current sense and control element 202 to maintain a constant current despite variations in the drain-to-source voltage across MOSFET 203.

Figure 22C:
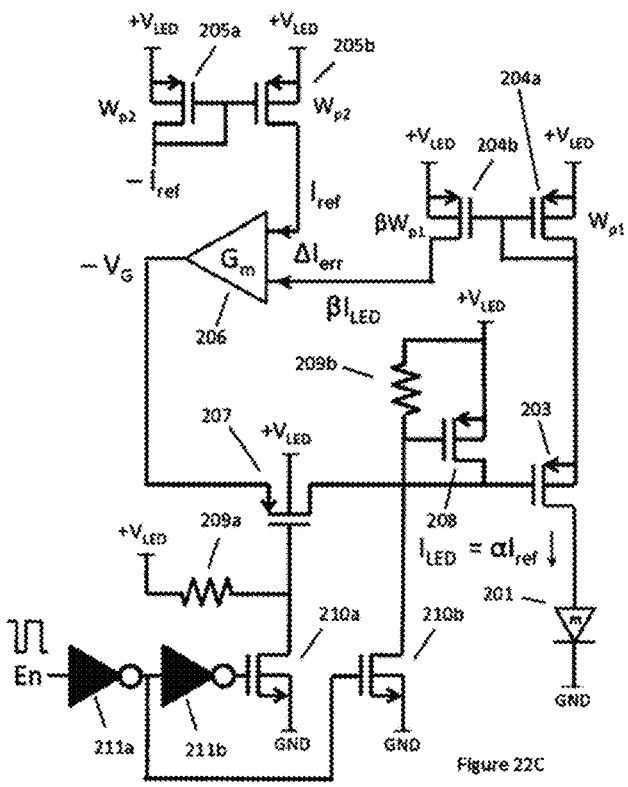
FIG. 22C is a schematic representation of an exemplary current-source type switched high-side LED driver implementation comprising a current mirror sensor, a transconductance amplifier bias circuit with reference current input $(-T_{ref})$ and a transmission gate with digital input.

FIG. 22C illustrates one implementation of the constant current source 200a, wherein P-channel current mirror MOSFETs 204a and 204b provide a current $\beta I_{LED}$ reflecting the magnitude of the load current $I_{LED}$. The ratio of the gate width of MOSFET 204A to the gate wide of MOSFET 204b is $\beta$, where $\beta<1$, meaning the current in mirror MOSFET 204b is a fraction of, but in a precise ratio to, the LED load current $I_{LED}$. The current $\beta I_{LED}$, representing a $+V_{LED}$ high-voltage supply-referenced current, is then input into a differential transconductance amplifier 206 wherein it is compared to reference current $I_{ref}$, a current also mirrored to the $+V_{LED}$ high voltage supply rail. The differential "error" signal Men, representing the difference between $I_{ref}$ and $\beta I_{LED}$, is then amplified and converted proportionally into a voltage $-V_G$ by transconductance amplifier 206 and fed to the gate of the current controlling element, P-channel current source MOSFET 203, forming a closed loop feedback path. In operation the gain $G_m$ of transconductance amplifier 206 results in a gate bias voltage $-V_G$ that drives its error signal $\Delta I_{err}$ to zero, thereby forcing $I_{ref}=\beta I_{LED}$. For convenience's sake we redefine $\beta=1/\alpha$ whereby we can express the current source transfer function as $I_{LED}=\alpha I_{ref}$. The reference current $I_{ref}$ is distributed to all the LED strings within the same LED pad to insure uniform brightness across all LEDs.

In the implementation of switched current source 200a shown in FIG. 22C, digital inverters 211a and 211b and an analog transmission gate comprising P-channel MOSFET 207 and a $+V_{LED}$ connected P-channel MOSFET 208 perform the digital enable function of the En input, controlling the gate of P-channel current source MOSFET 203. Specifically, when the enable signal En is high, the output of inverter 211a is at ground and the output of inverter 211b is at 5 V, turning on high-voltage level shift N-channel MOSFET 210a and turning off high-voltage level shift N-channel MOSFET 210b. With high-voltage level shift N-channel MOSFET 210a in its on state, current is conducted through resistor 209a pulling the gate of P-channel transmission gate MOSFET 207 down to a voltage near ground, turning it on. Because the P-channel MOSFET 207 has a gate biased near ground, the device operates in its linear region, i.e. fully on, behaving like a resistor and passing the analog voltage $-V_G$ from the output of transconductance amplifier 206 to the gate of P-channel current source MOSFET 203. Simultaneously, since high-voltage level-shift N-channel MOSFET 210b is off, no current flows in resistor 209b, and the voltage of the gate of P-channel pull up MOSFET 208 is tied to its source, i.e. to $+V_{LED}$, and MOSFET 208 is turned off. Thus, whenever P-channel current source MOSFET 203 is turned on, P-channel pull up MOSFET 208 is turned off and has no effect on the gate voltage of P-channel current source MOSFET 203.

Conversely, when the enable signal En is low (digital 0), the output of inverter 211b is biased at ground, turning off high-voltage level shift N-channel MOSFET 210a. With high-voltage level-shift N-channel MOSFET 210a turned off, no current flows in resistor 209a, and the voltage at the gate of P-channel transmission-gate MOSFET 207 is biased to $+V_{LED}$ turning P-channel transmission gate MOSFET 207 off and disconnecting the output of transconductance amplifier 206 from the gate of P-channel current source MOSFET 203. Concurrently, N-channel MOSFET 210b is turned on, allowing current to flow in resistor 209b and pulling the gate of P-channel pull-up MOSFET 208 down near to ground, turning MOSFET 208 on. With P-channel pull-up MOSFET 208 is an on state, the gate of P-channel current source MOSFET 203 is biased to $+V_{LED}$, whereby the current source MOSFET 203 is turned off and $I_{LED}=0$. In conclusion, the circuit of FIG. 22C represents one circuit to implement switched controlled current source 200a. When the current source 200a is enabled (En=digital 1), the current source MOSFET 203 conducts and carries a controlled current $I_{LED}=\alpha I_{ref}$. When the current source 200a is disabled (En=digital 0), the current source MOSFET 203 is turned off and $I_{LED}=0$.

It should be noted that the current sink circuit implementation of FIG. 20C is essentially a low voltage circuit. The only component requiring a specification capable of surviving high-voltage LED supply+$V_{LED}$ is the N-channel current sink MOSFET 167. This is not the case with the current source circuit of FIG. 22C, which requires MOSFETs with high off-state drain-to-source blocking capability, especially P-channel current source MOSFET 203, which must conduct a controlled current while simultaneously sustaining a high-voltage, i.e. the current source MOSFET 203 must exhibit a wide safe operating area free from second breakdown (snapback) and hot carrier reliability concerns. Of particular concern is the maximum gate-to-source voltage rating of P-channel MOSFETs 207 and 208, i.e. $V_{GSp}$(max). To avoid damaging the gate oxide of these devices, the values of resistors 209a and 209b must be chosen carefully not to produce an on-state gate drive exceeding $V_{GSp}$ (max) of the devices. As a precaution, a zener diode can be included across the gate to source terminals of MOSFETs 207 and 208, respectively, to clamp the maximum gate bias to a safe level. In some integrated circuit processes, fabricated high voltage P-channel transistors may optionally utilize a thicker "high voltage" gate, but this option depends of the wafer foundry used to produce the IC.

FIG. 23A illustrates another implementation of a switched current source for controlling the current through LED string 201. In this case the analog current control circuit is separated from the digital enable function, whereby LED string 201 is series connected between a controlled current source 220a and a grounded N-channel enable MOSFET 212. The block diagram of this circuit, shown in FIG. 23B, illustrates that the realization of current source 220a includes a current sense and control circuit 222 and a high-voltage P-channel current source MOSFET 203. The circuit implementation of a "low-side switched" current source, shown in FIG. 23C, is considerably simpler than that of the fully integrated switched current source of FIG. 22C. As shown, the current sensing remains unchanged, using a current sensing mirror comprising P-channel MOSFETs 204a and 204b, a current reference mirror comprising P-channel MOSFETs 205a and 205b and a differential input transconductance amplifier 206. In FIG. 23C, however, the high voltage level shift, transmission gate, and gate pull up circuitry is completely eliminated and replaced by a single grounded N-channel MOSFET 212 driven by low-voltage gate drive inverters 221a and 211b.

In the high-voltage current source circuits of both FIG. 22C and FIG. 23C, the required reference current is a ground referenced current sink current $-I_{ref}$. Since most current references source current rather than sink it, a source-to-sink current mirror is required. This mirror is depicted in FIG. 23C by a threshold connected N-channel MOSFET 213a with a current reference input $I_{ref}$ mirrored by N-channel MOSFET 213b to produce a current sink reference current $-I_{ref}$ used to power $+V_{LED}$ referenced P-channel current mirror MOSFET 205b. It should be understood that the converse of the circuit shown in FIG. 23C uses a high-voltage P-channel MOSFET and level shift circuit for the enable function and a grounded current sink for current control. But in general, a high-side switched current sink has no specific advantage over the fully integrated switched current sink shown in FIG. 20C and therefore is not described in this application.

In all the aforementioned circuits, LED current control depends on a common reference current. To achieve the required precision for controlling LED brightness, reference current $I_{ref}$ requires active trimming during manufacturing.

Figure 21A:
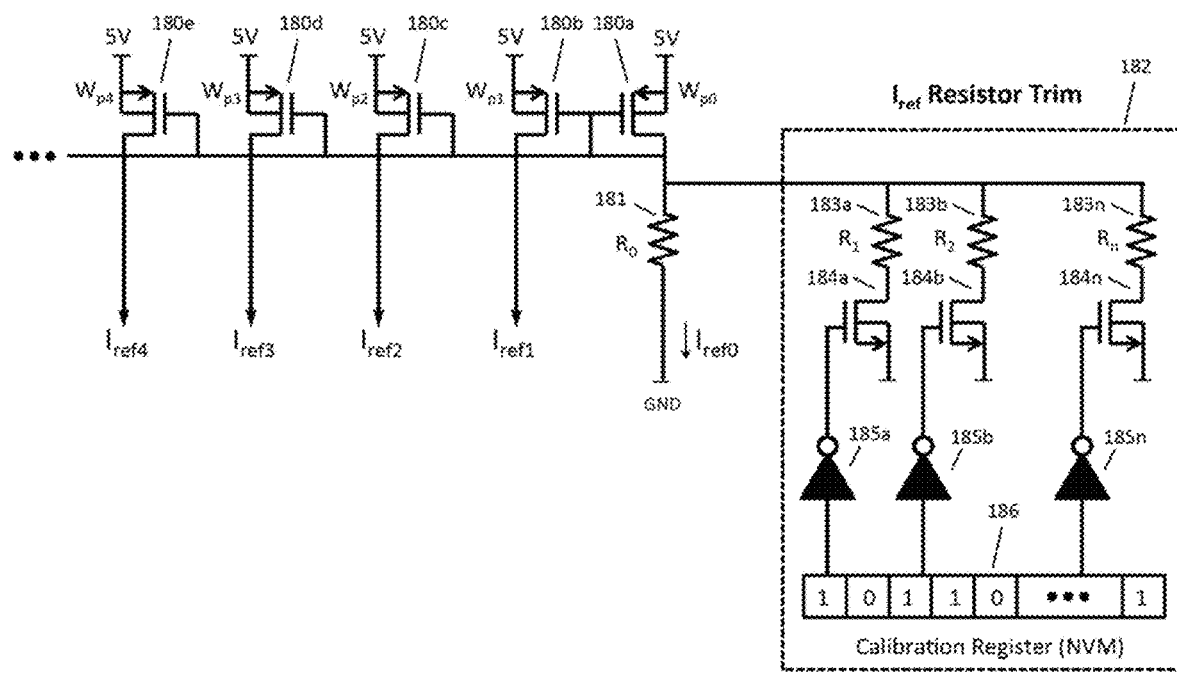
FIG. 21A is a schematic representation of an exemplary multi-channel current reference generator with DAC resistor current trim.

One method for trimming the reference current, using resistors, is shown in FIG. 21A. The reference current $I_{ref0}$ is determined by threshold-connected P-channel MOSFET 180a in series with resistor 181. Threshold connection refers to a MOSFET WITH ITS GATE CONNECTED TO ITS DRAIN TO CREATE A TWO TERMINAL DEVICE WHERE $V_{GS}=V_{DS}$. The term "threshold" is used because it represents the voltage where a rapid increase in drain current occurs, at a voltage near the threshold voltage $V_{tp}$ of the device, i.e. $V_{GS}=V_{DS}≈V_t$. So the current in P-channel MOSFET 180a is approximately $I_{ref0}≈(5V-V_{tp})/R_o$. This reference current is mirrored to other reference MOSFETs 180b to 180e of identical construction and gate width by a shared gate connection to produce multiple matched reference currents $I_{ref1}$, $I_{ref2}$, $I_{ref3}$, $I_{ref4}$ and more. Mismatch of the gate widths $W_{p0}=W_{p1}=W_{p2}=W_{p3}=W_{p4}$ etc. is not a significant source of variability in comparison to the variability of the resistance $R_0$ of the integrated circuit resistor 181. To be able to electronically trim the circuit to compensate for manufacturing variances, $I_{ref}$ resistor trim circuit 182 includes an array of switched resistors 183a, 183b . . . 183n having corresponding resistances $R_1$, $R_2$ . . . $R_n$ that can by connected electrically in parallel with resistor 181 (or not) depending on whether N-channel MOSFETs 184a, 184b . . . 184n are biased into a conducting state by gate drivers 185a, 185b . . . 185n respectively. For each transistor activated, its corresponding resistor is placed in parallel with resistor 181, reducing the effective resistance $R_0$ and increasing the magnitude of current $L_{ref0}$. Such a trimming method is a unidirectional trim down in resistance and up in current, meaning the initial value is the highest resistance and the lowest current. In manufacturing, the LED current is measured and the combination of which trim MOSFETs are turned on and off are adjusted by changing the digital value calibration register 186 until the target current is reached whereby the contents of calibration register 186 are written into non-volatile memory. Although this method describing switched parallel resistances represents one resistor trim method, an alternative method involves series connected resistors shorted out by conducting MOSFETs. In this series trim method, the resistor value with all the MOSFETs turned off starts at the highest value with the lowest current, and the current increases as the trim proceeds and MOSFETs are turned on shorting out more resistors.

Figure 21B:
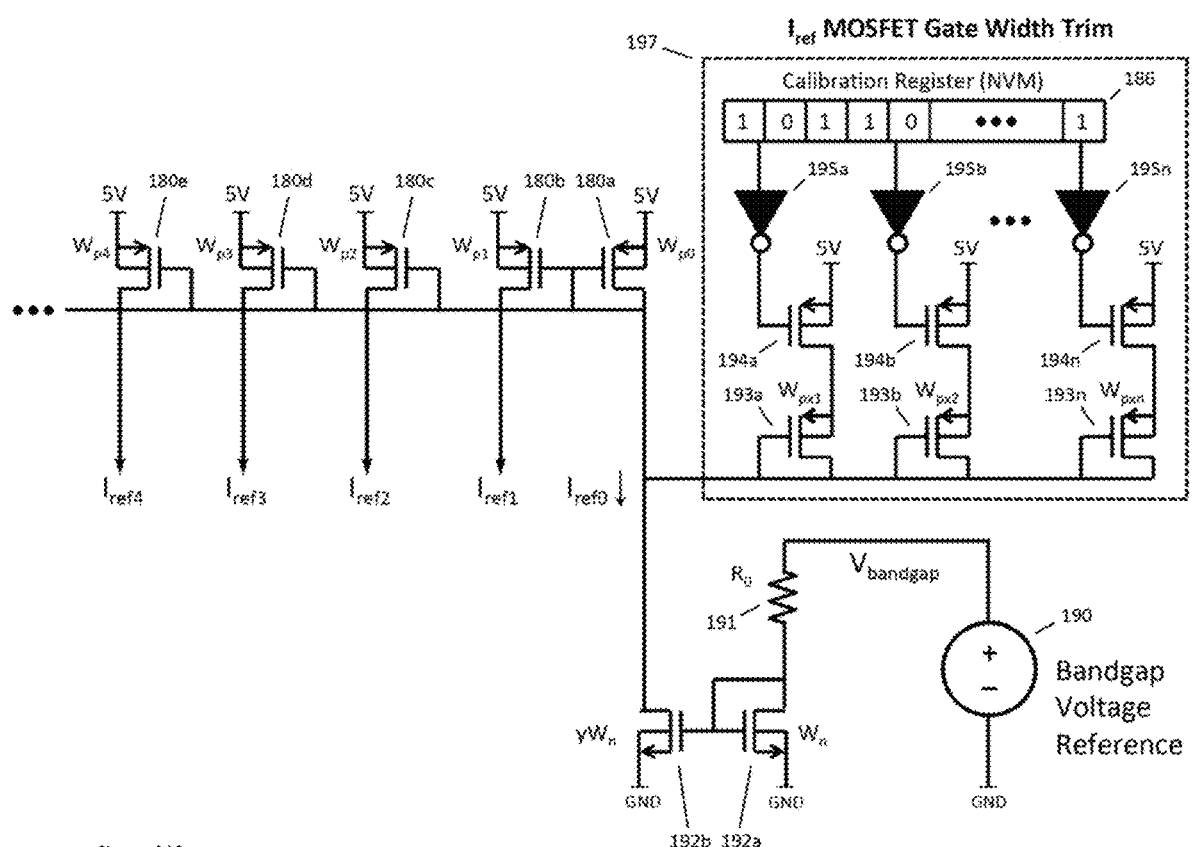
FIG. 21B is a schematic representation of an exemplary multi-channel current reference generator with DAC MOSFET gate width current trim.

FIG. 21B illustrates an alternative trimming method using MOSFET gate width scaling. As in the resistor reference circuit of FIG. 21A, in this reference circuit a reference current $I_{ref0}$ conducted by a threshold connected P-channel MOSFET 180a is mirrored to multiple outputs through identically sized MOSFETs 180b through 180e. Unlike in the prior case however, a bandgap reference circuit 190 with an output $V_{bandgap}$ produces the reference current. The bandgap voltage is converted into a current by series resistor and mirrored by threshold connected current mirror N-channel MOSFET 192a with a gate width $W_n$ to mirror MOSFET 192b with gate width $γW_n$ to produce reference current $I_{ref0}$. The temperature-dependent output voltage $V_{bandgap}$ (T) of bandgap voltage reference 190 can be designed to largely offset the temperature variation of resistor 191 whereby γ $[V_{bandgap}(T)/R_0(T)]=I_{ref0}$ where $I_{ref0}$ becomes constant with temperature. Trimming occurs by changing the effective gate width of P-channel MOSFET 180a by paralleling any number of threshold-connected MOSFETs 193a, 193b 193n, having respective gate widths $W_{p1}$, $W_{p2}$, . . . $W_{pxn}$ in accordance with the digital on-off state of P-channel MOSFET switches 194a, 194b . . . 194n, which are controlled by digital inverters 195a, 195b . . . 195n. If for example, MOSFET 194*b* is turned on by inverter 195*b*, then MOSFET 193*b* is essentially in parallel with P-channel MOSFET 180*a* and the current mirror's gate width increases from $W_{p0}$ to a larger ($W_{p0}$+$W_{px2}$). The larger gate width of the threshold connected MOSFET pair means less voltage is needed to carry the same reference current so the current in the output reference currents is reduced. In other words, the current mirror ratio between $L_{ref0}$ and $I_{ref3}$, for example, changes from a ratio [$W_{p3}/W_{p0}$] to a smaller ratio [$W_{p3}/(W_{p0}+W_{px2})$] meaning the output current deceased with active trimming. As such, the trim is unidirectional starting with the highest output current when the trim MOSFETs are off and decreasing as more transistors are connected in parallel. In manufacturing, the LED current is measured and the combination of which trim MOSFETs are turned on and off is adjusted by changing the digital value calibration register 186 until the target current is reached whereupon the contents of calibration register 186 are written into non-volatile memory.

Figure 21C:
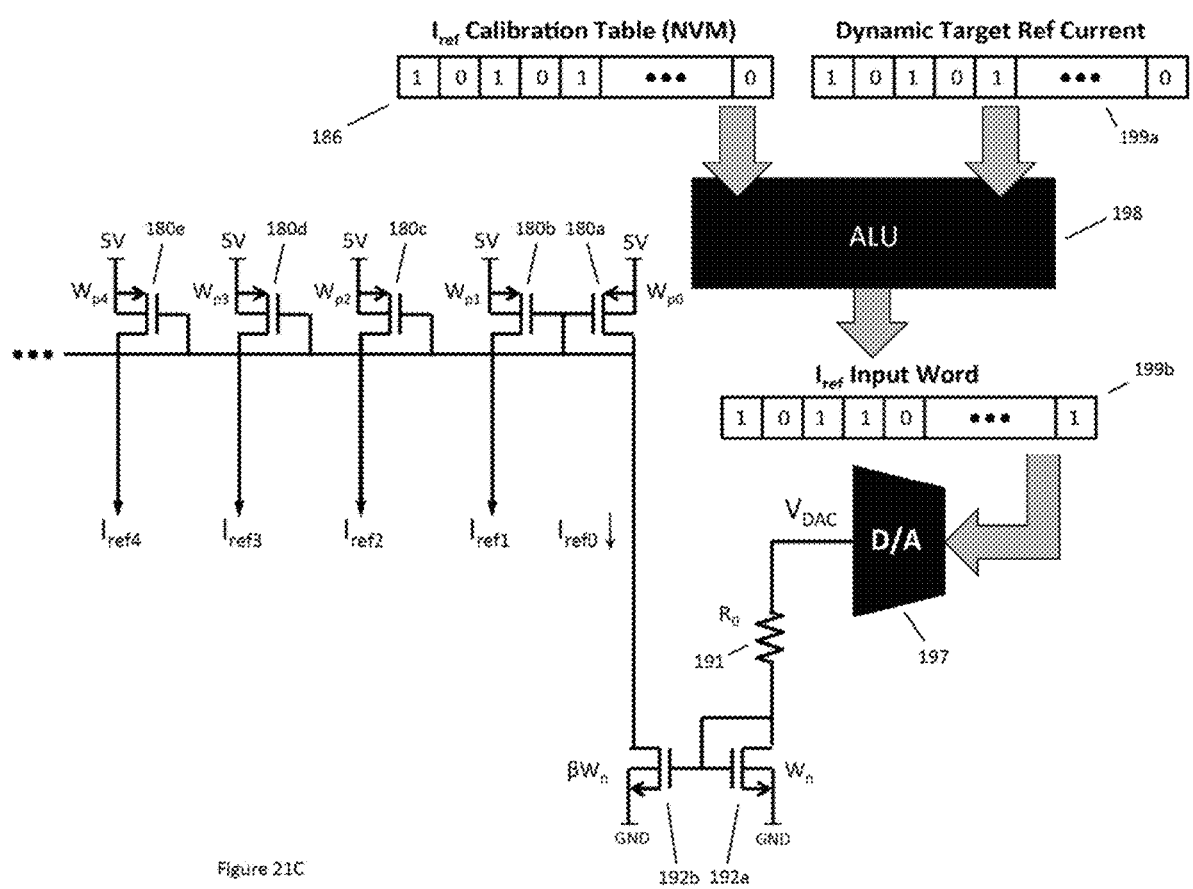
FIG. 21C is a schematic representation of an exemplary multi-channel reference current generator with DAC and arithmetic-logic-unit calculated input comprising current calibration and target reference input currents.

In order to vary the reference current and thereby the LED current dynamically, the value of the reference current can be changed digitally by overwriting the calibration register 186 with dynamic data adjusting or modulating LED brightness, but to do so is disadvantageous as it loses the accuracy achieved by a calibration reference trim during manufacturing. This problem is overcome by the dynamically programmable reference circuit of FIG. 21C, comprising two reference current registers—the aforementioned $I_{ref}$ calibration register 186, and a separate dynamic target reference current register 199*a* unique to a specific PBT treatment. The dynamic target reference current 199*a* varies with time while the calibration table does not. In this regard, the data in calibration table 186 can be considered as a fixed offset to the data in dynamic target reference current register 199*a*. The two registers are easily combined using simple subtraction performed by arithmetic logic unit ALU 198 to produce a compensated dynamic drive current register, specifically "$I_{ref}$ input word 199*b*". This digital word is used to drive a digital-to-analog (D/A) converter 197, which outputs an analog voltage as a function of its digital input. While the accuracy may range from 8 bits to 24 bits in resolution, 16-bit DACs, commonly available in many microcontrollers, produce 1,024 combinations—ample resolution for any required waveform synthesis. As shown, the D/A converter output voltage $V_{DAC}$ is converted to current by a resistor 191 and mirrored by N-channel MOSFETs 192*a* and 192*b* to produce reference current $I_{ref0}$, where $I_{ref0} \approx \beta [V_{DAC}-V_{tn})/R_0]$. The reference current $I_{ref0}$ is mirrored by threshold connected P-channel MOSFET 180*a* and matched MOSFETs 180*b*, 180*c*, 180*d*, 180*e* . . . to produce the corresponding current reference outputs $I_{ref1}$, $I_{ref2}$, $I_{ref3}$, $I_{ref4}$ and so on. D/A converter 197 may also comprise a current output D/A converter, producing an analog current instead of producing a voltage. In such cases the resistor 191 is unimportant and may even be eliminated.

Referring again to FIGS. 15 and 16, once components of a distributed PBT system are established through Layer-2 authentication, and Layer-3 and Layer-4 network and port address assignments, and the LED pad's configuration data is exchanged, the distributed PBT system is ready to execute treatments. Upon the PBT controller 120 receiving a user 'start' command, PBT treatment commences with an exchange of encryption keys or digital certificates between the PBT controller 120 and the network-connected intelligent LED pad 123 to establish a Layer-5 session. Once the session is opened, the PBT controller 120 and intelligent LED pad 123 maintain their secure link during the exchange of files and commands until the treatment is completed or is terminated. Additional network security can be performed using encryption on presentation Layer-6 or at the application Layer-7. Execution of a PBT treatment commences using either data streaming or file playback methods, as described below.

Data Streaming in Distributed PBT Systems

By incorporating all LED drive circuitry into an LED pad, as previously shown in FIG. 18, the PBT controller in a distributed PBT system need not concern itself with how the LED pad is able to select specific LED strings, how the LED current is controlled, or the methods used to the pulse or modulate the LEDs' conduction. Instead, the PBT controller performs the tasks of the user interface and in preparing the drive instructions for the selected treatment. These drive instructions can be transferred from the PBT controller to the LED pad in two ways. In one method, software called a LED player is first installed into the pad, which will later be used to interpret and execute the treatment, and then an instruction set called a playback file is transferred to the LED pad, instructing the LED player's executable code what to do. An alternative approach is for the PBT controller to send a streaming file to the LED pad.

Figure 24:
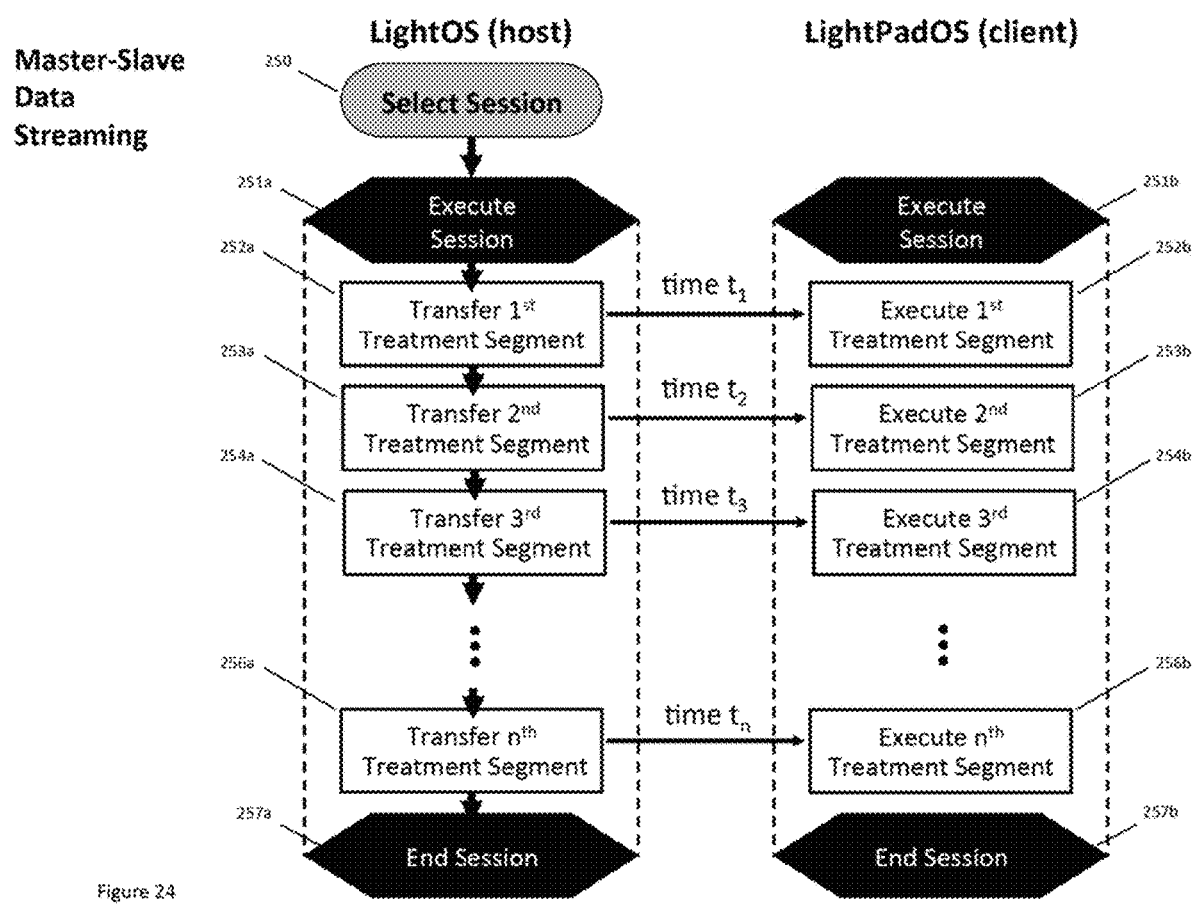
FIG. 24 is a flow chart describing a master-slave, data streaming based LED drive.

In master-slave data streaming, a series of LED instructions is sent sequentially and continuously instructing the LEDs when to turn on and off. Similar to an audio streaming file, the data transfer from the PBT controller to the intelligent LED pad must occur in advance of executing a particular step. The incoming instruction packets, sent in successive pieces, must stay ahead of the treatment's execution; otherwise the treatment will stall for lack of instructions. This process is illustrated in the flowchart of FIG. 24 showing the LightOS operations occurring in the PBT controller host and the LightPadOS operations occurring in tandem in the intelligent LED pad client. Specifically, after selecting a therapy session 250, both controller and pad operating systems commence execution 251*a* and 251*b* of the selected session 250. In step 252*a* and at time $t_1$ the LightOS transfers a $1^{st}$ treatment segment to the LED pad, whereupon in step 252*b* the LightPadOS executes the $1^{st}$ treatment segment. In step 253*a* and at time $t_2$ LightOS transfers a $2^{nd}$ treatment segment to the LED pad, whereupon in step 253*b* the LightPadOS executes the $2^{nd}$ treatment segment. In step 254*a* and at time $t_3$ LightOS transfers a $3^{rd}$ treatment segment to the LED pad, whereupon in step 254*b* the LightPadOS executes the $3^{rd}$ treatment segment, and so on. Finally, in step 256*a* at time to LightOS transfers a $n^{th}$ treatment segment to the LED pad, whereupon in step 256*b* the LightPadOS executes the $n^{th}$ treatment segment, after which both sessions 257*a* and 257*b* end.

Figure 25:
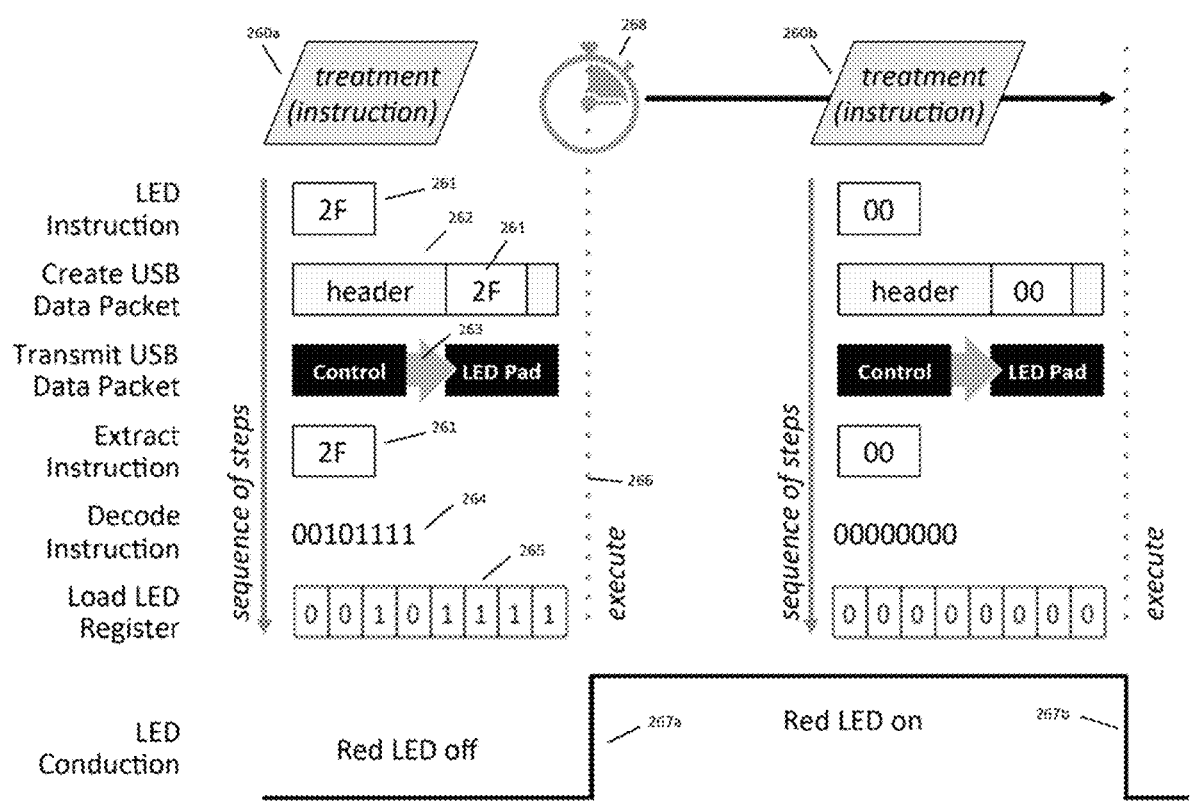
FIG. 25 illustrates real time streaming data transfer to an LED pad using packet transfer over USB.

An example of USB data packet transfer and instruction execution during master-slave streaming is shown in FIG. 25. Preparation of treatment instruction 260*a* occurs while the red LEDs are off, starting with LED instruction 261 represented by hexadecimal code representing a sample "turn-on LED" instruction. The instruction 261 is then embedded as the payload into a USB packet, combining the payload, instruction 261, with a header 262. In step 263 the packet is then transmitted 263 from the PBT controller to the LED pad. Instruction 261 is then extracted and decoded into bits 264, describing which LEDs are to be turned on and which ones are not. The bits are then loaded into an LED register 265 and executed at a time 266 when the red LED current changes from off to on, starting a timer to prepare and load the next instruction turning off all the LEDs. The switching of the red LEDs is illustrated by an off-to-on transition 267*a* and an on-to-off transition 267*b* in the graph at the bottom of FIG. 25.

Figure 26A:
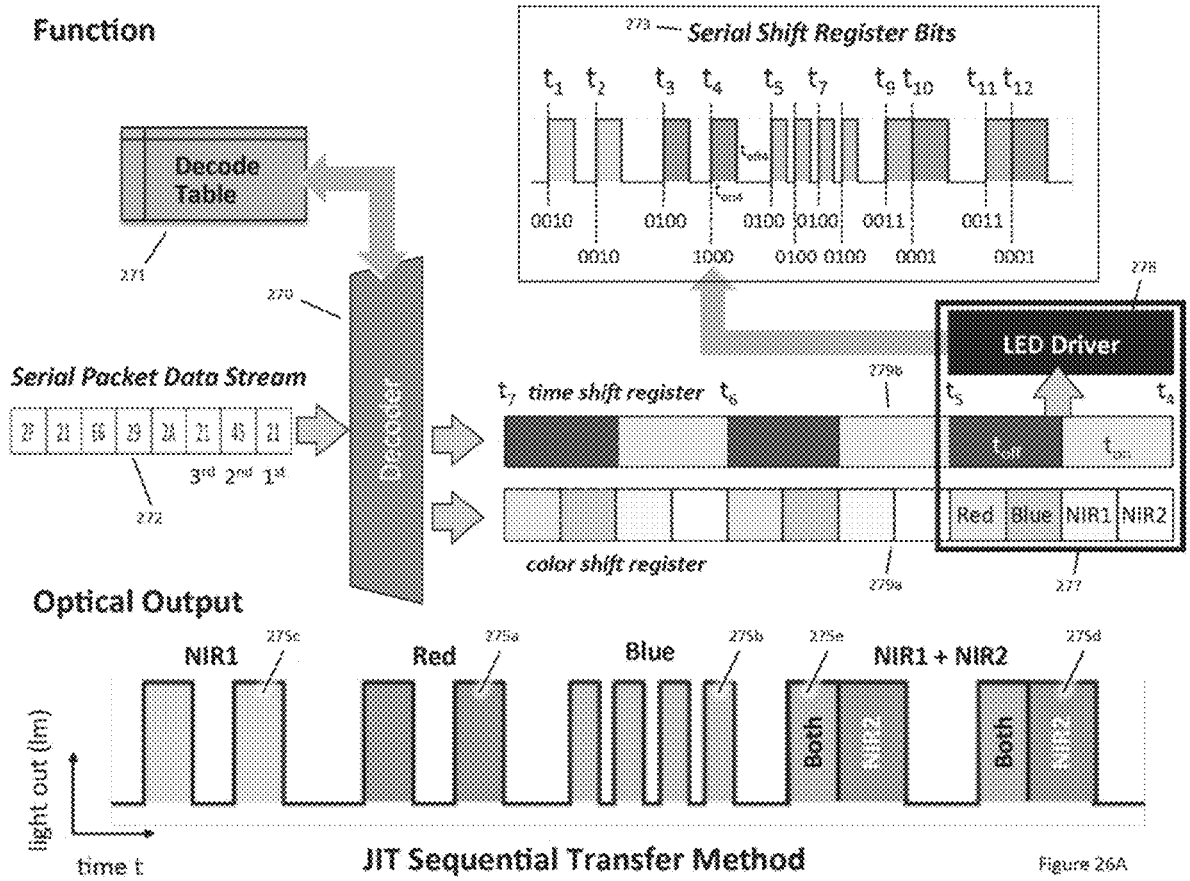
FIG. 26A illustrates a just-in-time or "JIT" sequential data transfer method for a stream-based LED drive.

Execution of streaming instructions can be performed using two techniques, the just-in-time (JIT) sequential transfer method and the transfer-ahead-and-shift method. In the JIT sequential transfer method shown in FIG. 26A, the serial packet data stream 272 transmitted from the PBT controller to the intelligent LED pad is interpreted by decoder 270 in accordance with decode table 271 resulting in two outputs to a color shift register 279a and a time shift register 279b, respectively. Each sequential interval, contains the on time and off time for the interval. The elapsed time is calculated one interval at a time as the shift register advances sequentially, for example $t_5=t_4+(t_{on4}+t_{off4})$. The process is executed using a first in, first out algorithm, where only the first out shift register data frame 277 drives LED driver 278. All subsequent frames and waiting in the queue, all prior frames, once executed, are discarded. The corresponding color shift register in data frame 277 specifies which LEDs are illuminated by LED driver 278. For example, the register [red|blue|NIR1|NIR2] having a bit sequence 0100 will illuminate only blue LEDs, 1000 will drive only red LEDs, and 0011 will drive both NIR1 and NIR2 LEDs. The resulting optical output includes red pulses 275a, blue pulses 275b, NIR1 pulses 275c, and NIR2 pulses 275d, and both concurrent NIR1 and NIR2 pulses 275e. In this method the shift register advances at a variable rate, speeding up or slowing down based on the values of $t_{on}$ and $t_{off}$.

Figure 26B:
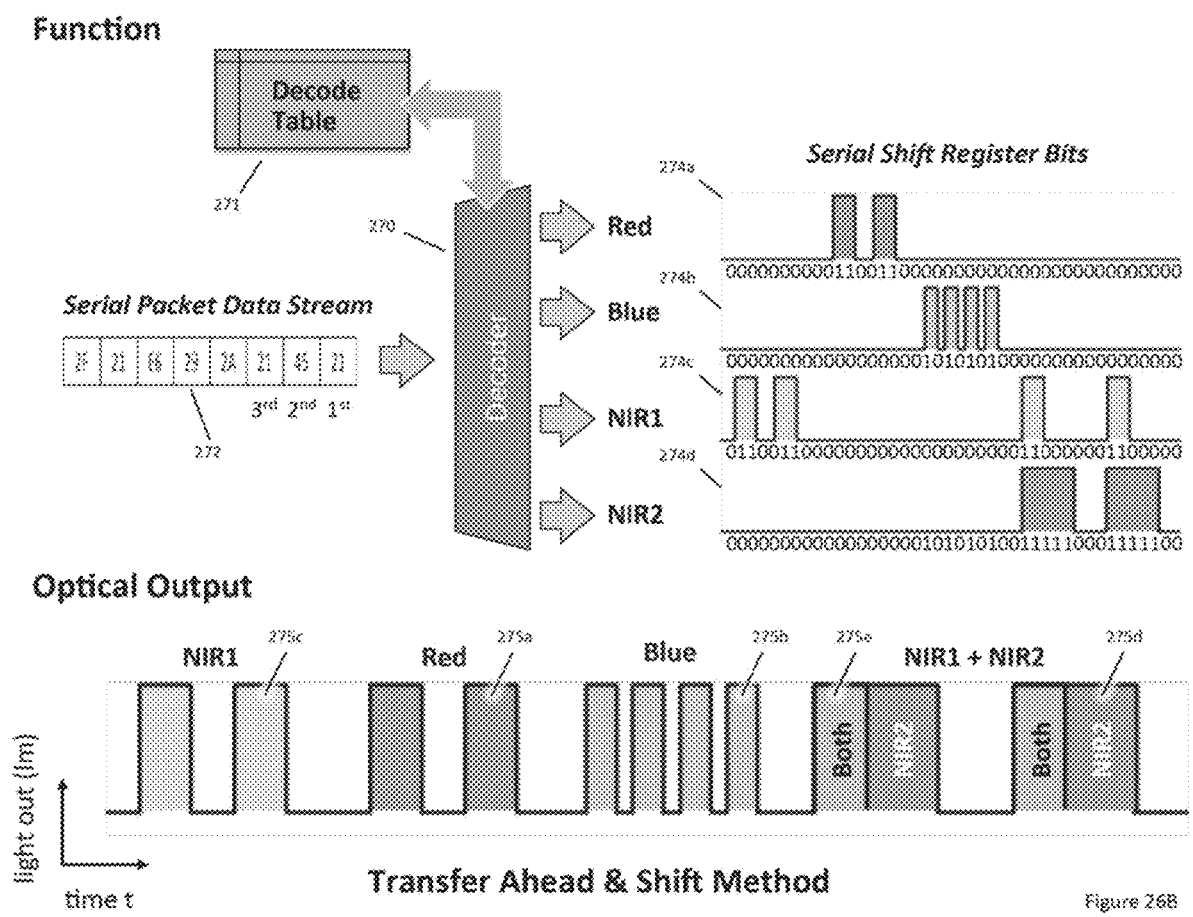
FIG. 26B illustrates a transfer-ahead-and-shift method for a stream-based LED drive.

In the transfer-ahead-and-shift method, shown in FIG. 26B, decoder 270 concurrently outputs four separate bit strings, 275a, 275b, 275c, and 275d for driving the red, blue, NIR1, and NIR2 LEDs, clocked against a fixed rate clock. To extend the duration of an LED's illumination, the on state bit is repeated for entire on duration. In the transfer-ahead-and-shift method, a file containing the illumination pattern is transferred to the LED pad and decoded in advance of LED playback.

Figure 26C:
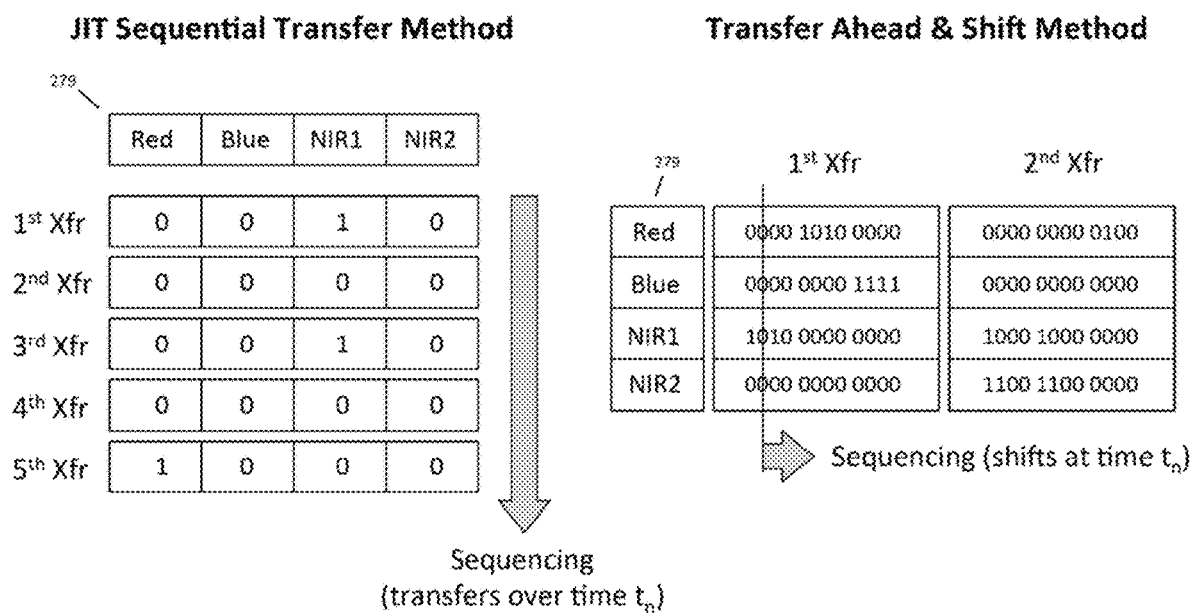
FIG. 26C compares JIT against the transfer-ahead-and-shift method of LED drive.

FIG. 26C contrasts the JIT sequential transfer method to the transfer-ahead-and-shift method. While the JIT method decodes the four LED color register 279 and drives the LEDs for a specified interval until the color register changes, in the transfer-ahead-and-shift method, the transfers are successively decoded into four bit sequences and stored then played in sequence from memory. In either method, data streaming has the advantage that the LED pad doesn't require significant memory for treatment data storage. It has the disadvantage that streaming requires a steady data flow from the PBT controller to the LED pad.

Figure 27:
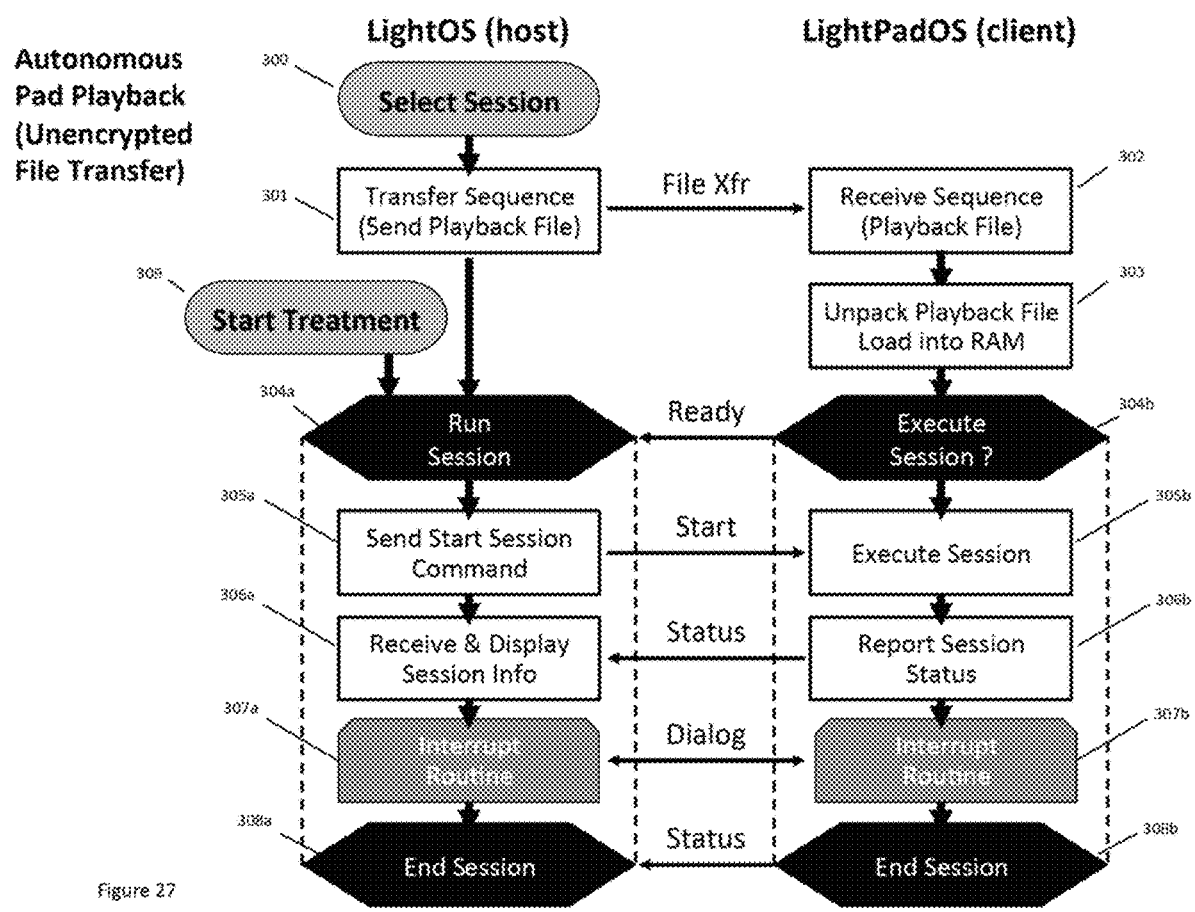
FIG. 27 is a flow chart of LED pad autonomous pad playback using unencrypted files.

An alternative approach is to transfer a complete and entire playback file from the PBT controller to the intelligent LED pad prior to commencing LED therapy. Shown in the flowchart of FIG. 27, this operation involves two parallel operations, one executed by the LightOS operating system within the PBT controller host, the other executed by the LightPadOS inside the LED pad client. As shown, after the file transfer program, execution occurs autonomously within the LED pad without intervention of the PBT controller. After a program is selected in step 300, the playback file for driving the LED sequence is transferred from the host to the client. The LED pad receives the file transfer in step 302, then in step 303 unpacks the file, stripping away the Layer 2 MAC data of the file such as the header, checksum bits, etc. to extract the payload data and loading it into volatile memory such as static RAM. This process is illustrated graphically in FIG. 28 where incoming USB packets 310 are transmitted over a physical media such as USB into a bus interface 338 of intelligent LED pad 337. Once received, payload 311 is extracted and then unpacked (step 312), executing any required decompression or file formatting to create executable code 313. Executable code 313 is subsequently stored in volatile memory 334a. Executable code 313 is self sufficient to run atop the LightPadOS operating system without requiring any other files or subroutines other than the LED pad's operating system and contains the hard-coded data of the algorithms 314 used in the PBT therapy, either a single treatment or an entire PBT session. This code could for example be realized in C++ or any other common programming language.

Figure 28:
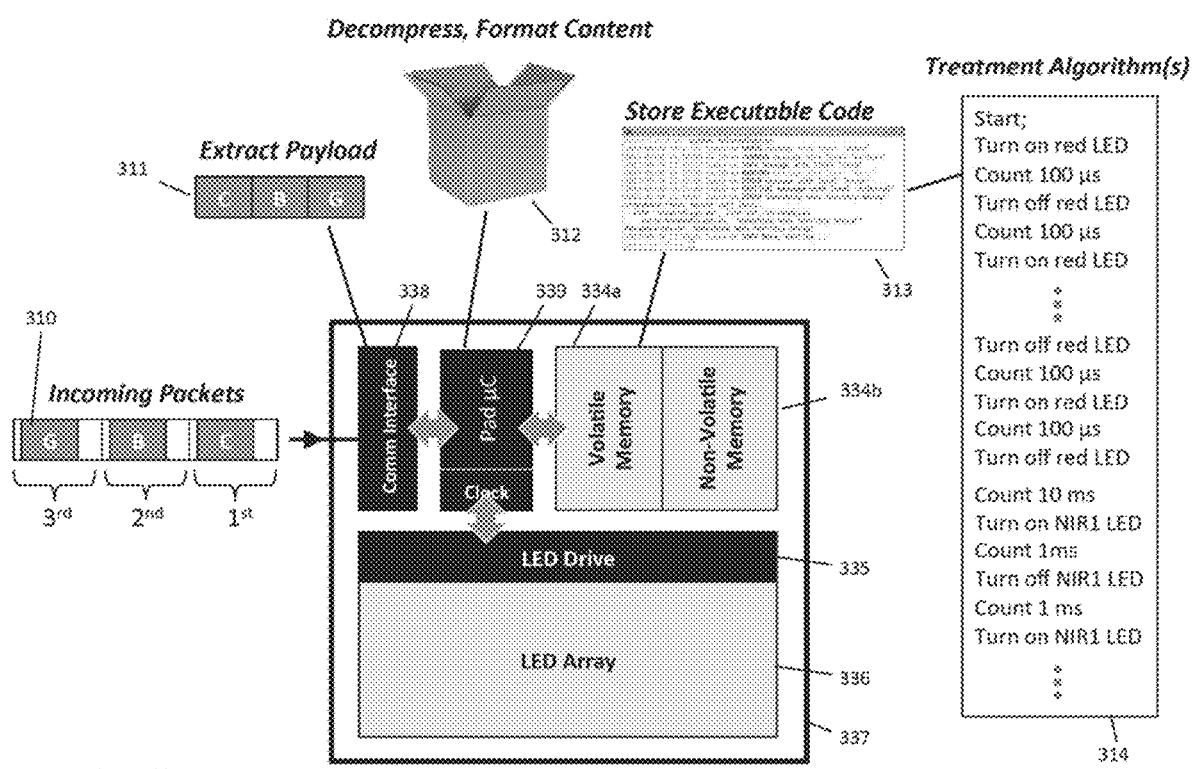
FIG. 28 illustrates executable code file storage in active LED pad.

Returning to FIG. 27, once the playback file is unpacked and stored in RAM in step 303 then in step 304b the LightPadOS informs the host PBT controller that it is ready to commence the session. Once the user confirms that they are ready by selecting the start treatment button 309 then in step 304a the run session instruction is enabled starting in step 305a where the start session command is sent to the LED pad. LightPadOS responds in step 305b by commencing treatment by executing treatment algorithm 314 (FIG. 28). As the treatment progresses, the LED pad occasionally reports its status (step 306b) to the host PBT controller including time, temperature, or other relevant program status information, which the PBT controller may display in step 306a. Should a fault condition occur in the LED pad, then interrupt service routine 307b in LightPadOS and 307a in LightOS communicate and possibly negotiate what is to be done about the condition causing the interrupt. For example, if during the session, the LED pads were unplugged and then reconnected incorrectly the session would pause, inform the user of the connection error, and tell them how to correct the fault. Once the fault is corrected, the interrupt routine is closed and treatment resumes until in step 308b the LED pad informs the host PBT controller that the treatment program has been completed. In response, in end session step 308a, the PBT controller informs the user the session or treatment has been completed.

Figure 29A:
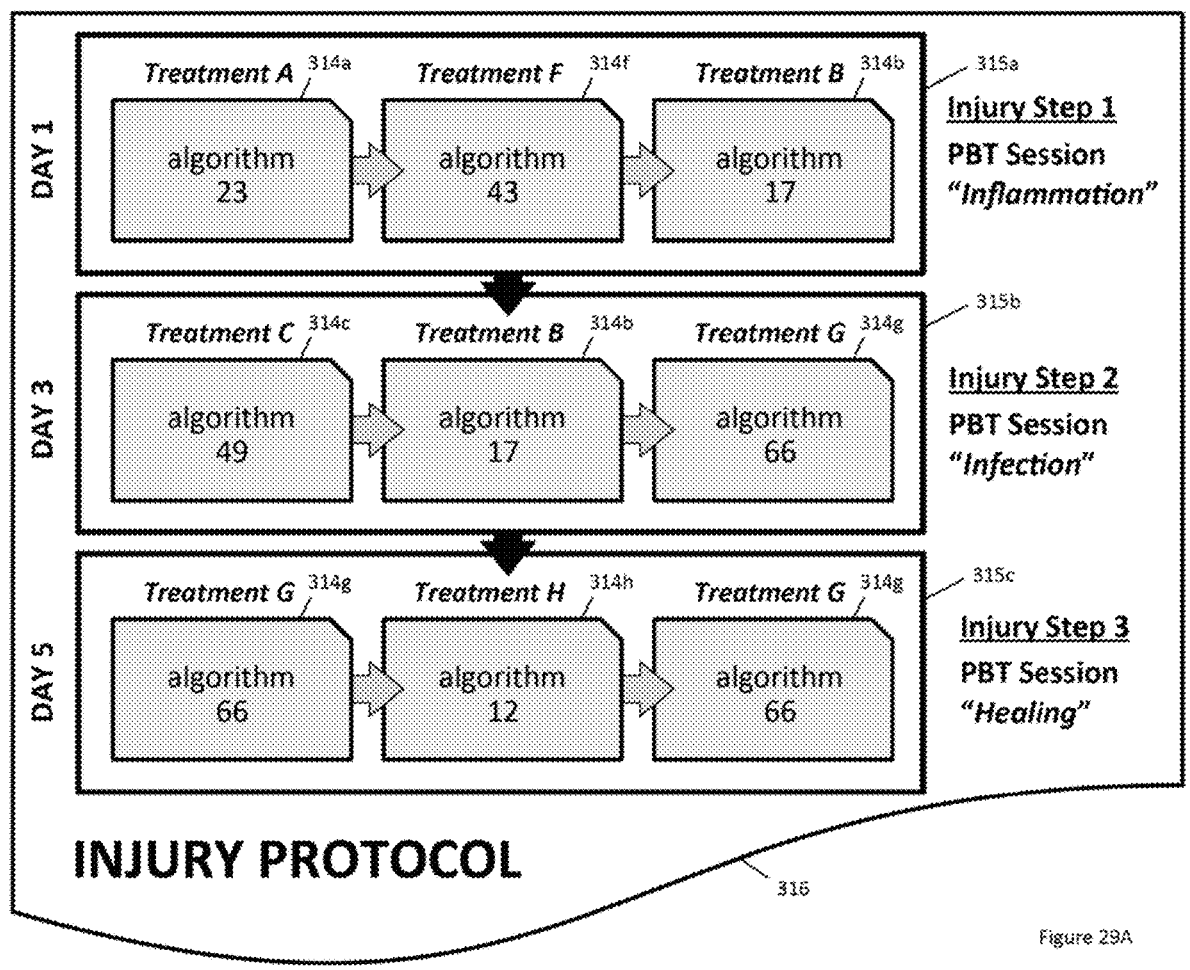
FIG. 29A illustrates an exemplary treatment protocol comprising three PBT "sessions" each constituting three sequential treatment algorithms.
Figure 29B:
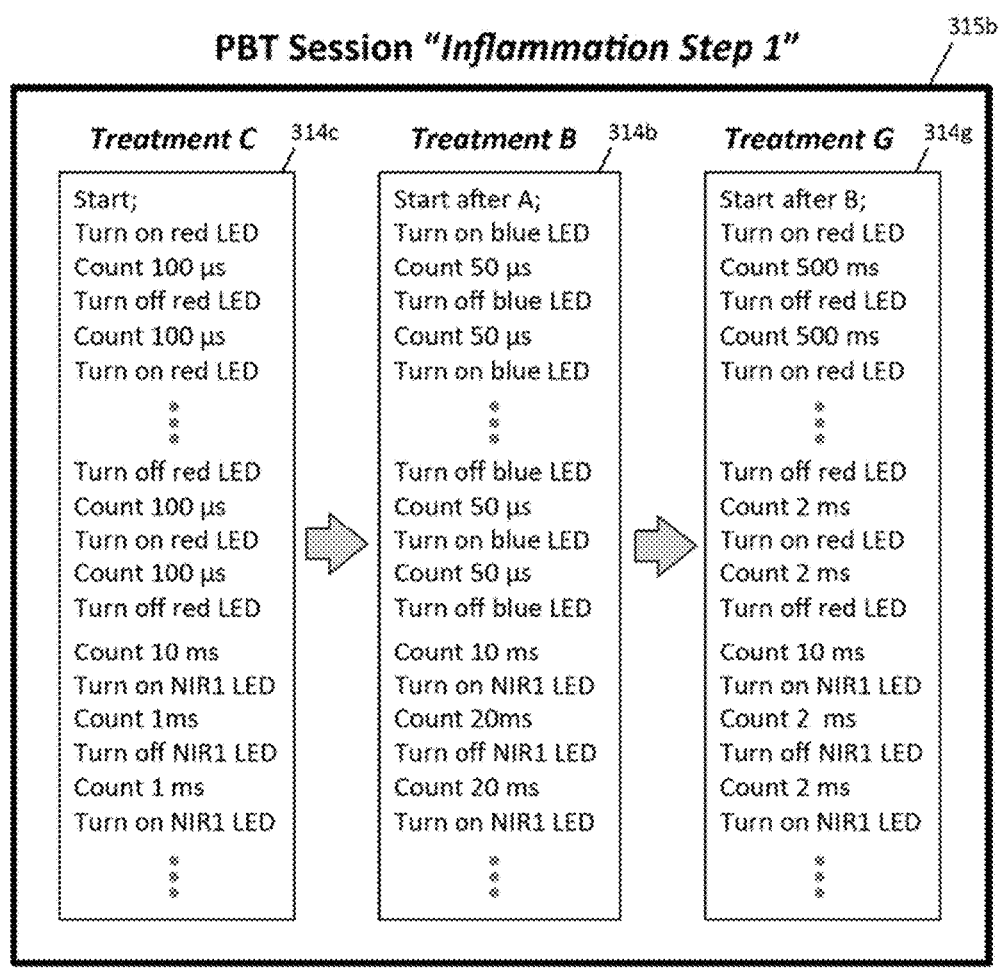
FIG. 29B illustrates exemplary treatments, each illustrating an LED control sequence of on and off commends and durations.

In this discussion, the term "treatment" is defined as a single therapeutic procedure, typically 20 minutes in duration and designed to invoke photobiomodulation on a specific tissue type or organ. Furthermore a "session" comprises a sequential series of treatments. As shown in FIG. 29A, for example, a therapeutic protocol for recovering from an injury (e.g. treating a sprained and cut ankle from a bicycle accident), may involve three "injury" sessions 315a, 315b, and 315c performed successively every other day, where each session involves the sequential therapy of three successive treatments comprising different algorithms varying light wavelengths, power levels, modulating frequencies, and durations. For example, PBT session 315a, referred to as "inflammation," is intended to expedite healing by accelerating (but not eliminating) the inflammation phase of the healing process. Session 315a comprises a sequence of three steps 314a, 314f, and 314b comprising algorithms 23, 43, and 17 respectively. Session 315b, entitled "infection," shown in FIG. 29B comprises a sequence of three steps 314c, 314b, and 314g comprising algorithms 49, 17, and 66 respectively. Note that treatment 314b comprising algorithm 17 was utilized in both the inflammation and infection sessions. Session 315c entitled "healing" comprises a sequence of three steps 314g, 314h, and 314g comprising algorithms 66, 12, and 66 respectively. Note that treatment algorithm 66 was utilized once in infection session 315b and twice in the healing session 315c.

Figure 30:
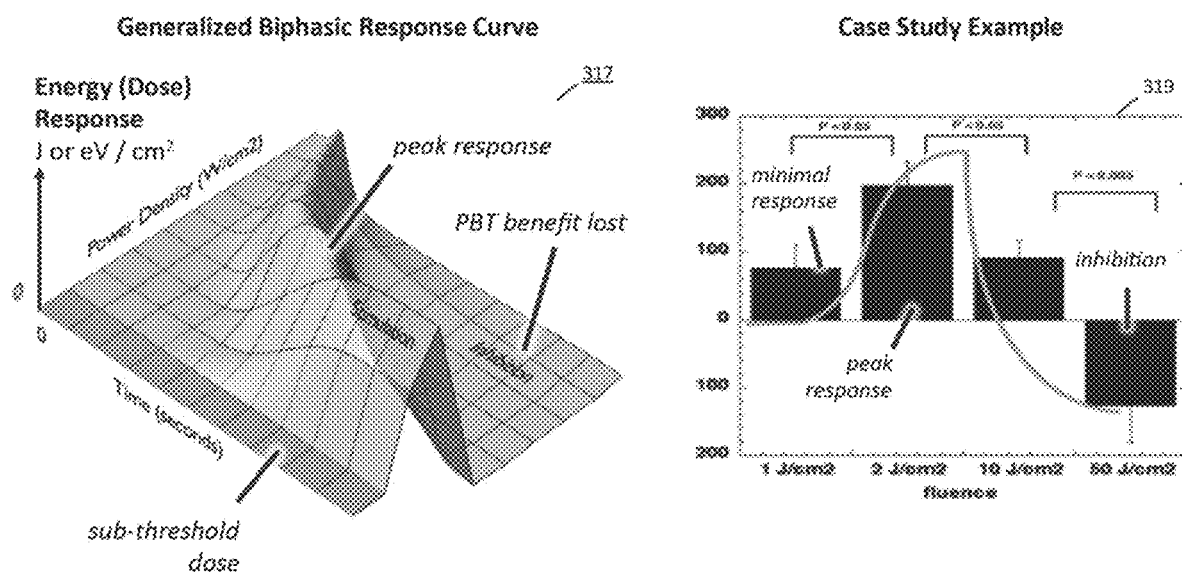
FIG. 30 illustrates an Arndt-Schultz biphasic dose response model for PBT.

The step sequence of performing sessions for inflammation, infection, and healing, together make injury protocol 316, first by speeding up the inflammatory phase of healing involving fibroblast and collagen scaffolding, cell apoptosis, and phagocytosis, then by combatting secondary microbial infections opportunistically attempting to colonize the wound. Finally, after inflammation subsides and all infection is removed, the final step in the injury protocol promotes healing of the wound by improving the thermodynamics and energy supply needed to feed healthy tissue regrowth. Injury protocol 316 does not employ daily therapy sessions, but by intent spreads the first three sessions over a five-day period. Rather than daily therapy, the need for intervening days off is explained by graph 317, shown in FIG. 30, describing a generalized biphasic dose-response model in accordance with the work of Arndt-Schultz [https://en.wikipedia.org/wiki/Arndt % E2%80%93Schulz_rule]. According to Wikipedia the "Arndt-Schulz rule or Schulz' law is an observed law concerning the effects of pharmaceuticals or poisons in various concentrations. It states that for every substance: small doses stimulate; moderate doses inhibit; large doses kill. Because of a large number of exceptions in pharmacology, e.g. where a small drug dose does nothing at all, the theory has evolved into its modern counterpart "hormesis", yet the underlying principle remains the same, that in medicine there is an optimum treatment dose beyond which treatment efficacy is reduced or recovery may actually be inhibited.

Despite controversy regarding the results of pharmacological studies, the biphasic model in "energy medicine" has been reconfirmed by numerous studies from radiation therapy of carcinoma to photobiomodulation. For example, in cancer therapy a small radiation dose is unable to adequately kill cancer cells while a large radiation dose is toxic and may rapidly kill the patient, far faster than leaving the cancer untreated. Adapting the biphasic model to photobiomodulation, graph 317 represents a pseudo-3D representation of PBT conditions where the x-axis represents treatment time; the orthogonally projected y-axis describes the power density of the PBT treatment measure in $W/cm^2$, and the vertical z-axis measure the effective energy dose in $J/cm^2$ or eV/cm2, i.e. the product of power and time and scaled by the observed magnitude of photobiomodulation, otherwise observed treatment efficacy. Topographically, the graph appears as two coasts, a mountain range and an interior valley. As shown for low dose treatments known as a sub-threshold dose, the treatment has an inadequate power, i.e. the rate of energy delivery, to do anything. Similarly for very short durations, no matter what the power level is there is not enough energy delivered to invoke photobiomodulation. In other words, too fast or too little energy does not invoke photobiomodulation.

For a combination of moderate power densities and durations, stimulation occurs resulting in a peak response curve for power densities or total energy doses above this level, beneficial PBT response and treatment efficacy declines rapidly and may even inhibit healing. Of course, excessively powerful levels lasers can cause burns, tissue damage, and ablation (cutting). And although LEDs are incapable of the power densities of lasers, they still can be driven at high currents causing overheating. These treatment conditions occur, however, far beyond the power levels and energy doses shown in the graph. The graph 319 on the right from a case study confirms the dose (fluence) dependence of PBT efficacy is indeed biphasic with a minimal response at 1 $J/cm^2$, a peak response at 2 $J/cm^2$, reduced benefits at 10 $J/cm^2$, and inhibition at 50 $J/cm^2$. Inhibition means the impact of the PBT treatment was worse than doing nothing. So for this reason along with concerns with safety and patient comfort PBT treatments should be spread over time and limited in power and dose (duration).

Data Security in Distributed PBT Systems

To effectuate multi-layer secure communication in the disclosed distributed PBT system, the operating system of the PBT controller (LightOS) and the operating system of the intelligent LED pads (LightPadOS) comprise parallel communication stacks using consistent protocols and shared secrets not discernable to a device operator, hackers, or unauthorized developers. As a result, the distributed PBT system operates as a protected communication network with the ability to execute security on any number of communication layers including data link Layer-2, network Layer-3, transport Layer-4 during setup, and on session Layer-5, presentation Layer-6, or application Layer-7 during operation.

As disclosed, "treatments, sessions, and protocols" define sequences of photoexcitation patterns and operating parameters including LED wavelength, modulation pattern and frequency, treatment durations, and the LED intensity (brightness), together determining the instantaneous power, average power, therapeutic dose (total energy), and ultimately therapeutic efficacy. In order to discourage copying or duplication, these sequences should be stored and communicated securely, using encryption and other methods. Although some data security methods and related security credentials can be executed as part of the application, i.e. in LightOS and LightPadOS, a added level of security can be achieved by inclusion of a "presentation" Layer-5 in the communication stack of the PBT controller host and any network connected intelligent LED pad clients.

Figure 31:
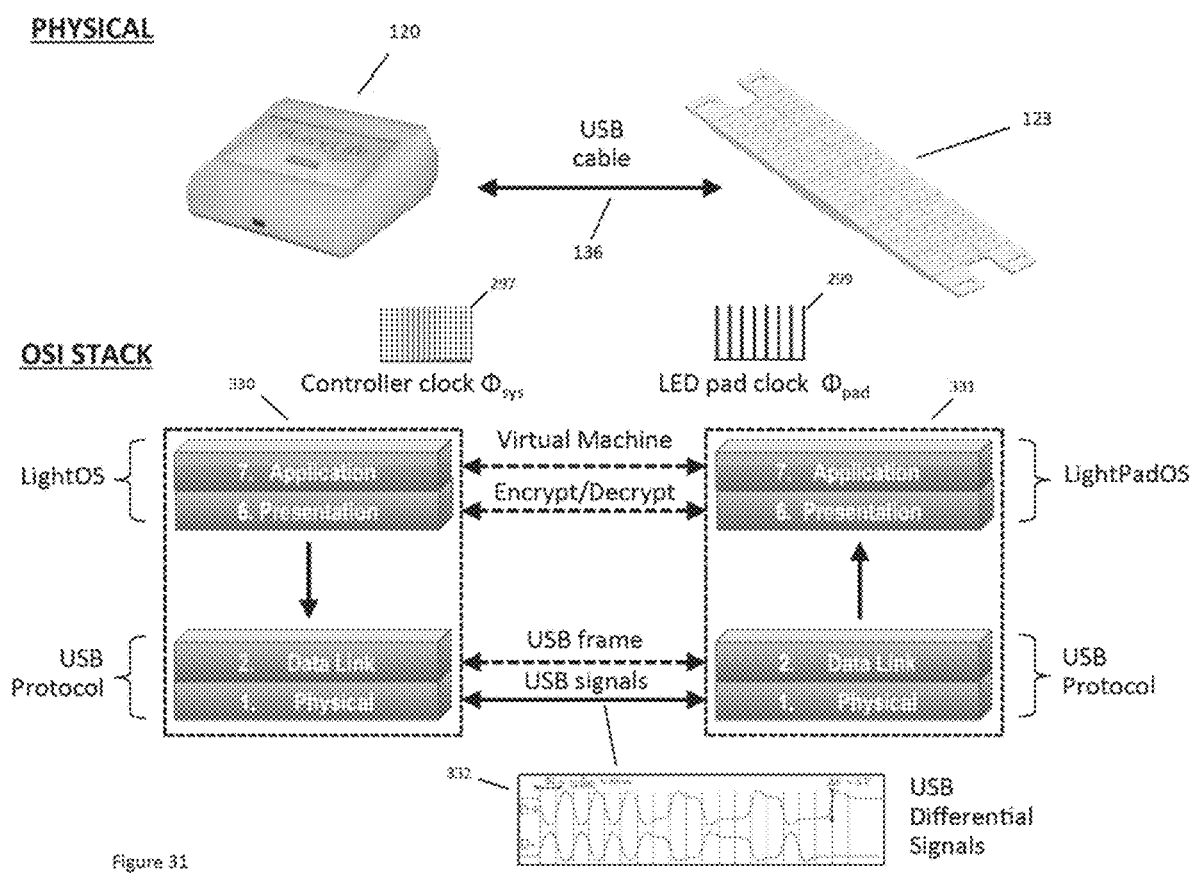
FIG. 31 illustrates a 4-layer serial bus based LightOS communication protocol stack.

The presentation layer is schematically represented in FIG. 31, where PBT controller 120 includes OSI communication stack 330 comprising application Layer-7, presentation Layer-6, data link Layer-2 and physical Layer-1. As previously stated, within PBT controller 120, application Layer-7 is implemented using the PBT specific operating system called LightOS. In operation, Layer-7 LightOS program execution results in actions requiring communication to the intelligent LED pad. These actions are encrypted in the presentation Layer-6 then passed to the lower level communication layers in encrypted form, i.e. as ciphertext. Specifically, the ciphertext passed down to the Layer-2 data link layer is then packetized, i.e. converted into a series of communication packets comprising a non-encrypted header and a ciphertext payload in accordance with a particular communication protocol such as USB, $I^2C$, FireWire, then communicated over the physical PHY Layer 1 to the LED pad. For example, PHY Layer 1 may communicate using the USB protocol using USB differential signals 332 to the corresponding PHY Layer-1 of communication stack 331 resident within intelligent LED pad 123. So although electrical signals comprise Layer-1 communications, the data constructs of USB behave as though the PBT controller 120 and intelligent LED pad 123 are communicating on Layer-2 with the packets arranged in time as USB data "frames".

Once communication stack 331 receives a USB packet, the ciphertext payload is extracted is transferred up to the presentation Layer-6, where it is decrypted and converted into plaintext. The plaintext file is then passed to the application Layer-7, where it is executed by the LED pad's operating system LightPadOS. Provided that the PBT controller's LightOS and the intelligent LED pad's operating system LightPadOS are designed to communicate and execute instructions in a self-consistent manner, the bidirectional link between communication stacks 330 and 331 functions as a virtual machine at the application Layer-7, meaning the distributed device behaves the same as if it were a single piece of hardware, and at the presentation layer to bidirectionally execute encryption and decryption. In this manner data can be transferred between the PBT controller and the intelligent LED pad. To prevent copying of the source code, however, the library of treatments is stored in encrypted form. For added security, the encryption key used for storing the algorithms in different than the key used for communication. So before a treatment file can be securely communicated it must first be decrypted.

Figure 32:
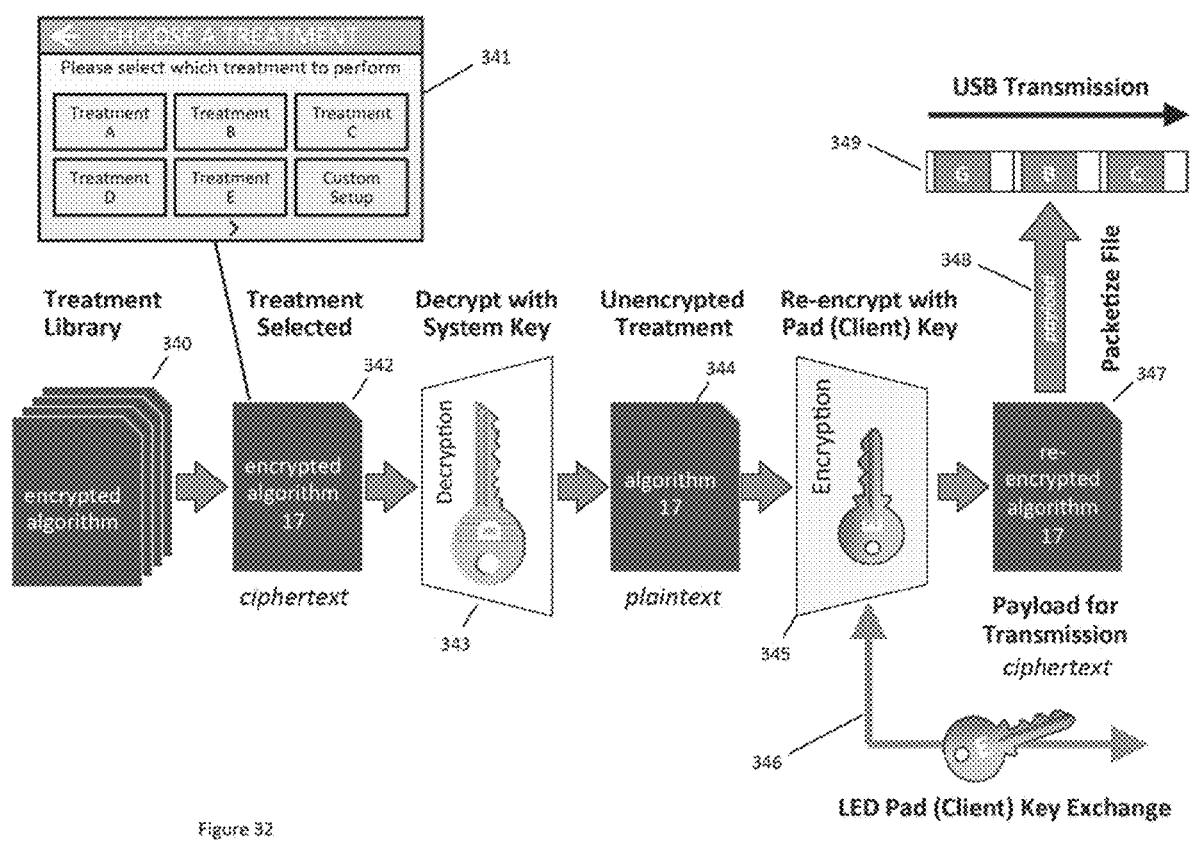
FIG. 32 illustrates encrypted packet preparation of PBT treatment file.

The process for preparing, communicating, and executing an encrypted treatment is represented schematically in FIG. 32, where through a graphical UI 341, in step 342 a user chooses a treatment that is based on an encrypted version of algorithm 17 from a library 340 of encrypted algorithms. Encrypted algorithm 17 is then decrypted using the system key (step 343), converting ciphertext into plaintext and restoring the unencrypted treatment 344, which references a plaintext version of algorithm 17. In step 345 the plaintext file of algorithm 17 is re-encrypted using an encryption key exchanged with the intelligent LED pad client (step 346). The resulting ciphertext 347 comprising re-encrypted algorithm 17 is then packetized (step 348) and transmitted to a PBT controller (step 349) using USB or another appropriate communication medium.

Figure 33:
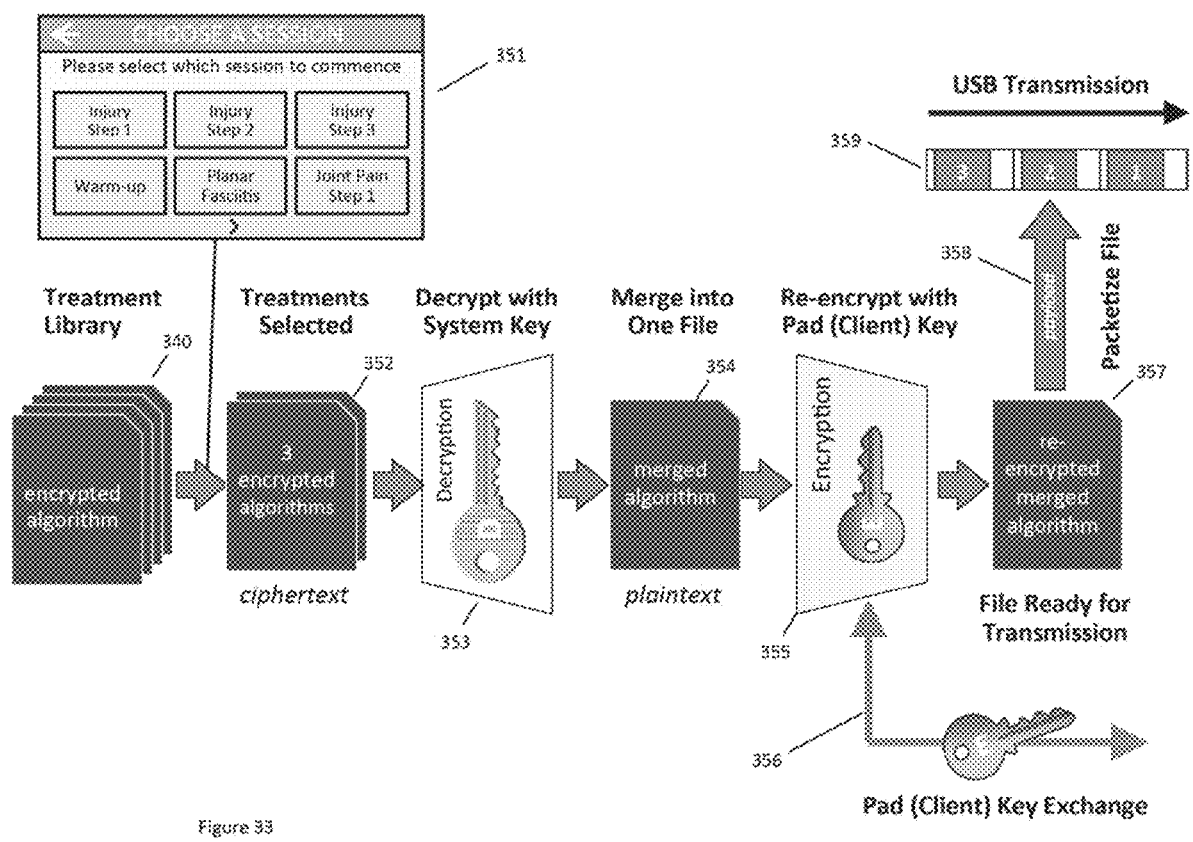
FIG. 33 illustrates encrypted packet preparation of a PBT session file.

In addition to treatment data, the same method can be used to prepare and transfer PBT session data from the PBT controller to the LED pad. This process is shown in the schematic diagram of FIG. 33 where through a graphical UI 351, a user chooses a session 352 constructed from the library 340 of encrypted algorithms, in the example shown comprising three encrypted algorithms. Using the system encryption key, the ciphertext is then decrypted in step 353, converting ciphertext into plaintext. The three plaintext files are then merged in step 354 and then in step 355 re-encrypted, using an encryption key exchanged with the intelligent LED pad client in step 356. The resulting ciphertext 357 comprising the encrypted merged algorithm is then packetized (step 358) and the packets 359 are transmitted to the LED pad using USB or another appropriate communication medium.

Figure 34:
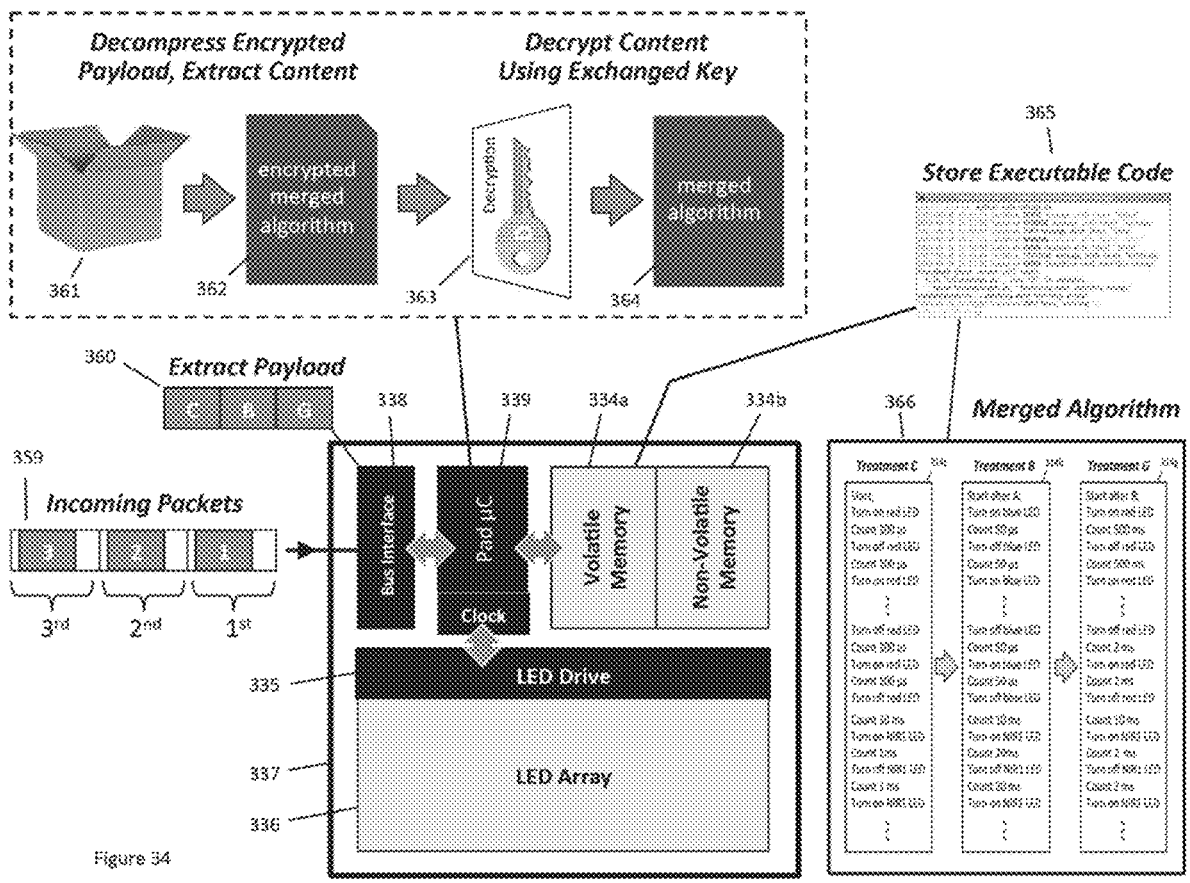
FIG. 34 illustrates active LED pad decryption and storage of an incoming encrypted packet.
Figure 35:
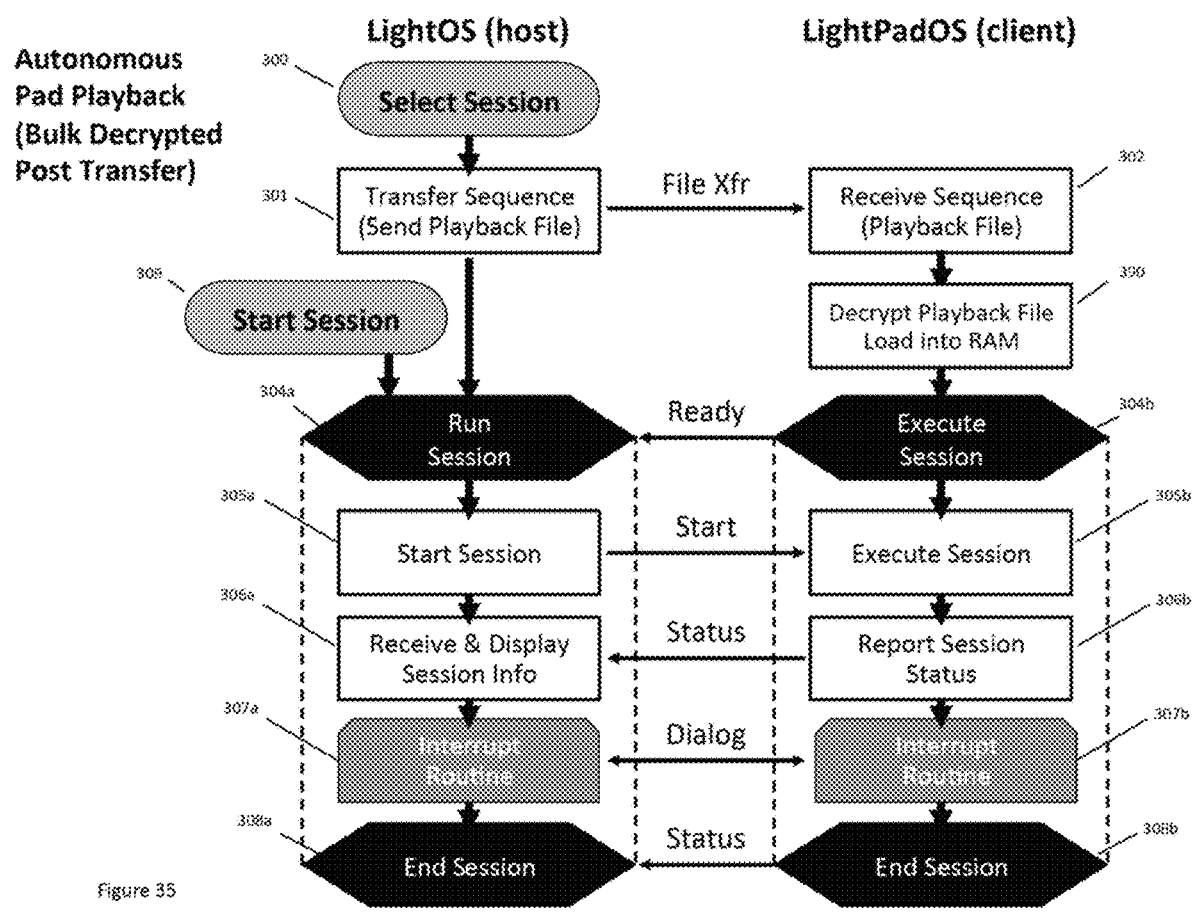
FIG. 35 is a flow chart of LED pad autonomous pad playback using post transfer file decryption.

As shown in FIG. 34, incoming data packets 359 received by bus interface 338 in LED pad 337 are first processed to remove packet headers extracting payload 360. Pad μC 339 then decompresses the payload 360 (step 361) to extract encrypted merged algorithm 362. The ciphertext is then decrypted (step 363) using the key exchange to extract plaintext file 364 comprising the treatment algorithm or in the cases of a session file, the merged algorithm. The algorithm or merged algorithm 366 comprising executable code 365 is stored in volatile memory 334a. Since the treatment is saved in RAM, any interruption in power will erase the file, making copying of the unencrypted executable code difficult. As shown in FIG. 35, autonomous pad playback of the PBT sequence with post transfer (pre-playback) bulk decryption involves user selection of the session (step 300) and transferring (step 301) the encrypted file which once received (step 302) by the LED pad is decrypted (step 390) and loaded into RAM. In step 304b the LightPadOS informs the host PBT controller it is ready to commence the session. Once the user confirms they are ready by selecting the start treatment button (step 309) then in step 304a the run session instruction is enabled starting in step 305a where the start session command is sent to the LED pad. LightPadOS responds in step 305b by commencing treatment by executing the treatment algorithm in file 364. As the treatment progresses, the LED pad occasionally reports its status (step 306b) to the host PBT controller, including time, temperature, or other relevant status information, and which PBT controller may display in step 306a. Should a fault condition occur in the LED pad, then an interrupt service routine is activated in the LED pad and PBT controller (steps 307a, 307b), allowing their operating systems LightPadOS and LightOS to communicate and possibly negotiate what is to be done about the condition causing the interrupt. Once the fault is corrected the interrupt routine is closed and treatment resumes until in step 308b the LED pad informs the host PBT controller that the treatment program has been completed. In response, in end session step 308a, the PBT controller informs the user the session or treatment has been completed.

Figure 36:
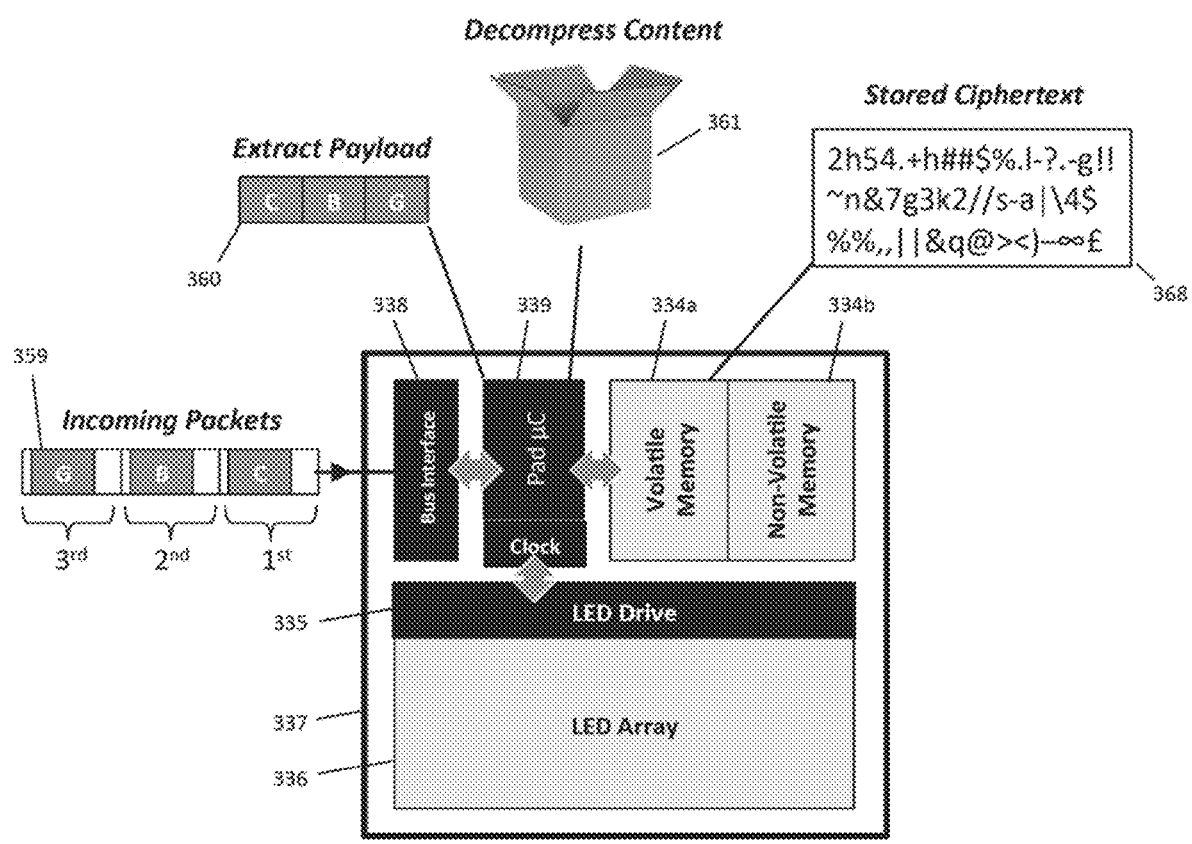
FIG. 36 illustrates ciphertext file storage in an active LED pad.
Figure 37:
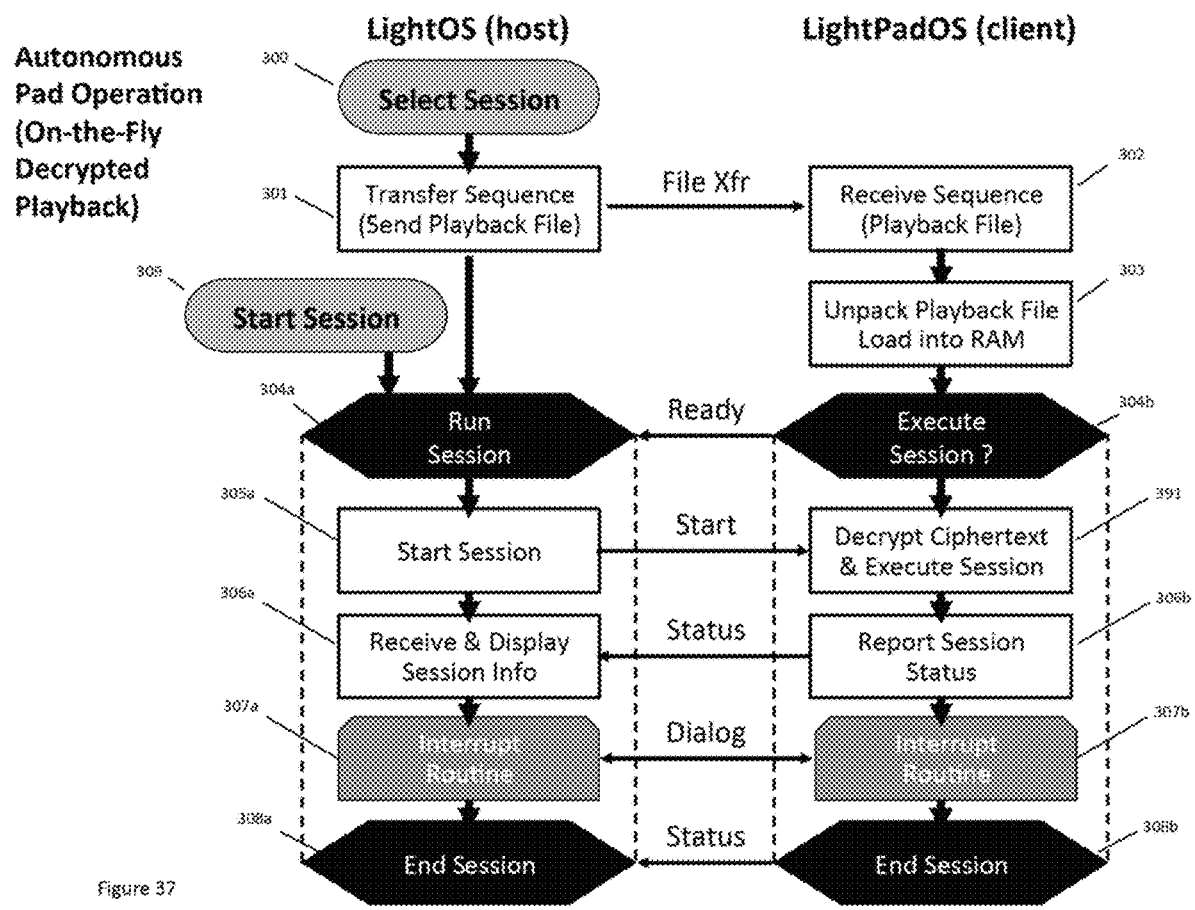
FIG. 37 is a flow chart of LED pad autonomous pad playback using on-the-fly decryption during playback.

Even greater security can be achieved by storing the algorithm in the LED pad in its encrypted form. As shown in FIG. 36, incoming packets 359 received by bus interface 338 in LED pad 337 are processed to extract payload 360, subsequently decompressed in step 361, and then stored as ciphertext 368 in volatile memory 334a. The file is played at the time the user starts the session by decrypting the file during playback as the file is executed, i.e. during autonomous playback. This process, known as "on the fly" decrypted playback, is illustrated in the flow chart of FIG. 37. The process is identical to that of bulk decrypted process flow shown in FIG. 35 except that after LED pad receives the sequence file 302 the next step is simply to unpack and as needed decompress the file 303 but not to decompress it. During playback in step 391, the ciphertext is read from SRAM volatile memory and executed on the fly, i.e. as playback proceeds.

Figure 38:
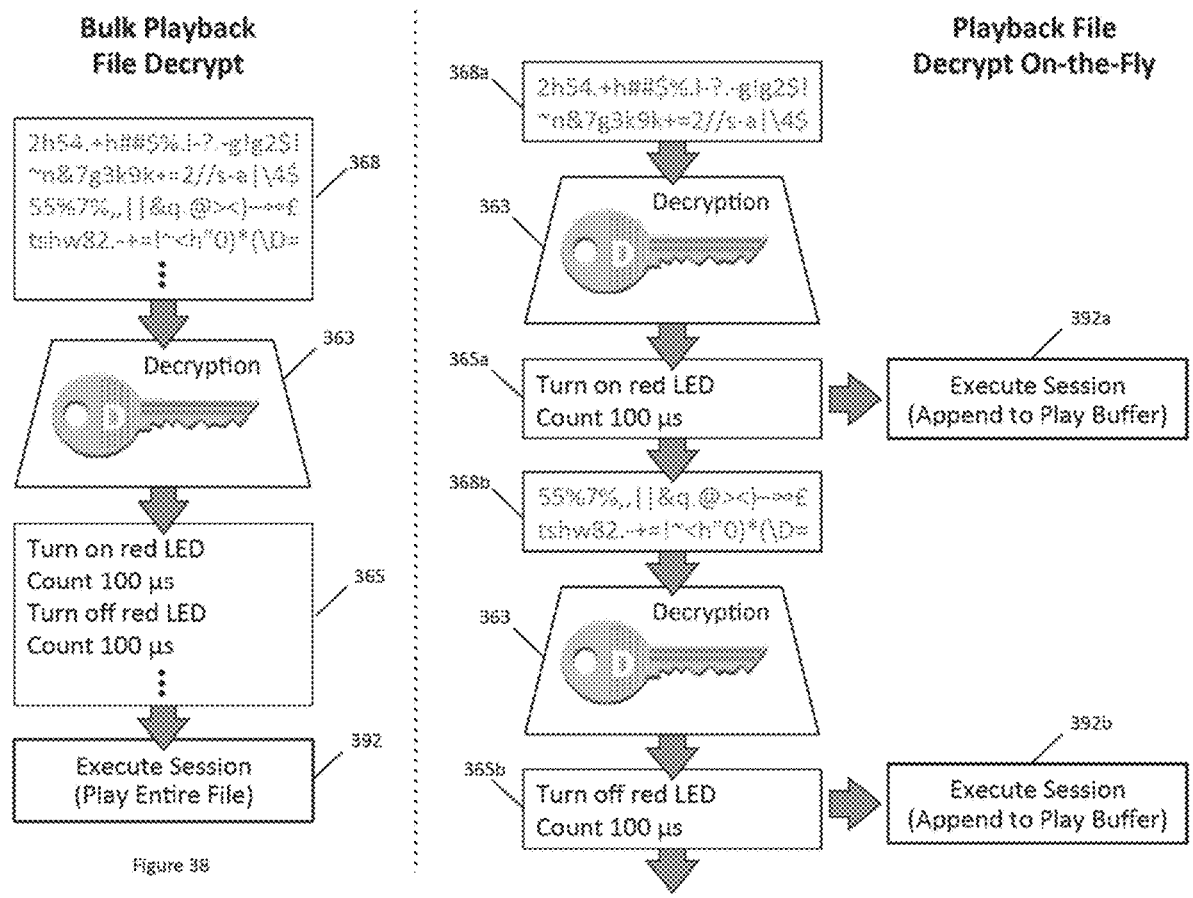
FIG. 38 is a file comparison of pre-playback bulk file decryption and on-the fly decryption during playback.

FIG. 38 contrasts bulk discount and on the fly playback methods. In a bulk decryption, the entire playback file 368 stored in ciphertext is read from volatile memory, decrypted (step 363) to extract the plaintext instruction set 365, and then executed to play back the entire file (step 392). By contrast, in decrypt on the fly playback, a portion 368a of the stored playback file is read and decrypted in step 363 and the resulting plaintext 365a is then executed in step 392a by appending the new plaintext instructions to the play buffer. In the meantime, another section 368a of the stored ciphertext playback file is read from the volatile memory, decrypted in step 363 to recover the plaintext executable file 365b, and then executed in step 392b by appending this file onto the end of the playlist.

Distributed PBT System with LED Pad Player

Although JIT or transfer-ahead-and-shift-based data streaming for LED drive control may be used for controlling an LED pad in a distributed PBT system, the delivery of real time data over the communication network connecting the PBT controller and one or more LED pads becomes problematic when more sophisticated algorithms are required. Even when high bandwidth communication is available, the streaming of clock signals or multi-MHz digital data represents a dubious command and control method, particularly in safety-focused applications such as medical devices. An alternative made possible by the disclosed distributed PBT system is to employ a two-step process for driving the LEDs, first to download a "LED player" into the LED pads, then to download a "LED playback file" defining the specific PBT treatment or PBT session to be performed. In this method as disclosed, execution of LED drive is performed autonomously within the intelligent pad based on commands from the PBT controller. Because the LED driver is local within the LED pad, advanced functions such as waveform synthesis and sinusoidal drive can be realized. If more than one treatment or session is performed, only the new "LED playback" file need be downloaded anew. The original LED player can be retained.

Figure 39:
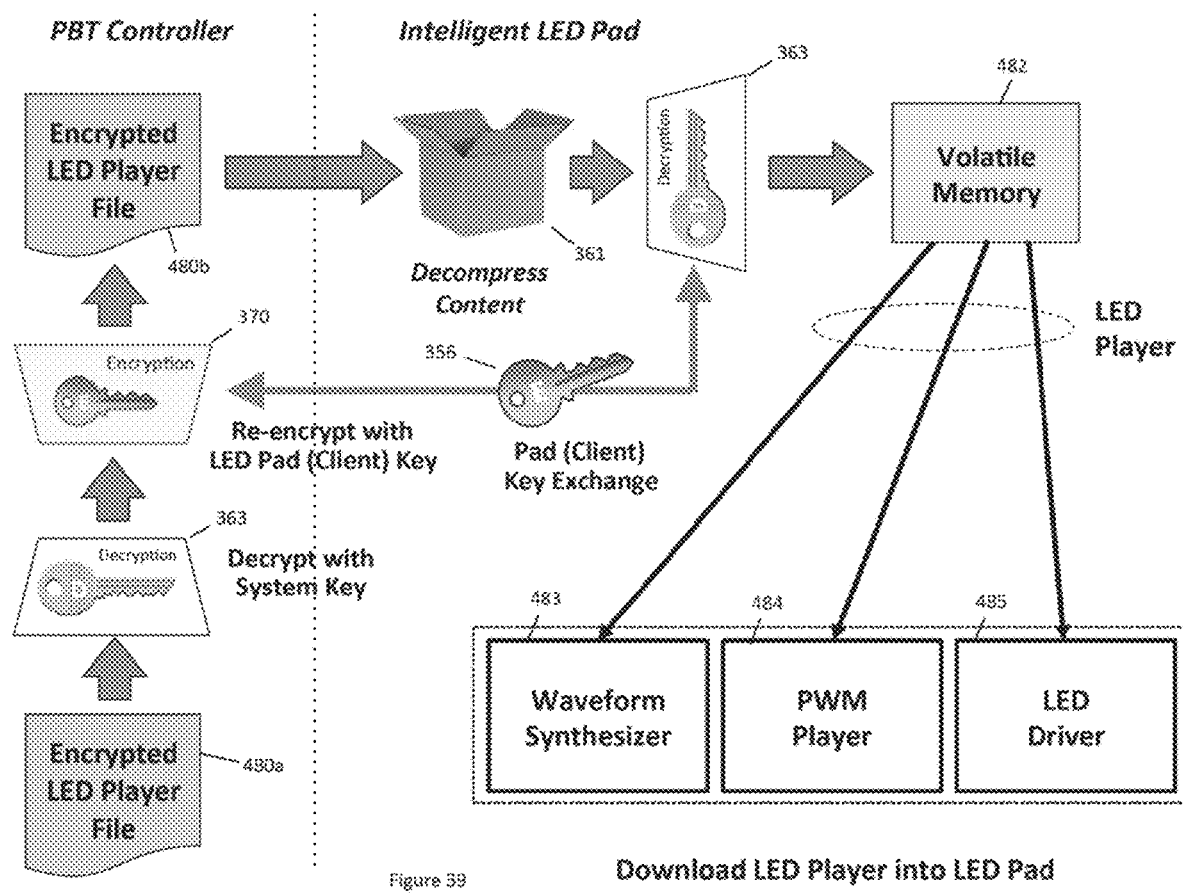
FIG. 39 illustrates file download from an LED player into an LED pad.

The first step in intelligent LED pad playback is to download the LED player from the PBT controller into the LED pad. In a manner similar to the transfer process for streaming files shown in FIG. 36, the download process shown in FIG. 39 involves transfer of an encrypted player file 480b from the PBT controller into the intelligent LED pad. The download process involves encrypted LED player file 480a being decrypted (step 363) with a system key and then re-encrypted (step 370) with the LED pad (client) key 356 to create encrypted LED player file 480b. The ciphertext LED player file 480b is then transmitted to the intelligent LED pad, where the payload is extracted and decompressed in step 361 and then decrypted in step 363 and stored into volatile memory 482. The content of the downloaded LED player file 480b includes a waveform synthesizer 483, a PWM player 484, and a LED driver 485.

Figure 40:
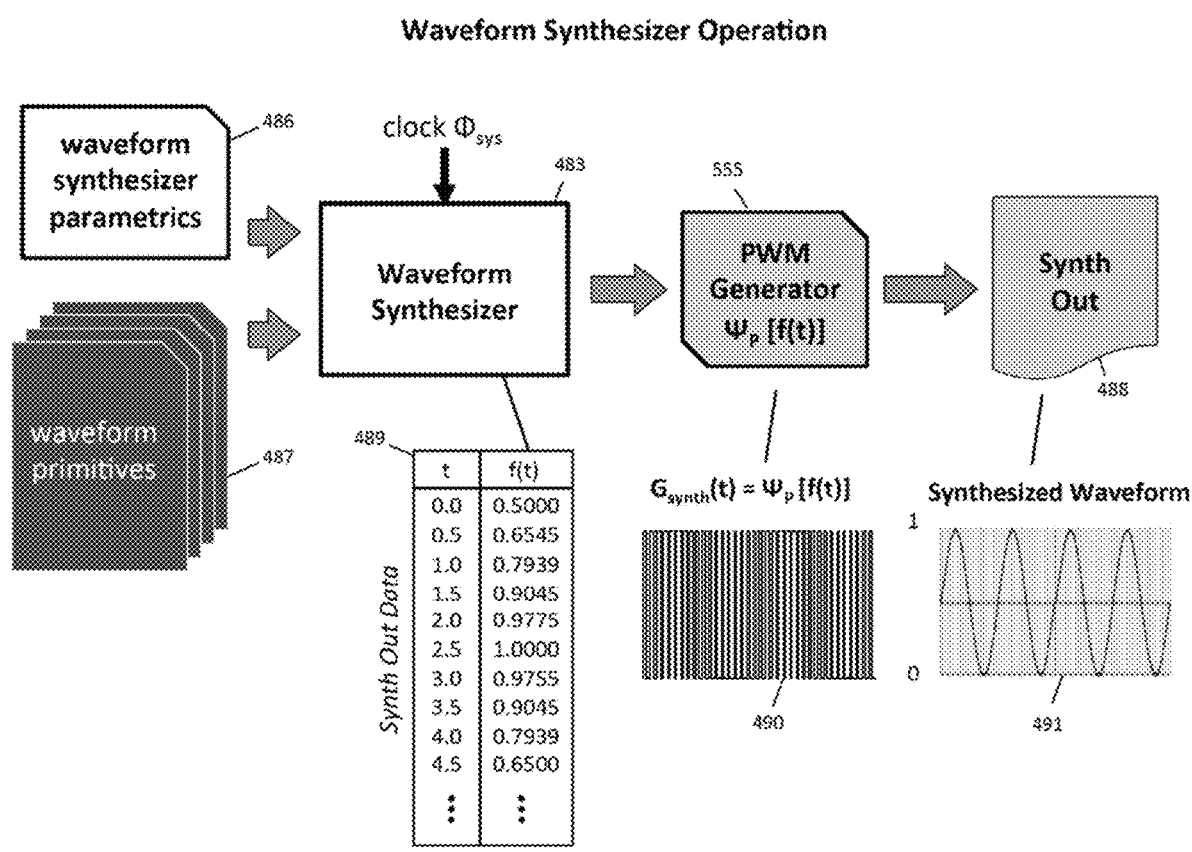
FIG. 40 is a flow chart describing the operation of a "waveform synthesizer" module.

Waveform synthesis is an algorithmic generation of excitation patterns such as sine waves and chords of sine waves but is also able to generate triangle waves, sawtooth waves, and to reproduce audio samples. The operation of waveform synthesizer 483, shown in FIG. 40, involves using waveform synthesizer 483 to convert a waveform synthesizer parametrics file 486 with system clock $\Phi_{sys}$ to produce a synth out data table 489, i.e. comprising a table showing a function f(t) paired against elapsed time t. A PWM (pulse width modulation) generator 555 then converts the function shown in data table 489 into a high frequency PWM pulse train 490 to produce a synth out file 488 including a synthesized waveform 491 embedded within the PWM output 490. Depending on the algorithm, waveform synthesizer 483 may also utilize waveform primitives 487. While the synthesizer can be realized in hardware, for waveforms up to 20 kHz, i.e. within the audio range, it can easily be implemented using software. For example, in synth out table 489, from 0.5 to 1.0 ms the value of f(t)=0.6545. The process $\Psi_P$ [f(t)] performed in PWM generator 555 converts the function f(t) into a PWM pulse train of on time and off time, where the output has a high (on) state 65.45% of the specified interval, i.e. from 0.500 to 0.827 ms, and has a low (off) state from 0.827 to 1.000 ms. So the on time duration $t_{on}$=0.827 ms−0.500 ms=0.327 ms, and the off time duration $t_{off}$=0.500 ms−0.327 ms=0.173 ms. In other words, the value f(t) is the duty factor D during the period, where D=$t_{on}$/$T_{PWM}$ and where $T_{PWM}$=$t_{on}$+$t_{off}$.

Since the duty factor D is an analog value limited between 0% and 100%, for convenience f(t) is limited to any value between 0.0000 and 1.0000. If f(t) is allowed to exceed 1.000 then the value must be scaled by the function's maximum value i.e. f(t)=[f(t)$_{unscaled}$)/f(t)$_{max}$] or the waveform will be clipped to the value 1.000 by the process $\Psi_P$ [f(t)]. The PWM clock frequency called the symbol rate clock $\Phi_{sym}$ is given by $\Phi_{sym}$=1/$T_{PWM}$. The symbol rate is derived from the system clock $\Phi_{sys}$ and must exceed the highest frequency waveform f(t) being synthesized, or described mathematically as $\Phi_{sys}$>$\Phi_{sym}$>f(t). The table below describes the time intervals where $t_x$=(x−1) $T_{PWM}$ breaking each 500 ms interval into its start time $t_x$ (on) and $t_x$ (off).

| $t_x$ | $t_x$ + $T_{PWM}$ | f (t) = D | $t_{on}$ | $t_{off}$ | $t_x$ (on) | $t_x$ (off) |
|---|---|---|---|---|---|---|
| 0.0000 | 0.5000 | 0.6545 | 0.3225 | 0.1775 | 0.0000 | 0.3225 |
| 0.5000 | 1.0000 | 0.7939 | 0.3970 | 0.1030 | 0.5000 | 0.8970 |
| 1.0000 | 1.5000 | 0.9045 | 0.4523 | 0.0477 | 1.0000 | 1.4523 |
| 1.5000 | 2.0000 | 0.9775 | 0.4888 | 0.0112 | 1.5000 | 1.9888 |
| 2.0000 | 2.5000 | 1.0000 | 0.5000 | 0.000 | 2.0000 | 2.5000 |
| 2.5000 | 3.0000 | 0.9775 | 0.4888 | 0.0112 | 2.5000 | 2.9888 |
| . | | | | | | |
| . | | | | | | |

Figure 41:
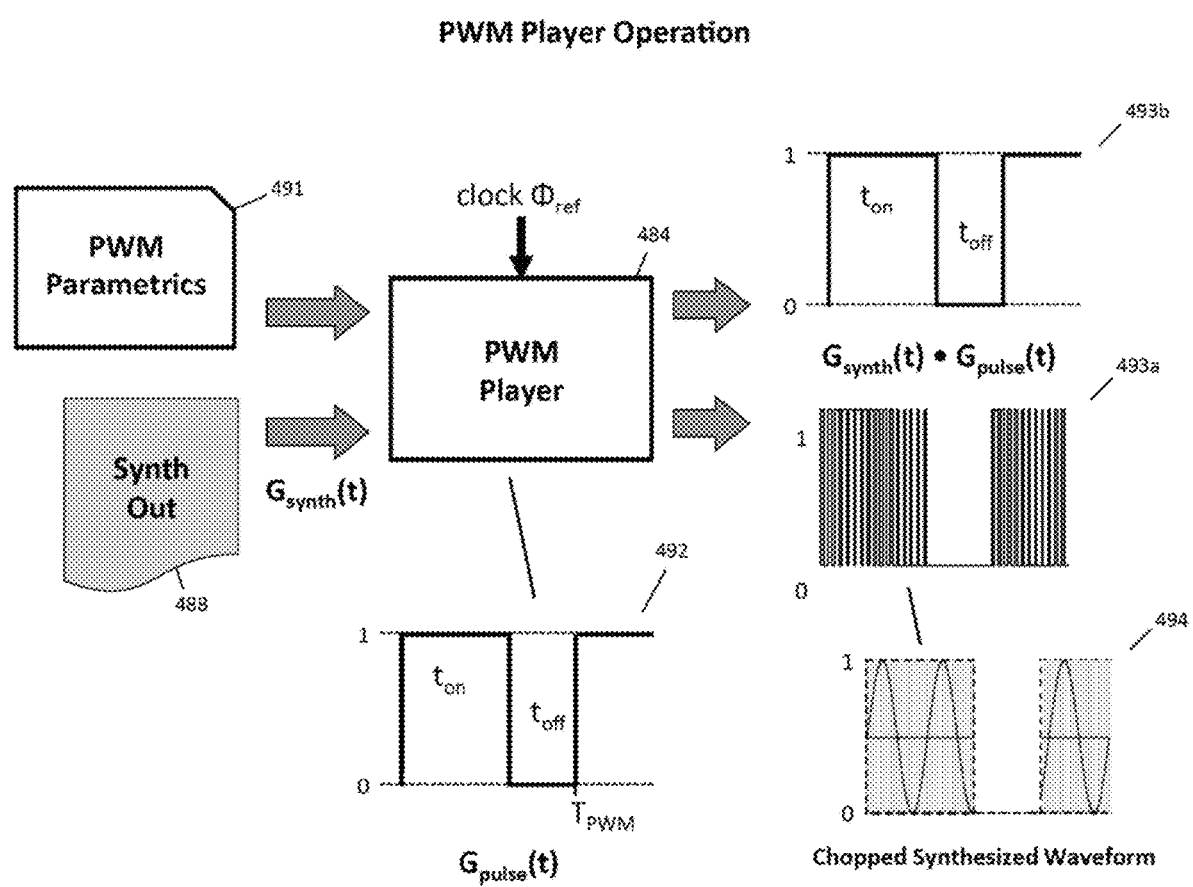
FIG. 41 is a flow chart describing the operation of a "PWM player" module.

The second process in the LED player is the PWM Player 484, shown in FIG. 41, which in response to its input PWM parametrics 491 and reference clock $\Phi_{ref}$ processes synth out data file 488 to produce PWM player outputs 493a and 493b. In operation, PWM player 484 generates a pulse width modulated (PWM) pulse train 492 $G_{pulse}$(t) comprising the algebraic product $G_{synth}$(t)·$G_{pulse}$(t). The waveform of $G_{pulse}$(t) comprises a repeating pulse having an on-time $t_{on}$=D$T_{PWM}$ and and an off-time $t_{off}$=(1−D) $T_{PWM}$.

Although the PWM player function can be performed in hardware, it is easily performed in software. Described in logical pseudo-code in terms of a fast counter and x (incremented on each loop), then:

If (t≥x$T_{PWM}$) AND (t<((x+D) $T_{PWM}$))
Then OUT=$G_{synth}$(t)
Else OUT=0 which means that in each cycle of duration $T_{PWM}$ from time x$T_{PWM}$≤t<(x$T_{PWM}$+D$T_{PWM}$) the PWM player's output is equal in magnitude to the input (on state), and for an interval (x$T_{PWM}$+D$T_{PWM}$)≤t<(x+1) $T_{PWM}$ the PWM player's output is grounded, a digital "0". By chopping the input $G_{synth}$(t) with the PWM pulse $G_{pulse}$(t), the output 493a waveform is digital with an equivalent value of $G_{synth}$(t)·$G_{pulse}$(t). The underlying waveform is shown superimposed atop the PWM signal 494. Although typically PWM player 484 outputs only a single digital waveform, it can produce more than one output as needed. In the example shown, although output 493a includes the multiplicative combination of two PWM pulses, output 493b is identical to $G_{pulse}$(t), meaning $G_{synth}$(t)=1. PWM Player 484 can also output a constant time-invariant value $G_{synth}$(t)·$G_{pulse}$(t)=1.

Figure 42:
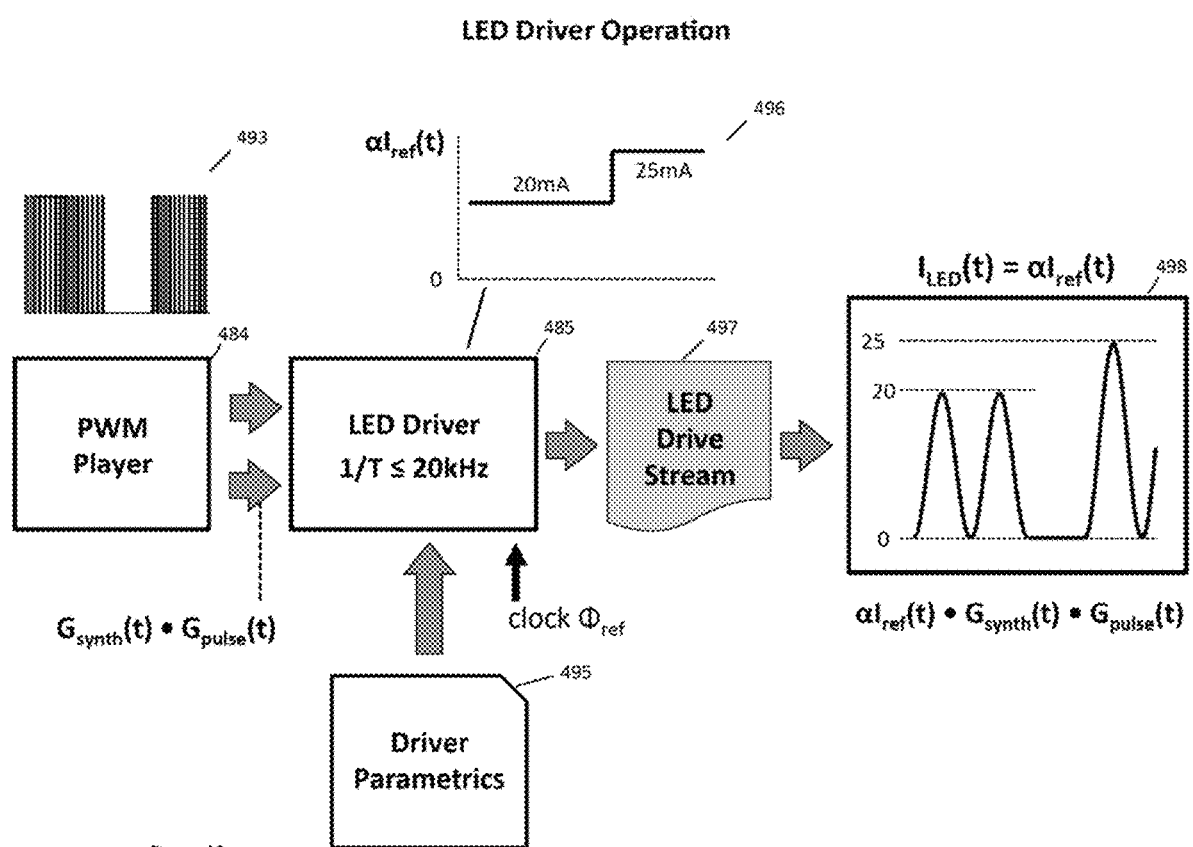
FIG. 42 is a flow chart describing the operation of an "LED driver" module.

The third component of the LED player is LED driver 485. As shown in FIG. 42, LED driver 485 is synchronized to reference clock $\Phi_{ref}$ and combines driver parametrics 495 with the output of PWM player 484 to produce an LED drive stream 497. Unlike waveform synthesizer 483 and PWM player 484, which outputs digital signals, the output of LED driver 485 is analog. Using driver parametrics 495 a programmable reference current 496 is generated with magnitude α$I_{ref}$(t) and multiplied by the output of PWM player 484, specifically $G_{synth}$(t)·$G_{pulse}$(t) to produce an LED drive stream 497 comprising α$I_{ref}$(t)·$G_{synth}$(t)·$G_{pulse}$ (t). The output waveform LED shown in graph 498 reveals a time varying waveform, specifically sinusoid, digitally pulsed, and varied in current over time. Although PWM player 484 may output a single output as an input to LED driver 485, it is also possible to provide two or more different outputs if necessary. Such cases could for example be useful in large PBT systems where many zones are required to treat each part of the body uniquely, i.e. with good tissue specificity.

Figure 43:
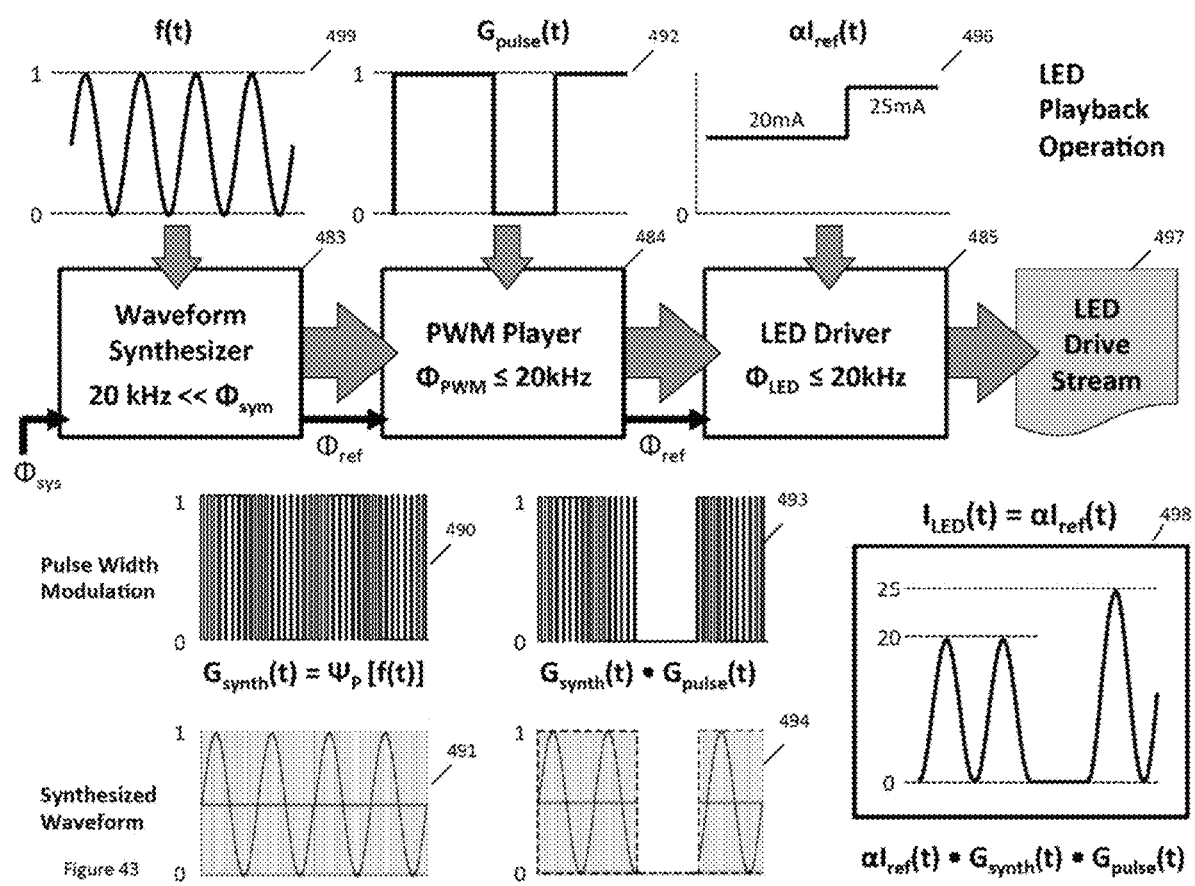
FIG. 43 is a block diagram showing waveform generation using a waveform synthesizer, PWM player, and LED driver modules.

The entire process of LED playback is summarized in FIG. 43 sequentially utilizing waveform synthesizer 483, PWM player 484, and LED driver 485 to generate LED drive stream 497. Unlike in prior-art methods, LED drive in the disclosed distributed PBT system is generated entirely within an LED pad while advantageously maintaining all treatment libraries and PBT system control in a common PBT controller, separate and distinct from the LED pad or pads. The waveform generation process utilizes a system clock of frequency $\Phi_{sys}$ produced within the LED to perform its tasks, thereby eliminating the need for distributing high-speed clocks over long lines. To insure synchronization of the PWM player 484 and the LED driver 485 with the waveform synthesizer 483, system clock $\Phi_{sys}$ is divided, using software or hardware counters to produce reference clock $\Phi_{ref}$. As a result, LED playback within a given LED pad is fully synchronous. While both waveform synthesizer 493 and PWM player 484 output digital PWM signals comprising repeating transitions between digital 0 and 1 states of varying duration, the output of LED driver 485 is analog, capable of regulating LED brightness in accordance with any waveform, including without limitation, square waves, sine waves, chords of sine waves, triangle waves, sawtooth waves, audio samples of acoustic or electronic music, audio samples of cymbal crashes and other noise sources and at any frequency within the audio spectrum from 20 Hz to 20 kHz, i.e. from the $0^{th}$ to the $9^{th}$ musical octave. It is also capable of modulating LED conduction in the infrasound range, i.e. in the $-1^{st}$ and $-2^{nd}$ octaves, e.g. down to 0.1 Hz, or to drive LEDs with direct current (0 Hz), i.e. providing continuous wave (CW) operation.

It should be noted that since each pad independently communicates asynchronously with the PBT controller and since each LED pad generates its own internal time reference for LED playback, strictly speaking the disclosed distributed PBT is an asynchronous system. That said, because of the high clock rates, precision time references, and high-speed communication network, timing mismatch between the LED pads is in the range of microseconds, imperceptible in UI control and UX response and having no impact on PBT efficacy.

Waveform Synthesis in Distributed PBT Systems

In distributed PBT systems, one PBT controller may control many intelligent LED pads, e.g. 3, 6 or more. Because of the number of intelligent LED pads required, economic considerations mandate limiting the complexity of a LED pad, specifically the cost and processing power of pad μP 339. Likewise, to manage product costs, the total memory within a LED pad must also be limited. Limited in computing power and memory, synthesis of waveforms within an LED pad in a distributed PBT system requires several criteria be met:

The amount of data transferred to or stored in the LED pad should be limited.

Calculations performed in LED pad should preferably comprise simple arithmetic calculations such as addition and subtraction, avoiding complex iterative processes such as functions, matrix operations, etc. unless absolutely unavoidable and even then, infrequently.

Calculations should be made in real time with minimal power consumption or heating.

Figure 44:
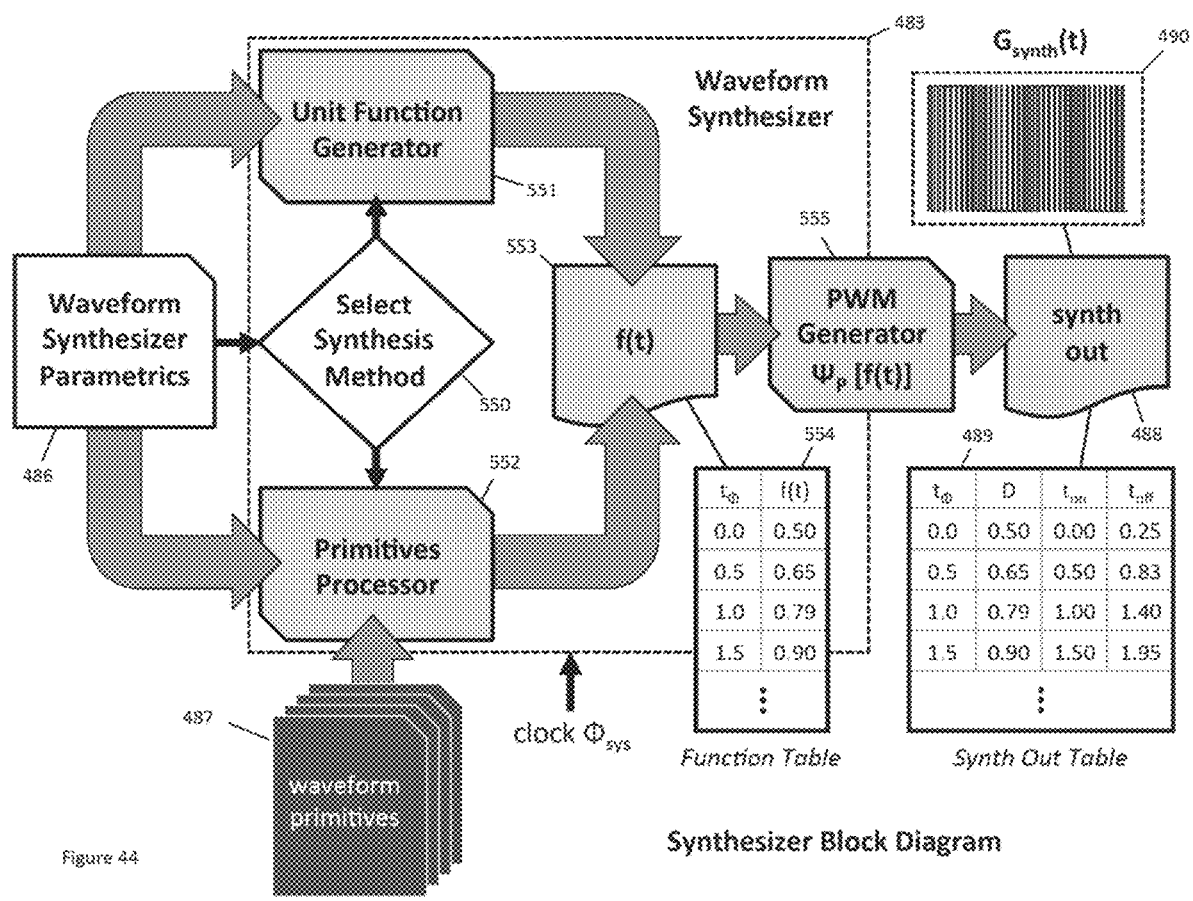
FIG. 44 is a block diagram showing details of waveform synthesizer operation including synthesis through either a unit function generator or primitives-processor.

Detailed operation of waveform synthesizer 483 is illustrated in FIG. 44 where an input file comprising waveform synthesizer parametrics 486, once loaded into waveform synthesizer 483, selects a synthesis method 550 used to calculate a function f(t) 553, either utilizing unit function generator 551 or primitives processor 552, all performed synchronous to system clock $\Phi_{sys}$. In the case of waveform synthesis, primitives-processor 552 requires access to detailed waveform descriptions, specifically waveform primitives 487. The resulting function f(t) 553 comprises Cartesian pairs of time t versus f(t) illustrated graphically in function table 554. Function table 554 is then converted into time varying digital data by PWM generator 555 using the process $\Psi_P[f(t)]$ to produce synth out file 488. Synth out file 488 comprises a digital PWM file numerically equivalent to synth out table 489 represented graphically as $G_{synth}(t)$ 490.

Waveform Synthesis With Unit Function Generator

Figure 45:
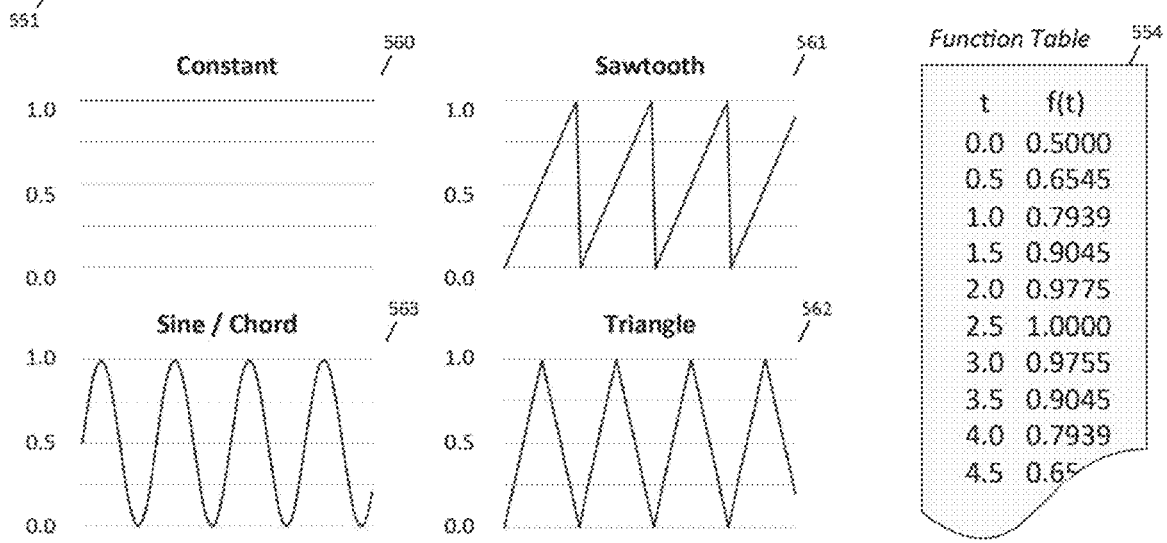
FIG. 45 illustrates examples of unit function generated waveforms including constant, sawtooth, triangle, sine, and sine chord waveforms.

The operation of unit function generator 551, illustrated in FIG. 45, involves selecting a mathematical function then calculating the value of the function for a series of times to generate a function table 554. These functions are referred to as "unit" functions because they have analog values limited to real numbers between 0.0000 and 1.0000. One example of a unit function is the time variant function f(t)=1, or "constant" is shown in the graph of 560. Another function, a unit sawtooth shown in graph 561 is described by equation f(t)=MOD (tf, 1) where (tf) is the argument of the modulus function and 1 is the base, meaning the function is a linear decimal fraction between 0 and 1. For any number over a multiple of 1, the modulus function returns the remainder, for example if (tf)=2.4 then MOD (2.4)=0.4. In a sawtooth, the functions ramps up to one then drops back to zero and repeats. Another function that ramps up to one and ramps back down to zero symmetrically is the triangle wave shown in graph 562 which is given by the equation f(t)=1−2·ABS [MOD (tf, 1)−0.5].

Figure 46:
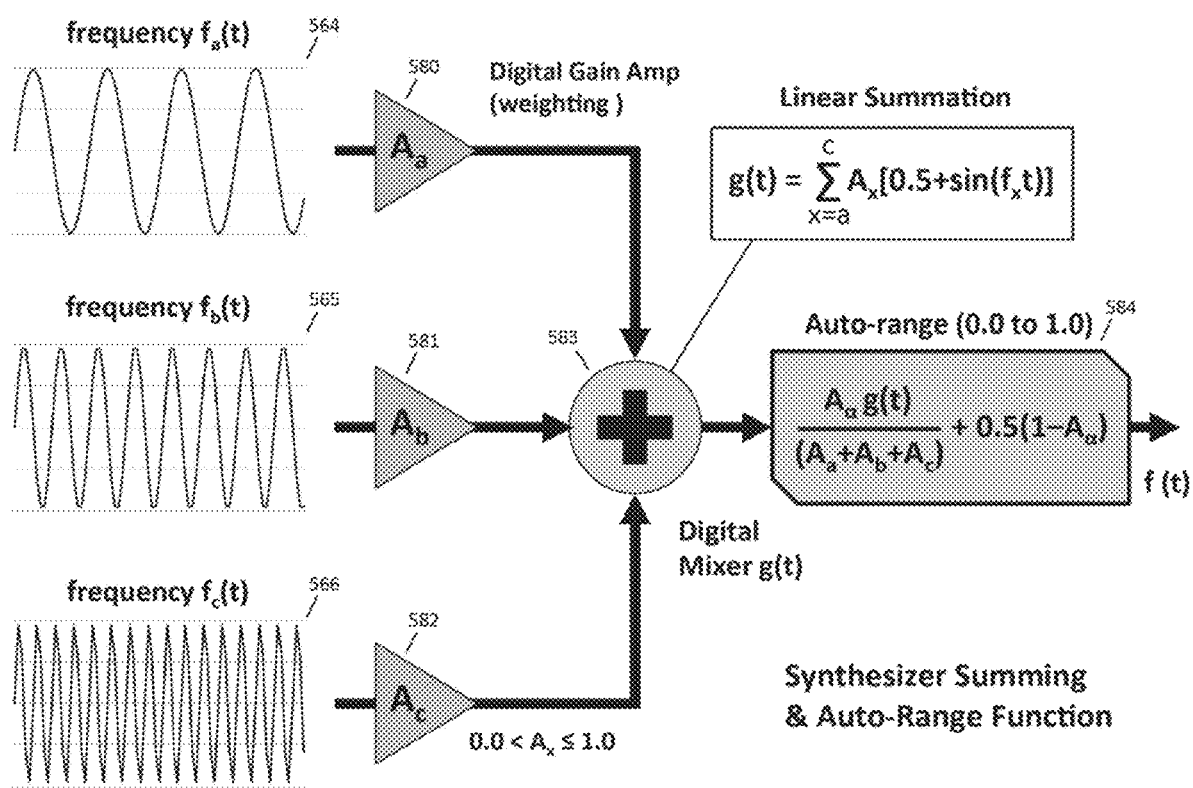
FIG. 46 is a functional description of a synthesizer summing-node and auto-range operation used in waveform synthesis.

Synthesis of a single sine wave or a chord of three or more sine waves of frequencies $f_a$, $f_b$, $f_c$, and relative magnitudes $A_a$, $A_b$, $A_c$, respectively can be described by the equation f(t)=Aα (0.5+0.5[$A_a$ sin (2π$tf_a$)+$A_b$ sin (2π$tf_b$)+$A_c$ sin (2π$tf_c$)]/[($A_a$+$A_b$+$A_c$)])+0.5(1−$A_α$). This mathematical process, shown in FIG. 46, mixes three sine waves 564, 565, and 566 with gains 580, 581, and 582 respectively, summed in a digital mixer 583 using a linear summation of digital words.

Digital summation, the arithmetic addition of binary, octal, or hexadecimal numbers, is identical to the addition of decimal numbers except that the numbers comprise binary or binary equivalent representations of numbers, i.e. base two (b2), base eight (b8), or base sixteen (b16), rather than base ten (b10). Although digital summation can be performed using dedicated devices, the arithmetic logic unit (ALU) resident within the LED pad's microcontroller 339 can easily perform the required tasks in binary mathematics. Converting numbers into another base then adding them in the alternate base and converting them back to base 10 produces identical results. This equivalency principle is shown in the example table below for the addition of three numbers in different bases. In the context of waveform synthesis, the numbers being added represent the instantaneous values of three sine waves at any given moment, added together to produce a digital summation of the three numbers. For illustrative purposes, the values of the sine wave have been magnified by ten times, i.e. where $A_x f_x(t_1)$ and where $A_x$=10 for x=1 to 3. For example, at a specific time $t_1$, the value of the functions $f_a(t_1)$)=1, $f_b(t_1)$)=0.5, and $f_c(t_1)$)=0.5. In a case where the gain factors are evenly weighted, i.e. where $A_a$=10, $A_b$=10, and $A_c$=10, then the summation 10(Σ$f_x(t_1)$)=20. To convert this number into a unit function, the resulting sum must be scaled to a fractional number between a result between 0.000 and 1.000–a task performed by auto-range function 584.

| Item | f (t) | Gain $A_x$ | Decimal g(t) | Binary g(t) | Octal g(t) | Hexadecimal g(t) |
|---|---|---|---|---|---|---|
| $A_x f_a(t_1)$ | 0.5 | 10 | 5 | 0000 0101 | 05 | 05 |
| $A_x f_b(t_1)$ | 0.5 | 10 | 5 | 0000 0101 | 05 | 05 |
| $A_x f_c(t_1)$ | 1 | 10 | 10 | 0000 1010 | 12 | 0A |

| Item | f (t) | Gain $A_x$ | Decimal g(t) | Binary g(t) | Octal g(t) | Hexadecimal g(t) |
|---|---|---|---|---|---|---|
| $A_x$ ($\Sigma f_x (t_1)$) | 2.0 | 30 | 20 | 0001 0100 | 24 | 14 |

For each time point $t_x$, dividing $A_x$ ($\Sigma f_x (t_x)$) by the sum of the gain multipliers ($A_a+A_b+A_c$) provides an average of the blended chord. In the case of even weighting, i.e. where $A_x=10$, the sum of these gain factors ($A_a+A_b+A_c$)=30. Applied to the above summation, auto-range scaling converts the summation of 20 to the auto-range scaled number 20/30=0.666, the same number as found by averaging three numbers having instantaneous values of 1.0, 0.5, and 0.5. The auto-range function also works when the sine waves are blended with non-even weighting, where one or more sine wave frequency components dominate the mix. For example, a blend where $A_a$ is 20% of the total, $A_b$ is 40%, and where $A_c$=40% yields the following mix of signals of the

| Item | f (t) | Gain $A_x$ | Decimal g(t) | Binary g(t) | Octal g(t) | Hexadecimal g(t) |
|---|---|---|---|---|---|---|
| $A_x f_a (t_1)$ | 0.5 | 20 | 10 | 0000 1010 | 12 | 0A |
| $A_x f_b (t_1)$ | 0.5 | 40 | 20 | 0001 0100 | 24 | 14 |
| $A_x f_c (t_1)$ | 1.0 | 40 | 40 | 0010 1000 | 50 | 28 |
| $A_x$ ($\Sigma f_x (t_1)$) | 2.0 | 100 | 70 | 0100 0110 | 106 | 46 |

In this case ($A_a+A_b+A_c$)=100 while g(t)=70, so that the output of the auto-range function is 0.7. The auto-range function employs positive multiplier $A_\alpha>0$ to scale the signal to compensate for magnitude compression. Because the scalar $A_\alpha$ shifts not only the function but also shifts its average value, the DC offset correction term 0.5 (1−$A_\alpha$) is added to the sum of sine waves to re-center the function's average back down to 0.5.

Figure 47:
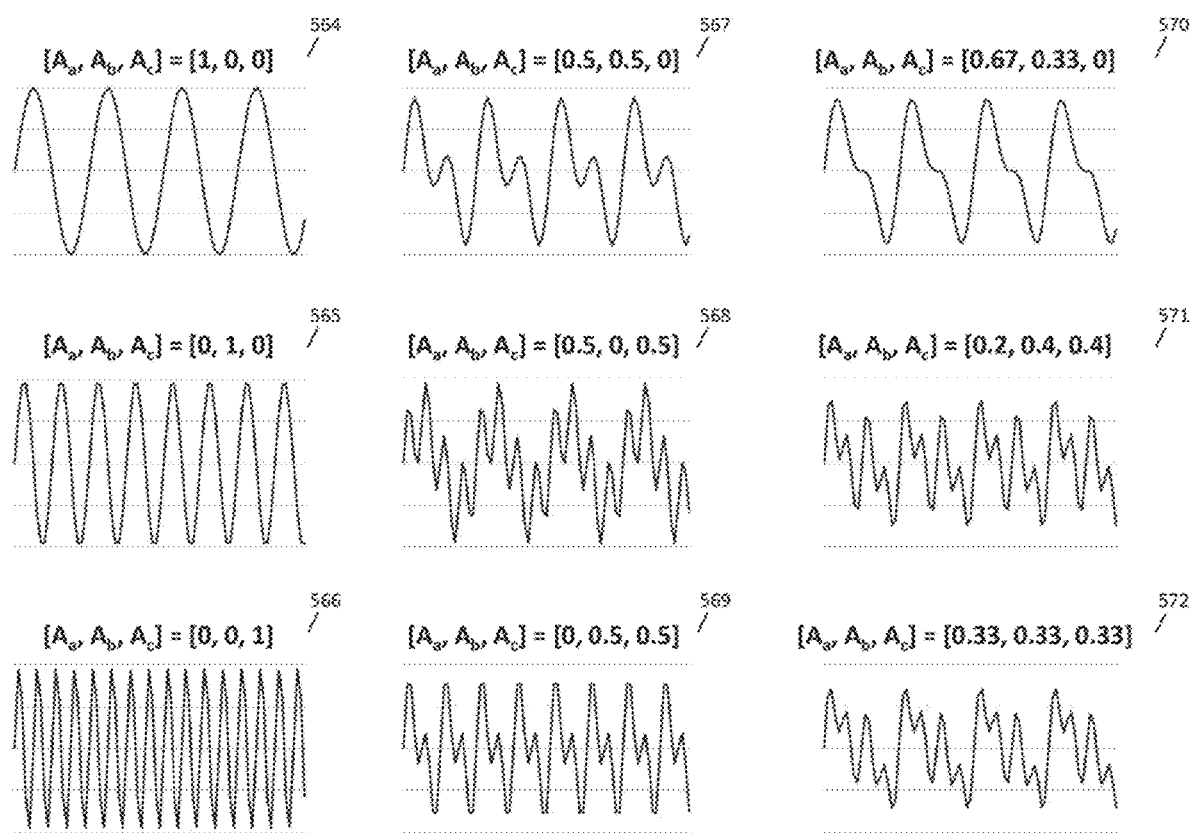
FIG. 47 illustrates examples of varying frequency sine waves and blended chords thereof.

FIG. 47 illustrates several sine waves and sine wave chords made in accordance with the unit function generator 551. In the examples shown, three sine waves each an octave apart (i.e. $f_c=2f_b=4f_a$) are generated with various gain factors to produce a variety of complex functions. The gain factors [$A_a$, $A_b$, $A_c$] control the mix or "blend" of frequency components. Because the components are averaged, the gain factors can be any positive real number. For convenience sake, however, the three factors can be scaled into percentages. In some cases, the weighting factors are zero, meaning the particular frequency sine wave is absent from the mix. For example, in graph 564, [$A_a$, $A_b$, $A_c$]=[1, 0, 0] so that only sinusoid $f_a$ is present. Similarly, in graph 565 where [$A_a$, $A_b$, $A_c$]=[0, 1, 0], only the middle octave sinusoid $f_b$ is present and in graph 566 where [$A_a$, $A_b$, $A_c$]=[0, 0, 1], only the highest octave sinusoid is present.

The figure also illustrates a variety of mixed blend chords. Graph 567 depicts an evenly weighted mix blend of sinusoids of frequencies $f_a$ and $f_b$, graph 568 depicts an evenly weighted mix blend of sinusoids of frequencies $f_a$ and $f_c$, and graph 569 depicts an evenly weighted mix blend of sinusoids of frequencies $f_b$ and G. Unevenly mixed blends of two sine waves with a ⅔rd weighting of frequency $f_a$ and a ⅓rd weighting of frequency $f_b$ are shown in graph 570. Three sine wave mixes include an evenly weighted chord 572 and an unevenly weighted chord 571, where [$A_a$, $A_b$, $A_c$]=[0.2, 0.4, 0.4]. Algebraic calculation of sin (θ) where θ=$f_x t$ for x=a, b, c . . . requires computation of a power series [http://www2.clarku.edu/~djoyce/trig/compute.html] for each sin (θ) evaluation where $$\sin(f_a t) = (f_a t) - \frac{(f_a t)^3}{3!} + \frac{(f_a t)^5}{5!} - \frac{(f_a t)^7}{7!} + \frac{(f_a t)^9}{9!} - \frac{(f_a t)^{11}}{11!} + \frac{(f_a t)^{13}}{13!} - \ldots$$

$$\sin(f_b t) = (f_b t) - \frac{(f_b t)^3}{3!} + \frac{(f_b t)^5}{5!} - \frac{(f_b t)^7}{7!} + \frac{(f_b t)^9}{9!} - \frac{(f_b t)^{11}}{11!} + \frac{(f_b t)^{13}}{13!} - \ldots$$

$$\sin(f_c t) = (f_c t) - \frac{(f_c t)^3}{3!} + \frac{(f_c t)^5}{5!} - \frac{(f_c t)^7}{7!} + \frac{(f_c t)^9}{9!} - \frac{(f_c t)^{11}}{11!} + \frac{(f_c t)^{13}}{13!} - \ldots$$

where n!=n·(n−1) . . . (n−2) . . . 3.2.1. Note the same method can be used to produce cosine waveforms, which are nothing more than since waves shifted in phase by 90°. To produce a three sine wave chord $A_x(\Sigma f_x(t_x))$ with the highest frequency sine wave in the 9$^{th}$ octave, approximately 20 kHz, with 360 degrees of precision requires that all the foregoing calculations along PWM generation $\Psi_P$ [f(t)] must occur at a rate of 7.2 MHz, i.e. within 138 ns. This approach is computationally intensive, wasting compute cycles and burning power, especially when synthesizing high frequency since waves.

Waveform Synthesis With Primitives Processor

Primitives processor 552, shown in FIG. 44, uses an alternative method. This method, far less computationally intensive and better matched to the limited computing capability of LED pad μP 339, involves the use of a lookup table to evaluate a function. For periodic functions, the function's value at regular increments of the period, for example at fixed angles or fixed percentages, can be pre-calculated and loaded into lookup tables included in waveform primitives 487. For example, the value of a sin (θ) depends on the angle of its argument θ where sin 0°=0
sin 15°=($\sqrt{6}-\sqrt{2}$)/4
sin 30°=1/2
sin 45°=$\sqrt{2}$/2
sin 60°=$\sqrt{3}$/2
sin 75°=($\sqrt{6}+\sqrt{2}$)/4
sin 90°=1

Since the sine function is periodic, there is no reason to recalculate the same values each time evaluation sin (θ) is required. In such a case the use of a lookup table is potentially beneficial. Lookup tables, however, face several fundamental hurdles—for one, the table can only return a value of the function at the same input condition for which it was previously calculated, i.e. with the same argument. Just because the table contains the value of sin(45°) doesn't mean it knows the value of sin (22°). In a subroutine call to a lookup table, ensuring that the input argument matches its available arguments is not likely unless the two are co-developed to insure they employ the same values. Another issue in the use of lookup tables is the stiff equation problem, performing high-resolution waveform synthesis across over many orders-of-magnitudes of frequency. For example, if a 20 kHz sinusoid (9$^{rd}$ octave) is synthesized using PWM methods with 16-bit precision, the required sample rate is (20,000 Hz)(16$^2$)=1,310,726,000 Hz or roughly 1.3 GHz. If in the same simulation, an infrasound excitation pattern at 0.1 Hz (−2$^{nd}$ octave) is added to the chord, the period of the low frequency wave component is T=1/f=1/(0.1 Hz)=10 sec.

This means to maintain the required resolution in the ninth octave while synthesizing a single 10 second infrasound wave requires a table of (1.3 GHz)(10 sec)=13 billion data points. Such a huge data table not only requires too much time for the transfer from PBT controller into the intelligent LED pad, but it also requires too much memory.

To resolve the stiff equation issue while ensuring matching arguments between subroutine calls and lookup tables, an inventive method disclosed herein uses pre-defined periodic waveform primitives such as sin waves or linear (scalar) functions, combined with a series of counters sharing a common numeric base, e.g. base 2. The term "primitives" as used herein means tabular time independent description of a waveform—one where the waveform is described using arguments specified relative to the waveform's period T and to not absolute time. For example, in linear functions such as a sawtooth wave, inputting a rectilinear (Cartesian) argument to the lookup table returns a unique value. In a linear unit sawtooth ramping from 0 to 1 over a period T, the input p is unit-less, where at 25% of T the function "saw (p)" has a value of 0.25, at 78% of T the function saw (p) has a value 0.78, etc. To accommodate repeating cycles, it is beneficial to express the argument input "p" using the modulus function MOD (argument, limit) where MOD (p, 1) for positive inputs returns a value bounded between 0 and 1, i.e. the remainder after division by the largest integer multiple of the limit. For example, MOD (0.78, 1)=0.78, MOD (5.78, 1)=0.78, and MOD (z.78, 1)=0.78 for any value of z. As such only data covering one period T is required to describe any repeating waveform.

The same function applies to polar coordinates. Evaluation of sin (MOD (θ, 360°) produces a repeating sequence of values between sin(0°) and sin (359.99 . . . °). At 360° the entire cycle repeats because sin (MOD (360°, 360°)=sin (0°). Note that in actual code or in spreadsheets the angle arguments θ of sin or any other trigonometric functions are expressed in radians, not in degrees, but the principal of the modulus function and its application remain the same. Using the modulus function in the manner disclosed, the size of a lookup table for any periodic function can be limited to a single period, reducing the size of the table dramatically. The number of data pairs in each lookup table is therefore equal to the principal resolution $\xi$ providing a one-to-one correspondence between an input $\Phi_x$ to a lookup table and its output $f_x$ where for any octave x, the relation $\Phi_x \xi_x f_x$ describes the transformation performed by the lookup table subroutine call.

Although these function primitives comprise a collection of time independent states describing a mathematical function, waveform synthesis requires their combination with oscillators comprising either digital or analog clocks to produce a time varying waveform. Specifically for rectilinear functions of period T such as the triangle or sawtooth waves the argument x can be expressed as x=t/T, and for sine waves, sine wave chords, and other trigonometric unit functions θ=tf. In either case a source of time is required to transform a time independent wave form primitive into a time varying function. One such implementation to generate a range of time sources, represented algorithmically in FIG. 48A, combines a series of binary (±2) digital counters 590 to 598 generating ten synchronous clock frequencies $\Phi_0$ to $\Phi_9$ from a common clock, specifically symbol clock rate $\Phi_{sym}$ having a programmable frequency. The clocks are then used to synthesize periodic functions such as sine waves in the audio spectrum having corresponding frequencies $f_9$ in the ninth octave down to $f_0$ in octave zero and as desired to mix them in various combinations. The same methods, not shown, can be used for generating infrasound, i.e. oscillating waveforms below 20 Hz, and also (provided a proper transducer is employed) ultrasound comprising frequencies greater than 20 kHz.

During synthesis, each clock is converted to a time varying waveform f(t) using a lookup table of the periodic function, e.g. sine wave, sine wave chords, triangle waves, sawtooth waves, etc. Each clock is paired with the waveform it creates, for example $\Phi_8$ uses sine wave lookup table 618 with primitive resolution $\xi_2$ to generate sine wave frequency $f_8$, $\Phi_3$ uses sine wave lookup table 613 with primitive resolution $\xi_3$ to generate sine wave frequency $f_3$, and $\Phi_1$ uses sine wave lookup table 611 with primitive resolution $\xi_1$ to generate sine wave frequency $f_1$, where $$f_8 = \Phi_8/\xi_8$$

$$f_3 = \Phi_3/\xi_3$$

$$f_1 = \Phi_1/\xi_1$$

and, in general, $f_x = \Phi_x/\xi_x$. So, in operation, the 10-octave waveform-summing implementation primitives processor 552 uses nine binary counters 598 to 590 to generate ten clock frequencies comprising input $\Phi_9 = \Phi_{sym}$ and clocks $\Phi_8$ to $\Phi_0$ to drive corresponding sine wave lookup tables 619 to 610 to synthesize sine waves $f_9$ to $f_0$.

The mixing process involves selecting various combinations of the sine waves using octave selector switches 609 to 600, blending the selected sine wave components in a digital-mixer summing node 630 where the components are weighted in various percentages by digital gain amplifiers 620 to 629. The blended summation is scaled by auto range function 631 into the range as 0.000 to 1.000. Although the primitives processor 552 can be implemented in hardware or with firmware-controlled hardware, the function can be entirely emulated using software, wherein mixer 630 is executed digitally using binary addition, and the auto range function 631 can be performed using binary mathematics executing one of several division algorithms (https://en.wikipedia.org/wiki/Division_algorithm). To avoid performing unnecessary operations, primitives-processor 552 only executes operations on selected octave selector switches 600 to 609.

Using the method shown in FIG. 48A and described above, the implementation of primitives-processor 552 performs wide bandwidth waveform synthesis and chord building over three orders of magnitude in frequency, i.e. ten octaves, spanning a frequency range from 20 Hz to 20,000 Hz, using only lookup tables and a series of counters. The disclosed method is computationally efficient, requiring minimal memory or compute power to execute and unlike the unit function generator 551 of FIG. 44, does not involve real time evaluation of power series. A key feature of the synthesizer in wide bandwidth algorithmic waveform generation is the role of counter operation. Together counters 590 to 598 generate ten octaves of clock frequencies used as inputs feeding corresponding lookup tables 610 to 619. Because each octave is fed by its own dedicated clock frequency, the number of points in the corresponding table and the memory required to realize the table is limited to the required precision of that specific octave and does not involve data used in other frequency bands. In this manner, the disclosed combination of counters and lookup tables overcomes the aforementioned stiff equation problem. To further minimize computational intensity and avoid unnecessary computations, lookup table subroutine calls are limited to only those tables selected by the octave switches.

To avoid aliasing and phase shift distortions, counter cascade 598 to 590 is synchronized to a common clock called the symbol rate $\Phi_{sym}$ output from tuner (counter) 599. For convenience, symbol rate $\Phi_{sym}$ is equivalent to the clock signal $\Phi_9$ for ninth octave waveform synthesis, but this relationship is arbitrary. Any symbol rate higher than the PWM resolution of the highest synthesized frequency, where $\Phi_{sym} \geq \xi_{sym} f_{max}$ will suffice. The counter cascade can be realized using hardware or software. Although a ripple counter can be used, a synchronous counter is preferred to prevent clock phase shift. A ripple counter is a counter cascade where each counter stage's output is instantly available at the same time it is input into the next stage. Because of the propagation delay through each counter stage, the outputs of higher frequency clocks change state before the lower frequency clocks do. The state changes therefore "ripples" down the cascade, such that the first clock $\Phi_9$ changes state, followed a moment later by the clock $\Phi 8$ and then by the clocks $\Phi 7$, $\Phi 6$, $\Phi_5$, etc., rippling like a wave traversing a pond's surface.

In contrast, a synchronous counter operates synchronously, such that even though the digital count takes time to ripple through the counter chain, the outputs only change contemporaneously with a synchronizing clock pulse. In this manner, the signal ripple through the counter cascade is invisible to the user. More specifically, whether implemented in hardware or in software, a synchronous counter operates like a ripple counter but with D-type flip-flop [https://en.wikipedia.org/wiki/Flip-flop_(electronics)] latched outputs. The D flip-flop retains is prior state until it is enabled by a latch signal with the corresponding truth table, i.e. the data input high or low state is copied to the latch output only when the sync clock goes high, after which the sync clock can return low and the flip flop output will remain latched in what ever state was on the D input at the time of the last sync clock pulse until the next sync pulse occurs. During that interval between clock pulses, the output of each counter stage can change without the transition appearing on the counter's output. To avoid clutter in the schematic, counters 599 to 590 may represent a synchronous counter without explicitly depicting the D flip flop latch or any sync clock input. To ensure that the clock transitions ripple completely through the counter cascade before updating the state of clock outputs $\Phi_9$ through $\Phi_0$ the sync clock pulse is derived from state transition of the lowest synthesized frequency clock, in this exemplar represented as $\Phi_0$.

| Sync Clock C in | Counter Data D in | Flip Flop Q out |
|---|---|---|
| 0 | X | $Q_{prev}$ |
| 1 | 0 | 0 |
| 1 | 1 | 1 |

The symbol rate $\Phi_{sym}$ feeding the counter cascade is generated from system clock rate $\Phi_{sys}$ by using a programmable "tuner" counter 599. The symbol clock rate $\Phi_{sym}$ is generated to produce a maximum output frequency $f_{max}$ at a resolution $\xi_{sym}$. The value of the primitive resolution $\xi_{sym}$ is a programmable input to tuner counter 599 that can be changed depending on the waveform synthesis being performed. The numerical variable $\xi_{sym}$, referred to herein the "primitive symbol resolution" is defined as the resolution of the highest synthesized frequency where $\xi_{sym} = \Phi_{sym}/f_{max}$ having a value that may range from 24 to 65,536 depending on the synthesis precision required. For example, selecting $\xi_{sym} = 96$ in sine wave synthesis means for the highest pitch sine wave of the synthesizer is related to the symbol clock rate by the relationship $\Phi_{sym} = \xi_{sym} f_{max} = 96 f_{max}$ where 90° of arc uses 24 points, one point every 3.75°. In operation, setting tuner counter 599 produces the entire cascade of frequencies derived from and tuned to the symbol clock rate $\Phi_{sym}$. The resolution of the $\xi_{sym}$ need not match the resolution of lower octave lookup tables. Different precision levels $\xi_x$ can be employed for lookup tables 610 to 619, or alternatively the same precision lookup table may be employed to generate some or all the required frequency components. Alternatively, the same lookup table can be used for every generated sine wave. In such cases every sine wave frequency $f_x$ has an identical resolution $\xi_9 = \xi_8 = \xi_7 \ldots \xi_1 = \xi_0$.

Because the entire counter cascade is driven from a common symbol clock rate $\Phi_{sym}$ the exact frequency relationship of the synthesized waveforms is precisely defined by the counter frequency $\Phi_x$ and its corresponding lookup table's resolution $\xi_x$. Although this relationship is shown using binary (divide by 2) counters, there is no restriction in what the counter's divisor may be. Dividing by two is convenient because it is equivalent to a halving of frequency, equivalent in musical scales to one octave or twelve half steps. The counters however can utilize any cascade combination of counters each with different divisors. Alternatively, programmable counters, where the count is loaded into the counter, may be employed. Furthermore, since the counters operate at fixed clock rates and complete one complete oscillating period in every data points, i.e. one complete cycle of a lookup table, then the relative timing and phase of any two periodic functions is precisely known. Given, for example, two sine waves having frequencies $f_x$ and $f_y$, where $$f_x = \Phi_x/\xi_x$$

$$f_y = \Phi_y/\xi_y$$

then the frequency ratio of waveforms is given by $$\frac{f_x}{f_y} = \frac{\Phi_x \xi_y}{\Phi_y \xi_x}$$

This ratio is illustrative that frequency scaling can be performed by changing the clock $\Phi_x$ or by changing the resolution $\xi_x$ of the lookup table. For example, if a constant resolution lookup table is used where $\xi_x = \xi_y = 24$ then the frequency ratio $f_x/f_y$ of the synthesized sine waves depends only the ratio of clock rates $\Phi_x/\Phi_y$ or $$\frac{f_x}{f_y} = \frac{\Phi_x}{\Phi_y}$$

Figure 48B:
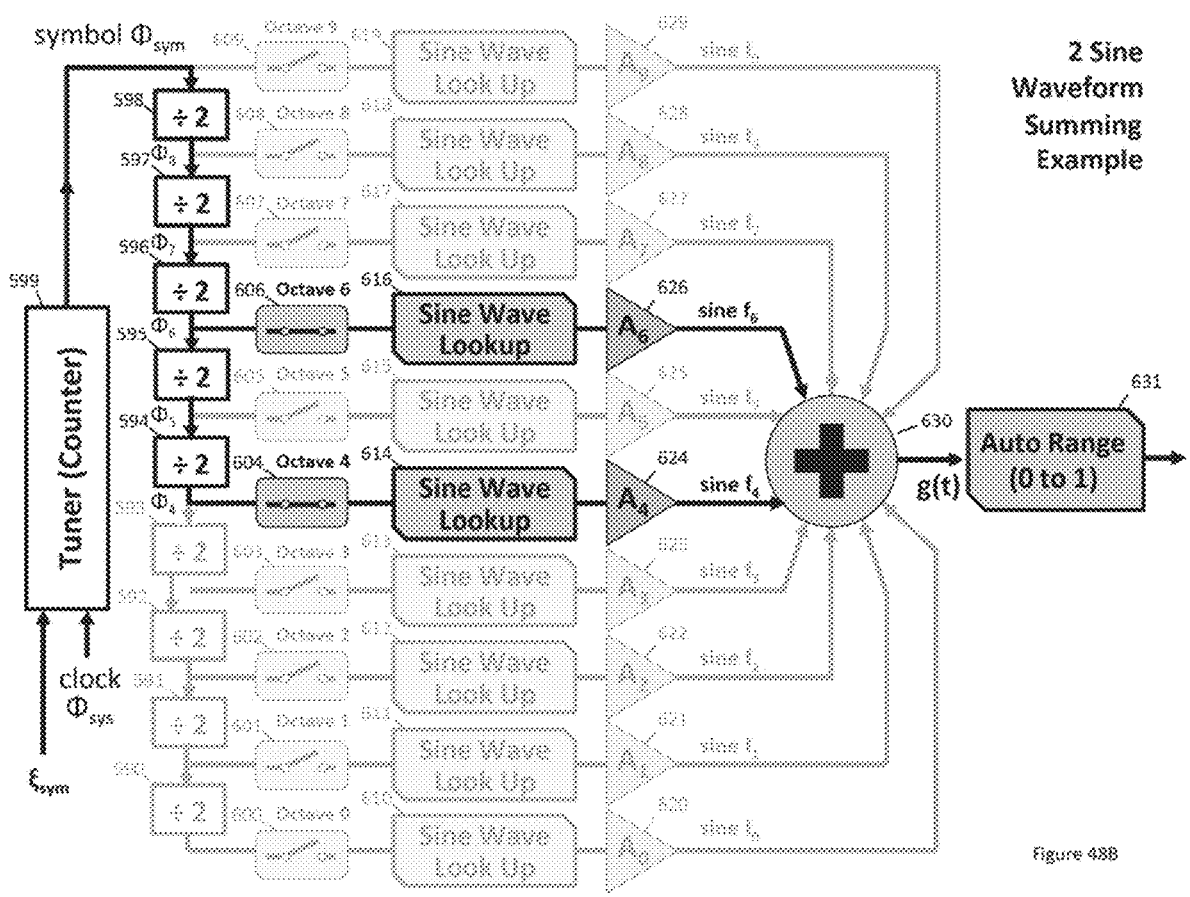
FIG. 48B illustrates two-sine-wave chord synthesis employing a counter-based sinusoidal synthesis system.

In such cases, a clock frequency ratio $\Phi_x/\Phi_y = 4$, results in two sine waves of the same note but two octaves apart, for example the musical note A at 1,760 Hz in the $6^{th}$ octave and the musical note A at 440 Hz in the $4^{th}$ octave. FIG. 48B illustrates a dual sine wave summing example wherein only the $6^{th}$ and $4^{th}$ octave selector switches 606 and 604 are enabled and used to access data in sine wave lookup tables 616 and 614 each waveform having a primitive resolution $\xi_6 = \xi_4 = 24$. The outputs are amplified by digital gain amps 626 and 624 then mixed in digital summing node 630 to produce a blended waveform output. In operation, tuner (counter) 599 generates symbol clock $\Phi_{sym}$ from the system clock $\Phi_{sys}$. The cascade of ±2 counters 598, 597, and 596 divides the symbol clock $\Phi_{sym}$ to produce $6^{th}$ octave clock $\Phi_6$ and by counters 595 and 594 to generate $4^{th}$ octave clock $\Phi_4$.

| Note, Octave | Clock | Resolution | Frequency | Ratio |
|---|---|---|---|---|
| A, $9^{th}$ | $\Phi_{sym} = \Phi_9 = $ 337,920 Hz | $\xi_{sym} = 24$ | $f_9 = 14,080$ Hz | $\Phi_{sym}/f_9 = 24$ |
| A, $6^{th}$ | $\Phi_6 = 42,240$ Hz | $\xi_6 = 24$ | $f_6 = 1,760$ Hz | $\Phi_{sym}/f_6 = 192$ |
| A, $4^{th}$ | $\Phi_4 = 10,560$ Hz | $\xi_4 = 24$ | $f_4 = 440$ Hz | $\Phi_{sym}/f_4 = 768$ |

The resulting 2 sine-wave chord is given by the summation $$g(t)=0.5+0.5[A_6 \sin(f_6 t)+A_4 \sin(f_4 t)]=0.5+0.5[A_6 \sin(\Phi_{sym}t/192)+A_4 \sin(\Phi_{sym}t/768)]$$

Figure 48C:
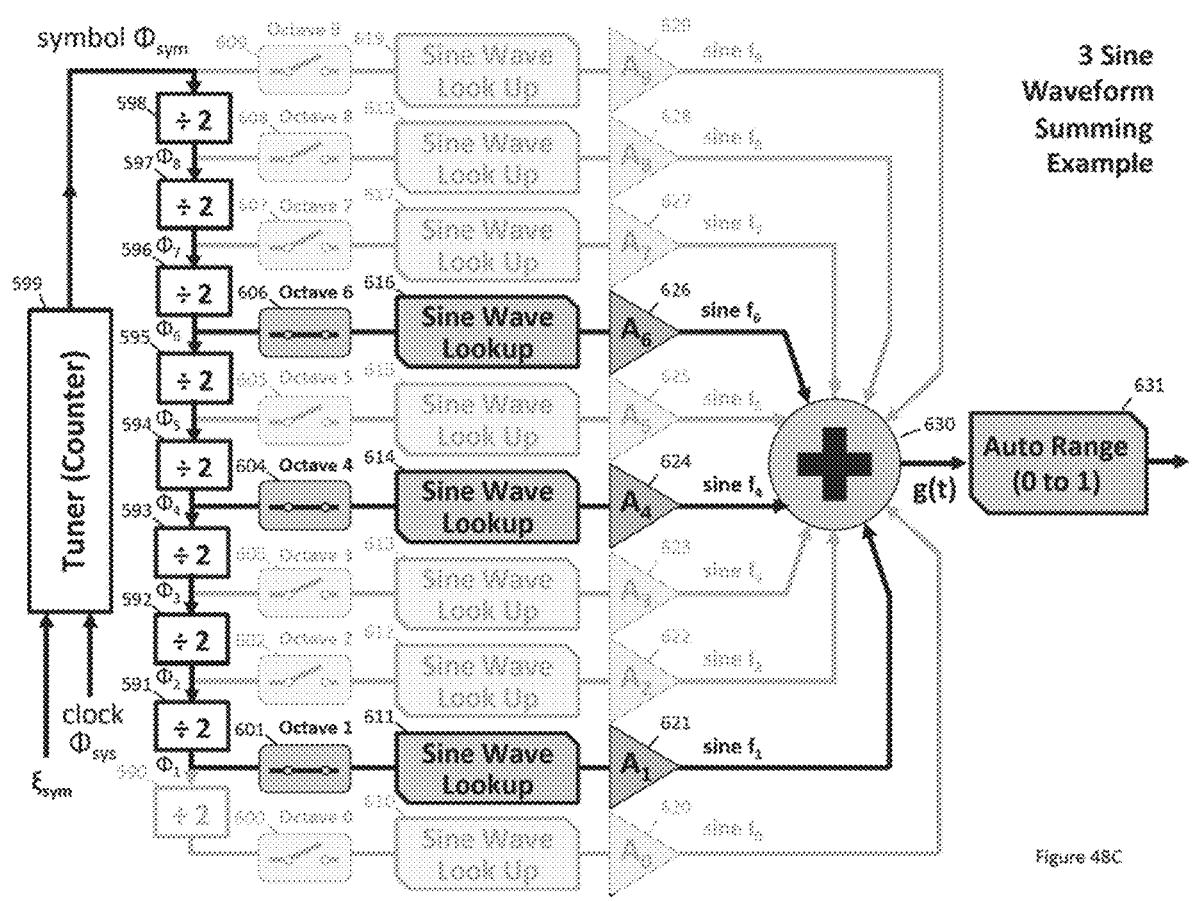
FIG. 48C illustrates three-sine-wave chord synthesis employing a counter-based sinusoidal synthesis system.

The multiplier 0.5+0.5[periodic expression] is used to scare the peak magnitude of the sine wave from ±1 to ±0.5 centered on an average value of zero. The adder 0.5 shifts the curve up by +0.5 to span a positive range between 0.000 and 1.000. By enabling octave selector switch 601 as shown in FIG. 48C, the components of lookup table 611 driven by clock $\Phi_1$ are added into the chord. Clock $\Phi_1$ is generated from Clock $\Phi_4$ using counters 593, 592, and 591. The added $1^{st}$ octave frequency component is given by

| Note, Octave | Clock | Resolution | Frequency | Ratio |
|---|---|---|---|---|
| A, $1^{st}$ | $\Phi_1 = 1,320$ Hz | $\xi_1 = 24$ | $f_1 = 55$ Hz | $\Phi_{sym}/f_1 = 6,144$ | and the resulting 3 sine-wave chord is given by the summation $$g(t)=0.5+0.5[A_6 \sin(f_6 t)+A_4 \sin(f_4 t)]=0.5+0.5[A_6 \sin(\Phi_{sym}t/192)+A_4 \sin(\Phi_{sym}t/768)+A_1 \sin](\Phi_{sym}t/6144)]$$

As described the above synthesis method utilizes a single waveform primitive to concurrently generate chords consisting of two or three sine waves.

Additional details of the operation of primitives-processor 552 are illustrated in the single primitive chord synthesis illustrated in FIG. 49. As shown, tuner counter 599 comprises two counters—a system clock counter 640 and a symbol clock counter 641. System clock counter 640 is a counter that converts the frequency $\Phi_{sys}$ of the clock 124 which drives the μC 134 in PBT controller 131 (shown in FIG. 14) to a reference clock frequency $\Phi_{ref}$ at a convenient fixed frequency (e.g. 5 MHz). Symbol clock counter then converts $\Phi_{ref}$ to the symbol clock rate $\Phi_{sym}$ used to define the reference frequency of the counter cascade for sinusoidal synthesis. In the example shown, counters 598 through 593 comprise binary ±2 counters, generating multiple sinusoidal frequencies each one octave apart as described in the above table. Further inspection reveals for a binary counter cascade:

The clock rate $\Phi_x$ in every octave is a multiple of 2 of the symbol rate $\Phi_{sym}$.

The frequency $f_x$ of every octave is a multiple of 2 of the maximum synthesized frequency $f_{max}$ which is, without limitation, illustrated as being in the $9^{th}$ octave of the musical scale.

The relationship between the symbol clock rate $\Phi_{sym}$ and the maximum synthesized frequency $f_{max}$ is determined by $\xi_{sym}$, the resolution of the highest frequency waveform synthesized. The multiplicative product $f_{max} \xi_{sym}=\Phi_{sym}$ setting the highest clock rate in the counter cascade.

The relationship between the symbol clock rate $\Phi_x$ and the synthesized frequency $f_x$ in each octave x is determined by $\xi_x$, the primitive resolution of the waveform in that octave.

Since all the relationships between clock rates and frequencies in a single primitive binary counter cascade comprise precise ratios to other frequencies present in the primitives processor 552, setting the frequency and resolution of any one synthesized waveform of frequency $f_x$ and $\xi$ automatically determines the frequency of every other synthesized frequency and clock in the entire counter cascade including the symbol rate $\Phi_{sym}$ and the maximum frequency $f_{max}$. Frequency scaling of the primitives process is summarized in the following table:

| Octave | Clock | Resolution | Frequency | Ratio to $\Phi_{sym}$ Clock |
|---|---|---|---|---|
| $9^{th}$ | $\Phi_{sym} = \Phi_9$ | $\xi_9 = \xi_{sym}$ | $f_9 = \Phi_{sym}/\xi_{sym} = f_{max}$ | $\Phi_{sym}/f_9 = \xi_{sym}$ |
| $8^{th}$ | $\Phi_8 = \Phi_9/2 = \Phi_{sym}/2$ | $\xi_8 = \xi_{sym}$ | $f_8 = \Phi_8/\xi_8 = f_{max}/2$ | $\Phi_{sym}/f_8 = 2\ \xi_{sym}$ |
| $7^{th}$ | $\Phi_7 = \Phi_8/2 = \Phi_{sym}/4$ | $\xi_7 = \xi_{sym}$ | $f_7 = \Phi_7/\xi_7 = f_{max}/4$ | $\Phi_{sym}/f_7 = 4\ \xi_{sym}$ |
| $6^{th}$ | $\Phi_6 = \Phi_7/2 = \Phi_{sym}/8$ | $\xi_6 = \xi_{sym}$ | $f_6 = \Phi_6/\xi_6 = f_{max}/8$ | $\Phi_{sym}/f_6 = 8\ \xi_{sym}$ |
| $5^{th}$ | $\Phi_5 = \Phi_6/2 = \Phi_{sym}/16$ | $\xi_5 = \xi_{sym}$ | $f_5 = \Phi_5/\xi_5 = f_{max}/16$ | $\Phi_{sym}/f_5 = 16\ \xi_{sym}$ |
| $4^{th}$ | $\Phi_4 = \Phi_5/2 = \Phi_{sym}/32$ | $\xi_4 = \xi_{sym}$ | $f_4 = \Phi_4/\xi_4 = f_{max}/32$ | $\Phi_{sym}/f_4 = 32\ \xi_{sym}$ |
| $3^{rd}$ | $\Phi_3 = \Phi_4/2 = \Phi_{sym}/64$ | $\xi_3 = \xi_{sym}$ | $f_3 = \Phi_3/\xi_3 = f_{max}/64$ | $\Phi_{sym}/f_3 = 64\ \xi_{sym}$ |
| $2^{nd}$ | $\Phi_2 = \Phi_3/2 = \Phi_{sym}/128$ | $\xi_2 = \xi_{sym}$ | $f_2 = \Phi_2/\xi_2 = f_{max}/128$ | $\Phi_{sym}/f_2 = 128\ \xi_{sym}$ |
| $1^{st}$ | $\Phi_1 = \Phi_2/2 = \Phi_{sym}/256$ | $\xi_1 = \xi_{sym}$ | $f_1 = \Phi_1/\xi_1 = f_{max}/256$ | $\Phi_{sym}/f_1 = 256\ \xi_{sym}$ |
| $0^{th}$ | $\Phi_0 = \Phi_1/2 = \Phi_{sym}/512$ | $\xi_0 = \xi_{sym}$ | $f_0 = \Phi_0/\xi_0 = f_{max}/512$ | $\Phi_{sym}/f_0 = 512\ \xi_{sym}$ |
| $-1^{st}$ | $\Phi_{-1} = \Phi_0/2 = \Phi_{sym}/1024$ | $\xi_{-1} = \xi_{sym}$ | $f_{-1} = \Phi_{-1}/\xi_{-1} = f_{max}/1024$ | $\Phi_{sym}/f_{-1} = 1024\ \xi_{sym}$ |
| $-2^{nd}$ | $\Phi_{-2} = \Phi_{-1}/2 = \Phi_{sym}/2048$ | $\xi_{-2} = \xi_{sym}$ | $f_{-2} = \Phi_{-2}/\xi_{-2} = f_{max}/2048$ | $\Phi_{sym}/f_{-2} = 2048\ \xi_{sym}$ |

The primitive processor 552 whose operation is depicted in FIG. 49 represents a "tuned" system wherein the entire multi-octave synthesizer is set to a single "key" frequency analogous to tuning a monophonic musical instrument to a single note or key, e.g. an instrument tuned in the key of A. For this reason, operation of symbol clock counter 641 is set by two parameters, namely $f_{key}$ key select 642 and the lookup table 645 having primitive resolution $\xi_{sym}$. As shown lookup table 645, stored in either volatile memory 334a or non-volatile memory 334b within the LED pad 337, is selected by some identifier such as hexadecimal code 643, or some binary equivalent code 644 thereof.

Since the entire synthesizer is tuned to octave multiples, choice of the $f_{key}$ key select input 642 is arbitrary. For convenience, digital tuning can be based in accordance with international frequency standards for pitch. For example, the pitch "A" above middle C in the fourth octave has a frequency 440 Hz. This 440 Hz tone is considered the general tuning standard for musical pitch [https://en.wikipedia.org/wiki/A440_(pitch_standard)]. Referred to as A440, A$_4$, or the Stuttgart pitch, the International Organization for Standardization classifies it as ISO-16. Adapting this standard for the primitive processor, the disclosed synthesizer is tuned to a specific key by selecting a note or frequency in the fourth octave.

Specifically, the input "key select" 642 sets the note or frequency in the 4$^{th}$ octave to which the entire synthesizer is tuned. If the maximum synthesized frequency is chosen to be in the ninth octave of the audio spectrum, and arbitrarily we select the 4$^{th}$ octave as the frequency input range for tuning the synthesizer, then the 9$^{th}$ octave and the fourth octave differ by 5 octaves. Since $2^5=32$, it means that $f_{max}=f_9=32f_4$ and set in accordance key select 642 the maximum frequency $f_{max}=32\ f_{key}$. Given $\Phi_{sym}=\xi_{sym}f_{max}$ then $\Phi_{sym}=\xi$sym $(32f_{key})$. For example, setting "key select" to 440 Hz (standard A above middle C) where $f_4=440$ Hz and where $f_{max}=32\ f_{key}=32(440\ Hz)=14,080$ Hz automatically scales the entire spectrum of available synthesized frequencies so that $f_9=14,080$ Hz, $f_8=7,040$ Hz, $f_7=3,520$ Hz, $f_6=1,760$ Hz, $f_5=880$ Hz, $f_4=4400$ Hz, $f_3=220$ Hz, $f_2=110$ Hz, $f_1=55$ Hz, $f_0=22.5$ Hz, and $f_{-1}=11.25$ Hz. Should $f_{key}$ be set to middle D then all the synthesized frequencies $f_x$ will also be multiples of D. Or if $f_{key}$ is set to middle A$^\#$ then all the binary synthesized frequencies will also be multiples of A$^\#$. The synthesis of sine waves having frequencies other than octave multiples will be discussed later in this disclosure.

Referring again to the primitive processor implementation of FIG. 49, lookup table 645 comprises an exemplar primitive description of a sine wave with 24-point resolution. This tabular primitive description of a sine wave is time independent, based only on the argument θ of sin (θ) as its input. After key $f_{key}$ of the primitive processor is selected by key select 642, e.g. to be 440 Hz, and the resolution $\xi_{sym}$ is established by selecting primitives waveform table 645 to be $\xi_{sym}=24$, then the symbol clock rate $\Phi_{sym}$ and corresponding period $T_{sym}$ is given by $\Phi_{sym}=\xi_{sym}(32f_{key})=24(32)(440\ Hz)=337,920$ Hz, $T_{sym}=1/\Phi_{sym}=1/(337,920\ Hz)=2.96$ μs This symbol rate corresponds to a synthesized maximum frequency $f_{max}$ in the ninth octave where $f_{max}=f_9=\Phi_{sym}/\xi_{sym}=(337,920\ Hz)/24=14,080$ Hz with a corresponding period $T_9=1/f_9=71.02$ μs which is also equivalent to $T_{sym}\xi_{sym}=(2.9592\ldots\ \mu s)(24)=71.02$ μs.

By establishing a time reference used the binary counter cascade, the time-independent sine primitive table 645 is transformed into a time-based description of the function 646*a*, specifically g (t). The same clock symbol clock $\Phi_{sym}$ is the time base for generating clocks $\Phi_6$ and $\Phi_4$ used to synthesize 6$^{th}$ and 4$^{th}$ octave sinusoids 647*a* and 648*a*, specifically $\Phi_6=\Phi_{sym}/8=(337,920\ Hz)/8=42,240$ Hz, having a period $1/\Omega_6=1/(42,240\ Hz)=23.67$ μs $\Phi_4=\Phi_{sym}/32=(337,920\ Hz)/32=10,560$ Hz having a period $1/\Phi_4=1/(10,560\ Hz)=94.79$ μs These clocks are used to synthesize two synchronous sine waves having frequencies $f_6$ and $f_4$ with the following frequencies $f_6=\Phi_6/\xi_6=(42,240\ Hz)/24=1,760$ Hz with a corresponding period $T_6=1/f_6=568$ μs $f_4=\Phi_4/\xi_4=(10,560\ Hz)/24=440$ Hz with a corresponding period $T_4=1/f_4=2,273$ μs In the prescribed manner, the sine waves of equal resolution but of differing frequency can be synthesized with a common clock and a single waveform primitive. In other words, the primitive table sets the shape of the waveform while the resolution ξ and the counter clocks determine the frequencies of the generated sine waves. The exemplary table below shows the relationship between the argument of the sine function θ measured in degrees (or in radians), the normalized unit sine wave function 0.5+0.5 sin (θ), and the times corresponding to the states for sinusoids oscillating at frequencies $f_{max}$ in the ninth octave, $f_6$ in the sixth octave, and $f_4$ in the fourth octave.

Although the table reveals a detailed pattern between 0° and 90°, for brevity's sake detailed 15° descriptions of the other three quadrants are redundant and have been excluded (because the sinusoid is a symmetric function, all four quadrants can be constructed from the data of one quadrant). The time required to complete a sine wave's 360° cycle, i.e. the period T, depends on the sine wave's frequency. For example, consistent with the foregoing calculations, sine waves having frequencies $f_9$, $f_6$, and $f_4$ comprise periods of 71 μs, 568 μs, and 2,273 μs respectively. Specifically, the value of the function 0.5+0.5 sin (θ)=1 when the argument θ=90° =π/2. The period of the sine wave T occurs at four times this duration, when 0=360°=2π. For example, a sixth octave sine wave tuned to the key of A requires 142 μs to complete one quarter of its cycle, so its period is $T_{6=4}$ (142.05)=569.2 μs.

| Argument θ (radians) | 0.5 + 0.5sin (θ) | t ($f_{max}$) | t ($f_6$) | t ($f_4$) |
| --- | --- | --- | --- | --- |
| 0° (0) | 0.5000 | 0.00 μs | 0.00 μs | 0.00 μs |
| 15° (π/12) | 0.6294 | 2.96 μs | 23.67 μs | 94.70 μs |
| 30° (π/6) | 0.7500 | 5.92 μs | 47.35 μs | 189.39 μs |
| 45° (π/4) | 0.8536 | 8.88 μs | 71.02 μs | 284.09 μs |
| 60° (π/3) | 0.9330 | 11.84 μs | 94.70 μs | 378.79 μs |
| 75° (5π/12) | 0.9830 | 14.80 μs | 118.37 μs | 473.48 μs |
| 90° (π/2) | 1.0000 | 17.76 μs | 142.05 μs | 568.18 μs |
| 180° (π) | 0.5000 | 35.51 μs | 284.09 μs | 1,136.36 μs |
| 270° (3π/2) | 0.0000 | 53.27 μs | 426.14 μs | 1,704.56 μs |
| 360° (2π or 0) | 0.5000 | 71.02 μs | 568.18 μs | 2,272.73 μs |

Figure 50:
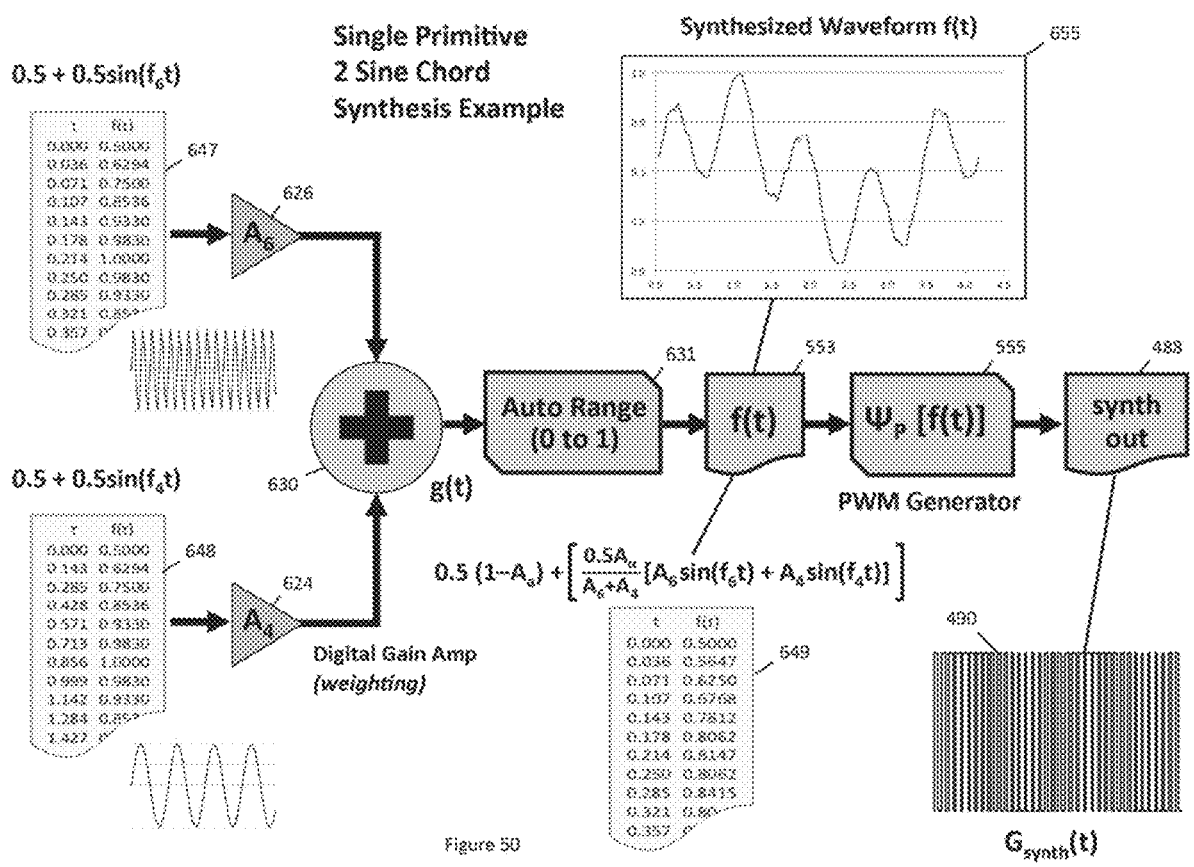
FIG. 50 is an example of two-sine-wave chord synthesis using a single fixed-resolution primitive.

FIG. 50 illustrates chord synthesis by blending two sine waves using a single waveform primitive, Using clocks generated from a binary cascade counter, the time independent time-based waveform primitive, in this example having a resolution $\xi_{sym}=\xi_x=24$ (not shown), is transformed into time-based sine wave tables 647 and 648 in a key of D comprising frequencies of $f_6=1,168$ Hz and $f_4=292$ Hz respectively. The component sine waves are then increased or decreased in amplitude by digital gain amps 626 and 624 having gain multipliers $A_6$ and $A_4$ performed arithmetically using digital multiply operations. The two sine waves are then mixed by digital summing node 630 to produce the summation g (t) where . . .

$g(t) = A_6[0.5 + 0.5\ \sin(f_6t)] + A_4[0.5 + 0.5\ \sin(f_4t)]$ $= 0.5[A_6 + A_4] + 0.5[A_6\ \sin(f_6t) + A_4\ \sin(f_4t)]$ Using a weighted average with a divisor $(A_6+A_4)$ yields ...

$$AVE[g(t)] = \frac{1}{[A_6 + A_4]} 0.5[A_6 + A_4] +$$
$$[0.5[A_6 \sin(f_6 t) + A_4 \sin(f_4 t)]]$$
$$= 0.5 + \frac{0.5}{[A_6 + A_4]}[A_6 \sin(f_6 t) + A_4 \sin(f_4 t)]$$

During averaging, the term $[A_6+A_4]$ does not affect the 0.5 offset because it appears in both the numerator and denominator of the fraction modifying the average value of the function. The second purpose of the Auto Range function, i.e. maximizing the sine component by $A_\alpha$ to full scale, does in fact change the average of the function. To avoid shifting the 0.5 average value the auto range function disclosed herein uses an additive correction factor $0.5 (1-A_\alpha)$ $$\text{Auto Range}[g(t)] = 0.5 + \frac{0.5 A_\alpha}{[A_6 + A_4]}[A_6 \sin(f_6 t) + A_4 \sin(f_4 t)]$$
$$= A_\alpha \left[0.5 + \frac{0.5}{[A_6 + A_4]}[A_6 \sin(f_6 t) + A_4 \sin(f_4 t)]\right] + (0.5 - 0.5 A_\alpha)$$
$$= \frac{0.5 A_\alpha}{[A_6 + A_4]}[A_6 \sin(f_6 t) + A_4 \sin(f_4 t)] + 0.5(1 - A_\alpha)$$
$$= A_\alpha \frac{g(t)}{[A_6 + A_4]} + 0.5(1 - A_\alpha)$$

As described the summation g (t) is scaled by auto-range function 631 by the scalar $[A_\alpha/(A_6+A_4)]$ performing a weighted average of the sine wave components along with digital multiplication by the gain factor $A_\alpha$. The resulting time varying waveform f(t) 553, shown in table 649, describes a chord 655 consisting of two sine waves of frequencies $f_6$ and $f_4$ having an average value of 0.5 and the ability to maximize the amplitude of the periodic function over the range from 0.000 to 1.000 with no signal clipping or distortion. PWM generator 555 then processes f(t) by the PWM transformation $\Psi_P[f(t)]$ producing synth out data 488 comprising a PWM string of pulses 499, referred to as $G_{synth}(t)$. Unlike f(t) which is analog, the $G_{synth}(t)$ is digital in amplitude, transitioning between a 0 (low) and 1 (high) state as a sequential series of pulses, embedding analog information in its varying pulse widths.

Figure 51A:
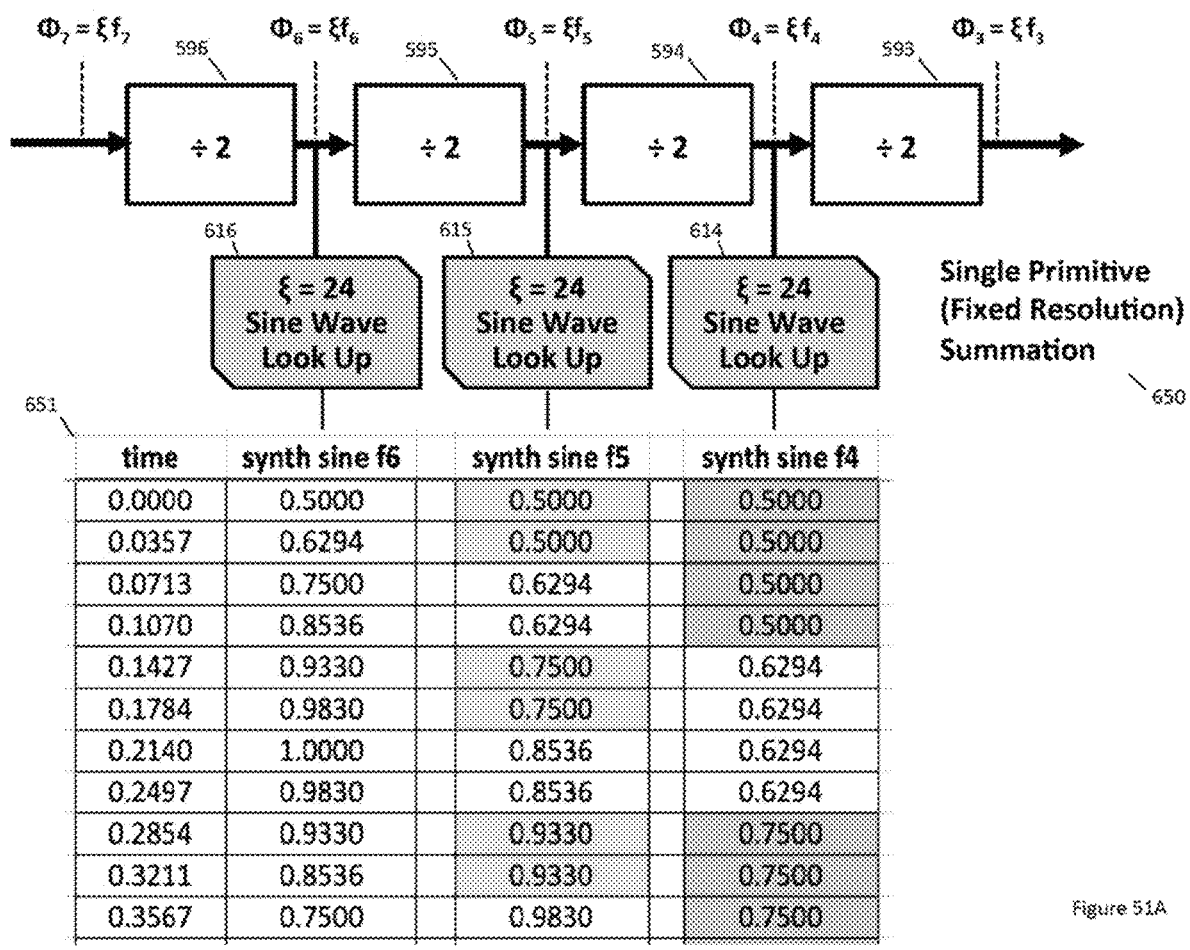
FIG. 51A is an example of three-sine-wave chord synthesis using a single fixed-resolution sine primitive.

One issue arising from the disclosed synthesis method is quantization noise. Although a single sine wave does not suffer from this issue, when two or more sine waves are added the noise appears in the waveform. This origin of the noise is illustrated in FIG. 51A where a cascade of ±2 binary counters 596 to 594 is used to produce three clocks $\Phi_6$, $\Phi_5$, and $\Phi_4$, each at half the frequency of its input. Using a fixed primitive resolution of $\xi=24$, the resulting sine waves of frequencies $f_6$, $f_5$, and $f_4$ are shown in tabular form in data table 651. Inspection reveals that although the data for frequency $f_6$ has a unique one-to-one correspondence to the clock time $\Phi_6$, the other frequencies do not change as rapidly. For example, for both t=0.1727 and t=0.1784, the data value of sine wave $f_5$ remains constant at 0.7500 even though sine wave $f_6$ changes. Similarly, for lower frequency sine wave $f_4$, the data output during the interval from t=0.1427 to 0.2497 remains constant at 0.6294, even though the $f_6$ data changes four times.

Figure 51B:
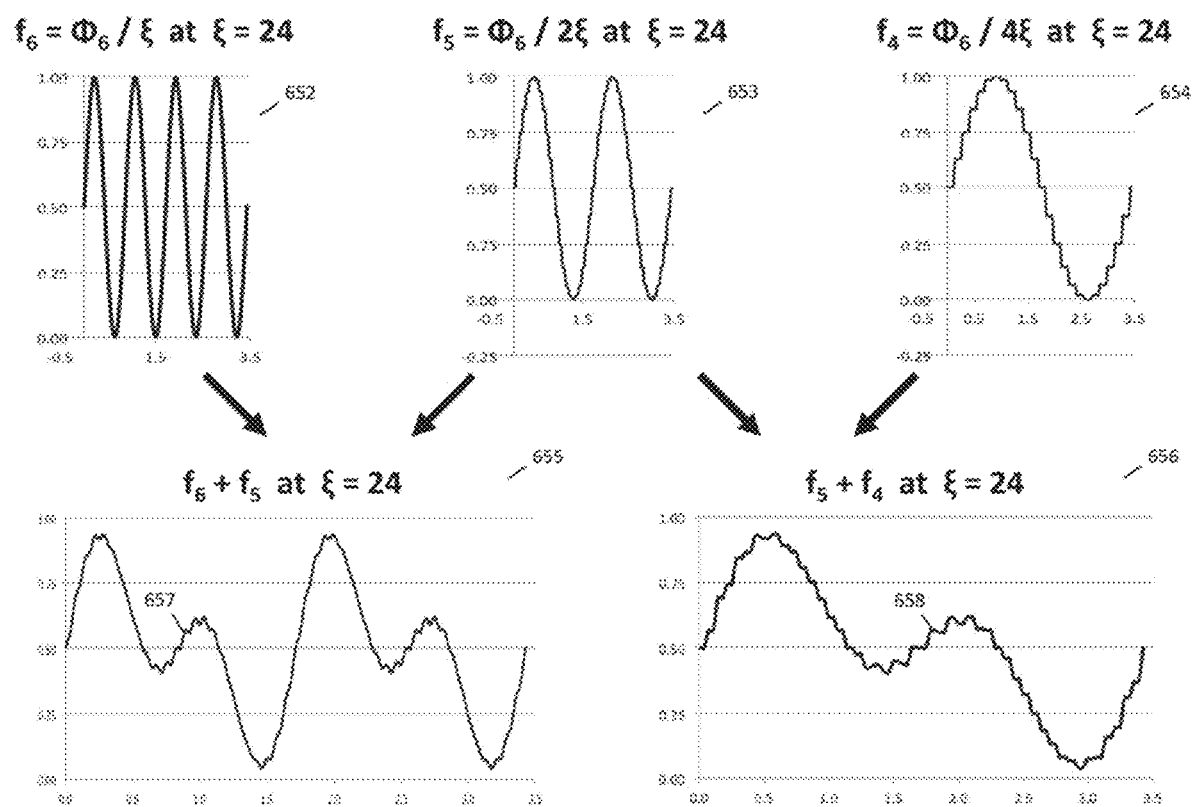
FIG. 51B illustrates exemplary sine waves and blended chords using a single fixed-resolution sine primitive highlighting quantization noise.

The impact of using a fixed resolution primitive with different clock rates is shown in FIG. 51B, where for a fixed interval in time a variety of curves are contrasted. For the duration shown, the sine wave of frequency $f_6$ shown in graph 652 exhibits no digitization noise. In contrast, sine wave of frequency $f_5$ generated by $\Phi_6/2\xi$ shown in graph 653 exhibits a small but noticeable degree of noise. The $f_4$ sine wave of graph 654 two octaves below $f_6$, i.e. where $f_4=\Phi_6/4\xi$ at $\xi=24$, shows substantial noise. The noise problem is pronounced in the two-sine chord of graph 655 combining $f_6$ and $f_5$ and even more exaggerated in graph 656 illustrating the sinusoidal summation of frequencies $f_5$ and $f_4$.

Figure 52A:
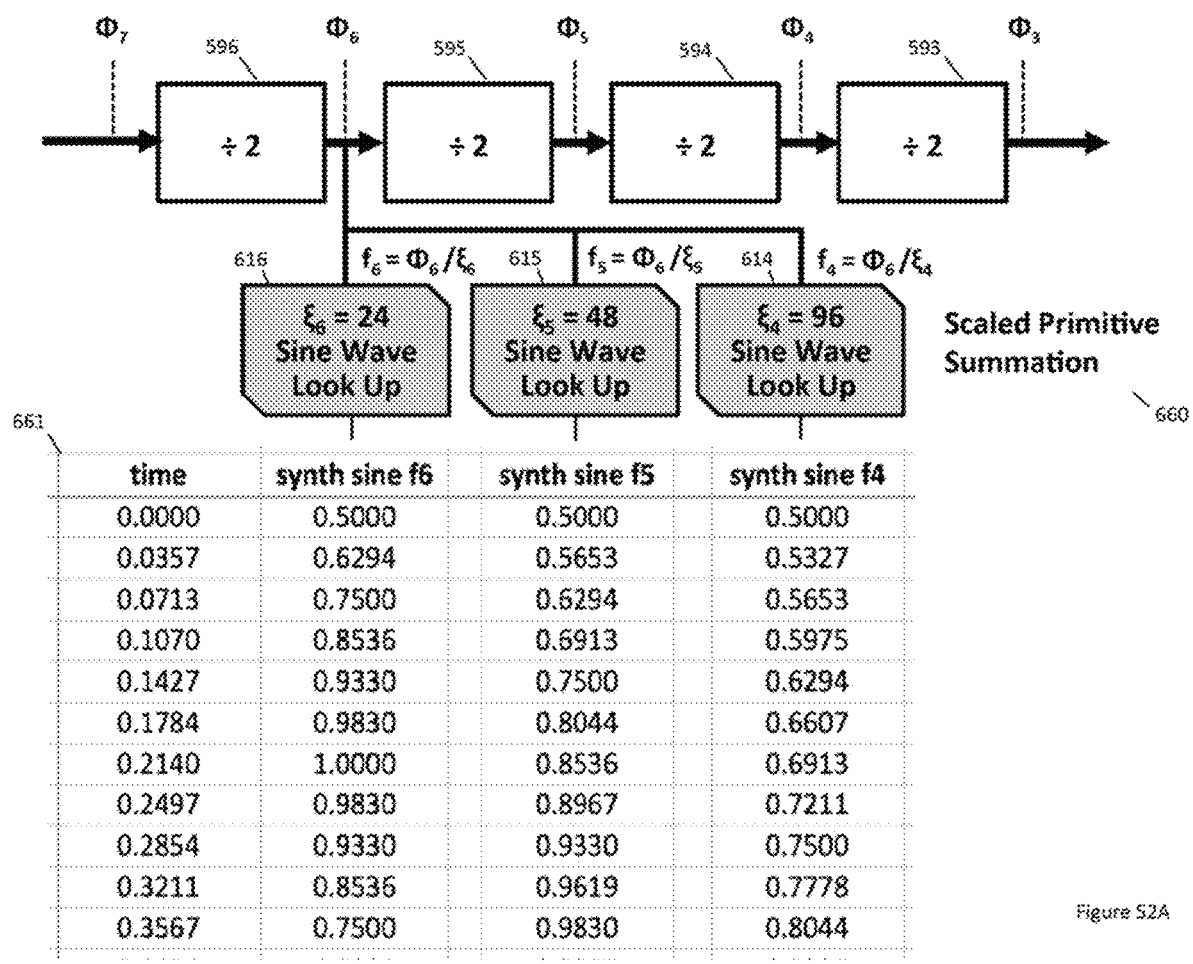
FIG. 52A is an example of three-sine-wave chord synthesis using multiple scaled-resolution sine primitives.

One resolution to this problem is illustrated in FIG. 52A where three different frequencies $f_6$, $f_5$, and $f_4$ are generated from a common clock frequency $\Phi_6$. Rather than scaling the clock frequency, instead the resolution is scaled, using higher resolution primitives to generate lower sinusoidal frequencies. Specifically, in lookup table 616, $\xi_6=24$ while in lookup table 615 the primitive resolution is doubled to $\xi_5=2\xi_6=48$ and similarly $\xi_4=4\xi_6=96$ in lookup table 614. The resulting waveforms have frequencies $$f_6=\Phi_6/\xi_6$$
$$f_5=\Phi_6/\xi_5=\Phi_6/(2\xi_6)$$
$$f_4=\Phi_6/\xi_4=\Phi_6/(4\xi_6)$$

Figure 52B:
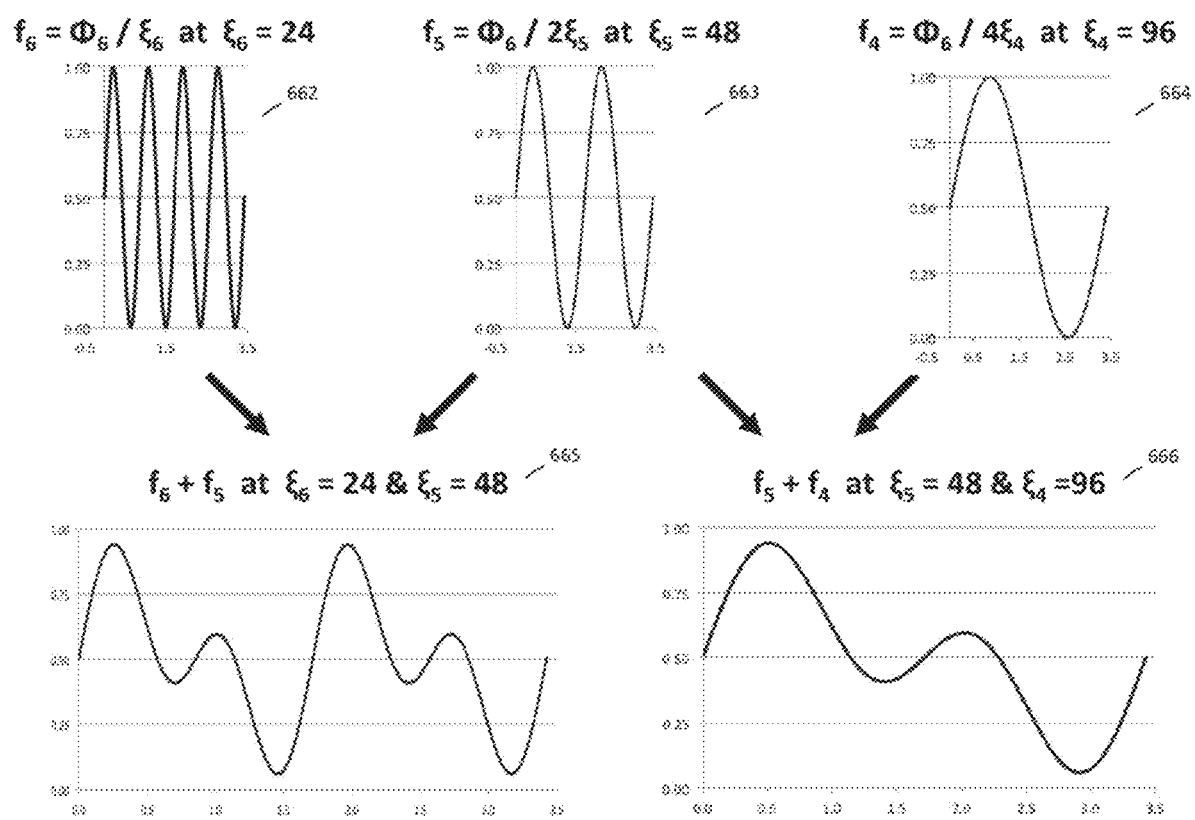
FIG. 52B illustrates exemplary sine waves and blended chords using multiple scaled-resolution sine primitives to completely eliminate quantization noise.

As indicated, sinusoidal frequencies $f_6$, $f_5$, and $f_4$, generated from a common clock $\Phi_6$, are all factors of two from one another, as shown in table 661. In this manner, the time steps are constant for all the generated frequencies. The resulting curves, shown in FIG. 52B, including sine waves 662, 623, and 624 as well as chords 665 and 666 show no signs of quantization errors at this resolution. The frequency ratio of any two sine waves using this method remains precise because the previously defined criteria $$\frac{f_x}{f_y} = \frac{\Phi_x \xi_y}{\Phi_y \xi_x} = \frac{\xi_y}{\xi_x}$$

is maintained when $\Phi_x=\Phi_y$.

In FIG. 52C this method, referred to as scaled primitive summation (block diagram 660) is contrasted to a single primitive summation (block diagram 650) for a chord blending three synthesized sine waves. In the block diagram 650 of single primitive summation, the sine wave lookup tables 616, 615 and 614 are identical in their resolution $\xi=24$ but are fed by three different clocks $\Phi_6$, $\Phi_5=\Phi_6/2$, and $\Phi_4=\Phi_6/4$, generated from a binary cascade counter. A time graph 659 of the resulting chord 671 shows significant digitization noise. In contrast, scaled primitive summation, shown in block diagram 660, employs a common clock $\Phi_6$ to drive three different resolution lookup tables 616, 615, and 614 with increasing resolutions $\xi_x=24$, 48, and 96 for x=6, 5, and 4 in corresponding order. The resulting waveform, shown in block diagram 669, shows no signs of digitization noise at this resolution.

To limit the maximum size of the primitive look up tables, the audio spectrum can be broken up into bands, e.g. upper, middle, and lower scales as well as an infrasound band (i.e. below 20 Hz) for zero and negative octaves. Such an approach is employed in the quad-range scaled-primitive synthesis block diagram shown in FIG. 53. As in the primitive processor shown in FIG. 49, the tuner counter 599 includes system clock counter 640 that converts system clock $\Phi_{sys}$ to a fixed reference frequency $\Phi_{ref}$, e.g. 5 MHz, and symbol clock counter 641 that converts the reference frequency $\Phi_{ref}$ to clock frequency $\Phi_{sym}$, where the clock frequency $\Phi_{sym}$ is defined by the ratio $\Phi_{sym}/\Phi_{ref} = (32 \xi_{key})/(5 \text{ MHz})$ in accordance with key select input 642, a note or key in the fourth octave. In the cascade of counters comprising tuner 590, and three divide-by-8 counters 672, 673 and 674, four frequencies are cogenerated to produce the clocks $\Phi_{sym}$, $\Phi_6 = \Phi_{sym}/8$, $\Phi_3 = \Phi_{sym}/64$, and $\Phi_0 = \Phi_{sym}/512$. Although counters 672 through 674 each comprise a three-stage binary cascade counter, for brevity's sake have been represented as single ±8 counters.

The highest frequency clock of the cascade, the symbol clock $\Phi_{sym}$, is then used to synthesize sine waves in four bands or scales. In the upper scale $\Phi_{sym}$ is used to generate sine waves $f_9$, $f_8$ and $f_7$ in accordance with selector switches 609, 608, and 607 respectively. If a selector switch is enabled, the clock pulse for $\Phi_{sym}$ is passed to the corresponding sine wave lookup table 699, 698, or 697 to produce sine waves $f_9$, $f_8$ and $f_7$ as desired.

Specifically, sine wave lookup table 699 with resolution $\xi=24$, if enabled, produces a sine wave $f_9$ with a frequency $f_9 = \Phi_{sym}/\xi_9$. Sine wave $f_9$ has a frequency 32 times the $f_{key}$ key select frequency and $1/24^{th}$ of the symbol frequency $\Phi_{sym}$. In the same upper scale, sine wave lookup table 698 with resolution $\xi_8=48$, if enabled, produces a sine wave $f_8$ with a frequency $f_8 = \Phi_{sym}/\xi_8 = \Phi_{sym}/(2 \xi_9)$. Sine wave $f_8$ has a frequency 16 times the $f_{key}$ key select frequency and $1/48^{th}$ of the symbol frequency $\Phi_{sym}$. Similarly, sine wave lookup table 697 with resolution $\xi_7=96$, if enabled, produces a sine wave $f_7$ with a frequency $f_7 = \Phi_{sym}/\xi_7 = \Phi_{sym}/(4\xi_9)$. Sine wave $f_7$ has a frequency 8 times the $f_{key}$ key select frequency and $1/96^{th}$ of the symbol frequency $\Phi_{sym}$. Because generation of sinusoids with frequencies $f_9$, $f_8$ and $f_7$ comes from the same clock frequency $\Phi_{sym}$, their waveform synthesis employs the same time increments, thereby avoiding the aforementioned issue of digitization error within the upper scale.

The same clock $\Phi_{sym}$ is also divided by 8 in counter 672 to produce a lower frequency rate clock $\Phi_6$ used for sinusoid synthesis of sine waves $f_6$, $f_5$, and $f_4$ in the middle scale. If any selector switch 606, 605, and 604 is enabled, the clock pulse comprising $\Phi_6 = \Phi_{sym}/8$ is passed to the corresponding sine wave lookup table 696, 695, or 694 to produce sine waves $f_6$, $f_5$ and $f_4$ as desired. Specifically, sine wave lookup table 696 with resolution $\xi_6=24$, if enabled, produces a sine wave $f_6$ with a frequency $f_6 = \Phi_6/\xi_6 = \Phi_{sym}/(86)$. Sine wave $f_6$ has a frequency four times the $f_{key}$ key select frequency and 1/192 of the symbol frequency $\Phi_{sym}$. In the same middle scale, sine wave lookup table 695 with resolution $\xi=48$, if enabled, produces a sine wave $f_5$ with a frequency $f_5 = \Phi_6/\xi_5 = \Phi_{sym}/(16 \xi_6)$. Sine wave $f_5$ has a frequency 2 times the $f_{key}$ key select frequency and 1/384 of the symbol frequency $\Phi_{sym}$. Similarly, sine wave lookup table 694 with resolution $\xi=96$, if enabled, produces a sine wave $f_4$ with a frequency $f_4 = \Phi_6/\xi_4 = \Phi_{sym}/(32 \xi_6)$. Sine wave $f_4$ has a frequency equal to the $f_{key}$ key select frequency and 1/768 of the symbol frequency $\Phi_{sym}$. Because generation of sinusoids with frequencies $f_6$, $f_5$ and $f_4$ comes from the same clock frequency $\Phi_6 = \Phi_{sym}/8$, the waveform synthesis employs the same time increments, thereby within the middle scale avoiding the aforementioned issue of digitization error.

To generate sinusoid $f_3$, $f_2$, and $f_1$ in the lower scale, clock $\Phi_6$ is divided by 8 in counter 673 to produce a lower frequency rate clock $\Phi_3$. If any selector switch 603, 602, and 601 is enabled, the clock pulse comprising $\Phi_3 = \Phi_{sym}/64$ is passed to the corresponding sine wave lookup table 693, 692, or 691 to produce sine waves $f_3$, $f_2$ and $f_1$ as desired. Specifically, sine wave lookup table 693 with resolution $\xi=24$, if enabled, produces a sine wave $f_3$ with a frequency $f_3 = \Phi_3 = \Phi_{sym}/(64\xi_3)$. Sine wave $f_3$ has a frequency $f_3$ of $\frac{1}{2}^{th}$ the $f_{key}$ key select frequency and 1/1,536 of the symbol frequency $\Phi_{sym}$. In the same lower scale, sine wave lookup table 692 with resolution a $\xi_2=48$, if enabled, produces a sine wave $f_2$ with a frequency $f_2 = \Phi_3/\xi_2 = \Phi_{sym}/(128 \xi_3)$. Sine wave $f_2$ has a frequency $\frac{1}{4}^{th}$ the $f_{key}$ key select frequency and 1/3,072 of the symbol frequency $\Phi_{sym}$. Similarly, sine wave lookup table 691 with resolution $\xi_1=96$, if enabled, produces a sine wave $f_1$ with a frequency $f_1 = \Phi_3/\xi_1 = \Phi_{sym}/(256 \xi_3)$. Sine wave $f_1$ has a frequency $\frac{1}{8}^{th}$ the $f_{key}$ key select frequency and 1/6,144 of the symbol frequency $\Phi_{sym}$. Because generation of sinusoids with frequencies $f_3$, $f_2$ and $f_1$ comes from the same clock frequency $\chi_3 = \Phi_{sym}/64$ the waveform synthesis employs the same time increments, thereby within the lower scale avoiding the aforementioned issue of digitization error.

The counter cascade can also be used to generate infrasound excitation of the LEDs, i.e. sine waves having frequencies below 20 Hz. As shown, the output of divide-by-8 counter 674 having a clock frequency $\Phi_0 = \Phi_{sym}/512$, if chosen by selector switch 600 produces a sine wave $f_0$ at a resolution $\xi_0=24$ where the generated frequency is given by $f_0 = \Phi_0/\xi_0 = \Phi_{sym}/(514\xi_0)$. Using the above principles, the scaling concept can be extended to produce two lower infrasound frequencies $f_{-1}$ and $f_{-2}$ (as desired) by including two additional sine look-up tables with respective resolutions 48 and 96 driven by clock $\Phi_0$.

In the foregoing discussion, the use of time increments comprising constant intervals minimizes quantization noise but requires larger higher-resolution look up tables increasing the required memory capacity within a LED pad.

Provided that a lookup table has the required number of data points, a single table can be used to generate multiple octaves of data from a single clock. For example, a table of 24,576 points can be used to synthesize sine waves spanning 11 octaves with an angle precision of 0.0146484375° per data point. Combining a 337,920 Hz clock with an 11 octave universal primitive table, frequencies can be generated, e.g. in the key-of-A ranging from $f_9 = \Phi_{sym}/\xi_{sym} = 14,080$ Hz in the $9^{th}$ octave down to 13.75 Hz in the −1st octave (including A at 440 Hz). This example is illustrated in the $4^{th}$ column of the table below. Using the same symbol clock rate, i.e. in the same table column, if the number of synthesized frequencies is reduced to only 7 octaves, the size of the universal primitive data table shrinks to 1,536 data points spanning a range from 14,080 Hz in the $9^{th}$ octave down to $f_3=220$ Hz.

Alternatively, using the same 7-octave universal primitive table, the frequency band covered can be shifted by employing a lower symbol clock rate. For example, as shown in the $5^{th}$ column of the table below, with symbol clock rate $\Phi_{sym}=168,960$ Hz, a 1,536 data point universal primitive, can cover a range from 7,040 Hz in the $8^{th}$ octave down to 110 Hz in the $2^{nd}$ octave. By shrinking the table size and lowering the symbol clock, a compromise in sine wave frequency range and data table size is also possible. Referring to the $6^{th}$ column of the table below, a symbol clock rate of $\Phi_{sym}=42,240$ Hz can generate sine waves from 1,760 Hz in the $6^{th}$ octave to 55 Hz in the $1^{st}$ octave using a look-up table with only 768 data points.

| # Oct | Resolution $\xi$ | Angle $\theta$ | $\Phi_{sym} =$ 337,920 Hz | $\Phi_{sym} =$ 168,960 Hz | $\Phi_{sym} = 42,240$ Hz |
|---|---|---|---|---|---|
| 1 | $\xi_{sym} = 24$ | 15° | $f_9 = 14,080$ Hz | $f_8 = 7,040$ Hz | $f_6 = 1,760$ Hz |
| 2 | 48 | 7.5° | $f_8 = 7,040$ Hz | $f_7 = 3,520$ Hz | $f_5 = 880$ Hz |
| 3 | 96 | 3.75° | $f_7 = 3,520$ Hz | $f_6 = 1,760$ Hz | $f_4 = 440$ Hz |
| 4 | 192 | 1.875° | $f_6 = 1,760$ Hz | $f_5 = 880$ Hz | $f_3 = 220$ Hz |
| 5 | 384 | 0.98375° | $f_5 = 880$ Hz | $f_4 = 440$ Hz | $f_2 = 110$ Hz |
| 6 | 768 | 0.46875° | $f_4 = 440$ Hz | $f_3 = 220$ Hz | $f_1 = 55$ Hz |
| 7 | 1,536 | 0.234375° | $f_3 = 220$ Hz | $f_2 = 110$ Hz | — |
| 8 | 3.072 | 0.1171875° | $f_2 = 110$ Hz | — | — |
| 9 | 6,144 | 0.05859375° | $f_1 = 55$ Hz | — | — |
| 10 | 12,288 | 0.029296875° | $f_0 = 27.5$ Hz | — | — |
| 11 | 24,576 | 0.0146484375° | $f_{-1} = 13.75$ Hz | — | — |

Figure 54:
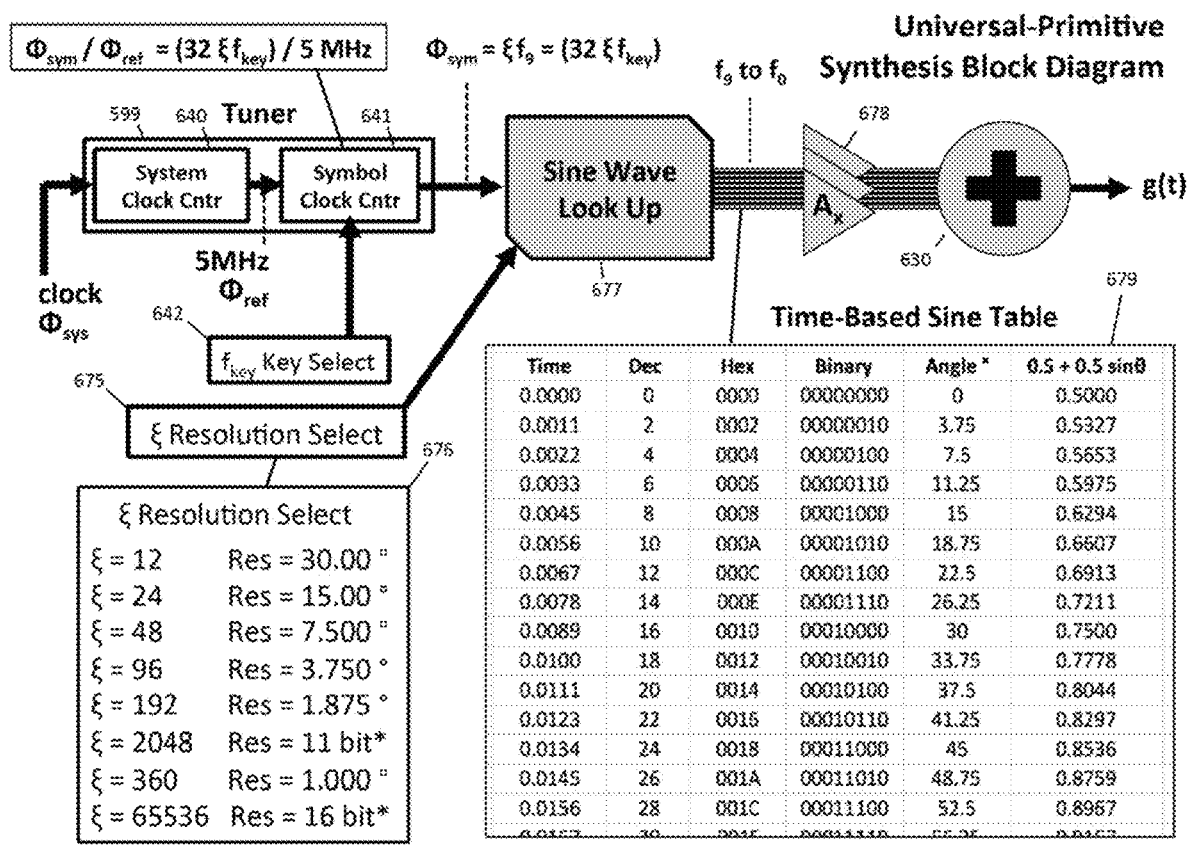
FIG. 54 is a block diagram of a universal-primitive sinusoidal chord synthesizer applicable for any resolution sine primitive.

The process of waveform synthesis using universal-primitive synthesis is shown in FIG. 54 where tuner counter 599 generates a programmable symbol clock $\Phi_{sym}=I_{ref}/(32\ \xi f_{key})$ in accordance with key select 642, transforming the clock into one or more sine waves varying in frequency, e.g. from $f_9$ to $f_0$, using universal primitive sine wave look up table 677. The sine waves are then blended in accordance with digital gain amps 678 with programmable gains $A_x$ and summed in a mixer 630 to produce g (t). As shown, for each sine wave synthesized, conversion from the clock $\Phi_{sym}$ to time-based sine table 679 depends on Resolution Select" input 675 and the resolution choices available. Table 676 is shown to, without limitation, demonstrate available table resolutions from a minimum of 12 points to 16-bit resolution having 65,536 data points. The number of data points in sine wave look-up table 677 determines the maximum resolution available.

In waveform synthesis using a universal primitive table, the same table is employed to generate any sine wave with equal or lower precision than the table's precision. For example, if the table 677 resolution is 96 points, i.e. increments of 3.75°, the same table can be used to generate sine waves with 48, 24 or 12 points, the higher the resolution, the lower the synthesized frequency.

| | | Symbol Clock $\Phi_{sym} = 224,256$ Hz, T = 4.5 μs | | | |
|---|---|---|---|---|---|
| | | Resolution | | | |
| Row | Angle | $\xi_{sym} = 24$ $f_{max} = 9,344$ Hz | $\xi_{sym} = 48$ $f_{max}/2 = 4,672$ Hz | $\xi_{sym} = 96$ $f_{max}/4 = 2,336$ Hz | $\xi_{sym} = 192$ $f_{max}/8 = 1,168$ Hz |
| 00 | 0.00 | 0.0000 | 0.0000 | 0.0000 | 0.0000 |
| 01 | 3.75 | — | — | — | 0.0011 |
| 02 | 7.50 | — | — | 0.0011 | 0.0022 |
| 03 | 11.25 | — | — | — | 0.0033 |
| 04 | 15.00 | — | 0.0011 | 0.0022 | 0.0045 |
| 05 | 18.75 | — | — | — | 0.0056 |
| 06 | 22.50 | — | — | 0.0033 | 0.0067 |
| 07 | 26.25 | — | — | — | 0.0078 |
| 08 | 30.00 | 0.0011 | 0.0022 | 0.0045 | 0.0089 |
| 09 | 33.75 | — | — | — | 0.0100 |
| 0A | 37.50 | — | — | 0.0056 | 0.0111 |
| 0B | 41.25 | — | — | — | 0.0123 |
| 0C | 45.00 | — | 0.0033 | 0.0067 | 0.0134 |
| 0D | 48.75 | — | — | — | 0.0145 |
| 0E | 52.50 | — | — | 0.0078 | 0.0156 |
| 0F | 56.25 | — | — | — | 0.0167 |
| 10 | 60.00 | 0.0022 | 0.0045 | 0.0089 | 0.0178 |

Various frequency sine waves are synthesized by looking up the data for every angle or by systematically skipping angles. For example, in the table above, using a symbol clock with a frequency $\Phi_{sym}=224,256$ Hz with rows 00, 04, 08, 0C, 10 . . . results in a 5,672 Hz sine wave while selecting every row in table produces a 1,168 Hz sine wave.

Key Select and Custom Waveform Synthesis

As described previously, because the periodic waveform generation involves a cascade counter with fixed frequency-multiples, the waveform synthesizer is essentially "tuned" to specific key. The user interface (UI) and resulting operation (UX or user experience) is shown in FIG. 55A, where a user selects the "CHOOSE A KEY" menu 701 facilitating key selection for various "Musical" scales, "Physiological" (reported medical frequencies) scales, "Custom" scales including manual entry, and "Other" scales. It also includes a provision to return to "default" scales settings. Upon selecting the "musical" setting the "ENTER A KEY" menu 702 appears. Choosing a note in menu 702 selects a predefined scale to be loaded into the LED pad into "$f_{key}$ key select" input 641, ranging from middle C at 261.626 Hz to middle B at 493.883 Hz. as stored in table 703. If middle A is selected, then table 703 will transfer the value of "A" 440 Hz into the symbol clock counter 642 in accordance with $\Phi_{sym}\Phi_{ref}=(32\ \xi f_{key})/(5\ \text{MHz})$ generating a symbol rate $\Phi_{sym}=(32\ f_{key})$ from whence various frequency sine waves based on this scale are synthesized, e.g. $f_9=\Phi_{sym}/\xi_9$. A table of exemplary frequencies by octave is shown below for a variety of tunings for musical keys of C through F (https://en.wikipedia.org/wiki/Scientific_pitch_notation). The scales shown are referred to as "equal tempered" tuning.

| Key | C | C#/Db | D | D#/Eb | E | F |
|---|---|---|---|---|---|---|
| $f_9 = f_{max}$ | 8372.0 (120) | 8869.8 (121) | 9397.3 (122) | 9956.1 (123) | 10548 (124) | 11175 (125) |
| $f_8$ | 4186.0 (108) | 4434.9 (109) | 4698.6 (110) | 4978.0 (111) | 5274.0 (112) | 5587.7 (113) |
| $f_7$ | 2093.0 (96) | 2217.5 (97) | 2349.3 (98) | 2489.0 (99) | 2637.0 (100) | 2793.8 (101) |
| $f_6$ | 1046.5 (84) | 1108.7 (85) | 1174.7 (86) | 1244.5 (87) | 1318.5 (88) | 1396.9 (89) |
| $f_5$ | 523.25 (72) | 554.37 (73) | 587.33 (74) | 622.25 (75) | 659.26 (76) | 698.46 (77) |
| $f_4 = f_{key}$ | 261.63 (60) | 277.18 (61) | 293.66 (62) | 311.13 (63) | 329.63 (64) | 349.23 (65) |
| $f_3$ | 130.81 (48) | 138.59 (49) | 146.83 (50) | 155.56 (51) | 164.81 (52) | 174.61 (53) |
| $f_2$ | 65.406 (36) | 69.296 (37) | 73.416 (38) | 77.782 (39) | 82.407 (40) | 87.307 (41) |
| $f_1$ | 32.703 (24) | 34.648 (25) | 36.708 (26) | 38.891 (27) | 41.203 (28) | 43.654 (23) |
| $f_0$ | 16.352 (12) | 17.324 (13) | 18.354 (14) | 19.445 (15) | 20.602 (16) | 21.827 (17) |
| $f_{-1}$ | 8.176 (0) | 8.662 (1) | 9.177 (2) | 9.723 (3) | 10.301 (4) | 10.914 (5) |

A table of exemplary frequencies by octave is shown below for a variety of tunings for musical keys of F#/Gb through B. The scales shown are referred to as "equal tempered".

| Key | F#/Gb | G | G#/Ab | A | A#/Bb | B |
|---|---|---|---|---|---|---|
| $f_9 = f_{max}$ | 11838.8 (126) | 12543.8 (127) | 13289.8 (—) | 14,080.0 (—) | 14917.2 (—) | 15804.0 (—) |
| $f_8$ | 5919.9 (114) | 6271.9 (115) | 6644.9 (116) | 7040.0 (117) | 7458.6 (118) | 7902 (119) |
| $f_7$ | 2960.0 (102) | 3136.0 (103) | 3322.4 (104) | 3520.0 (105) | 3729.3 (106) | 3951 (107) |
| $f_6$ | 1480.0 (90) | 1568.0 (91) | 1661.2 (92) | 1,760.0 (93) | 1864.7 (94) | 1975.5 (95) |
| $f_5$ | 739.99 (78) | 783.99 (79) | 830.61 (80) | 880.00 (81) | 932.33 (82) | 987.77 (83) |
| $f_4 = f_{key}$ | 369.99 (66) | 392.00 (67) | 415.30 (68) | 440.00 (69) | 466.16 (70) | 493.88 (71) |
| $f_3$ | 185.00 (54) | 196.00 (55) | 207.55 (56) | 220.00 (57) | 233.08 (58) | 246.94 (59) |
| $f_2$ | 92.499 (42) | 97.999 (43) | 103.83 (44) | 110.00 (45) | 116.54 (46) | 123.47 (47) |
| $f_1$ | 46.125 (30) | 48.999 (31) | 51.913 (32) | 55.000 (33) | 58.270 (34) | 61.735 (35) |
| $f_0$ | 23.125 (18) | 24.500 (19) | 25.957 (20) | 27.500 (21) | 29.135 (22) | 30.868 (23) |
| $f_{-1}$ | 11.563 (6) | 12.250 (7) | 12.979 (8) | 13.750 (9) | 14.568 (10) | 15.434 (11) |

Another option in UI menu 701 is the selection "Other", in which case other scales are used to modulate the LEDs. These scales, including Pythagorean, Just Major, Mean-tone, and Werckmeister, shown in the table below, share the frequency for middle C at 261.626 Hz with the even-tempered scale but differ in the relative frequency relationships between the twelve half steps spanning an octave. For example, in an even-tempered scale, the tone of $A_4$ above middle C is set to 440 Hz but in other scales varies from 436.05 Hz to 441.49 Hz.

In "Other" mode, the user interface (UI) and resulting operation (UX user experience) is shown in FIG. 55B, where a user selects the "CHOOSE A KEY" menu 701 and selects "OTHER" opening "CHOOSE A SCALE" menu 700. The user then selects an alternative tuning from the menu—either Pythagorean, Just Major, Mean-tone, and Werckmeister, opening submenu 702 entitled ENTER A KEY. Once the key (note) is selected, the frequency is selected from the tuning table below and loaded into "$f_{key}$ Key Select" key register 641 which is subsequently transferred to the LED pad and ultimately loaded into symbol clock counter 642. For example, if the key "A" is selected from the Werckmeister scale, then the value of "A" at 437.05 Hz will be loaded into the symbol clock counter 642 in accordance with $\Phi_{sym}/\Phi_{ref}=(32\ \xi f_{key})/(5\ \text{MHz})$. Accordingly, the symbol counter generates a symbol rate $\Phi_{sym}=(32\ \xi f_{key})$ from whence various frequency sine waves based on this scale are synthesized, e.g. $f_9=\Phi_{sym}/\xi_9$. Since the key frequency $f_{key}$ is used to generate then $\Phi_{sym}$ then the entire nine-octave scale is adjusted accordingly. For example, if $f_{key}=f_4$ is set to 437.05 Hz, then $f_5=2f_4=874.1$ Hz, $f_6=4f_4=1,748.2$ Hz, etc.

| Note | Equal Tempered | Werckmeister | Note | Pythagorean | Just Major | Mean Tone |
|---|---|---|---|---|---|---|
| $C_5$ | 523.25 | 523.25 | $C_5$ | 523.25 | 523.25 | 523.25 |
| $B_4$ | 493.88 | 491.67 | B | 496.67 | 490.55 | 489.03 |
| A#/Bb | 466.16 | 465.12 | $B^b$ | 465.12 | 470.93 | 468.02 |
| A | 440.00 | 437.05 | A | 441.49 | 436.05 | 437.41 |
| G#/Ab | 415.30 | 413.42 | $A^b$ | 413.42 | 418.60 | 418.60 |
| G | 392.00 | 391.16 | G | 392.44 | 392.44 | 391.21 |
| F#/Gb | 369.99 | 367.51 | F# | 372.52 | 367.92 | 365.62 |
| F | 349.23 | 348.83 | F | 348.83 | 348.83 | 349.92 |
| E | 329.62 | 327.76 | E | 331.11 | 327.03 | 327.03 |
| D#/Eb | 311.13 | 310.08 | $E^b$ | 310.08 | 313.96 | 312.98 |
| D | 293.66 | 292.37 | D | 294.33 | 294.33 | 292.50 |
| C#/Db | 277.18 | 275.62 | C# | 279.39 | 272.54 | 273.37 |
| $C_4$ | 261.63 | 261.63 | $C_4$ | 261.63 | 261.63 | 261.63 |

And although the scales vary throughout the octave, they all match one another for the frequency C. For example, as shown for comparative purposes, the fifth octave Cs frequencies shown in the below table all match at $f_5=525.25$ Hz$=2f_4$. The notation used by Pythagorean, Just Major, and Mean-tone, scales differ slightly from the Werckmeister and even-tempered scales in their use of sharps # and flats b. Although the exact effects of tuning on PBT efficacy are not well characterized, scientific studies have confirmed that therapeutic efficacy of PBT treatments is clearly frequency dependent. If on UI menu 701, the item "Physio" is selected, frequency scales reported in these medical studies to be therapeutically beneficial are used for the value of $f_{key}$. If instead the Custom button in menu 701 is selected, as shown in FIG. 56, a UX response comprising the custom "ENTER A KEY" menu 704 will appear. Upon entering a number on the keypad, e.g. 444 Hz as shown, and depressing the DONE button, the $f_{key}$ key select register 641 is loaded with the custom key value 444 Hz and transferred to symbol clock generator 642. This value is then used to calculate the symbol clock rate using symbol clock counter 642 in accordance with the relation $\Phi_{sym}/\Phi_{ref}=(32\ \xi f_{key})/(5\ MHz)$ to produce an output $\Phi_{sym}=(32\ \xi f_{key})$.

Figure 57A:
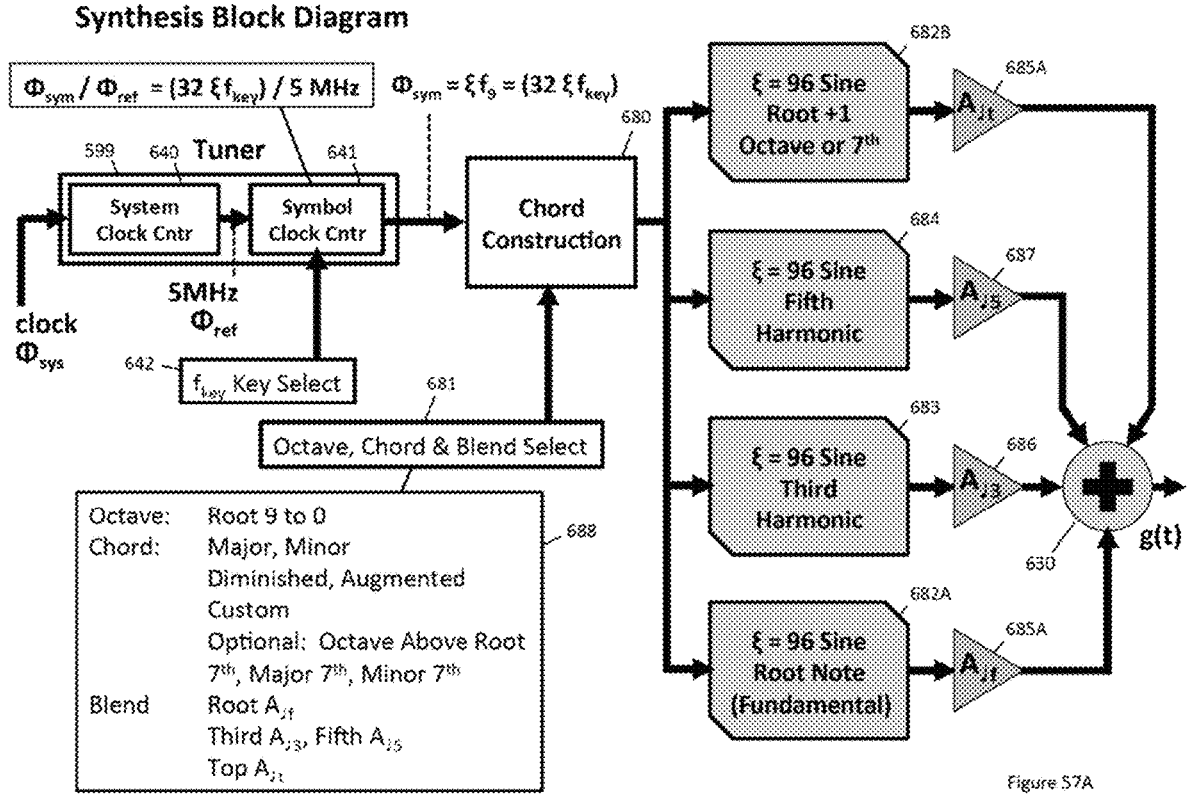
FIG. 57A is a block diagram of an algorithmic chord builder for musical-chord triad/quad synthesis (with optional+1 octave note), including major, minor, augmented, and diminished chords.

The disclosed PBT system is also capable of generating excitation patterns comprising a chord of three frequencies within the same octave, i.e. a triad, and optionally with an additional frequency as a $7^{th}$ or one octave higher than the root note of the chord. A block diagram of an algorithmic chord builder is shown in FIG. 57A, where tuner counter 599 set in accordance with $f_{key}$ key select 642 produces a symbol clock with frequency $\Phi_{sym}=(32\ f_{key})$ which is fed into a chord construction algorithm 680. The chord builder in turn, uses well-known mathematical relationships to generate the frequency components of various common chord types in accordance with "Octave, Chord & Blend Select" input 681 selected from chord builder menu 688. Triad chords include selection of the octave of the root note in which the chord will be constructed and the type of chord to be implemented, i.e. major, minor, diminished, augmented, or custom. Quad chords include a $7^{th}$, a minor $7^{th}$, a major $7^{th}$ or any of the aforementioned triads with an added note one octave above the root. The relative amplitude or "blend" of the component frequencies are also specified in table 688 comprising the volume of the chord's root note, its third, fifth, and optionally a $7^{th}$ or a note one octave above the root.

In operation, chord construction algorithm 680 uses a scaled fraction of symbol clock $\Phi_{sym}$ to drive four lookup up tables 682B, 684, 683 and 682A to synthesize four sine waves with a fundamental root at frequency $f_{\downarrow}f$, a third at a frequency $f_{\downarrow}3$, a fifth at a frequency $f_{\downarrow}5$ and a top note either a $7^{th}$ or a note one octave higher than the root (depending on the selection) with a frequency $f_{\downarrow}t$. The three or four frequencies are then blended in accordance with digital gain amps 685A, 686, 687, and 685B with gains $A_{\downarrow}f$, $A_{\downarrow}3$, $A_{\downarrow}5$ and $A_{\downarrow}t$ respectively, and mixed in summing node 630 to create g (t).

The exact frequencies of the notes in the chord depend on the value of the selected octave 681 and by the value of $f_{key}$ key select 642, i.e. the tuning or key of the binary cascade counters. Together these synthesizer settings determine the frequency or the root note, also referred to as the fundamental of chord. The remaining notes in the chord are calculated as a ratio to the chord's fundamental frequency in accordance with the following table describing the frequency ratio of common musical chords (https://pages.mt-u.edu/~suits/chords.html):

the chord, the root note of the chord, the note of the $3^{rd}$, i.e. the next higher note, the note of the $5^{th}$, i.e. the third highest note, and optionally whether to include a note one octave above the root. Once the root note is selected, the $3^{rd}$, $5^{th}$, and +1 octave notes are monotonically arranged in ascending frequency, even if the notes extend into the next higher octave. The second and third inversion of any chord must be entered as a custom chord using the lowest pitch note as the chord's root. The notes are evenly weighted in volume unless otherwise adjusted using the up and down arrows. Once the parameters are entered, after a time-out period or as signaled by other means such as a double screen tap, the parameters are formatted into data table 688 and eventually transferred to the chord construction algorithm block 680 within the intelligent LED pads where sine wave look up tables 677, digital gain stages 678, and mixer 630 create g (t). In the event that another menu item is selected from the CHOOSE A CHORD menu 705, a different submenu (not shown) will open allowing the user to select the octave and the relative amplitude mix of the constituent frequency components. The submenu, however, does not allow a user to change the notes since the relative frequencies present in a minor, major, diminished, etc. chord are precisely defined.

Returning to the synthesizer block diagram of FIG. 44, regardless of the synthesized waveform or how it was created, the waveform g (t) must be processed to create f(t) 553 by limiting its range between 0.000 and 1.000 in order for PWM generator 555 to perform the value-to-PWM-duty-factor transformation $\Psi_P[f(t)]$ required to create synth out file 488. Since the maximum duty factor of a PWM modulated pulse is 100%, i.e. one lasting the full clock cycle, a PWM representation of data over 1.000 is not possible. As such the PWM transformation is limited to $0\% \le \Psi_P[f(t)] \le 100\%$, and therefore $0.000 \le f(t) \le 1.000$. The autorange operation 584 (shown in FIG. 46) averages the function g (t) while limiting the range of the data and f(t) to that of unit function, i.e. between 0.000 and 1.000.

An example of autorange operation 584 is illustrated in FIG. 58A, wherein the sum of sine waves 662, 663, and 664 results in chord 669. Although each of these sine waves extends over the full range from 0.000 to 1.000, the sum of the sine waves in chord 669 does not span the full extent of a unit function. As shown, the mathematical average of the chord, specifically 0.5, remains constant, but the periodic time-varying function does not extend over the full range of $0.5 \pm 0.5$. As shown in FIG. 58B, chord 669 only extends

| Chord (+Option) | Half Steps | Integer Freq. Ratios | Ratiometric Chord Frequencies |
|---|---|---|---|
| Major (+Octave) | 4, 3, (5) | 4:5:6:(8) | $f_{\downarrow f}$, $f_{\downarrow 3} = 1.25\ f_{\downarrow f}$, $f_{\downarrow 5} = 1.5\ f_{\downarrow f}$, $f_{\downarrow t} = 2\ f_{\downarrow f}$ |
| Minor (+Octave) | 3, 4, (5) | 10:12:15:(20) | $f_{\downarrow f}$, $f_{\downarrow 3} = 1.2\ f_{\downarrow f}$, $f_{\downarrow 5} = 1.5\ f_{\downarrow f}$, $f_{\downarrow t} = 2\ f_{\downarrow f}$ |
| Diminished (+Octave) | 3, 3, (6) | 160:192:231:(320) | $f_{\downarrow f}$, $f_{\downarrow 3} = 1.2\ f_{\downarrow f}$, $f_{\downarrow 3} = 1.444\ f_{\downarrow f}$, $f_{\downarrow t} = 2\ f_{\downarrow f}$ |
| $7^{th}$ | 4, 3, 3 | 20:25:30:36 | $f_{\downarrow f}$, $f_{\downarrow 3} = 1.25\ f_{\downarrow f}$, $f_{\downarrow 5} = 1.5\ f_{\downarrow f}$, $f_{\downarrow t} = 1.8\ f_{\downarrow f}$ |
| Minor $7^{th}$ | 3, 4, 3 | 10:12:15:18 | $f_{\downarrow f}$, $f_{\downarrow 3} = 1.2\ f_{\downarrow f}$, $f_{\downarrow 5} = 1.5\ f_{\downarrow f}$, $f_{\downarrow t} = 1.8\ f_{\downarrow f}$ |
| Major $7^{th}$ | 4, 3, 4 | 8:10:12:15 | $f_{\downarrow f}$, $f_{\downarrow 3} = 1.25\ f_{\downarrow f}$, $f_{\downarrow 5} = 1.5\ f_{\downarrow f}$, $f_{\downarrow t} = 1.875\ f_{\downarrow f}$ |

Figure 57B:
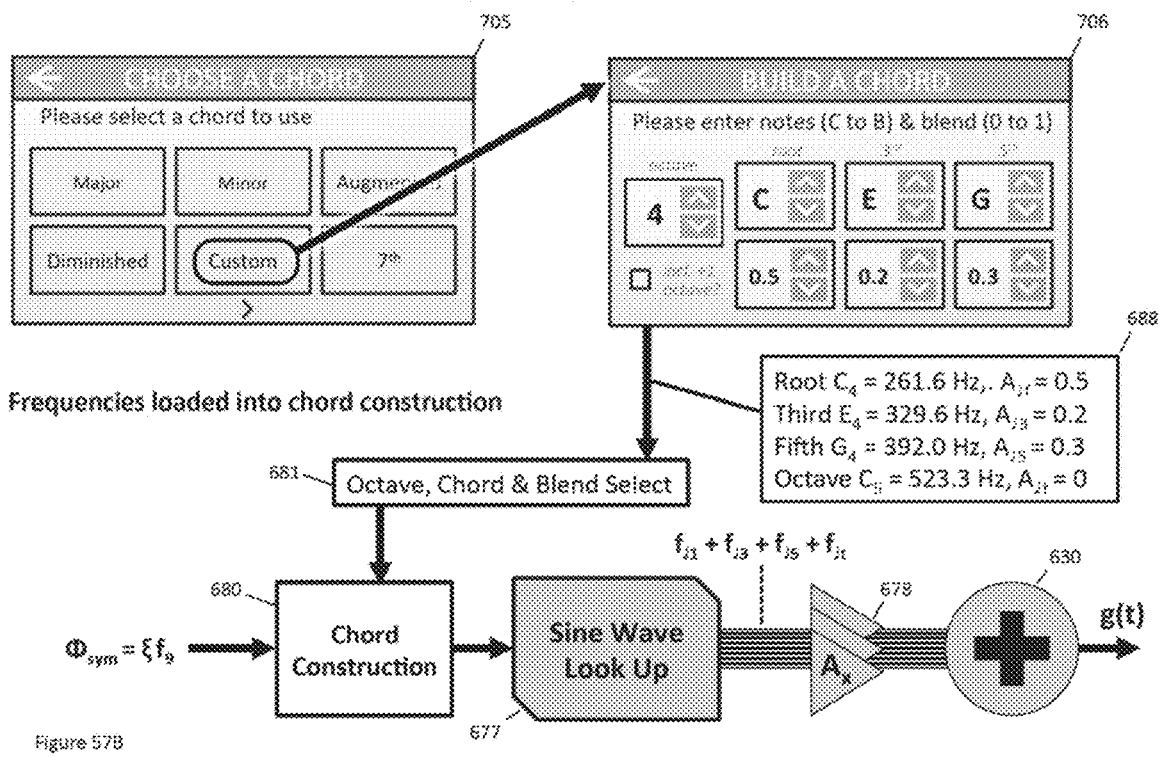
FIG. 57B illustrates the UI/UX interface for a custom triad chord builder with optional+1 octave note.

Although the chord builder can be a library element used in predefined treatments and sessions, chords can also be created using a UI menu such as shown in the exemplar of FIG. 57B where a chord may be selected from CHOOSE A CHORD menu 705 including major, minor, diminished, augmented, diminished, custom, $7^{th}$, minor $7^{th}$ and major $7^{th}$ chords. Selecting a custom chord opens the BUILD A CHORD menu 706 where the user can select the octave of from 0.13 to 0.87, representing 74.4% of the full range. To increase the amplitude of the time varying component the averaging function is amplified by the scalar $A_\alpha$. By setting $A_\alpha = 1.344$, chord 669 is increased to full range, as shown by chord 689. To prevent a shift in the function's average value, the correction term $0.5(1-\alpha)$ is included to ensure that the function remains centered on 0.5 and prevent clipping. The result is a unit function f(t) having an average value of 0.5 and having the same dynamic time varying frequency components as the synthesized waveform g (t).

Figure 59:
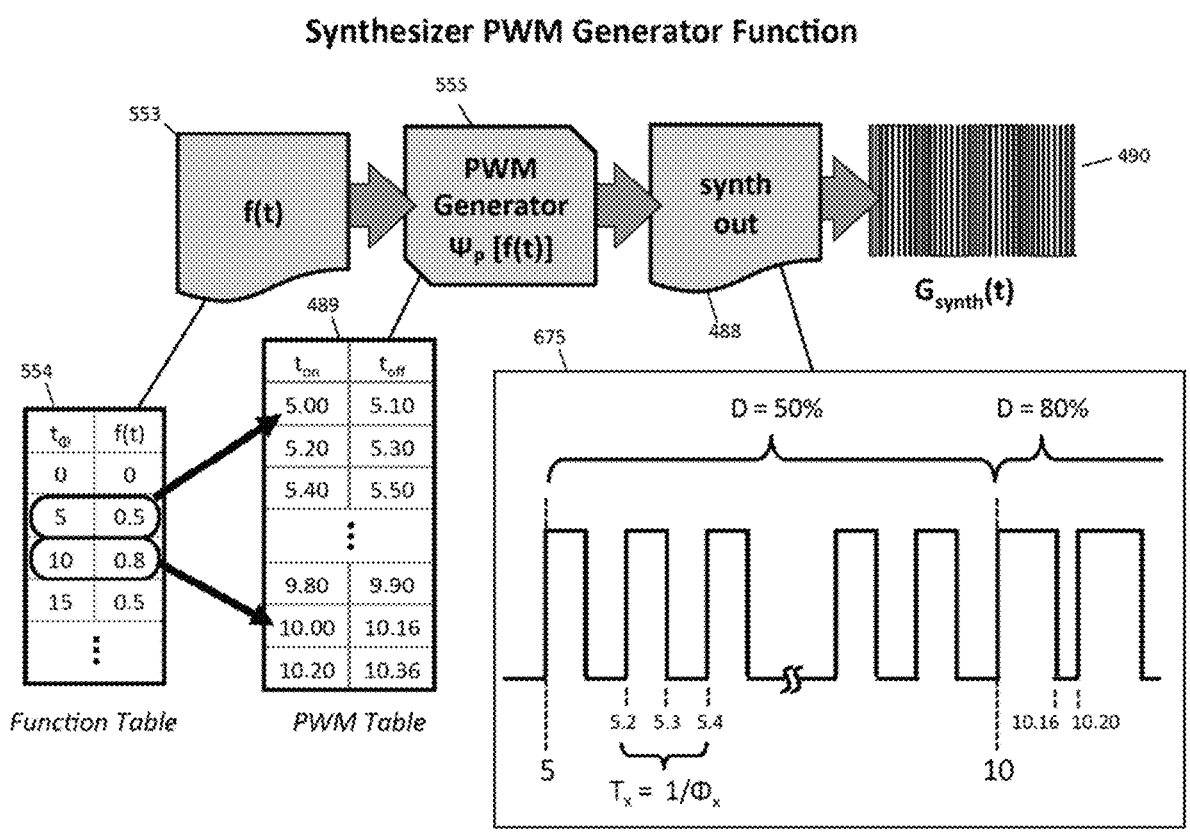
FIG. 59 is a functional illustration of a PWM generator function used in waveform synthesizer.

FIG. 59 illustrates the process by which PWM generator 555 converts unit function f(t) 553 into synth out file 488 describing PWM waveform $G_{synth}(t)$ 490. As shown, the function table 554 contains a description of time to versus the function's value f(t) at each time increment. For example, at $t_\Phi$=5 μs the function f(t)=0.5 and remains at that value until at $t_\Phi$=10 μs the function's value changes to f(t)=0.8. The output of the transformation $\Psi_P[f(t)]$ changes this time dependent table into a PWM table 489 where at time $t_{on}$=5.00 μs the state goes high, i.e. the LEDs turn on and time $t_\Phi$=5.10 μs the LEDs turn off until at time $t_{101}$=5.20 the LEDs turn on again. Since the LEDs were on from time 5.00 to 5.10 for a duration of 0.10 μs and the period T=1/$\Phi_x$ until the LEDs turn on again is from 5.00 to 5.20, or a duration of 0.20 μs, the duty factor of the pulse is D=$\Delta t_\Phi$/T=10 μs/20 μs=0.50 or 50% and the function f(t)=0.5 during this interval and until time $t_\Phi$=10 μs, when the duty factor switches to 0.8 or 80%. The resulting synth out file 488 is illustrated graphically in PWM pulse string 675.

Examples of PWM output 490 using the transformation $\Psi_P[f(t)]$ are shown for a variety of non-sinusoidal functions in FIG. 60, including PWM bit stream 670 for a constant function 560 where f(t)=1.000, PWM bit stream 671 for a sawtooth function 561, and PWM bit stream 672 for a triangle function 562. The same PWM transformation $\Psi_P[f(t)]$ can be used to encode audio samples of any audio sample including simple tones like a triangle, strings like a guitar or violin, complex tones such as a cymbal crash, or music.

PWM Player Operation

Revisiting the block diagram of FIG. 43, the output $G_{synth}(t)=\Psi_P[f(t)]$ of waveform synthesizer 483 is the input PWM player 484. PWM player 484 then combines $G_{synth}(t)$ with waveform $G_{pulse(t)}$ 492 to produce pulse string 493. The function of PWM player 484 is twofold:

To generate an audio spectrum PWM pulse string $G_{pulse}(t)$ with a dynamically controlled duty factor $D_{PWM}$.

To perform dynamic "gating", i.e. to block or pass the content of $G_{synth}(t)$ based on the state of $G_{pulse}(t)$.

The truth table for the above function can be described is logic pseudocode as

If $G_{pulse}$=1

Then PWM Player OUT=$G_{synth}(t)$

Else PWM Player OUT=0

Since $G_{pulse}(t)$ comprises a PWM string of pulses, the waveform alternates between high and low logic states. Specifically, whenever the function $G_{pulse}(t)$=1, i.e. the PWM pulse 492 is in its high or logic "1" state, the digital state of $G_{synth}(t)$ is precisely reproduced at the output of PWM player 484. For example, when $G_{pulse}(t)$=1 then if $G_{synth}(t)$=1 the output of PWM player 484 is high and if $G_{synth}(t)$=0 then the output of PWM player 484 is low. Whenever, however, the function $G_{pulse}(t)$=0, i.e. the PWM pulse 492 is in its low or logic "0" state, the digital state of $G_{synth}(t)$ is forced to zero, ignoring the state of the input $G_{synth}(t)$. Logically, this function is the same as an AND gate. Mathematically it is equivalent to a digital multiply where the output of PWM player 492 is given by the product $G_{synth}(t) \cdot G_{pulse}(t)$. Actual implementation of PWM player 492 may be achieved in hardware, software/firmware, or some combination thereof.

Figure 61A:
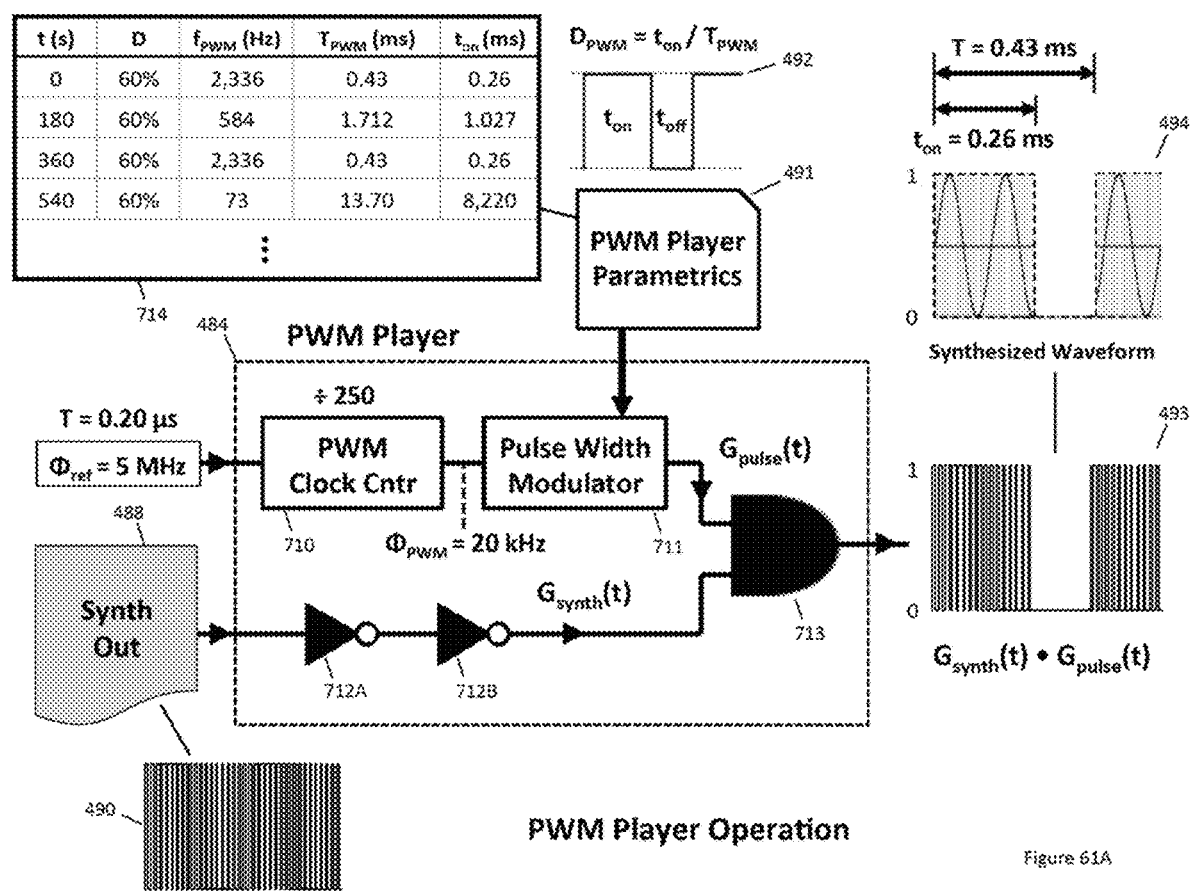
FIG. 61A illustrates the chopping function operation of the PWM player.

Illustrated schematically in FIG. 61A, PWM player 484 comprises a PWM clock counter 710, a pulse width modulator 711, digital inverters 712A and 712B, and a logical AND gate 713. Inputs to PWM player 491 include reference clock $\Phi_{ref}$, synth out 488, and PWM player parametrics 491. In operation, reference clock $\Phi_{ref}$=5 MHz provides a time reference with period $T_{ref}$=0.20 μs as an input to PWM counter 710, generating PWM clock $\Phi_{PWM}$=20 kHz. With a period $T_{PWM}$=5 μs, 250 times longer than the reference clock $\Phi_{ref}$ period, pulse width modulator 711 generates a sequence of PWM pulses 492 of varying duration $t_{on}$=$D_{PWM}T_{PWM}$ made in accordance with a table 714 defined in PWM player parametrics 491. For example, in table 714 from 0 to 180 seconds, $G_{pulse}(t)$ is pulsed at a frequency of 2,836 Hz with a duty factor of 60%, after which the pulse frequency changes to 584 Hz. At time t=360 sec, the pulse frequency returns to 2,836 Hz. In terms of pulse string 492, during the interval from 0 to 180 seconds the period $T_{PWM}$=0.43 ms and the on-time, the portion of the period when the pulse is in its high state, is given by $t_{on}$=$D_{PWM}T_{PWM}$=(60%)(0.43 ms)=0.26 ms.

The off portion of the pulse is given by $t_{off}$=$T_{PWM}$−$t_{on}$= (0.43 ms)−(0.26 ms)=17 ms. When the pulse frequency changes to 584 Hz, the period increases to 1.712 ms with an on-time of 1.027 ms. Thus, pulse string 492 is dynamically generated by pulse width modulator 711 in accordance with the dynamic conditions specified in table 491. The output of PWM player 484, shown as a gated PWM pulse string 493, includes the with embedded waveform 494 output from the waveform synthesizer 483.

Pulse width modulator 711 essentially comprises two sequential counters, one for counting the on time, the other for counting the off time, where $G_{pulse}(t)$=1 during the $t_{on}$ interval and $G_{pulse}(t)$=0 during the $t_{off}$ interval. In logic pseudo-code, operation of pulse width modulator 711 can be described by defining the following subroutine.

```
Begin subroutine "Pulse Width Modulator" loop:
    Load registers Pulse Width Modulator [Δt, T_PWM, t_on]
    Clear Counters
    Begin Count of (1/Φ_ref) pulses
Loop start
    If Count (1/ Φ_ref) > Δt, then exit subroutine
    Else
        Define t_off = (T_PWM − t_on)
        Set G_pulse = 1
        Count (1/Φ_PWM) pulses to t_on
        Reset G_pulse = 0
        Count (1/Φ_PWM) pulses to t_off
Loop end
```

The above subroutine entitled "Pulse Width Modulator" is a software pseudo-code description performing the same function as block 711, i.e. executing a loop for an interval Δt comprising alternating digital pulses in the logic 1 state for duration $t_{on}$ and a logic 0 state for a duration ($T_{PWM}$−$t_{on}$) repeatedly until the count of clock $T_{ref}$=1/$\Phi_{ref}$ exceeds Δt. The variables [Δt, $T_{PWM}$, $t_{on}$] are loaded into the subroutine from the sequence defined in table 714 in PWM player parametrics 491, as illustrated in the following exemplar executable pseudo-code where table look ups are specified by the value in the (row, column) pair, i.e. table (Row, column) where Row is a defined variable:

```
Executable code "Treatment Back Pain"
Load table [PWM Player Parametrics]
Set Row = 0
Loop start
    Set Δt = table ((Row+1), 1) − table (Row, 1)
    Set T_PWM = table (Row, 4)
    Set t_on = table (Row, 5)
```

```
        If T_PWM = 1
        Then
                Terminate execution
        Else
                Call subroutine Pulse Width Modulator [Δt, T_PWM, t_on]
                Increment Row by 1
Loop end
```

As described, the above executable pseudo-code repeatedly reads table 714, loading data into the subroutine call Pulse Width Modulator with the arguments for its duration $\Delta t$, the PWM pulse period $T_{PWM}$, and the PWM pulse on-time $t_{on}$, incrementing the row number after each loop is completed. For example, when commencing Row=0 so $\Delta t$ is calculated by the difference of the time entries in the second row and the first row in the table's first column, i.e. where table (2,1)=180 sec and where table (1,1)=0, therefore $\Delta t$=180 sec in the first loop of the code. Similarly, in the first row and fourth column, the data for the PWM period is $T_{PWM}$=table (1, 4)=0.43 ms, and in the first row and fifth column, the data for the PWM one time is $t_{on}$=table (1, 5)=0.26 ms. At the end of the loop, the row number is incremented from 1 to 2, so the new data is read from the second row where $\Delta t$=[table (3,1)−table (2,1)]=[360 s−180 s]=180 s, $T_{PWM}$=table (2, 4)=1.712 ms, and $t_{on}$=table (2, 5)=1.027 ms. This process continues until a null entry for $T_{PWM}$ is encountered, i.e. $T_{PWM}$=table (Row, 4)=0. At that point, program execution concludes. So as demonstrated, the functions of PWM Player 484 and pulse width modulator 711 can be executed using software or hardware, or some combination thereof.

Figure 61B:
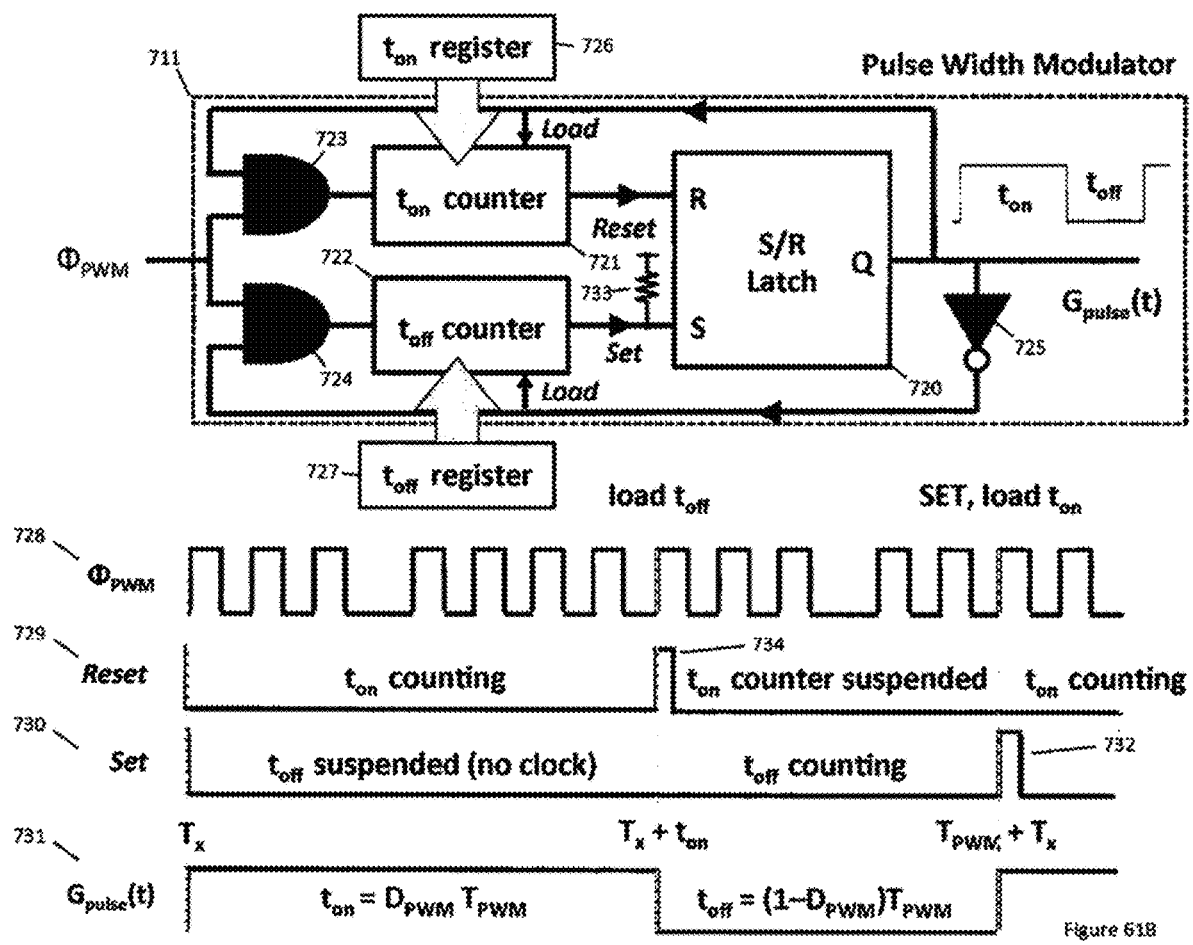
FIG. 61B illustrates a schematic functional equivalent of a pulse width modulator used in the PWM player.

For example, the function of pulse width modulator 711 is represented schematically in FIG. 61B, comprising a set/reset flip-flop or S/R latch 720, $t_{on}$ and $t_{off}$ counters 721 and 722, AND gates 723 and 724, an inverter 725, a startup resistor 733, as well as $t_{on}$ and $t_{off}$ registers 726 and 727. In operation, startup resistor 733 pulls up on the S input of S/R latch 720, which sets the Q output to a logic high or "1" state. The rising edge of this 0 to 1 logic transition triggers the load function of $t_{on}$ counter 721. loading the data from $t_{on}$ register 726 into the counter 721. The logic high state of the Q output also is an input to AND gate 723, and its inverse state, the output of inverter 725, presents a logic "0" to an input AND gate 724.

As a result, clock pulses from clock $\Phi_{PWM}$ are routed through AND gate 723 to $t_{on}$ counter 721 but blocked by AND gate 724 from reaching the $t_{off}$ counter 722. Accordingly, $t_{on}$ counter 721 counts down for a duration $t_{on}$. During its countdown, the output of $t_{on}$ counter 721 remains in a logic "0" state and has no effect on S/R latch 720. Concurrently, lacking a clock input, the operation of $t_{off}$ counter 722 is suspended. Referring to the associated timing diagrams 728-731, during the interval from $T_x$ to $(T_x+t_{on})$, PWM clock $\Phi_{PWM}$ 728 continues counting, reset signal 729 comprising the R input to S/R latch 720 remains low, set signal 730 comprising the S input to S/R latch 720 remains low (except for a startup pulse not shown), and the output $G_{pulse}(t)$ 731 remains high.

Once $t_{on}$ counter 721 completes its countdown of the interval $t_{on}$, the output of counter 721 goes high momentarily, as shown by reset pulse 734. The rising edge on the R input of S/R latch 720 resets the output Q to logic "0" and disables PWM clock $\Phi_{PWM}$ from passing through AND gate 723 and driving $t_{on}$ counter 721. Concurrently, the falling edge of the Q output produces a rising edge on the output of inverter 725 triggering a load of $t_{off}$ register 727 data into $t_{off}$ counter 722. The logic high input to AND gate 724 enables routing of the $\Phi_{PWM}$ clock to $t_{off}$ counter 722. Referring to the associated timing diagrams 728-731, during this interval from $(T_x+t_{on})$ to $(T_x+T_{PWM})$, PWM clock $\Phi_{PWM}$ continues counting (diagram 728), reset signal comprising the R input to S/R latch 720 remains low (except for reset pulse 734 at the beginning of the interval) (diagram 729), the set signal at the S input to S/R latch 720 remains low (diagram 730), and the output $G_{pulse}(t)$ remains low (diagram 731). Once $t_{off}$ counter 722 counts down to zero after an interval of $t_{off}$, its output generates a short set pulse 732, which toggles the Q output of S/R latch 720 back to a logic "1" state, loading the current value from $t_{on}$ register 726 into $t_{on}$ counter 721 and restarting the entire process.

As shown in diagram 731, the $G_{pulse}$ output toggles between a logic high state for a duration $t_{on}=D_{PWM} T_{PWM}$ to a logic low state for a duration $t_{off}=(1-D_{PWM}) T_{PWM}$. Each time a set pulse 732 is triggered, the current value of $t_{on}$ register 726 is loaded into the $t_{on}$ counter 721. Similarly, each time a reset pulse 734 is triggered, the current value of $t_{off}$ register 727 is loaded into the $t_{off}$ counter 722. In this manner, PWM player parametrics file 491 is able to dynamically change the PWM player's frequency and duty factor producing a waveform identical to its software equivalent implementation. Note that resistor 733 used to pull the S input to S/R latch 720 high during startup has a high resistance, and is unable to overcome the logic low state output from $t_{off}$ counter 722 once startup is concluded and power to the circuitry has stabilized.

In conclusion, in the PWM player 748 the frequency $f_{PWM}$ and a corresponding duty factor $D_{PWM}$ change over time in accordance with a specific playback file, thereby defining a PWM sequence of pulses of varying durations of $t_{on}$ and $t_{off}$. Note that the pulse frequency $f_{PWM}=1/T_{PWM}$ of the pulse width modulator 711 is lower in frequency than the PWM clock $\Phi_{PWM}$=20 kHz used to drive the pulse width modulator 711. Moreover, the PWM frequency $f_{PWM}$ is far below the oversampled clock $\Phi_{sym}$ used by in the PWM generator 555 $\Psi_F[f(t)]$ in the waveform synthesizer 483, i.e. $1/\Phi_{sym} \gg 1/\Phi_{PWM} \geq f_{PWM}$.

LED Driver Operation

The third stage in an LED player of a distributed PBT system is the LED driver circuitry. Referring to FIG. 43, the function if LED driver 485 is to convert its input $G_{synth}(t) \cdot G_{pulse}(t)$ along with an optional time dependent reference current 496 into one or more analog control signals, i.e. LED drive stream 497 The aggregate signal equal to $\alpha I_{ref}(t) \cdot G_{synth}(t) \cdot G_{pulse}(t)$ is then used to control the current in numerous LED strings as illustrated by exemplary waveform 498.

Figure 62:
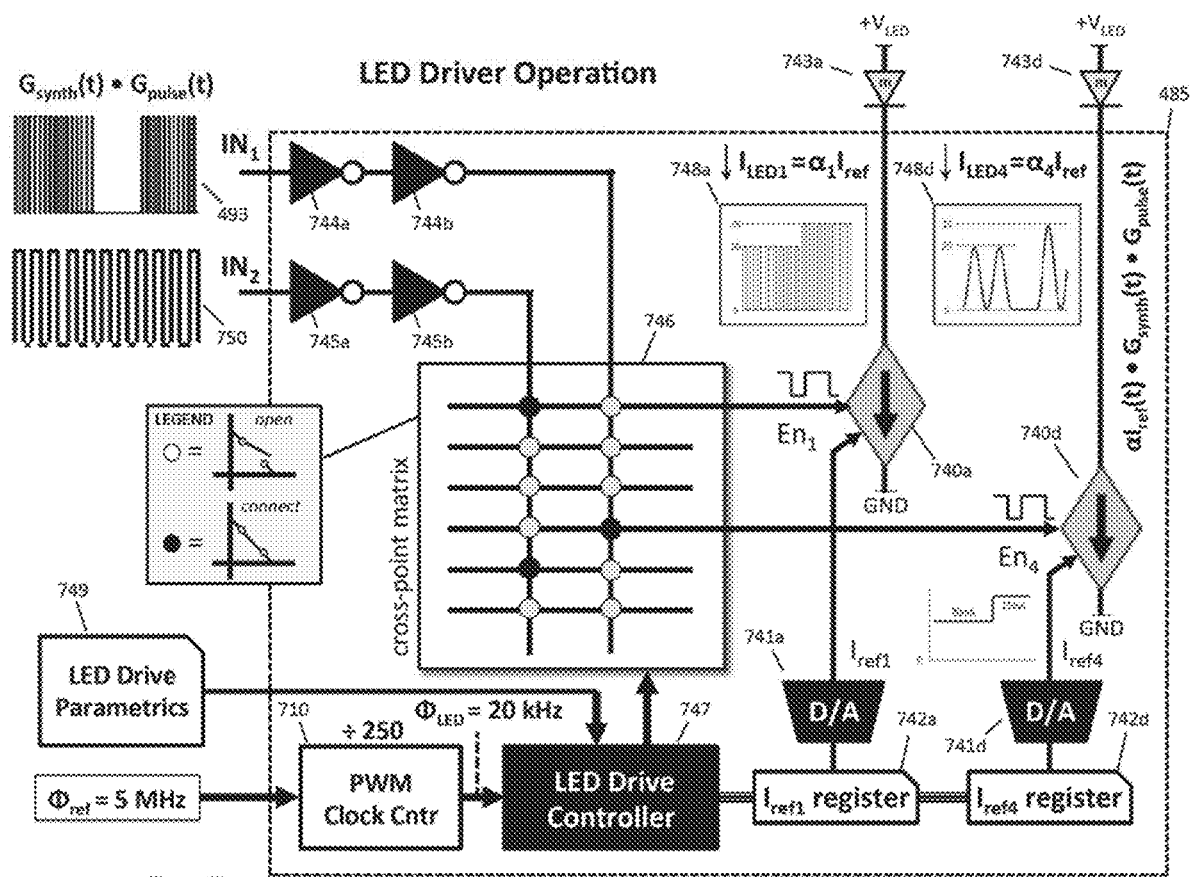
FIG. 62 illustrates a block diagram of LED driver operation.

Greater detail of the operation of LED driver 485 is shown in the block diagram of FIG. 62. Although the illustration shows two PWM pulse string inputs IN$_1$ 493 and IN$_2$ 750 and only two outputs for driving LED strings 743a and 743d, it will be understood to those skilled in the art of PBT that any number of synthesized waveforms, e.g. from 1 to 16 may be required, and that the number of LED strings may vary from n=1 to 36 strings (or even more in large devices) although for smaller LED pads the number of strings will likely range from 8 to 24. It is also understood that the number of series connected LEDs "m" can vary from string-to-string so long that the total number "m" of LEDs in a given LED string does not require a voltage greater than +$V_{LED}$ to properly operate.

As shown, LED driver 485 contains, two buffers per input, e.g. IN$_1$ is passed through inverters 744a and 744b and IN$_2$ is passed through inverters 745a and 745b, as well as a PWM clock counter 710, an LED drive controller 747, multiple channels carrying currents exemplified by $I_{LED1}$ and. $I_{LED4}$, wherein each channel includes an LED string, a controlled current source or sink and optionally a D/A converter and an associated $I_{ref}$ data register. For example, the channel carrying the current $I_{LED1}$ includes a controlled current sink 740a driving LED string 743a, a D/A converter 741a producing a reference current $I_{ref1}$, and an associated $I_{ref1}$ data register 742a. Similarly, the channel carrying the current $I_{LED4}$ includes a controlled current sink 740d driving LED string 743d, a D/A converter 741d producing a reference current $I_{ref4}$, and an associated $I_{ref4}$ data register 742d. An optional cross point matrix 746 is used to dynamically allocate, i.e. map, inputs $IN_1$, $IN_2$, etc. to the channels carrying $I_{LED1}$ and $I_{LED4}$ and any other channels, as required. Aside from its PWM waveform inputs $G_{synth}(t) \cdot G_{pulse}(t)$ LED driver 485 also requires inputs from LED driver parametrics file 749 and reference clock $\Phi_{ref}$.

In operation, input waveforms are mapped to the channels dynamically controlling the current for assigned LED strings. For example, waveform 493 is input to $IN_1$ then mapped through cross-point switch 746 to the digital $En_1$ input to current sink 740a and to other channels (not shown). As detailed in its accompanying legend, the blackened circle in cross-point switch indicates a closed switch, i.e. a connection, while an open circle indicates no connection, i.e. an open circuit. Similarly, waveform 750 is input to $IN_2$ then mapped through cross-point switch 746 to the digital $EN_4$ input to current sink 740d and to other channels (not shown). Concurrently, as synchronized by the clock $\Phi_{LE4}$ output from PMW clock counter 710, the analog signal $I_{ref1}$ is supplied to current sink 740a and the analog signal $I_{ref4}$ is supplied to current sink 740d. Currents $I_{ref1}$ and $I_{ref4}$ are set by the digital values loaded into $I_{ref1}$ register 742a and $I_{ref4}$ register 742d and by corresponding D/A converters 741a and 741d. The resulting waveforms 748a and 748d are represented in the currents $I_{LED1}=\alpha I_{ref1}$ and $I_{LED4}=\alpha I_{ref4}$. The design, implementation, and operation of current sinks (or alternatively current sources) are shown in FIGS. 20A-20C, FIGS. 22A-22C and FIGS. 23A-23C. The LED Driver function can also be specified and executed using software in two steps, first mapping the inputs to the outputs, e.g.

Set "I/O Mapping" where
$En_1=IN_2$
$En_4=IN_1$
$En_5=IN_2$

Although it is possible to change this mapping dynamically, the mapping is more likely to be executed only once per treatment and left unchanged throughout the treatment. In many cases only a single input is used. The executable code for current each channel's current can be fixed to constant value Set "Output Currents" where
$I_{LED1}=20$ mA
$I_{LED4}=20$ mA
$I_{LED5}=20$ mA During manufacturing calibration, an error term or curve $I_{calib}$ is stored in non-volatile memory for each channel, for example $I_{calib1}=1=1.04$ mA, $I_{calib4}=-0.10$ mA, $I_{calib4}=0.90$ mA. The LED pad also stores a value of the mirror ratio $\alpha$, e.g. $\alpha=1/\beta=1,000$, meaning a milliamp channel current $I_{LED}$ requires a corresponding microampere reference current $I_{ref}$. Before commencing playback, the pad μC 339 calculates and stores the values of $I_{ref}$ for each channel where $I_{ref1}=[I_{LED1}+I_{calib1}]/\alpha=[20 \text{ mA}+(1.04 \text{ mA})]/10^6=21.04$ μA $I_{ref4}=[I_{LED4}+I_{calib4}]/\alpha=[20 \text{ mA}+(-0.10 \text{ mA})]/10^6=19.99$ μA $I_{ref5}=[I_{LED5}+I_{calib5}]/\alpha=[20 \text{ mA}+(0.90 \text{ mA})]/10^6=20.90$ μA The $I_{ref}$ values are stored in the equivalent digital form in $I_{ref}$ registers 742a, 742d, 742e, etc. in volatile memory prior to program execution. If the value of the target LED current changes, the register value can be overwritten prior to program execution, or dynamically "on-the-fly" as the treatment progresses. For example, using executable pseudocode, dynamic LED drive may comprise

```
Executable code "Treatment Back Pain"
Load table "drive" [LED Drive Parametrics]
Load table "calib" [LED Calibration]
Set α = LED Configuration [row, col]
Set Row = 0
Loop start
    Set Δt = table "drive" ((Row+1), 1) – table "drive" (Row, 1)
    If Δt = 0
    Then
        Terminate execution
    Else
        Set
        I_ref1 = [table "drive" (Row, 2) + table "calib" (1,1)]/ α
        I_ref4 = [table "drive" (Row, 5) + table "calib" (4,1)]/ α
        I_ref4 = [table "drive" (Row, 6) + table "calib" (5,1)]/ α
        Count (1/Φ_PWM) pulses to table "drive" ((Row+1), 1)
        Increment Row by 1
Loop end
```

During execution the value of $I_{ref}$ for each channel is set by a $[I_{LED}+I_{calib}]/\alpha$ where $I_{LED1}=$"drive" (Row, 2), $I_{LED4}=$"drive" (Row, 5), etc. and where column 2 cells contain the LED current drive data for $I_{LED2}$, column 5 contains $I_{LED4}$ data, etc. The value of Row is used to define various intervals for a treatment, e.g. up to 540 sec conducting 20 mA and thereafter carrying 23 mA.

| Row | Col 1, time(s) | Col 2: $I_{LED1}$ | Col 3: $I_{LED2}$ | Col 4: $I_{LED3}$ | Col 5: $I_{LED4}$ | Col 6: $I_{LED5}$ |
|---|---|---|---|---|---|---|
| 1 | 0 | 20 mA | 20 mA | 15 mA | 20 mA | 20 mA |
| 2 | 180 | 20 mA | 20 mA | 15 mA | 20 mA | 20 mA |
| 3 | 540 | 23 mA | 20 mA | 20 mA | 23 mA | 23 mA |
| 4 | 900 | 23 mA | 20 mA | 20 mA | 23 mA | 23 mA |
| 5 | 900 | Terminate treatment | | | | |

If all the channels are carrying the same current, the channel specific columns can be eliminated from the table a replaced by a single column, as shown below

| Row | Col 1, time (s) | Col 2: $I_{LED}$ |
|---|---|---|
| 1 | 0 | 20 mA |
| 2 | 180 | 20 mA |
| 3 | 540 | 23 mA |
| 4 | 900 | 23 mA |
| 5 | 900 | Terminate |

The program can also invoke a function rather than a table, e.g. in Treatment Headache example

```
Executable code "Treatment Headache"
Load table "calib" [LED Calibration]
Set α = LED Configuration [row, col]
Set f_LED = 5.5
```

-continued

```
Begin Count of (1/Φ_ref) pulses
Set t = 0
Loop Start
    Set t = t+(1/(Φ_ref)
    If t ≥ t_end
    Then
        Set I_ref = 0
    Else
        Set I_LED (t) = [20mA] [0.5 +0.5sin (2πf_LED t)]
        Set "Reference Currents by Channel"
            I_ref1 = [I_LED (T) + table "calib" (1,1)]/ α
            I_ref4 = [I_LED (T) + table "calib" (4,1)]/ α
            I_ref4 = [I_LED (T) + table "calib" (5,1)]/ α
Loop end
```

In the foregoing example the 20 mA sine wave is generated by a mathematical function for the reference current LED (t) with a defined frequency, e.g. 5.5 Hz, using the $\Phi_{ref}$ clock (or optionally a multiple thereof). The desired output current LED (t) at each instance is corrected on a channel-by-channel basis by the calibration table data before being converted by mirror ratio α into the corresponding reference current $I_{ref1}$ registers 742a, 742, 742e, etc. According to the instruction "Set t=t+(1/$\Phi_{ref}$)," each loop at time t is incremented by a duration (1/$\Phi_{ref}$) and the summation stored back in the variable t, thereby overwriting the prior value. As such the variable t acts as a clock incremented with each loop of the program. The clock continues to count and repeatedly generate the sine wave with a fixed periodicity of $T_{LED}=1/f_{LED}$ until the terminus condition t≥$t_{end}$ is met.

LED Player in Distributed PBT System

In the LED playback operation illustrated in FIG. 43, the sequence of waveform synthesizer 483, PWM player 484, and LED driver 485 produces LED drive stream 497. Waveform synthesizer 483 operates at a clock frequency $\Phi_{sym}$ significantly above the audio frequency spectrum, i.e. $\Phi_{sym}$>>20 kHz, while the PWM clock $\Phi_{PWM}$ used by PWM player 484 and LED clock ILEA used by LED driver 485 operate in the audio spectrum, i.e., $\Phi_{PWM}$≤20 kHz and $\Phi_{LED}$≤20 kHz. In summary, the LED playback operation involves Generating a time dependent analog unit function f(t) either mathematically using a unit function generator or using an over-sampled look-up-table based primitive processor.

Converting unit function f(t) into a PWM pulse stream using transformation $G_{synth}(t)=\Psi_P[f(t)]$.

Generating an audio spectrum PWM pulse string $G_{pulse}(t)$.

Gating, i.e. performing a logical AND, of $G_{synth}(t)$ with PWM pulse string $G_{pulse}(t)$ to produce a multiplicative unit function output $G_{synth}(t) \cdot G_{pulse}(t)$.

Driving LEDs with a time varying analog current $\alpha I_{ref}(t)$ pulsed by unit function output of the LED player whereby the $I_{LED}=\alpha I_{ref}(t) \cdot G_{synth}(t) \cdot G_{pulse}(t)$.

FIGS. 63A-63H, 64A-64F and 65 illustrate examples demonstrating the versatility of the disclosed LED player for generating a variety of waveforms.

Figure 63A:
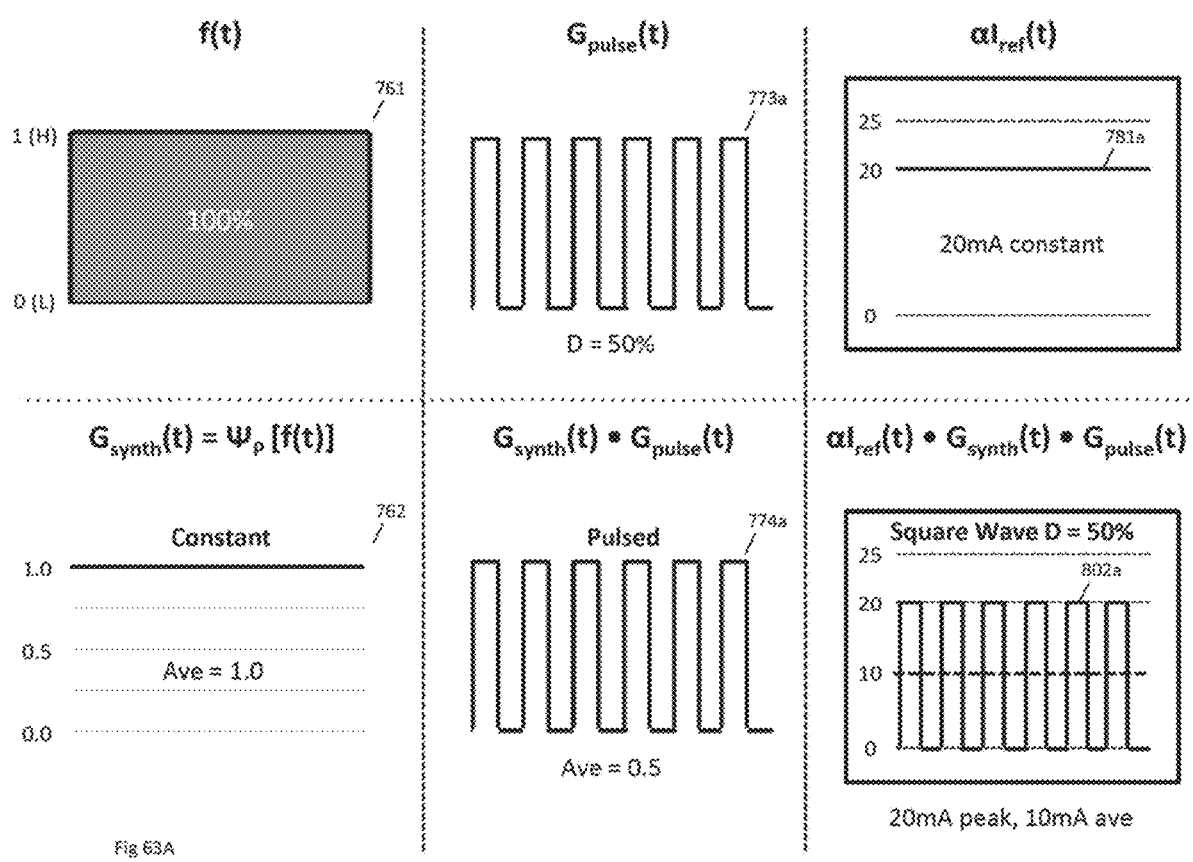
FIG. 63A illustrates the constituent waveforms for a PWM player generated square wave with 50% duty factor and a 10 mA average LED current.
Figure 63B:
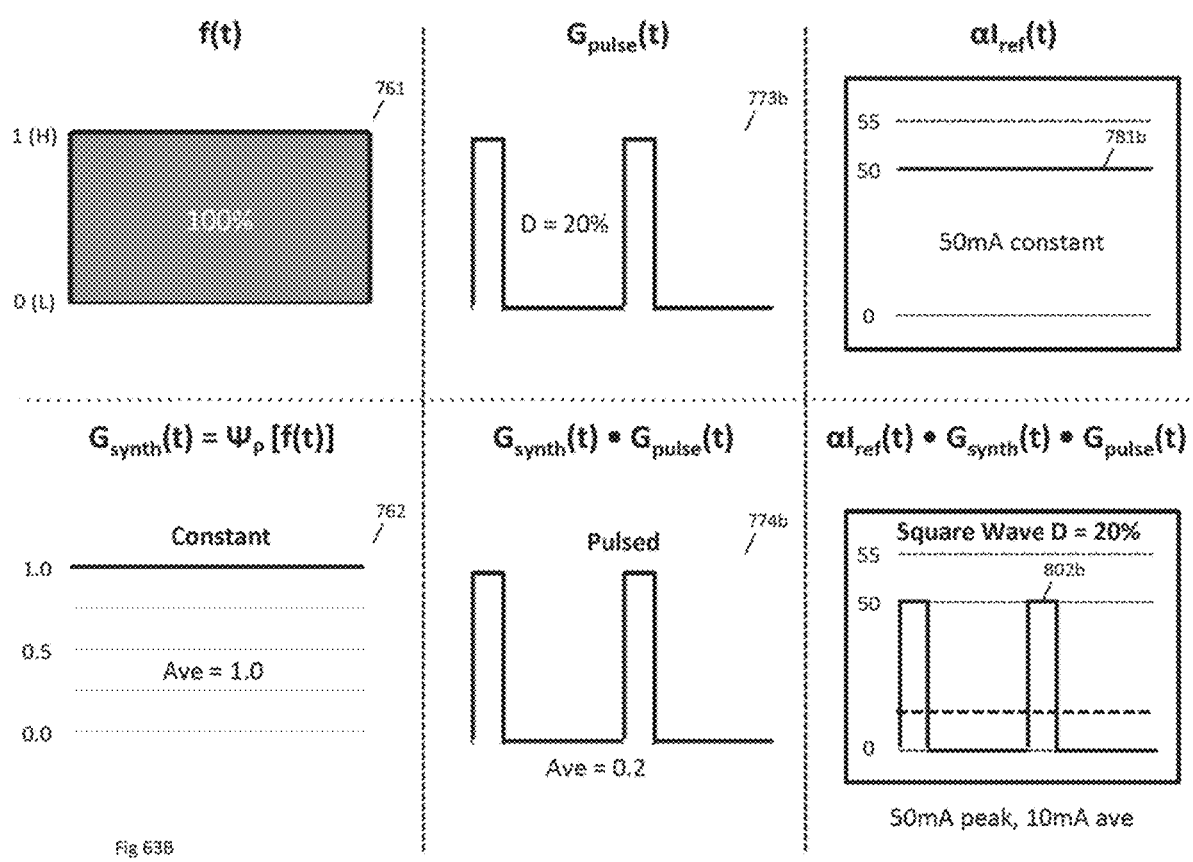
FIG. 63B illustrates the constituent waveforms for a PWM player generated square wave with 20% duty factor and a 10 mA average LED current.
Figure 63C:
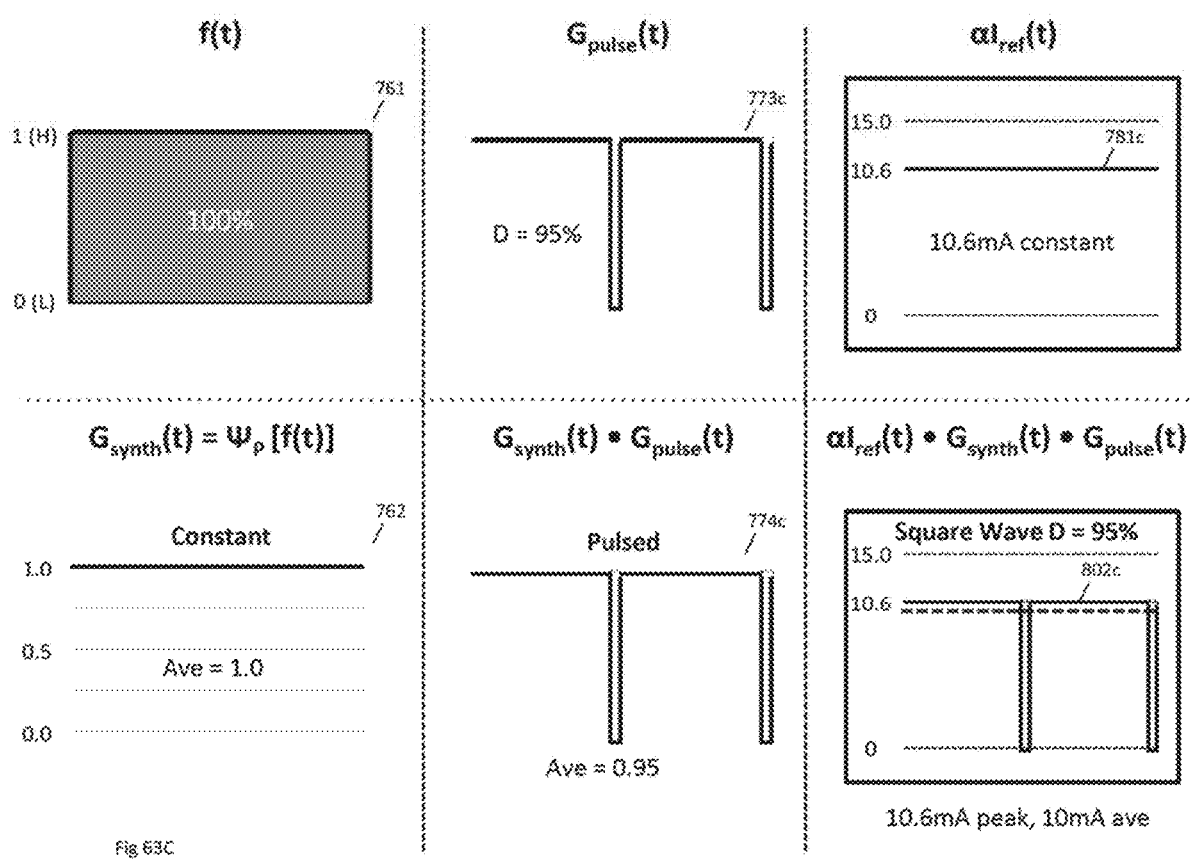
FIG. 63C illustrates the constituent waveforms for a PWM player generated square wave with 95% duty factor and a 10 mA average LED current.

FIG. 63A illustrates a constant f(t)=unit function 761, resulting in a constant time invariant $G_{synth}$ waveform 762 where $\Psi_P[f(t)]=100\%$. The constant $\Psi_P[f(t)]$ is then multiplied by a PWM pulse string 773a with D=50% producing a pulse string 774a equal to $G_{synth}(t) \cdot G_{pulse}(t)$. Multiplied by a constant reference current 781a, $\alpha I_{ref}=20$ mA, the resulting waveform $I_{LED}=\alpha I_{ref}(t) \cdot G_{synth}(t) \cdot G_{pulse}(t)$ is a 20 mA peak square wave 802a with a 50% duty factor and an average value of 10 mA.

FIG. 63B illustrates again constant f(t)=unit function 761 resulting in constant time invariant $G_{synth}$ waveform 762, where $\Psi_P[f(t)]=100\%$. The constant $\Psi_P[f(t)]$ is then multiplied by a PWM pulse string 773b with D=20%, producing a pulse string 774b having a value $G_{synth}(t) \cdot G_{pulse}(t)$. Multiplied by a constant reference current 781b, $\alpha I_{ref}=50$ mA, the resulting waveform $I_{LED}=\alpha I_{ref}(t) \cdot G_{synth}(t) \cdot G_{pulse}(t)$ is a 20 mA peak square wave 802b with a 20% duty factor and an average value of 10 mA.

FIG. 63C illustrates once again constant f(t)=unit function 761 resulting in constant time invariant $G_{synth}$ waveform 762, where $\Psi_P[f(t)]=100\%$. The constant $\Psi_P[f(t)]$ is then multiplied by a PWM pulse string 773c with D=95% producing a pulse string 774c comprising $G_{synth}(t) \cdot G_{pulse}(t)$. Multiplied by a constant reference current 781c, $\alpha I_{ref}=10.6$ mA, the resulting waveform $I_{LED}=\alpha I_{ref}(t) \cdot G_{synth}(t) \cdot G_{pulse}(t)$ is a 10.6 mA peak square wave 802c with a 95% duty factor and an average value of 10 mA.

FIG. 63D illustrates the constant f(t)=unit function 761 resulting in constant time invariant $G_{synth}$ waveform 762, where $\Psi_P[f(t)]=100\%$. The constant $\Psi_P[f(t)]$ is then multiplied by the PWM pulse string 773a with D=50% producing the pulse string 774a with a value $G_{synth}(t) \cdot G_{pulse}(t)$. Multiplied by a stepped reference current 781d, $\alpha I_{ref}=20$ mA and stepping up 25% to 25 mA., the resulting waveform $I_{LED}=\alpha I_{ref}(t) \cdot G_{synth}(t) \cdot G_{pulse}(t)$ is a 20 mA peak square wave 802c with a 50% duty factor and an average value of 10 mA, stepping up to a 25 mA peak square wave with a 50% duty factor and an average value of 112.5 mA.

Figure 63E:
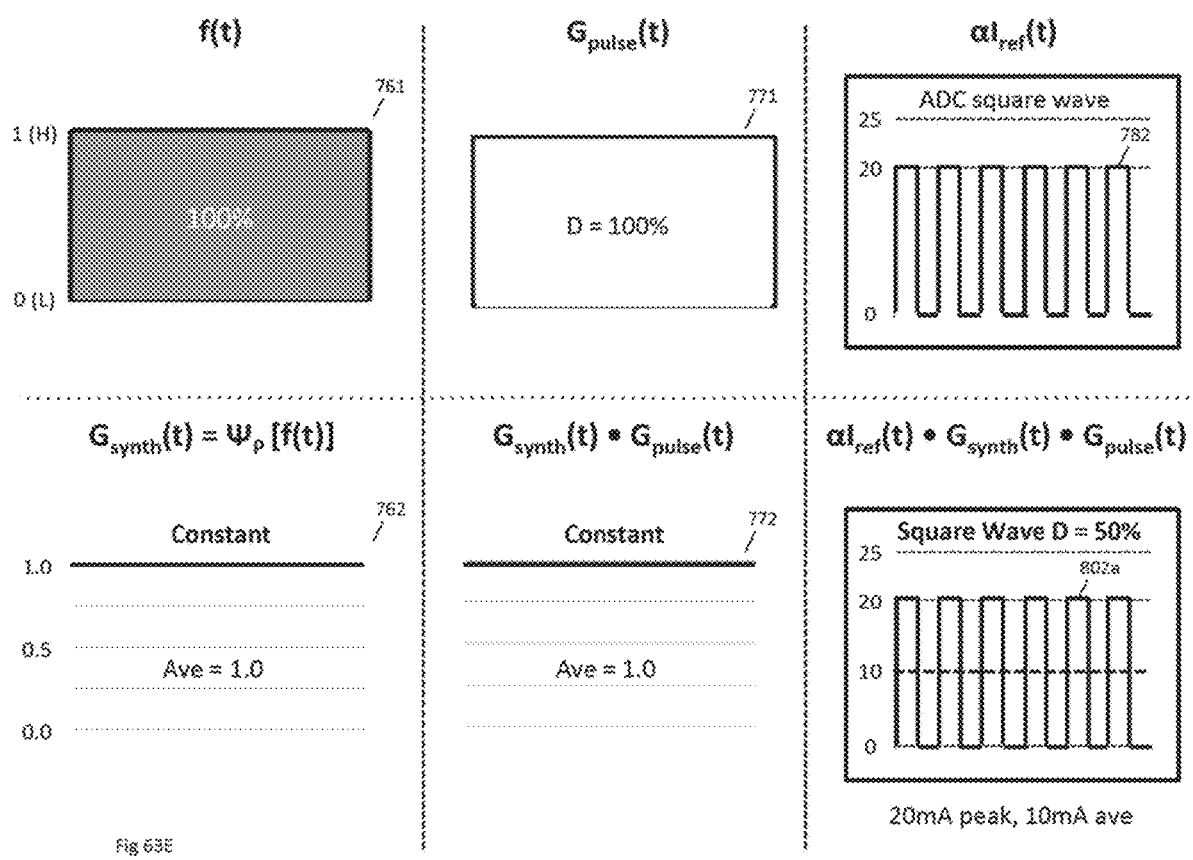
FIG. 63E illustrates the constituent waveforms for a LED driver generated square wave with 50% duty factor and a 10 mA average LED current.

FIG. 63E illustrates the constant f(t)=unit function 761 resulting in constant time invariant $G_{synth}$ waveform 762 where $\Psi_P[f(t)]=100\%$. The constant $\Psi_P[f(t)]$ is then multiplied by a constant value 771 with D=100%, producing constant value 772, where $G_{synth}(t) \cdot G_{pulse}(t)=100\%$. Multiplied by a pulsed reference current 782, $\alpha I_{ref}$ in the form of a 20 mA square wave, the resulting waveform $I_{LED}=\alpha I_{ref}(t) \cdot G_{synth}(t) \cdot G_{pulse}(t)$ is a 20 mA peak square wave 802a with a 50% duty factor and an average value of 10 mA.

Figure 63F:
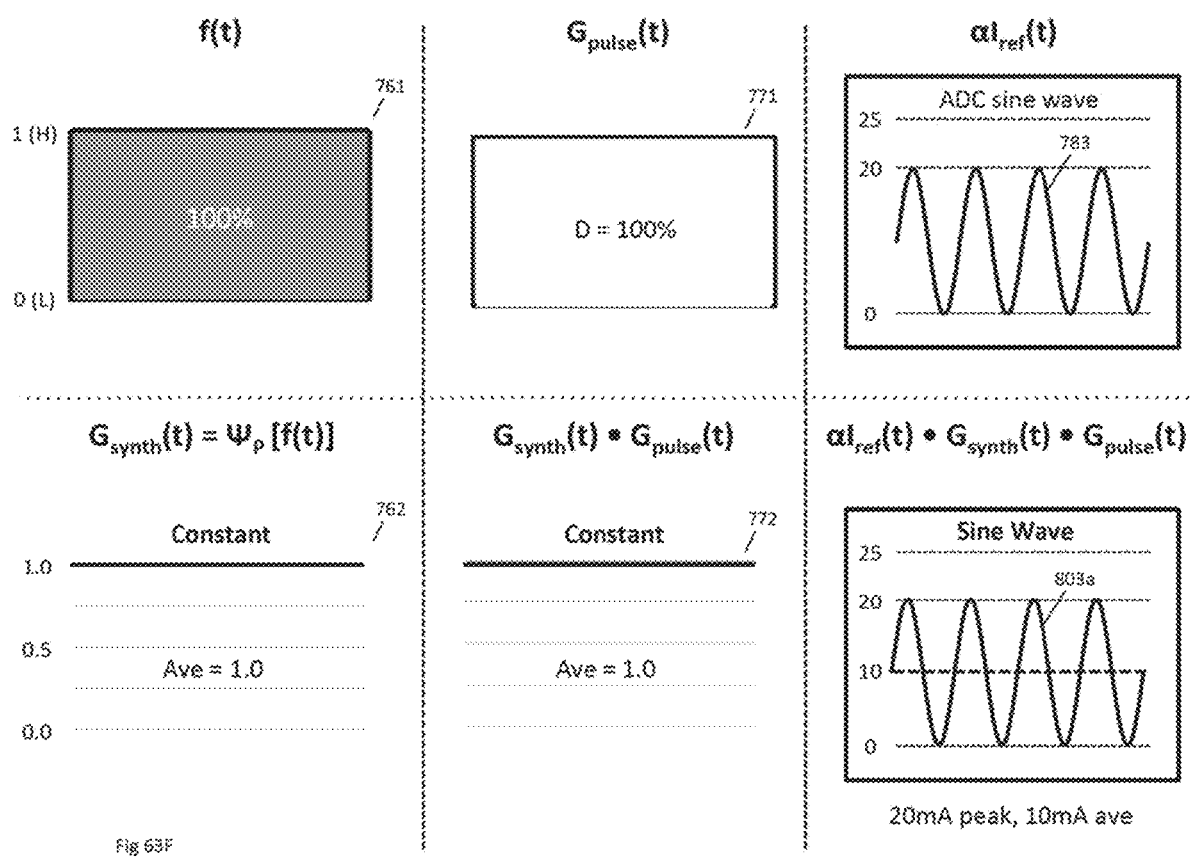
FIG. 63F illustrates the constituent waveforms for a LED driver ADC (analog-to-digital converter) generated sine wave with a 10 mA average LED current.

FIG. 63F illustrates the constant f(t)=unit function 761 resulting in constant time invariant $G_{synth}$ waveform 762 where $\Psi_P[f(t)]=100\%$. The constant $\Psi_P[f(t)]$ is then multiplied by constant value 771 with D=100%, producing constant value 772, where $G_{synth}(t) \cdot G_{pulse}(t)=100\%$. Multiplied by a sinusoidal reference current 783, $\alpha I_{ref}$ in the form of a 20 mA sine wave, the resulting waveform $I_{LED}=\alpha I_{ref}(t) \cdot G_{synth}(t) \cdot G_{pulse}(t)$ is a 20 mA sine wave 803a with an average value of 10 mA.

Figure 63G:
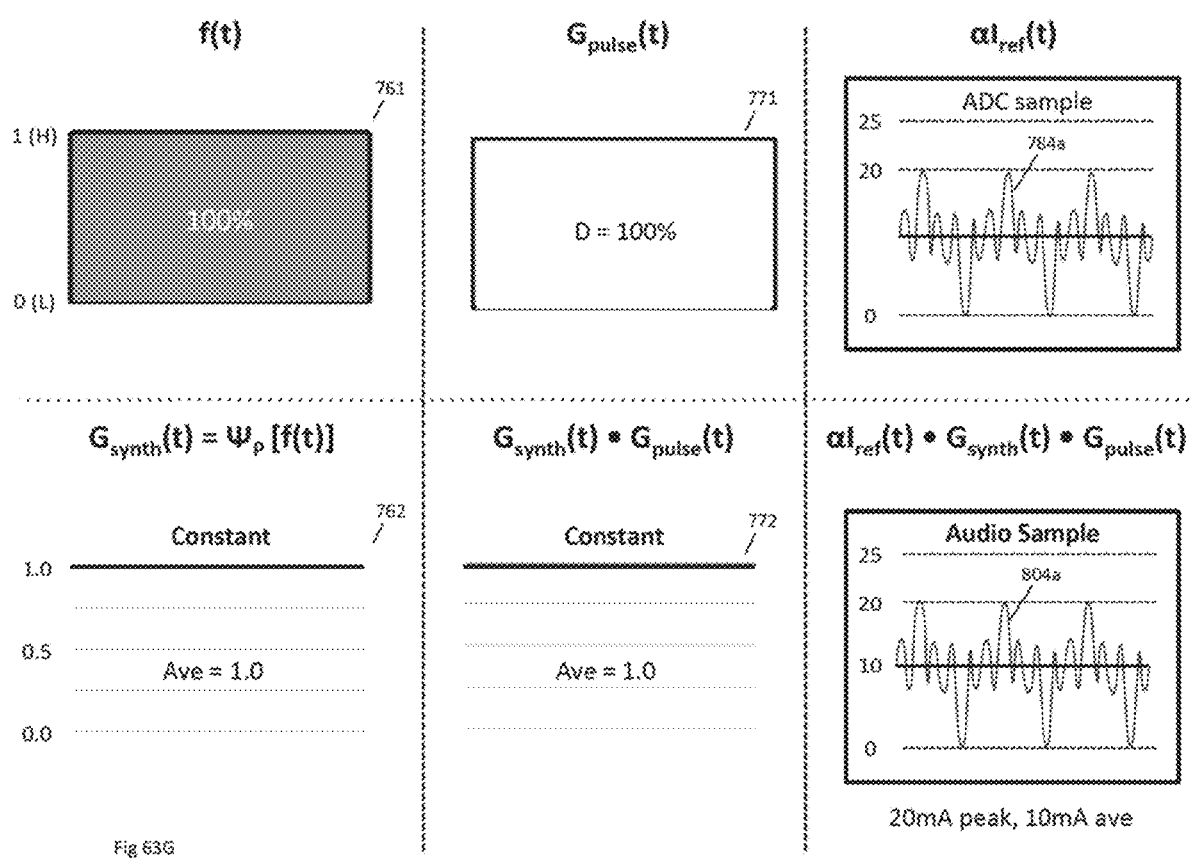
FIG. 63G illustrates the constituent waveforms for a LED driver ADC (analog-to-digital converter) generated audio sample of a guitar string pluck with a 10 mA average LED current.

FIG. 63G illustrates the constant f(t)=unit function 761 resulting in constant time invariant $G_{synth}$ waveform 762, where $\Psi_P[f(t)]=100\%$. The constant $\Psi_P[f(t)]$ is then multiplied by constant value 771 with D=100%, producing constant value 772, where $G_{synth}(t) \cdot G_{pulse}(t)=100\%$. Multiplied by a reference current 784a, $\alpha I_{ref}$, representing a plucked guitar string with a peak value of 20 mA, the resulting waveform $I_{LED}=\alpha I_{ref}((t) \cdot G_{synth}(t) \cdot G_{pulse}(t)$ is a waveform 804a with a peak value of 20 mA and an average value of 10 mA.

Figure 63H:
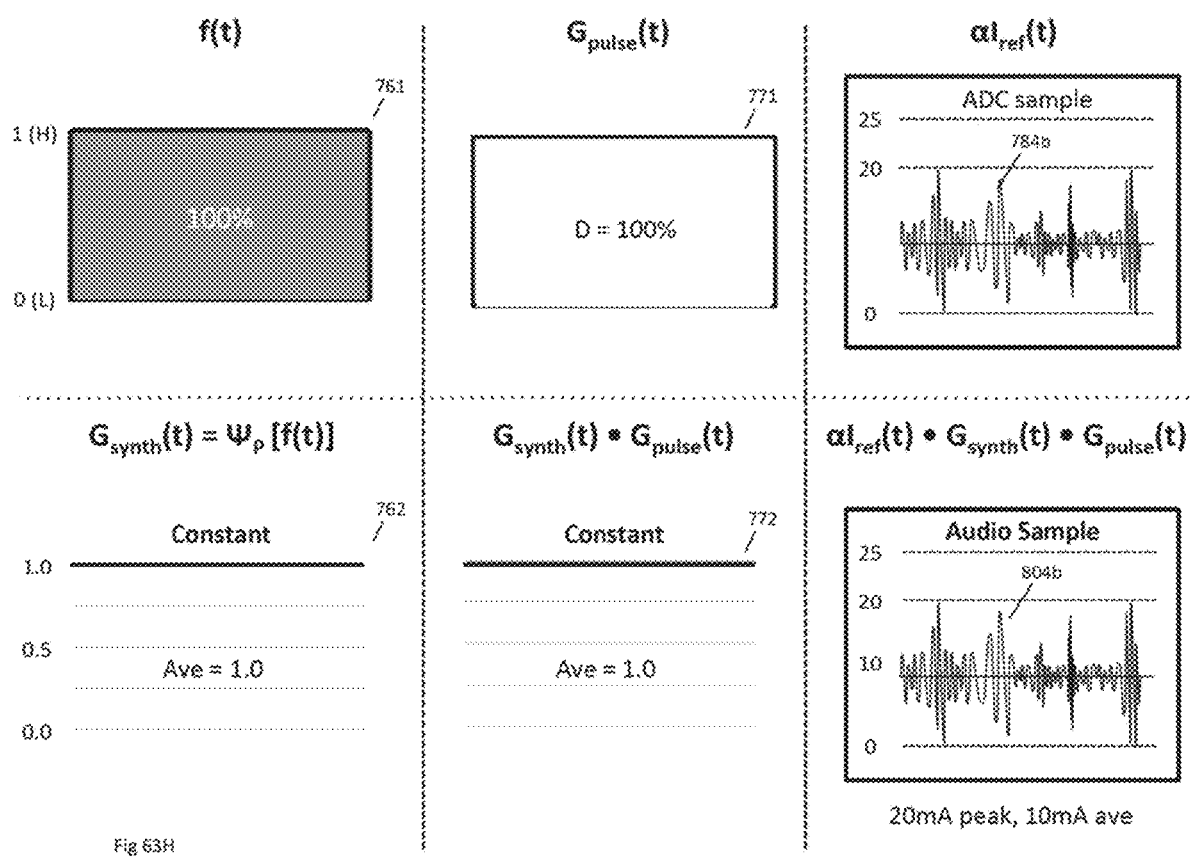
FIG. 63H illustrates the constituent waveforms for a LED driver ADC (analog-to-digital converter) generated audio sample of a cymbal crash with a 10 mA average LED current.

FIG. 63H illustrates the constant f(t)=unit function 761 resulting in constant time invariant $G_{synth}$ waveform 762 where $\Psi_P[f(t)]=100\%$. The constant $\Psi_P[f(t)]$ is then multiplied by constant value 771 with D=100% producing constant value 772 where $G_{synth}(t) \cdot G_{pulse}(t)=100\%$. Multiplied by a reference current 784b, $\alpha I_{ref}$, representing a cymbal crash with a peak value of 20 mA, the resulting waveform $I_{LED}=\alpha I_{ref}(t) \cdot G_{synth}(t) \cdot G_{pulse}(t)$ is a waveform 804b with a peak value of 20 mA and an average value of 10 mA.

Figure 64A:
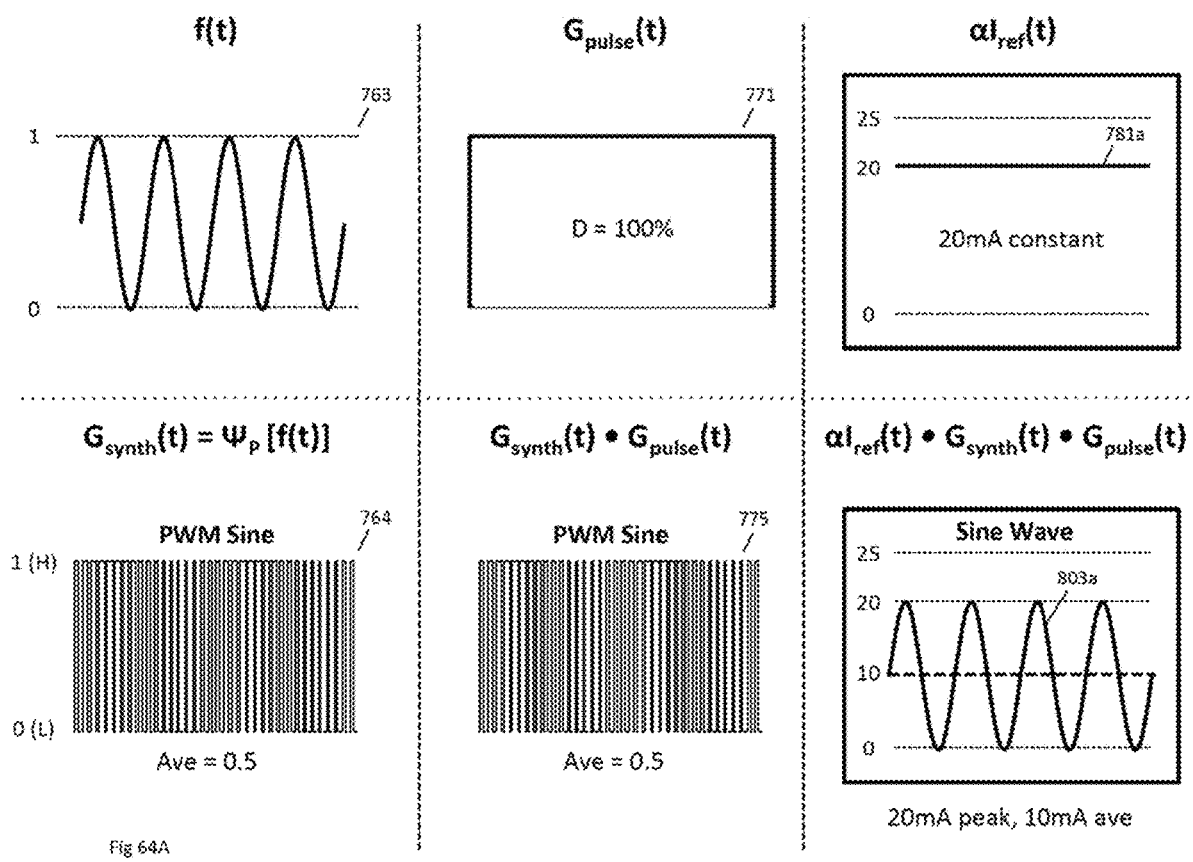
FIG. 64A illustrates the constituent waveforms for a PWM synthesized sine wave with a 10 mA average LED current.

FIG. 64A illustrates a sinusoidal function 763 off (t)=sin (t) resulting in $G_{synth}=\Psi_P[f(t)]$ as a continuously varying PWM pulse string waveform 764 with a defined period $T_{synth}$. The PWM string $\Psi_P[f(t)]$ is then multiplied by constant value 771 with D=100%, producing $G_{synth}(t) \cdot G_{pulse}(t)$, a PWM representation 775 of a sine wave. Multiplied by a constant reference current 781a, $\alpha I_{ref}$ of 20 mA, the resulting waveform $I_{LED}=\alpha I_{ref}(t) \cdot G_{synth}(t) \cdot G_{pulse}(t)$ is a sine wave 803a with a peak value of 20 mA and 50% average value of 10 mA.

Figure 64B:
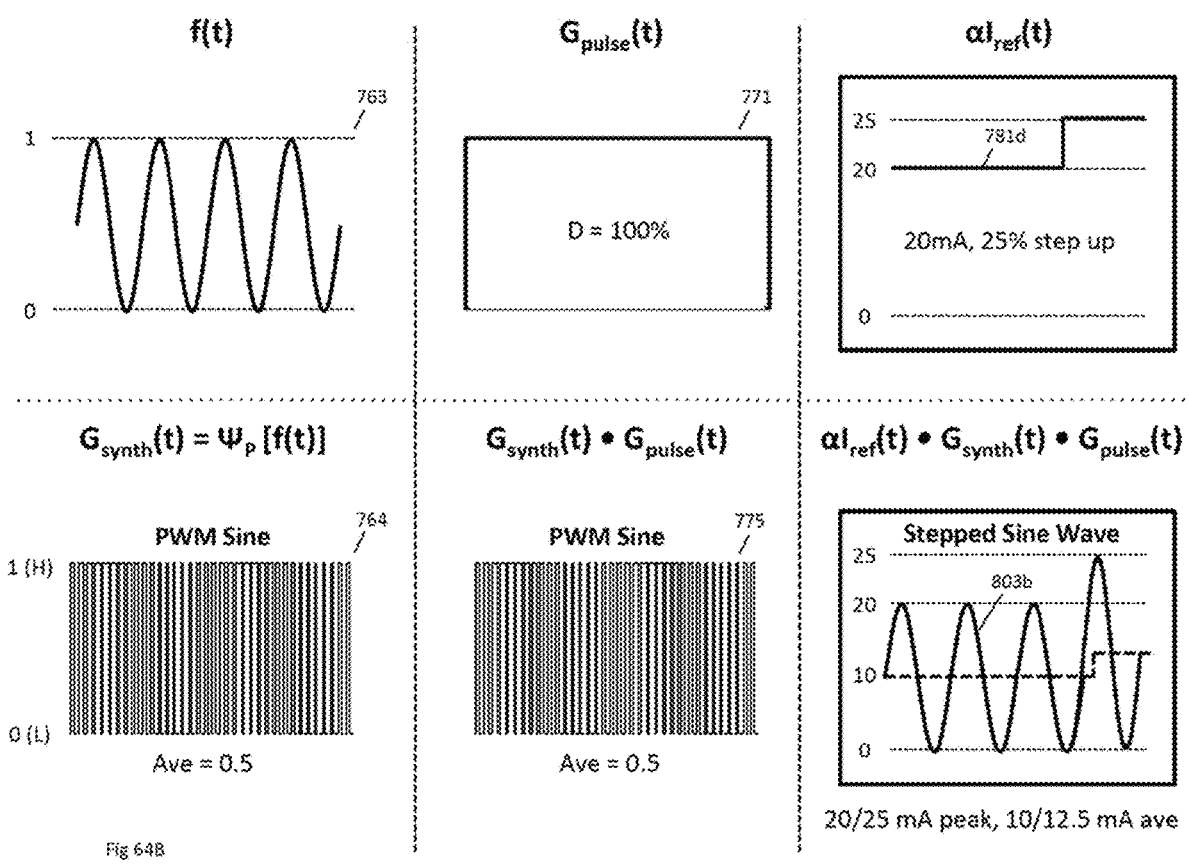
FIG. 64B illustrates the constituent waveforms for a PWM synthesized sine wave with a 10 mA average LED current subsequently stepped up to 13 mA.

FIG. 64B illustrates a sinusoidal function 763 where f(t)=sin (t), resulting in $G_{synth}=\Psi_P[f(t)]$ as the continuously varying PWM pulse string waveform 764 with a defined period $T_{synth}$. The PWM string $\Psi_P[f(t)]$ is then multiplied by constant value 771 with D=100%, producing $G_{synth}(t) \cdot G_{pulse}(t)$, PWM representation 775 of a sine wave. Multiplied by a stepped reference current 781d, $\alpha I_{ref}$ of 20 mA stepping up 25% to 25 mA., the resulting waveform $I_{LED}=\alpha I_{ref}(t) \cdot G_{synth}(t) \cdot G_{pulse}(t)$ is a sine wave 803b with a peak value of 20 mA and a 50% average value of 10 mA stepping up to a sine wave with a peak value of 25 mA and a 50% average value of 112.5 mA.

FIG. 64C illustrates a chord of sine waves 763 transformed by $G_{synth}=\Psi_P[f(t)]$ into a continuously varying PWM pulse string waveform 765 with a defined period $T_{synth}$. The PWM string $\Psi_P[f(t)]$ is then multiplied by constant value 771 with D=100%, producing $G_{synth}(t) \cdot G_{pulse}(t)$, a PWM representation 776 of a chord of sine waves. Multiplied by a constant reference current 781a, $\alpha I_{ref}$ of 20 mA, the resulting waveform $I_{LED}=\alpha I_{ref}(t) \cdot G_{synth}(t) \cdot G_{pulse}(t)$ is a chord of sine waves 803c with a peak value of 20 mA and a 50% average value of 10 mA.

Figure 64D:
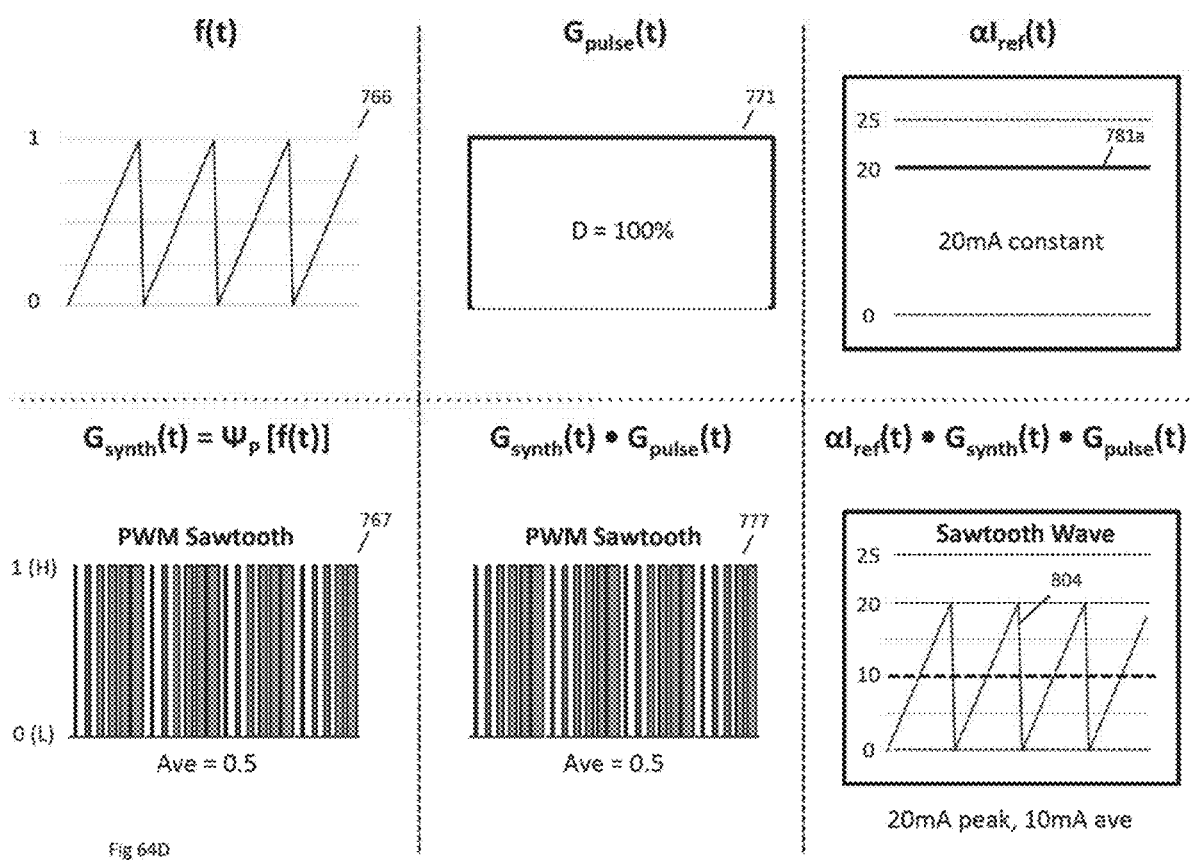
FIG. 64D illustrates the constituent waveforms for a PWM synthesized triangle wave with a 10 mA average LED current.

FIG. 64D illustrates a sawtooth wave 763 transformed by $G_{synth}=\Psi_P[f(t)]$ into a periodically varying PWM pulse string waveform 767 with a defined period $T_{synth}$. The PWM string $\Psi_P[f(t)]$ is then multiplied by constant value 771 with D=100%, producing $G_{synth}(t) \cdot G_{pulse}(t)$, a PWM representation 777 of a sawtooth wave. Multiplied by constant reference current 781a, $\alpha I_{ref}$ of 20 mA, the resulting waveform $I_{LED}=\alpha I_{ref}(t) \cdot G_{synth}(t) \cdot G_{pulse}(t)$ is a sawtooth wave 804 with a peak value of 20 Ma and a 50% average value of 10 mA.

Figure 64E:
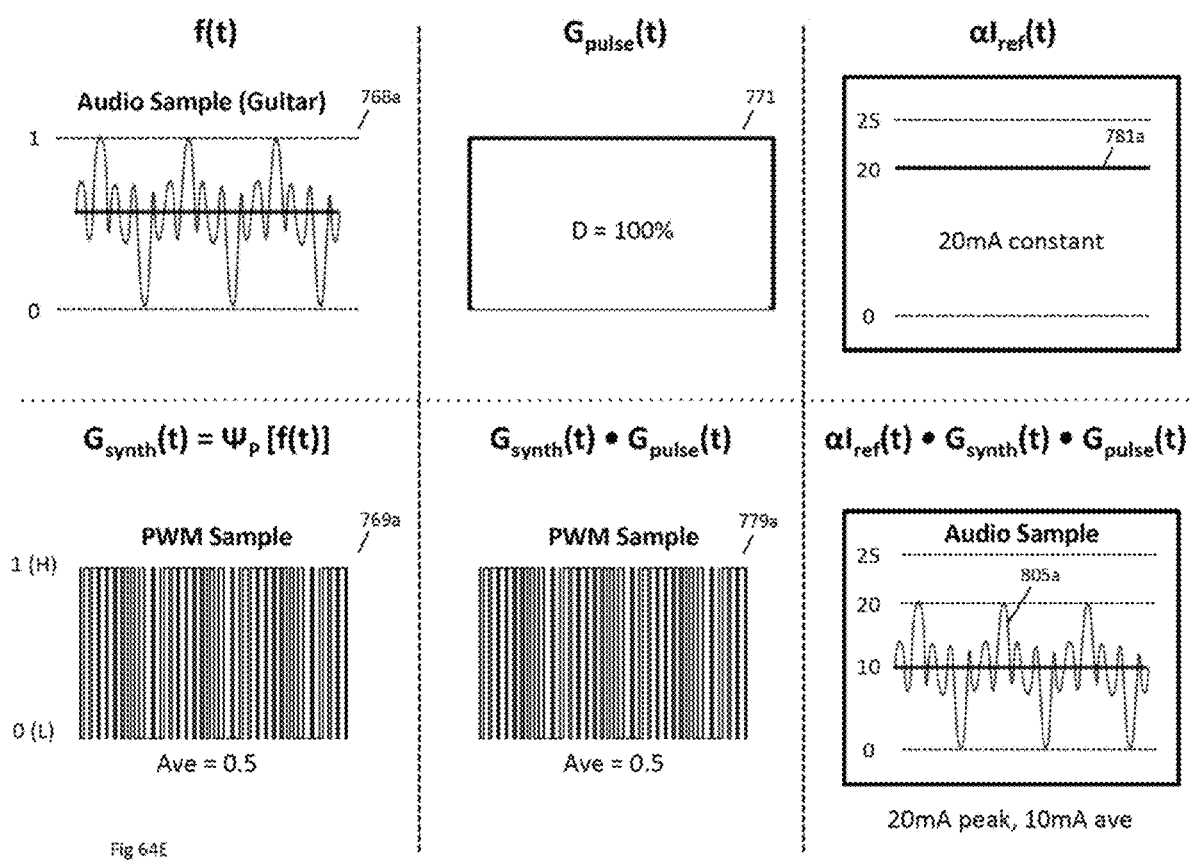
FIG. 64E illustrates the constituent waveforms for a PWM synthesized audio sample comprising a guitar string pluck with a 10 mA average LED current.

FIG. 64E illustrates an audio sample 768a of a guitar string transformed by $G_{synth}=\Psi_P[f(t)]$ into a periodically varying PWM pulse string waveform 769a with a defined period $T_{synth}$. The PWM string $\Psi_P[f(t)]$ is then multiplied by constant value 771 with D=100%, producing $G_{synth}(t) \cdot G_{pulse}(t)$, a PWM representation 779a of a audio sample 768a. Multiplied by constant reference current 781a, $\alpha I_{ref}$ of 20 mA, the resulting waveform $I_{LED}=\alpha I_{ref}(t) \cdot G_{synth}(t) \cdot G_{pulse}(t)$ is an audio sample 805a representing audio sample 768a with a peak value of 20 mA and a 50% average value of 10 mA.

FIG. 64F illustrates an audio sample 768b of a cymbal crash transformed by $G_{synth}=\Psi_P[f(t)]$ into a periodically varying PWM pulse string waveform 769b. The PWM string $\Psi_P[f(t)]$ is then multiplied by constant value 771 with D=100% producing $G_{synth}(t) \cdot G_{pulse}(t)$, a PWM representation 779b of a cymbal crash. Multiplied by constant reference current 781a, $\alpha I_{ref}$ of 20 mA, the resulting waveform $I_{LED}=\alpha I_{ref}(t) \cdot G_{synth}(t) \cdot G_{pulse}(t)$ is an audio sample 805b representing audio sample 768b with a peak value of 20 mA and a 50% average value of 10 mA.

Figure 65:
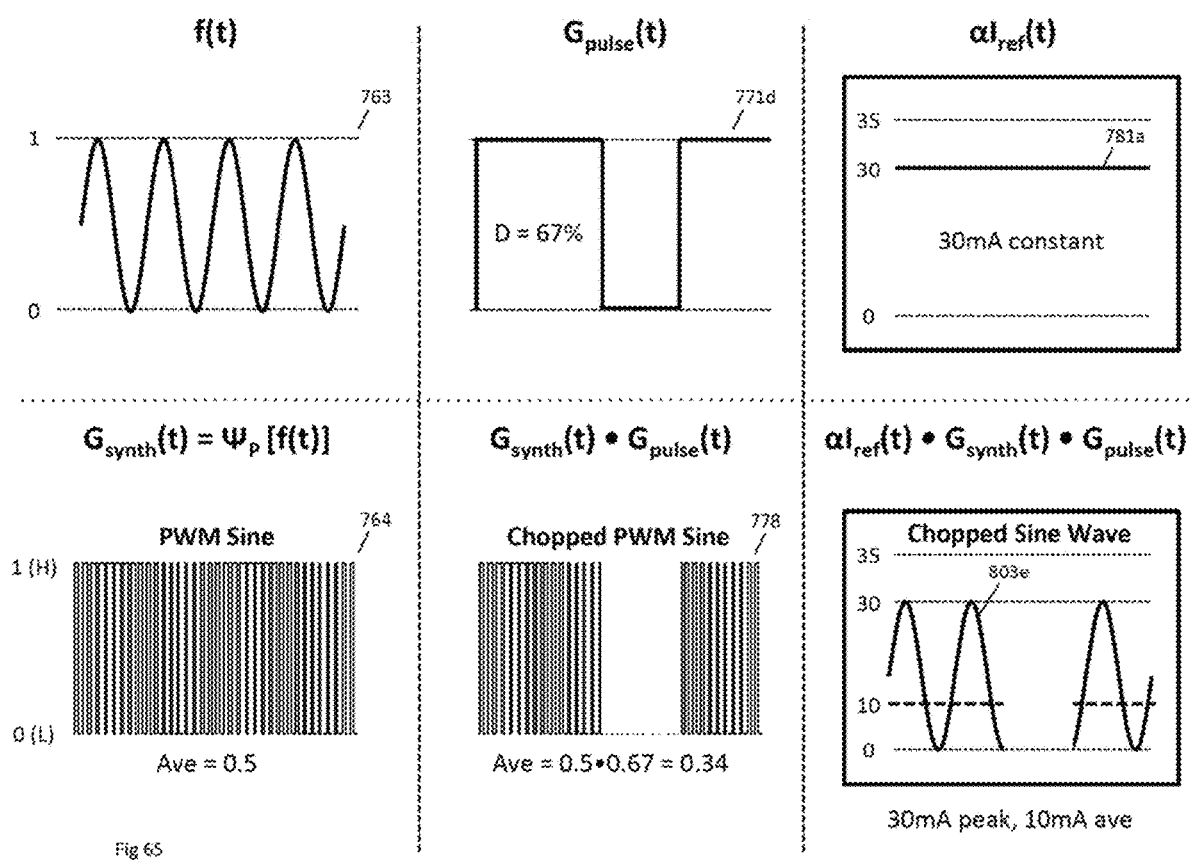
FIG. 65 illustrates the constituent waveforms for a PWM synthesized sine wave with a 10 mA average LED current subsequently stepped up to 13 mA chopped by a PWM player.

FIG. 65 illustrates a sinusoidal function 763 where f(t)=sin (t), resulting in $G_{synth}=\Psi_P[f(t)]$ as the continuously varying PWM pulse string waveform 764 with a defined period $T_{synth}$. The PWM string $\Psi_P[f(t)]$ is then multiplied by a PWM pulse 771d of a fixed period with D=67%, producing a digital pulse string $G_{synth}(t) \cdot G_{pulse}(t)$, a chopped PWM representation 778 of a sine wave gated by a lower frequency PWM pulse. Multiplied by a constant reference current, 781e, $\alpha I_{ref}$ of 30 mA, the resulting waveform $I_{LED}=\alpha I_{ref}(t) \cdot G_{synth}(t) \cdot G_{pulse}(t)$ is a chord of sine waves 803e with a peak value of 30 mA and an average value of 10 mA.

In order to execute PBT treatments, first the LED player is downloaded from the PBT controller into the LED pad, followed by the specific LED playback file to be executed. Once the LED player is downloaded, the LED player does not need to be reloaded each time a new treatment is selected. New playback files can be repeatedly loaded and new treatments or sessions executed so long as the LED player remains in the volatile memory of the LED pad. Turning off the PBT system or disconnecting a LED pad from the PBT controller, however, wipes the LED player software from the LED pad's volatile memory and it must be re-installed into the pad before a LED playback file can be executed and treatment or session commence. Although the program wipe issue can be avoided by storing the LED player file in non-volatile memory, for security purposes it is preferable to write the program in volatile memory such as SRAM or DRAM rather than in non-volatile EEPROM or flash. In that way any attempt to reverse engineer the program's contents are lost with a power interruption and a hacker's efforts to extract the program thwarted by the immediate loss of the executable code.

Figure 66:
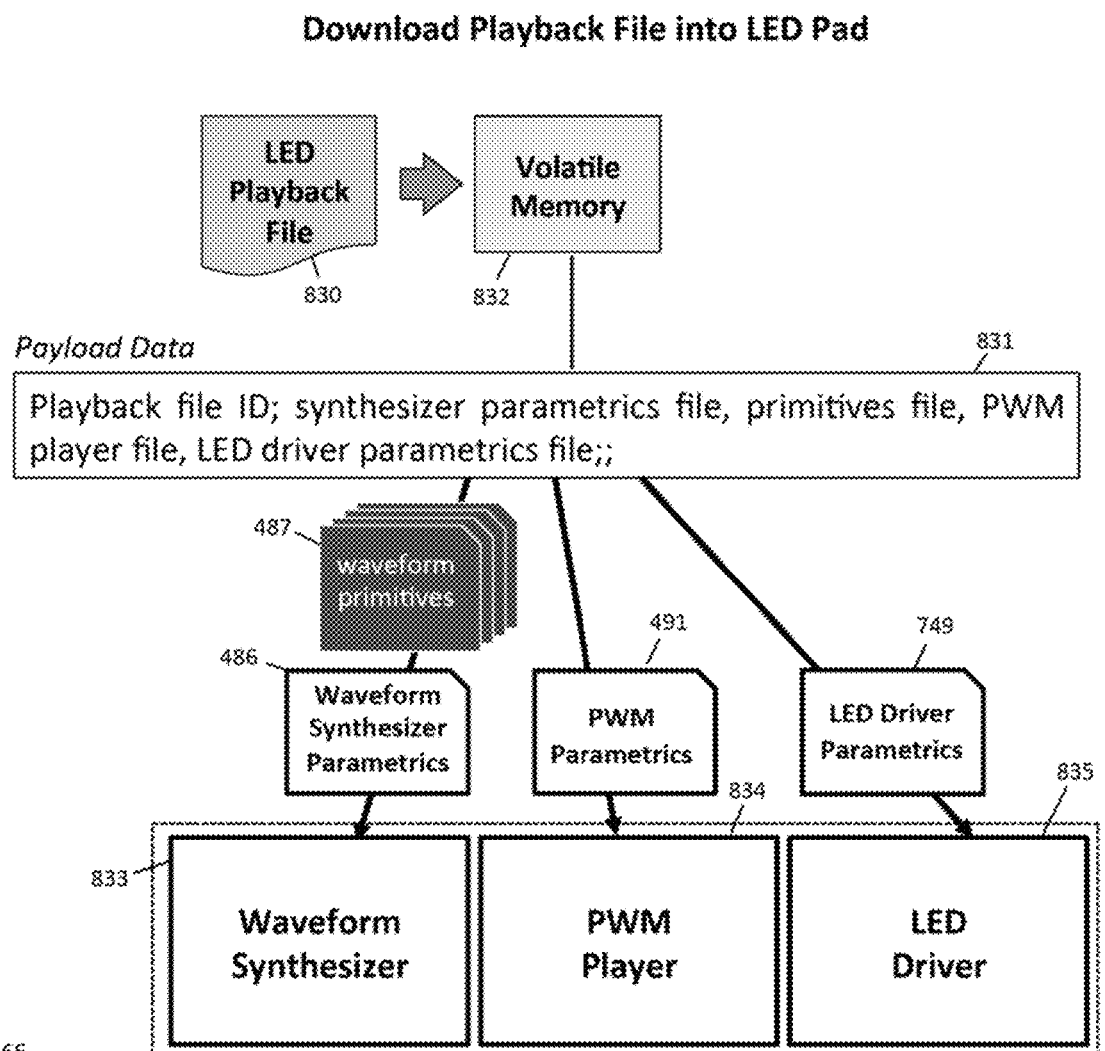
FIG. 66 illustrates download of a playback file into an LED pad.
Figure 67:
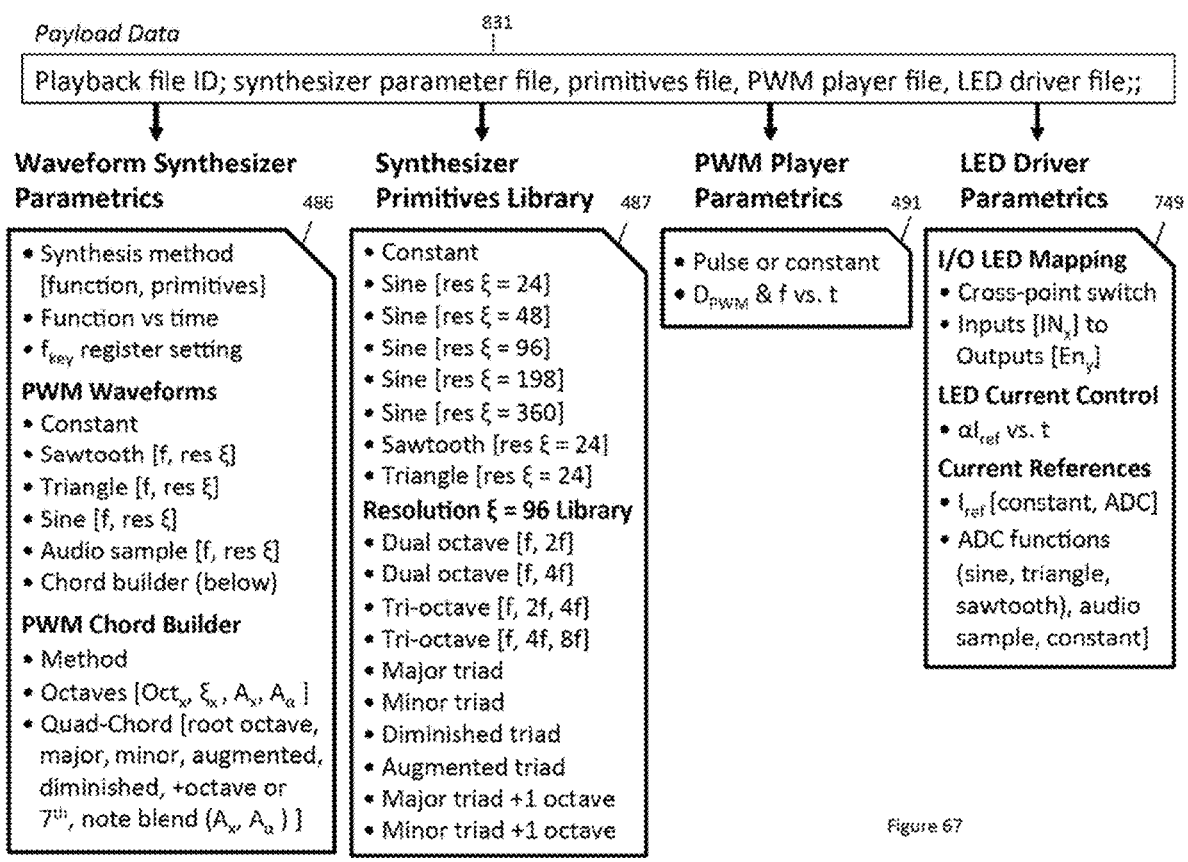
FIG. 67 illustrates an LED playback data file comprising a Playback file ID, synthesizer parameter file, primitives file, PWM player file, LED driver file, and components thereof.

As shown as FIG. 66, an LED playback file 830 containing payload data 831 is transferred into a volatile memory 832. The payload data 831 is then uncompressed to extract waveform primitives 487 and waveform synthesizer parametrics 486 which are loaded into waveform synthesizer 833, PWM player parametrics 491 are loaded into PWM player 834, and LED driver parametrics are 749 loaded into LED driver 835. An example of the contents of payload data 831 is shown in FIG. 67, including the contents of synthesizer primitives library 487, waveform synthesizer parametrics 486, PWM player parametrics 491, and LED driver parametrics 749. The waveform synthesizer parametrics 486 comprises the information needed to execute a specific treatment or session, i.e. an instruction file. The general instruction file for waveform synthesizer parametrics 486 includes the following:

The waveform synthesis method employed by the file, i.e. either function synthesis or primitive synthesis.

The tuning (key) of the program, i.e. the $f_{key}$ register setting for the synthesis. Available keys of PBT synthesis comprise predefined binary multiples of a $4^{th}$ octave note, the generated harmonic multiples spanning the audio spectrum from the $9^{th}$ to the $-1^{st}$ octaves. Scales include default, musical, physiological, other and custom. While default, and musical scales are even-tempered; the "other" submenu includes alternate tunings such as Werckmeister, Pythagorean, Just-Major and Mean-Tone scales. The physiological scale "physio" is based on empirically derived scales derived from observation. The "custom" UI/UX allows a user to manually set the value of $f_{key}$ as a $4^{th}$ octave frequency (entered in Hertz rather than by note) and passes this frequency into the $f_{key}$ register.

The waveform sequence to be synthesized, including the duration of each waveform "step" in the synthesis. A termination code is included at the program's terminus to signify the treatment or session has completed.

If function synthesis is used, the mathematical expression of each function and its frequency f Available periodic waveforms using function synthesis include constant, sawtooth, triangle, and single frequency sine wave.

If primitive synthesis is used, each primitive subroutine-call including the frequency $f_x$ and resolution $\xi_x$ of the primitive's playback subroutine. Available primitive based waveform subroutine calls include constant, sawtooth, triangle, or sine waves, or audio samples. Primitives-based synthesis of sinusoidal chords is also available using a "chord builder" subroutine.

Chord builder subroutines include specifying the chord construction method and the octaves and notes present. Chord builder algorithms include "octave" synthesis and "tri/quad" chord synthesis.

In octave synthesis, any chord can be described by its component octave "Oct" numbers (a number from −1 to 9 describing the frequency $f_x$ made in accordance with the $f_{key}$ register setting) along with each octave's corresponding primitive resolution $\xi_x$ and blend $A_x$. In a tri/quad chord builder, three or four fixed-resolution sine wave notes spanning a single octave can be blended using adjustable amplitude set by gain $A_\alpha$. Available chord triads include major, minor, diminished, augmented, each of which includes an optional fourth note +1 octave above the chord's root note. Alternatively a fourth note can be added to form a $7^{th}$ chord, specifically a quad note chord having a $7^{th}$, major $7^{th}$, and minor $7^{th}$ construction. A "custom" chord allows generation of any three note chord spanning one octave, even in dissoanance, with an option for a fourth note +1 octave above the chord's root note.

All chord builder outputs may be scaled to increase the chord's periodic amplitude by digital gain $A_\alpha$ without shifting the 0.5 Average value of the unit function.

All outputs of the waveform synthesizer 833 represent unit functions, i.e. having analog values between 0.000 and 1.000 converted into PWM pulse strings with a duty factor between 0% and 100%. Any synthesized waveform outside of this range will be truncated.

In operation, only waveform primitives 486 required by a playback file specified by the synthesizer primitives library 487 are downloaded into a LED pad. The downloadable synthesizer primitives library 487 includes a selection of sine wave primitives at various resolutions for example using 24, 46, 96, 198 or 360-point or 16-bit resolution. The exemplary synthesizer primitives library 487 shown in FIG. 67 also includes 24 point descriptions of triangle and sawtooth waveforms, although other resolutions may be included without limitation. Other components of synthesizer primitives library 487, for example with ξ=96, involve chords including dual octave chords comprising two sine waves one octave apart (f and 2f) or two octaves apart (f and 4f). Other possibilities (not shown) are chords four octaves apart (f and 16f) or five octaves apart (f and 32f).

Other options shown in FIG. 67 include tri-octave chords such as [f, 2f, 4f] spanning two octaves or such as [f, 4f, 8f] spanning three octaves or other triads, including major, minor, diminished, and augmented chords, e.g. [f, 1.25f, 1.5f], [f, 1.2f,1.5f], [f, 1.2 f,1.444f]. As shown, the triads may be modified into quad chords by including a note one octave above the root. Other options, not shown, include tri-octave chords [f, 2f, 8f] spanning three octaves or tri-octave chords [f, 2f, 16f], [f, 4f, 16f] or [f, 8f, 16f] spanning four octaves.

PWM player parametrics file 491 includes settings for constant or pulse mode. In pulse mode, the playback file comprises a sequence of PWM frequencies $F_{PWM}$ and a corresponding duty factor $D_{PWM}$ versus playback time, thereby defining a PWM sequence of pulses of varying durations of $t_{on}$ and $t_{off}$. Note that the pulse frequency $f_{PWM}$ Of the pulse width modulator 711 is lower in frequency than the PWM clock $\Phi_{PWM}$=20 kHz used to drive the pulse width modulator 711. To conclude, in PWM player operation, the PWM frequency $f_{PWM}$ is not fixed but varies with the playback program specified in PWM parametrics file 491. Although the frequency $f_{PWM}$ can be as high as the clock $\Phi_{PWM}$ in most cases it is lower so that $f_{PWM} \leq \Phi_{PWM}$. Moreover, the frequency $f_{PWM}$ is in the audio spectrum, far below the oversampled clock $\Psi_{sym}$ in the supersonic range used by in the PWM generator $\Psi_P[f(t)]$ in the waveform synthesizer block, i.e. mathematically $f_{PWM} \leq \Phi_{PWM} \ll \Phi_{sym}$.

In LED driver parametrics 749, the unit function digital PWM inputs $IN_x$ are mapped against the current sink enable $En_y$. For example, the input $IN_1$ maps to the channel 4 current sink enable $En_4$, the input $IN_2$ maps to current sink enables $En_1$ and $En_5$ (not shown) for channels 1 and 5, etc. LED current control comprises a playback file of $\alpha I_{ref}$ versus time. The value of $I_{ref}$ for each channel is set by the output of each corresponding D/A converter, which may comprise a constant, a periodic function, or an audio sample. Alternatively, one D/A converter may be used to supply the reference current of all output channels with the same function or constant value.

Commencing Playback in Distributed PBT Systems

Figure 68:
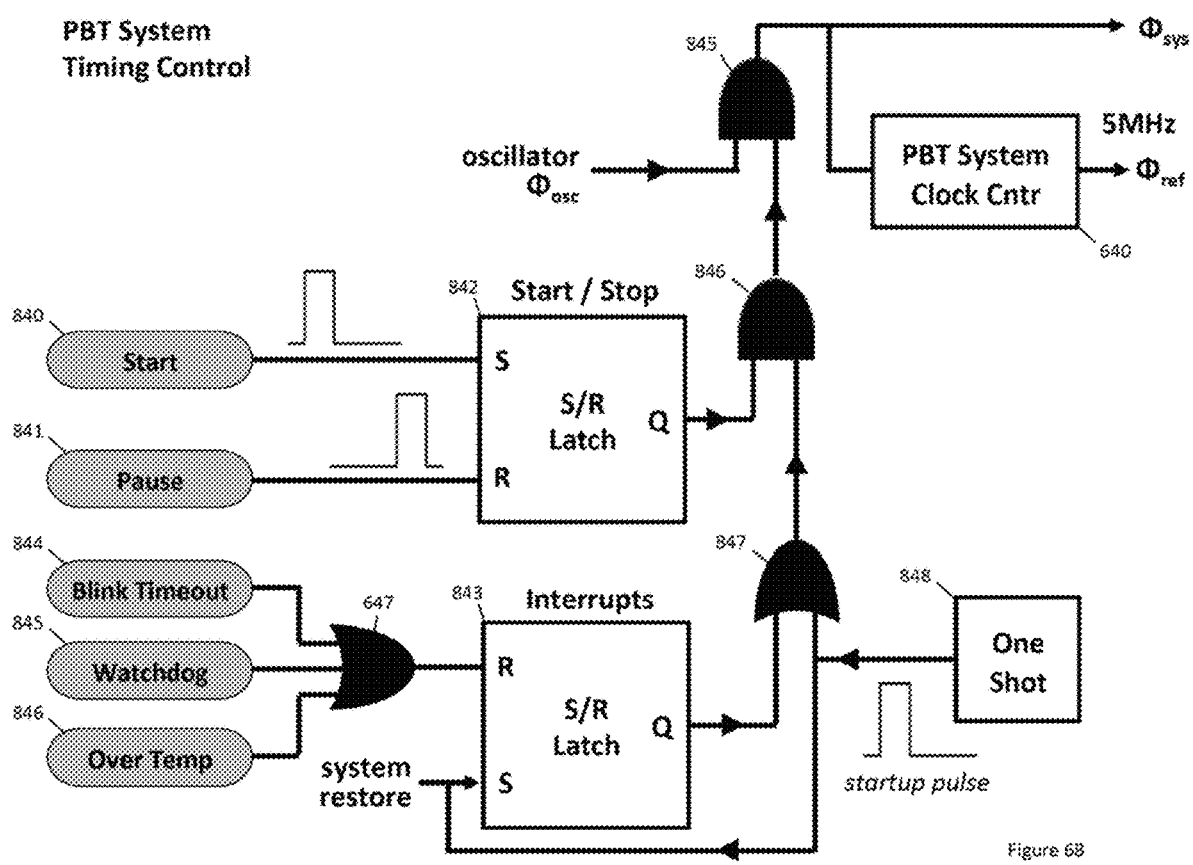
FIG. 68 is a schematic analog view of firmware used to control the PWM player clock $\Phi_{ref}$.

After downloading the LED player and LED playback file into an LED pad, playback is enabled by a start signal 840 in the PBT System timing control, which may be implemented in software or in hardware using the exemplary circuit of FIG. 68, including a start/stop latch 842 comprising a set/reset or S/R type flip flop, an interrupts latch 843, a PBT system clock counter 640, a start-up one shot 848, logical AND gates 845 and 846, and logical OR gates 846 and 847. The two-input AND gate 845 acts as a system clock enable of oscillator $\Phi_{osc}$ to the LED player, gated by start and pause signals 840 and 841, and by a variety of interrupts, specifically a blink timer timeout 844, a watchdog timer timeout 845, and an over-temperature flag 846.

At startup, one shot 848 generates a pulse that immediately drives the output of OR gate 847 to high. Concurrently the pulse from one shot 848 triggers the set input S of interrupts latch 843, setting its output Q to high. When user input "start" 840 is selected, it generates a positive pulse, setting the output Q of start/stop latch 842 to high. With the Q outputs of both start/stop latch 842 and interrupts latch 843 set high, AND gate 846 is enabled. As a result, the output of oscillator $\Phi_{osc}$ is delivered to the PWM player 834 as clock $\Phi_{sys}$, and divided by PBT system clock counter 640 to produce reference clock $\Phi_{ref}$.

Selecting "pause" 841 generates a pulse that resets the output of start/stop latch 842 to zero and suspends playback. Playback remains latched off until "start" 840 is selected, cancelling the pause command. As a result, start/stop latch 842 starts and stops program execution. In the event that an interrupt occurs for any reason, i.e. if any one of the inputs to OR gate 647 go high, output of OR gate 647 will also go high, thereby resetting the output Q of interrupts latch 843 to zero. With the Q output of interrupts latch low, the outputs of AND gates 846 and 845 also go low, disconnecting clock $\Phi_{osc}$ from the LED player and suspending treatment. This situation will persist until the cause of the interrupt is remedied, the inputs to OR gate 647 are reset to low and a system restore pulse is sent to the S input of interrupts latch 843. For example, if an over temperature condition occurs, the over temperature flag 846 will go high 846 disable LED pad operation until normal temperatures return and the over temperature flag 846 is reset.

A unique safety feature of the disclosed distributed PBT system is the blink timer. This timer operates within the intelligent LED pad itself and does not rely on the PBT controller. At regular intervals in the pad μC 339, e.g. every 20 or 30 seconds, the program counter interrupts operation to execute an interrupt service routine (ISR). During this interval, the blink timer timeout 844 is set to logic 1 while the LightPadOS software executes a safety check regarding LED pad electrical connections, any priority messages or file updates, file parity checks, etc. Once the safety check routine has been completed, the blink timer timeout 844 is reset to zero, the watchdog timer 845 is reset, and program execution is returned to the main routine. After completing the ISR, the pad μC 339 generates a system restore pulse to interrupts latch 843 and program operation recommences. If the software has for any reason frozen, the program will not resume operation and the LED strings in the pad will remain off. Otherwise, the LED pad will resume operation after a defined interval, e.g. 2 seconds.

Another failure mode involves frozen software while the LEDs are on and emitting light. If the condition persists the LEDs may overheat and present a burn risk to a patient. To prevent a dangerous condition from arising, watchdog timer 845 (whose operation is not dependent on software) counts down in parallel to the software program counter. Should the software timer become frozen in an on state, the watchdog timer 845 will not be reset, and the watchdog timer 845 will time out, generating an interrupt signal from blink timer timeout 844 and discontinuing operation of the PBT system until the fault condition is resolved.

In this manner the disclosed distributed PBT system can be used to control LED pad operation remotely. Furthermore, the methods disclosed herein can be adapted to control multiple intelligent LED pads simultaneously from a common PBT controller.

Component Communication Over Distributed PBT Systems

Implementing the required communication among components in a distributed PBT system requires a complex communication network and dedicated protocol designed to accommodate the mix of real time and file-based data transfers, some of which are linked to safety systems. In accordance with FDA regulations, safety is a major design consideration in medical devices. In distributed systems this concern is further exacerbated by autonomous operation of components. In the event that inter-device communication in the distributed PBT fails or is interrupted, the safety systems cannot malfunction. The topic of communication, safety, sensing and biofeedback are discussed in greater detail in related U.S. application Ser. No. 16/377,192, entitled "Distributed Photobiomodulation Therapy Devices, Methods, and Communication Protocols Thereof," filed contemporaneously with this application.

As described above, the delivery of LightOS data packets in a distributed PBT system can be achieved using a 4-layer communication protocol executed over a wired bus such as USB, I²C, SMBus, FireWire, Lightening and other wired communication mediums. If, however, distributed PBT system communication is performed over Ethernet, WiFi, telephonically over cellular networks (such as 3G/LTE/4G or 5G), or if data is passed through a public router, communication cannot be performed exclusively through the MAC address, i.e., a Layer-1 and Layer-2 communication stack is not sufficient to execute data routing through the network.

Figure 69:
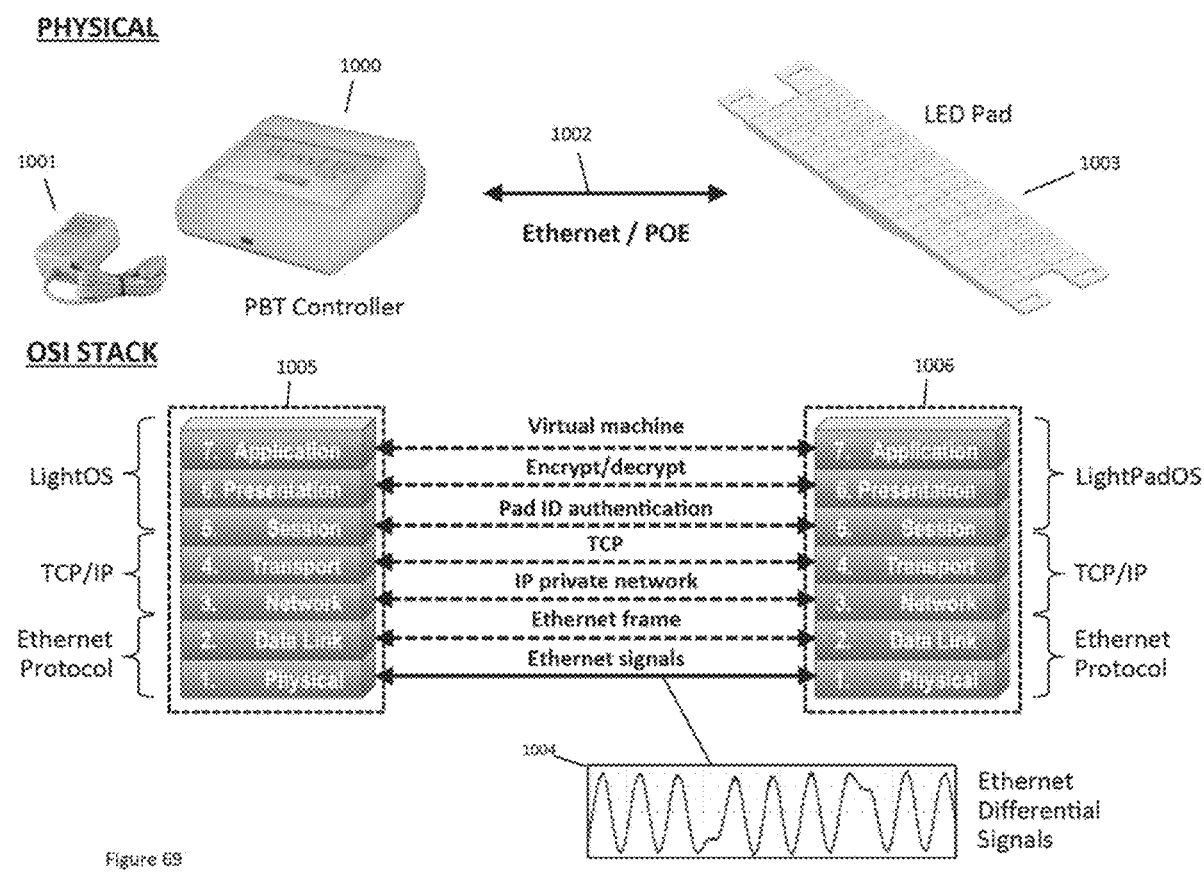
FIG. 69 illustrates the communication stack for an Ethernet based distributed PBT system.

For example, as shown in FIG. 69, a PBT controller 1000 communicates over Ethernet 1002 with an intelligent LED pad 1003 using a 7-layer OSI compliant communication stack 1005. Specifically, communication stack 1005 of PBT controller 1000 includes PHY Layer-1 and Data Link Layer-2, executing the Ethernet communication protocol over Ethernet differential signals 1004; Network Layer-3 and Transport Layer-4, executing network communication in accordance with the TCP/IP (transfer communication protocol over Internet protocol network); and LightOS operating system defined applications layers comprising Session Layer-5 for authentication, Presentation Layer-6 for security (encryption/decryption), and Application Layer 7 for PBT system control and therapy. Communication stack 1006 of LED light pad 1003 includes the corresponding Layer-1 and Layer-2 protocols for Ethernet and Layer-3 and Layer-4 for TCP/IP, along with LightPadOS defined layers 5 through 7. In point-to-point communication, i.e. for communication not involving an IP router, Ethernet connection 1002 operates as a private network over network Layer-3. The operating system LightPadOS of intelligent LED pad 1003 is a subset of LightOS, and therefore PBT controller 1000 and intelligent LED pad 1003 are able to communicate with one another as a single virtual machine (VM) despite being physically separated from one another.

Figure 70:
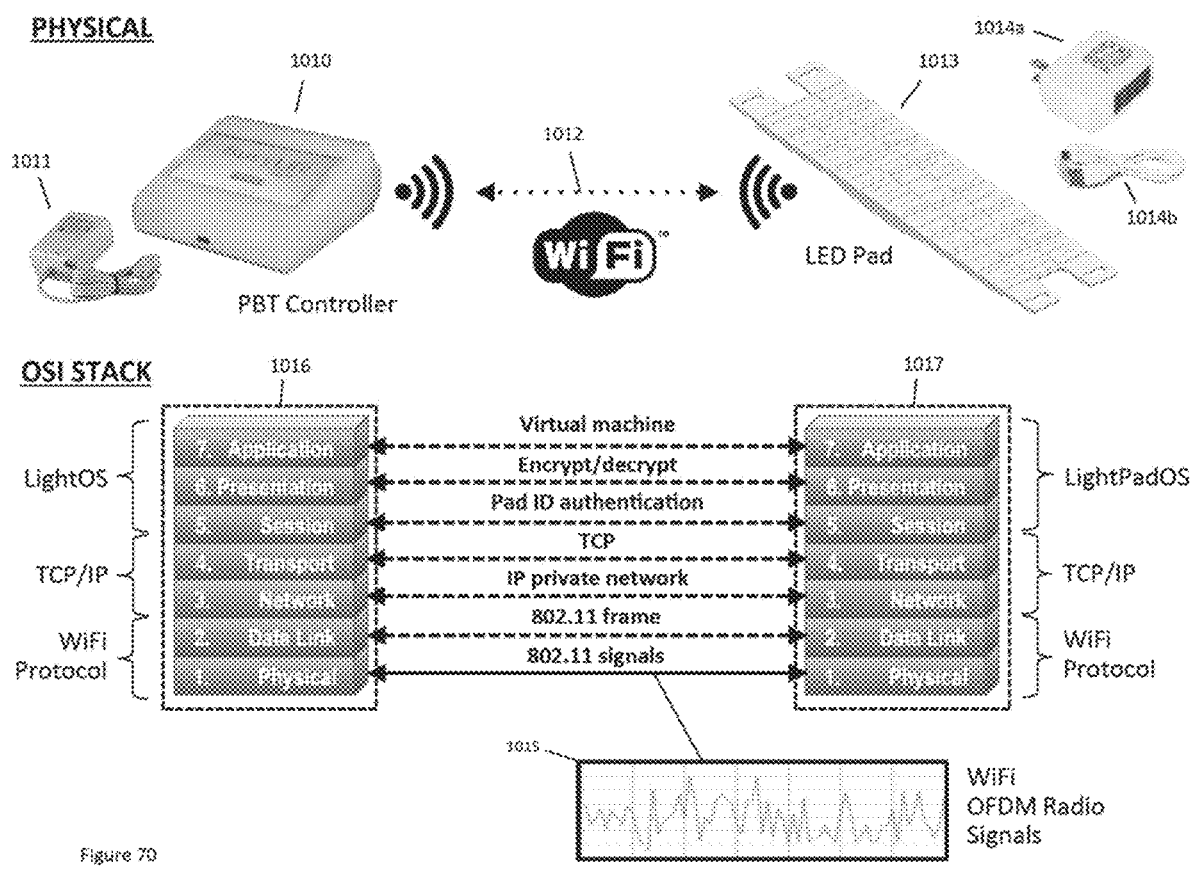
FIG. 70 comprises the communication stack for a WiFi based distributed PBT system.

Using the described 7-layer OSI communication stack, network communication in the PBT system can easily be adapted to WiFi wireless communication. In the distributed PBT system shown in FIG. 70, a WiFi enabled PBT controller 1010 powered by a power supply 1011 communicates by WiFi signal 1012 with an intelligent LED pad 1013 using OFDM radio signals 1015 in accordance with the IEEE standards for 802.11. WiFi communication protocols may include 802.11a, 802.1b, 802.11g, 8012.11n, or 802.11ac or other related versions depending on the chip sets employed in intelligent LED pad 1013. PBT controller 1010 can support the superset of all standard WiFi protocols. Because WiFi cannot carry power, intelligent LED pad 1013 must receive power through a USB cable 1014b, powered either by AC/DC converter and DC power supply (brick) 1014a or a USB storage battery (not shown). WiFi communication occurs over the full 7-layer OSI communication stack 1016 present in PBT controller 1010 connected to communication stack 1017 present in intelligent LED pad 1013.

Figure 71A:
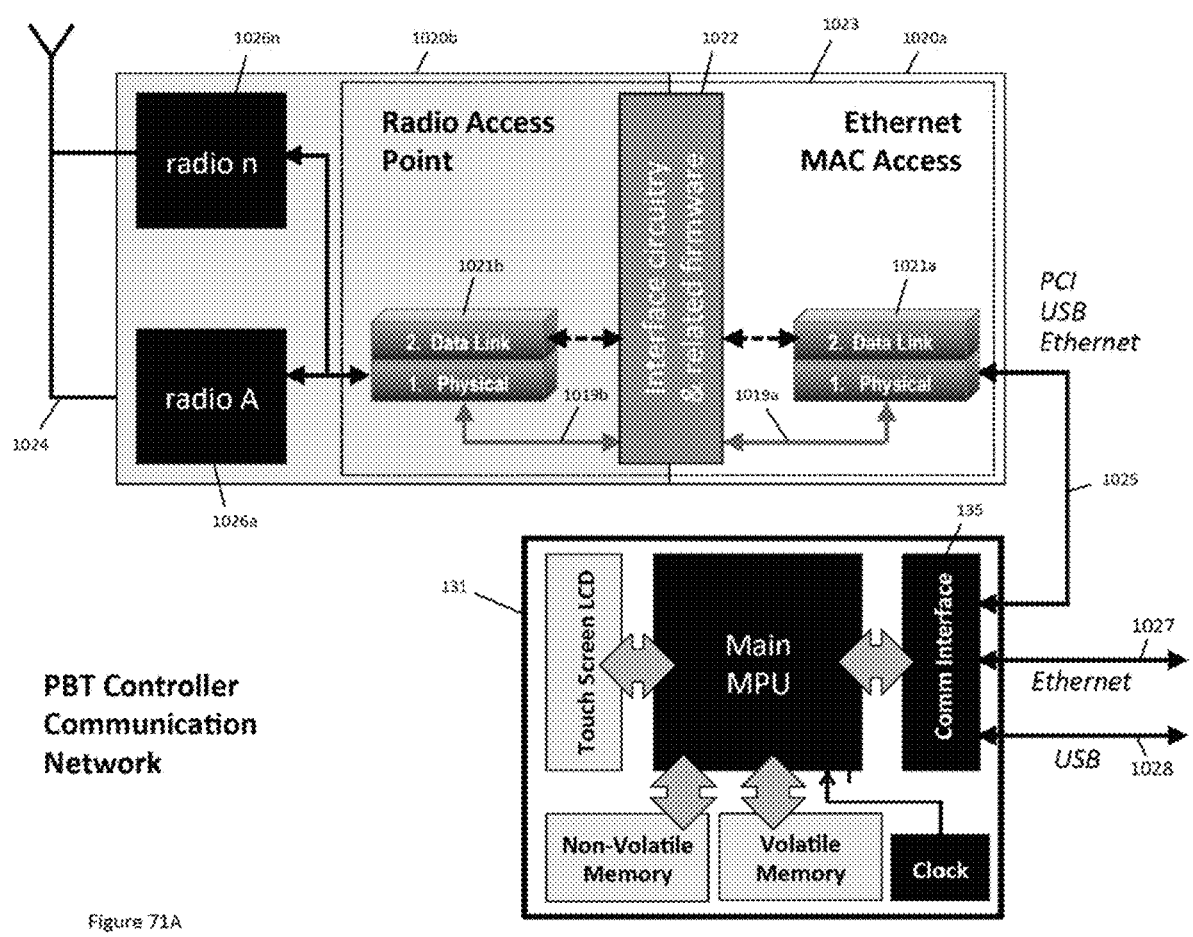
FIG. 71A is a block diagram of a WiFi communication enabled PBT controller for distributed PBT systems.

FIG. 71A is a block diagram of WiFi communication-enabled PBT controller 1010. In operation, a WiFi radio converts a wired communication link 1025 (e.g. PCI, USB, Ethernet) to a microwave radio link 1024, translating Ethernet MAC access 1020a to Radio Access Point 1020b using interface circuitry and related firmware 1022. Signals from communication link 1025 pass through communication stack 1021a as PHY signals 1119a, whose format is converted by interface 1022 to PHY signals 1119b, which are then sent into WiFi communication stack 1021b and on to radios 1026a through 1026n, operating over various radio frequencies transmitted over multi-band antenna array for microwave radio link 1024. Communication 1021a transfers data 1019a in accordance with the link communication Data Link Layer-2 protocol and interface circuitry and related firmware 1022 converts the data into WiFi data 1019b in accordance with Data Link Layer-2 of communication stack 1021b, formatted for radios 1026a through 1026n. This WiFi radio in turn connects to PBT controller 131 through 135 also connected to Ethernet 2017 ad USB 1028.

Figure 71B:
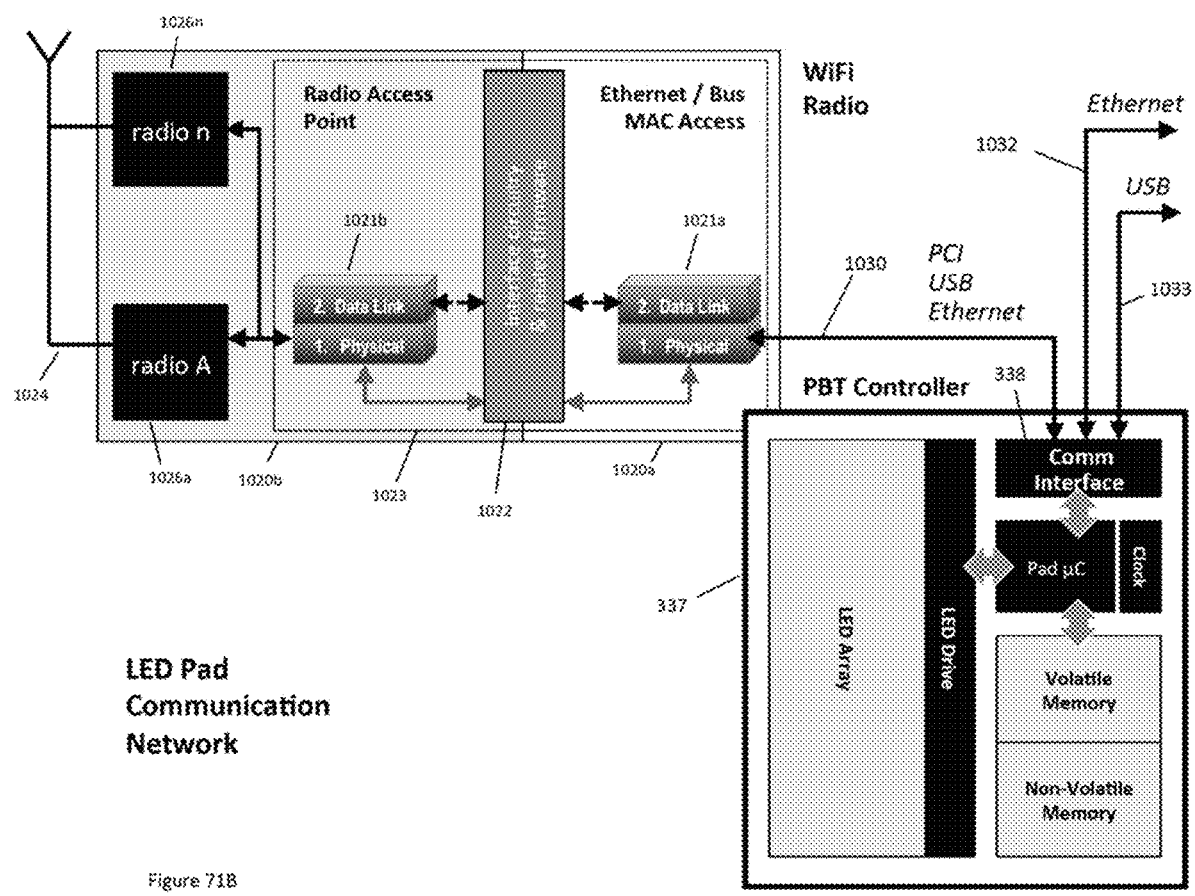
FIG. 71B is a block diagram of a WiFi communication enabled LED pad for distributed PBT systems.
Figure 72:
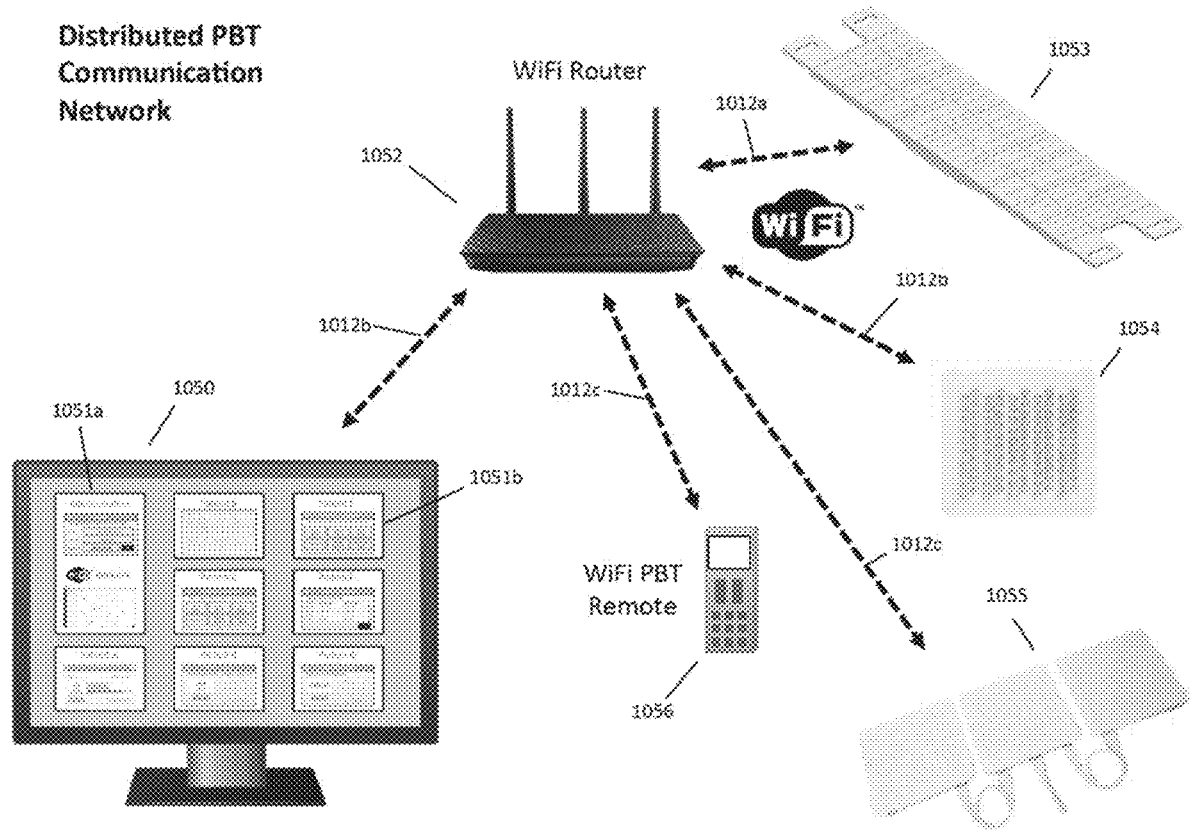
FIG. 72 is a multi-user distributed PBT system and communication network.

As shown in FIG. 71B, the microwave radio link 1024 extends to intelligent LED pad 1013 and then, via a wired data link 1030 using PCI, USB or Ethernet protocols, to communication interface 338 in LED pad 1013. Communication interface 338 also may connect to other devices or sensors via a USB link 1033 and an Ethernet link 1032. An example of a distributed PBT communication network is shown in FIG. 72, wherein a WiFi router 1052 communicates with intelligent LED pads 1053, 1054, and 1055 over WiFi links 1012a, 1012b, and 1012c, and with a central control UI/UX LCD display 1050, having a system control window 1051a and a patient window 1051b, over a WiFi link 1012b. The system also includes an inventive component, WiFi PBT remote control 1056, which enables a nurse to start a treatment in a patient's room without the need to return to central control UI/UX LCD display 1050.

Figure 73:
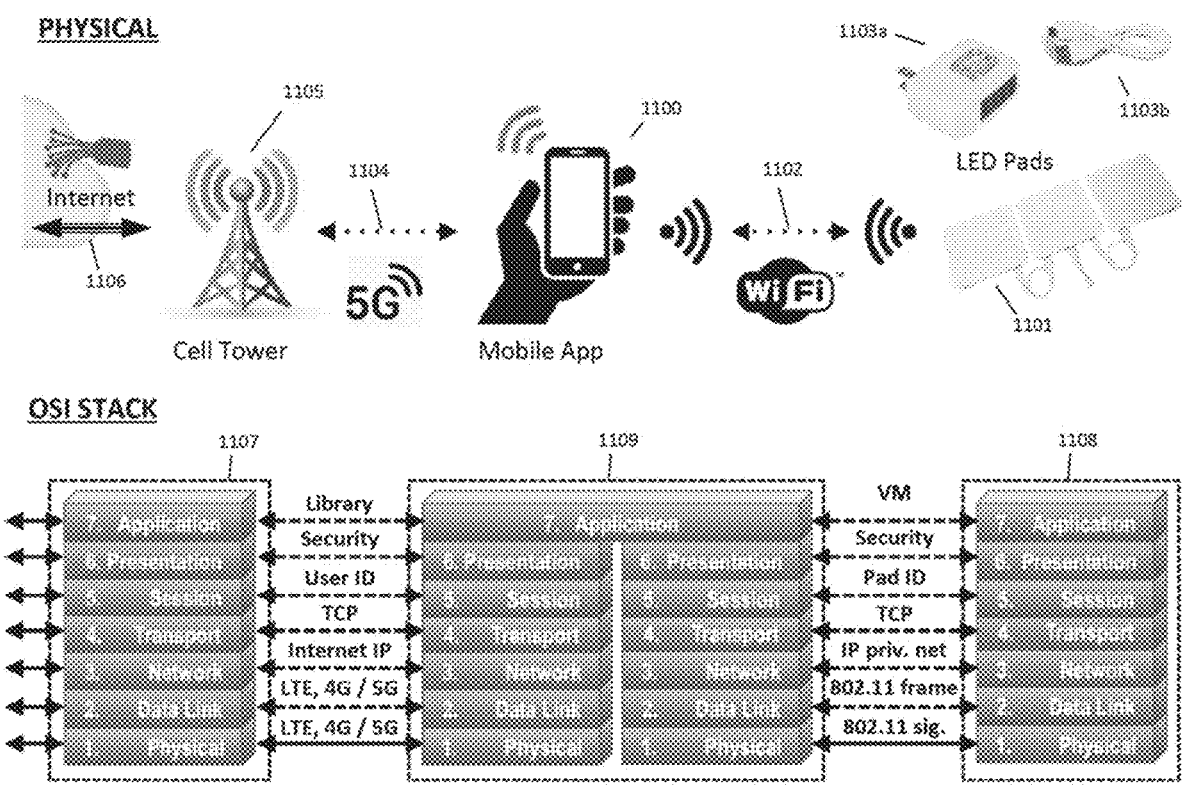
FIG. 73 comprises the communication stacks for a cell phone based distributed PBT system.

Using wireless connectivity, the PBT controller 1010 can be replaced an application program running on a mobile device such as a cell phone, tablet, or notebook computer. For example, in FIG. 73 a cell phone 1100 running PBT controller application software (e.g. PBT "Light app") connects to a cell tower 1105 over a cellular network 1104, e.g. 3G/LTE, 4G, and 5G. Cell tower 1105 in turn connects to Internet 11061706 by Ethernet, fiber, or other means. Cell phone 1105 running the aforementioned Light app also connects to an intelligent LED pad 1101 using WiFi 1102, where intelligent LED pad 1101 is powered by an AC adapter 1103a and a cord 1103b. A 7-layer OSI communication stack 1107 of cell tower 1105 uses mobile network data packets to connect with a communication stack 1109 of Light app running on cell phone 1100. In turn, the Light app also uses the 7-layer communication stack 1109 to connect to intelligent LED pad 1101 comprising communication stack 1108. As shown, PBT communication stack 1109, mixes two 7-layer communication stacks, one for dialog with communication stack 1107 of cell tower 1105 and through a router (not shown) to Internet 1106 and to a cloud based server (not shown), and another for connecting to intelligent LED pad 1101 via communication stack 1108, wherein only the Light Application Layer-7 bridges the two communication stacks in communication stack 1109. In this manner, cell phone 1100 running the aforementioned Light app operates as a PBT controller communicating separately to a cloud-based computer server (not shown) over Internet 1706 and to intelligent LED pad 1101 but without relinquishing local control.

Because PHY Layer-1 and Data Link Layer-2 are within the six data layers not shared in communication stack 1109, the cell tower 1105 communication stack 1107 is unable to directly access the intelligent LED pad 1101 communication stack 1108. Instead, only Application Layer-7 within communication stack 1109 bridges the two communication networks. The software in cell phone 1100 may comprise a dedicated Light app, which like LightPadOS, operates as reduced instruction set version of the LightOS operating system used in the dedicated hardware PBT controllers described previously. In essence, the Light app in cell phone 1100 emulates the operation of LightOS in facilitating PBT control functionality and its UI/UX touchscreen-based control. The Light app is realized as software designed for operating on the operating system used in the corresponding mobile device. For example, in smart phones and tablets, the Light app is created to run atop Android or iOS while in notebooks, the Light app is created to run on MacOS, Windows, Linux, or UNIX. The conversion of the source code, the basic logic and function of the Light app, into executable code adapted to run atop a specific platform is a conversion process referred to as a "compiler".

Figure 74:
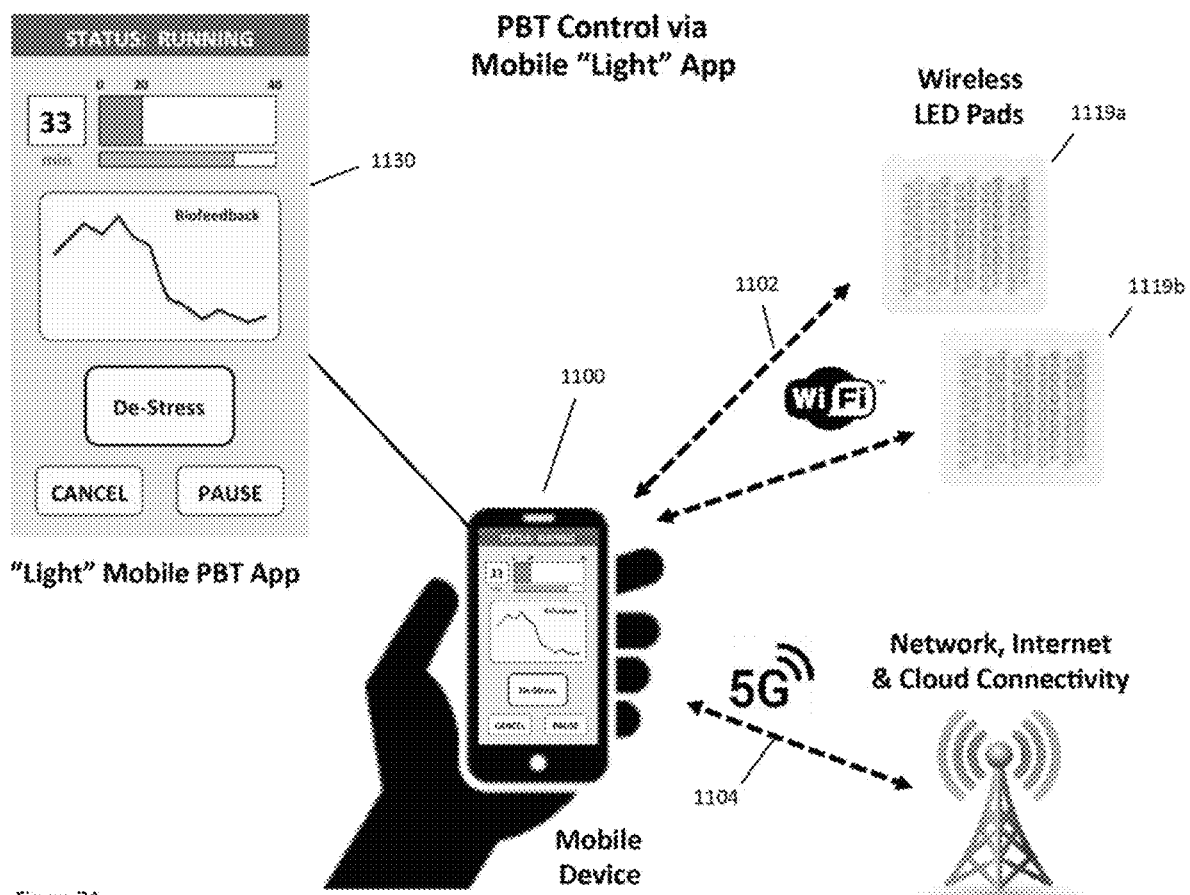
FIG. 74 illustrates a distributed PBT system using cell phone app and WiFi based control.

The translation of source code into compiled code is therefore platform-specific, meaning that multiple versions of the software must be distributed each time a software revision, patch, or new release occurs. Operation of a mobile device based distributed PBT system is shown in FIG. 74, where cell phone 1100 hosts Light app with a control UI/UX interface 1130 to control intelligent LED pads 1119a and 1119b over WiFi 1102. Cell phone 1100 is also able to connect to the Internet and cellular networks using cellular network 1104, e.g. using 3G/LTE, 4G, and 5G protocols.

Figure 75:
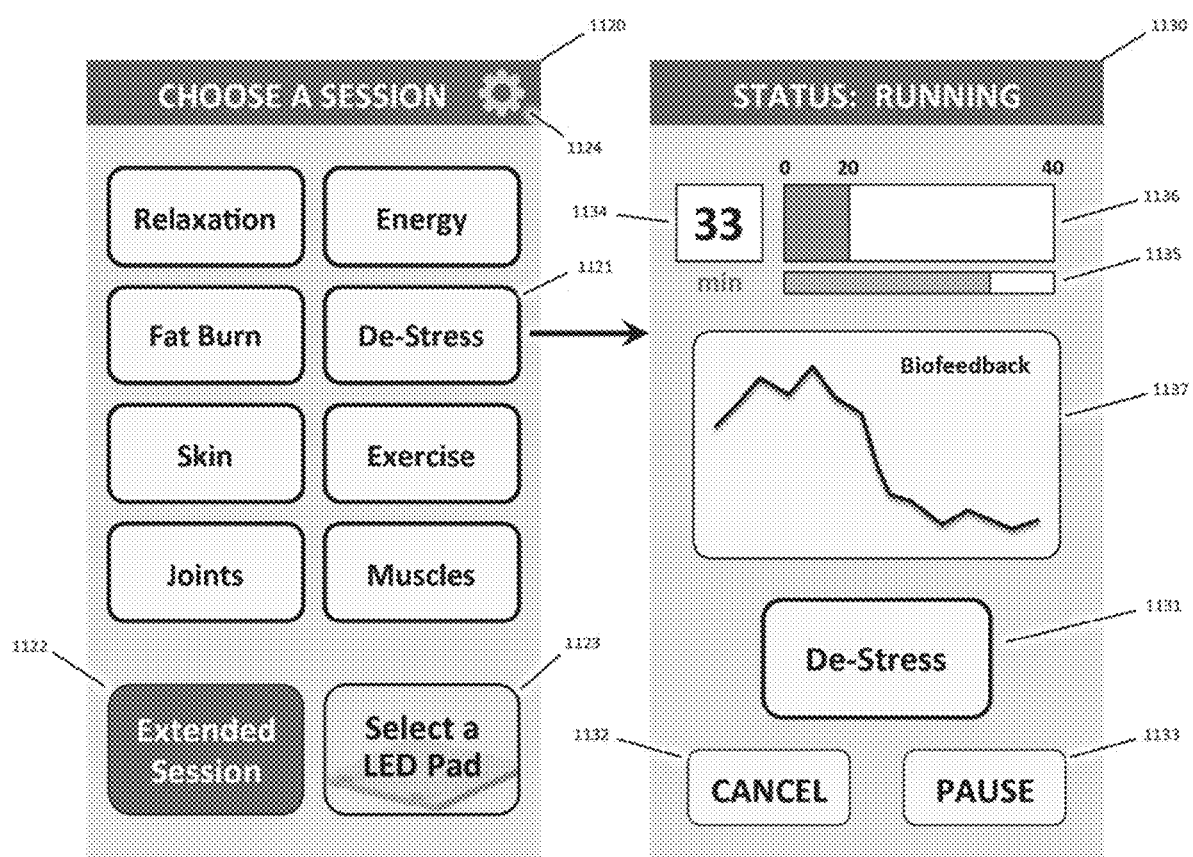
FIG. 75 is a UI/UX menu for PBT control using a mobile device application program.

An example of a user interface for software control of a PBT system is shown in a screen 1120 in FIG. 75, where the UI/UX screen entitled "choose a session" includes a treatment menu 1121 along with a button 1122 for selecting an "extended session" to increase the time of a PBT treatment. A "Select a LED pad" button 1122 is used to pair the mobile device to a specific intelligent LED pad. As shown, selecting the De-Stress treatment opens a second "Running" screen 1130 to monitor an ongoing treatment, with a window 1131 showing the treatment name, and buttons 1132 and 1133 to cancel or pause a treatment. The "Running" screen 1130 also has a window 1134 showing the time remaining in the treatment, a step progress bar 1135, a treatment progress bar 1136 and a biofeedback window 1137.

Driving Other Distributed Components

The PBT controller of this invention can also be used to control therapy devices other than LED pads. These peripheral components may comprise laser PBT wands and systems, autonomous LED pads programmed over a distributed PBT system, magnetotherapy pads and wands, LED masks, LED caps, LED ear and nose buds, and more. LED facemasks, head caps, and LED beds are simply multi-zone PBT systems using unique LED delivery systems. Electrical control of these other devices is generally similar to control of the intelligent LED pads with the aforementioned PBT system as disclosed herein. Broadly, the aforementioned distributed PBT system is not limited to driving LEDs but may be used to drive any energy emitter positioned adjacent to a patient in order to inject energy into living tissue, including a coherent light from a laser, time-varying magnetic fields (magneto-therapy), micro-electric currents (electrotherapy), ultrasonic energy, infrasound, far infrared electromagnetic radiation, or any combination thereof.

Figure 76:
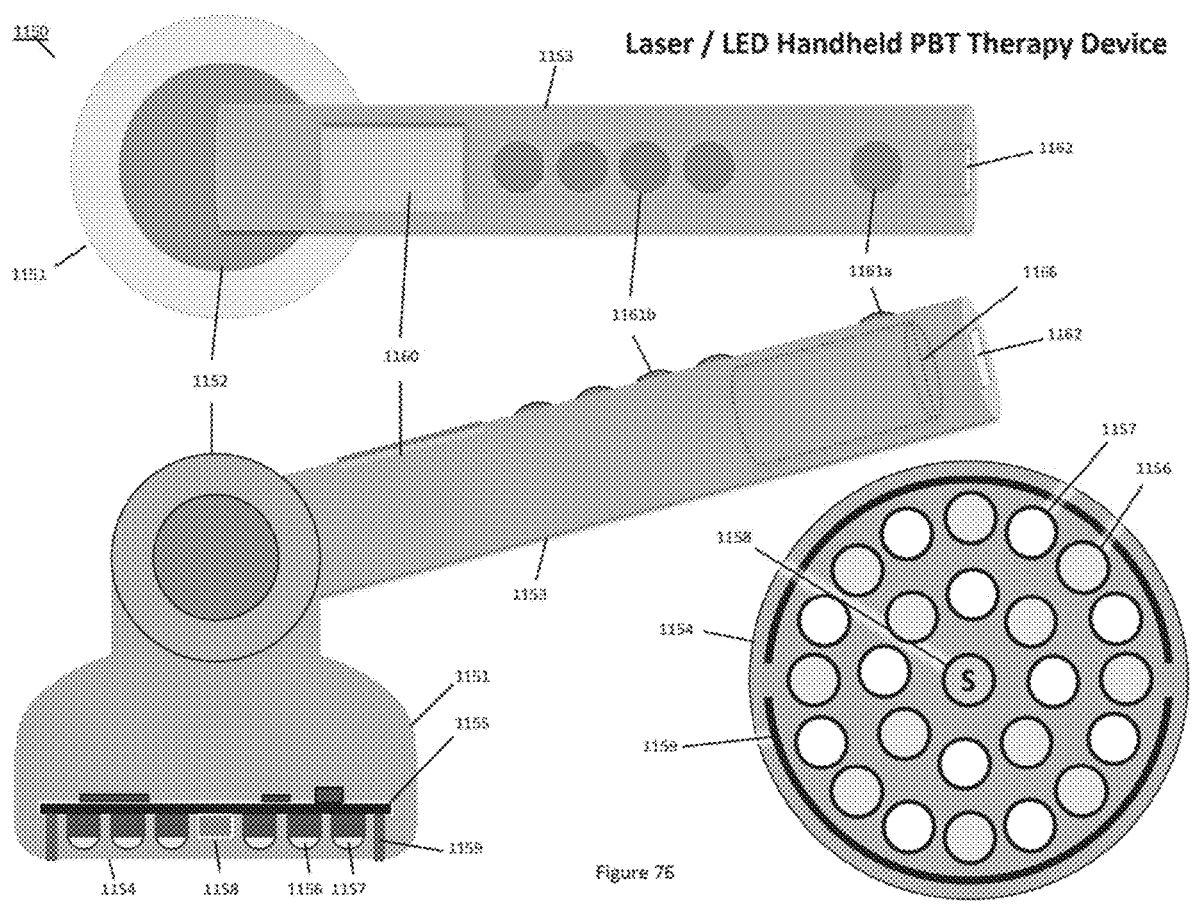
FIG. 76 is a cross section, top view, and underside view of a handheld PBT wand for LED or laser therapy.

Nonetheless, because these other distributed therapeutic systems, such as laser PBT, thermotherapy, magnetotherapy, and ultrasound therapy, use energy emitters other than LEDs, they require some modifications in order to drive the energy emitters using the disclosed PBT controller. Some examples of adapting the disclosed PBT system for alternate therapies are described below:

Laser PBT Systems—FIG. 76 illustrates a handheld PBT "wand" 1150 useful for laser PBT therapy. As shown, handheld wand 1150 includes a cylindrical handle 1153 with a liquid crystal display (LCD) 1160 and control buttons 1161a and 1162b. The bottom of the cylindrical handle 153 includes a USB port 1162 needed to charge a battery 1166. The handle 1153 connects through a gimbal 1152 to a PBT head 1151 with a transparent faceplate 1154 containing a printed circuit board (PCB) 1155 on which lasers 1156 and 1157 and a temperature sensor 1158 are mounted. One inventive feature is a circular conductive blade 1159 used to sense contact to the skin and thereby prevent illumination of the lasers unless the unit is in contact with tissue.

Figure 77:
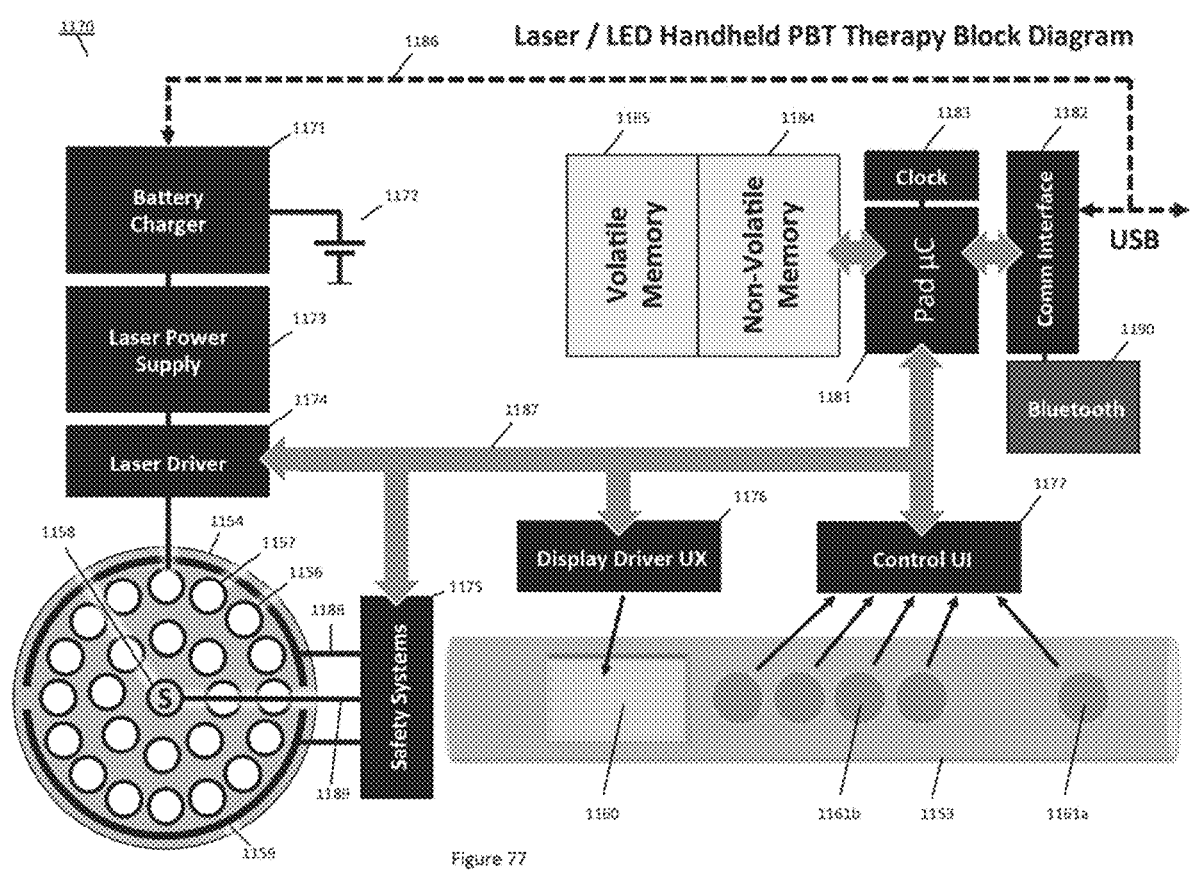
FIG. 77 is a block diagram of a handheld PBT wand for LED or laser therapy.

The block diagram of FIG. 77 shows that the handheld PBT wand 1150 includes a μC 1181, a clock 1183, a volatile memory 1185, a non-volatile memory 1184, a communication interface 1182 and Bluetooth 1190. μC 1181 communicates over a data bus 1187 to a control UI 1177 with buttons 1161a and 1161b, a display driver UX 1176 with an LCD 1160, a laser driver 1174, and safety systems 1175. As shown, laser driver 1174 drives laser-diodes 1156 and 1157. Concurrently, contact blade signal 1188 and temperature sensor signals 1189 are used by safety systems 1175. Laser driver 1174 is powered by a laser power supply 1173 which in turn is powered by a Li-Ion battery 1172 via a battery charger and regulator 1171, powered by a USB input 1186.

Figure 78:
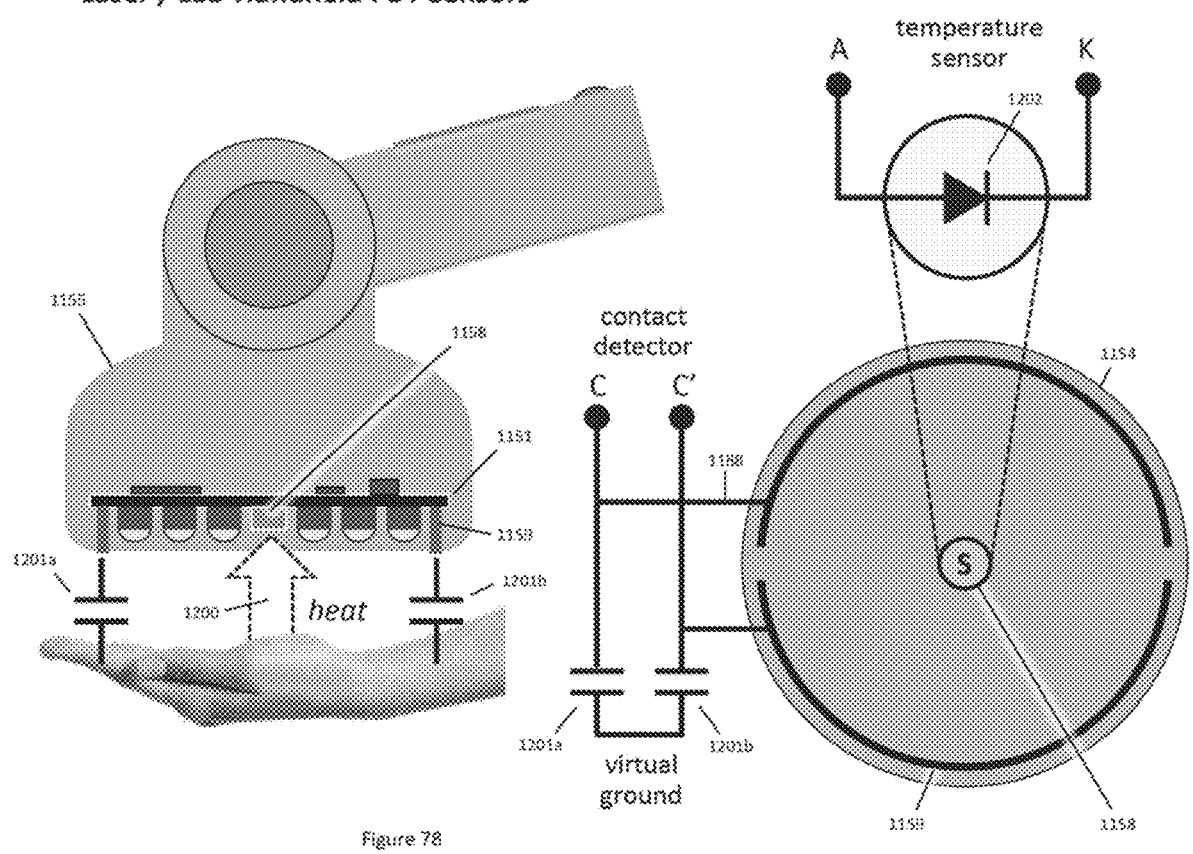
FIG. 78 is cross section and underside view of a PBT wand eye safety system for laser PBT utilizing capacitive contact sensing.
Figure 79:
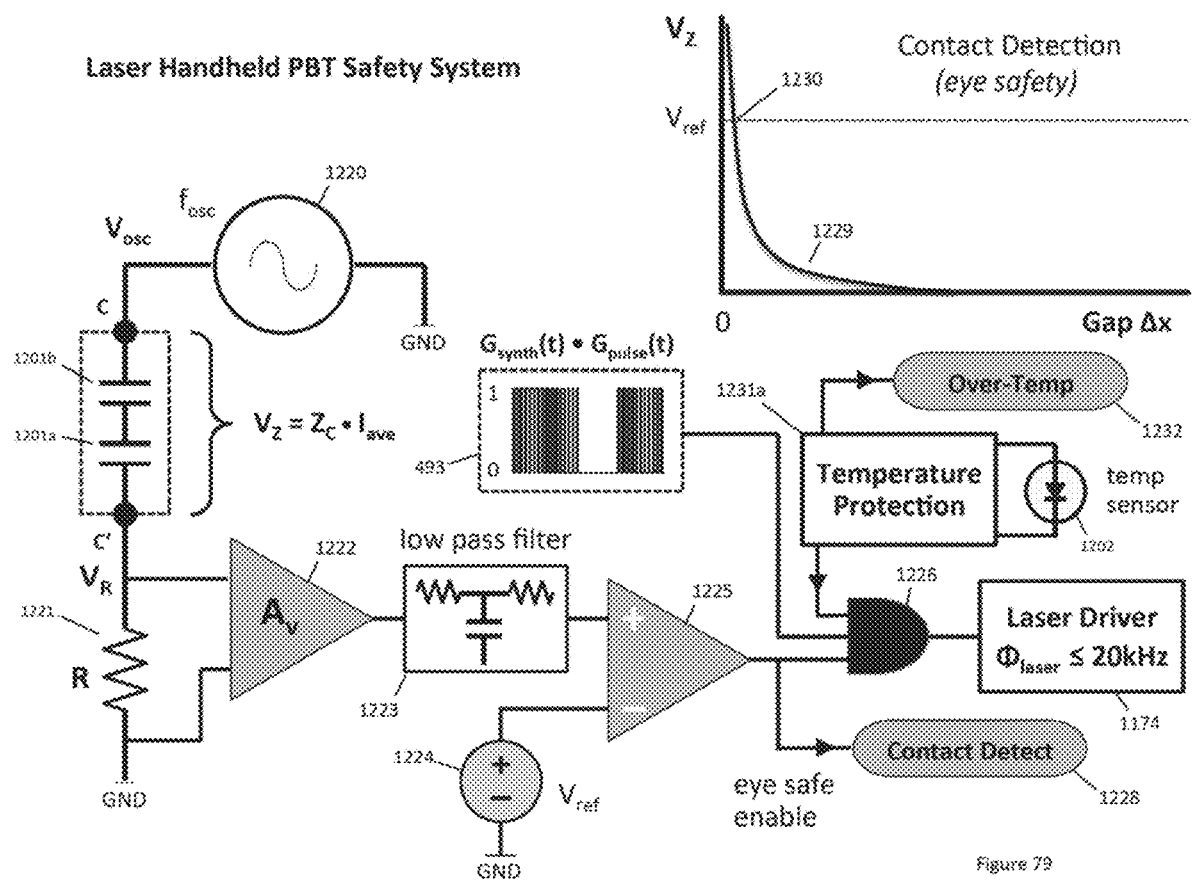
FIG. 79 is a schematic of an eye safety system for laser PBT utilizing capacitive contact sensing.

Details of the safety sensors, shown in FIG. 78, include a PN diode 1202 (terminals A and K) in the temperature sensor 1158 for sensing heat 1200 and capacitors 1201a and 120b connected to the two parts of conductive blade 1159, which form a closed circuit conducting AC current through a patient's tissue across terminals C and C'. FIG. 79 illustrates further details of the laser PBT handheld safety system, including an oscillator 1220, the contact sensor capacitors 1201a and 1201b, and a sense resistor 1221 along with a differential amplifier 1222, a low pass filter 1223, an eye safety comparator 1225 and a source 1224 of a reference voltage $V_{ref}$. In operation, oscillator 1220 injects a voltage $V_{osc}$ at a frequency $f_{osc}$ into a voltage divider formed by sense resistor 1221 and the series connection of capacitors 1201a and 1201b. At the switching frequency $f_{osc}$, the series connected capacitors 1201a and 1201b exhibit an equivalent impedance Z and drop a voltage network voltage between nodes C and C' of $V_Z = Z_C \cdot I_{ave}$ while the voltage drop across resistor 1221 is $V_R = R \cdot I_{ave}$. Equating the two equations $V_R = V_{osc} R/(R+Z_C)$. Thus, when the conductive blade 1159 is not contacting the patient's skin, the value of $Z_C$ is large, and $V_R$ approaches zero. In such a case, the output of differential amplifier 1222 is lower than $V_{ref}$, which is temperature independent. As such, the output of eye safety comparator 1225 is at ground, the associated input terminal and the output terminal of logical AND gate 1226 are at a logic low, and the laser driver 1174 is inhibited. If the sensor blade contacts the skin, the AC impedance $Z_C$ drops significantly so that, after removing the AC signal in low pass filter 1223, the average DC voltage across resistor 1221 is greater than $V_{ref}$, whereby the output of eye safety comparator 1225 switches to a logic high and sending a contact detect enable signal 1228 to the laser μC 1181. Similarly, the voltage across diode 1202 in temperature sensor 1158 is processed by temperature protection circuit 1231a. If an over-temperature condition occurs, an over temperature flag 1232 is sent to the laser μC 1181 and the input to logical AND gate 1226 goes low, disabling laser driver 1174. Conversely, in the absence of an over-temperature condition, and the presence of a contact detect enable signal 1228, the logical AND gate 1226 will pass the digital value of the output of PWM driver 493 to laser driver 1174.

Figure 80:
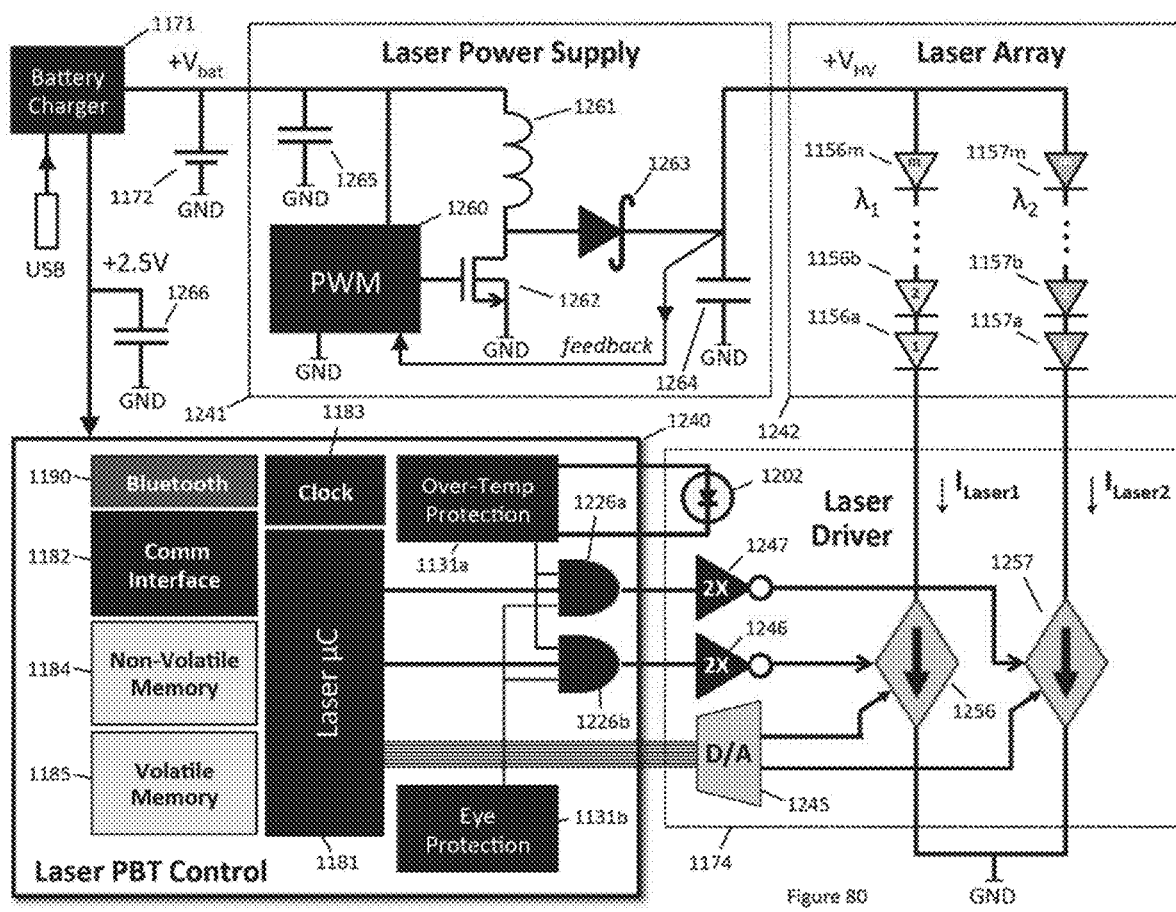
FIG. 80 is a schematic of a distributed-system laser PBT drive circuit.
Figure 83A:
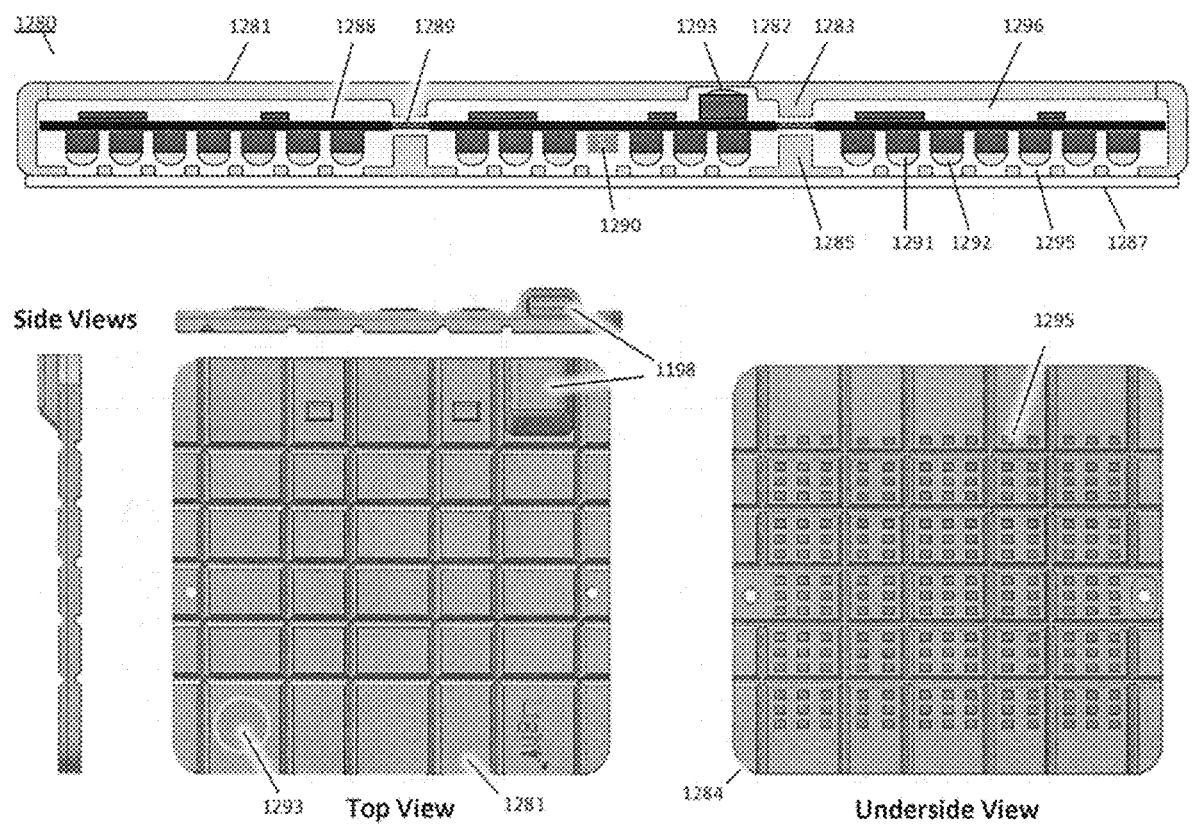
Figure 818:
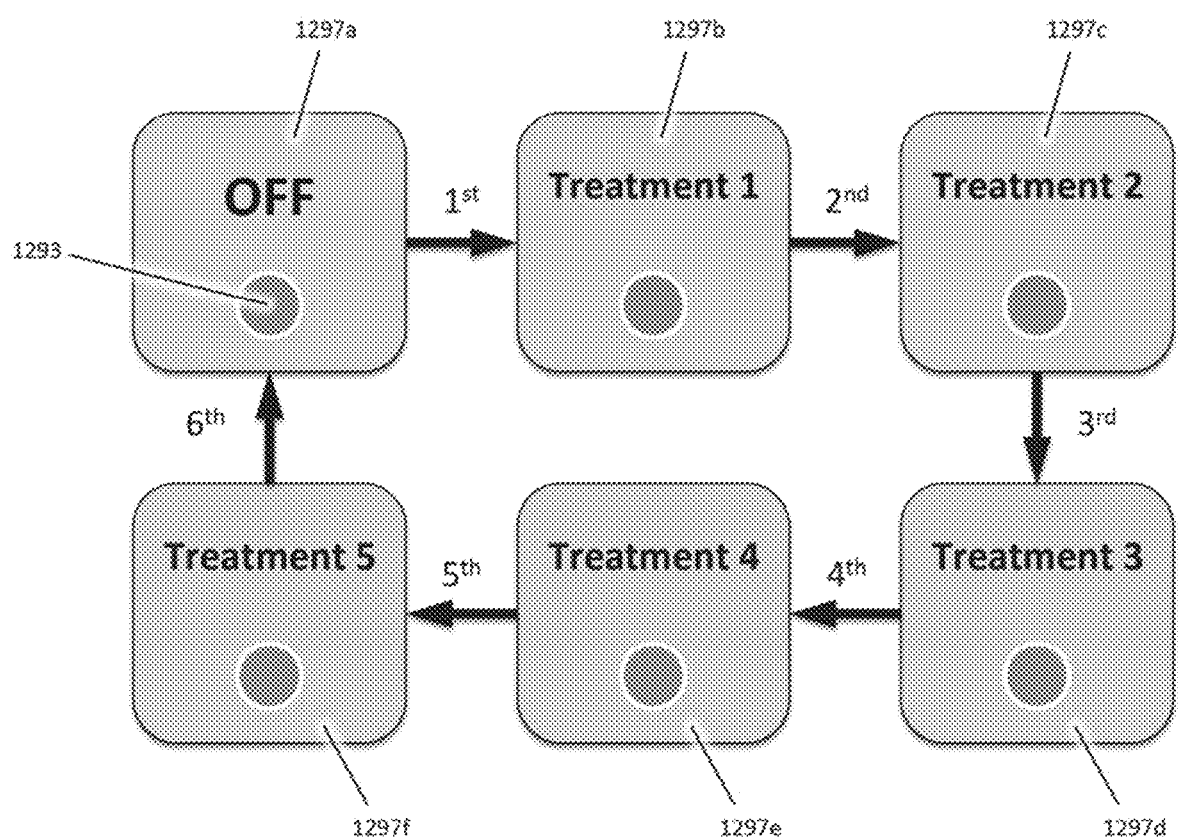

FIG. 80 illustrates an exemplary schematic for a dual channel laser driver. As shown laser PBT control 1240 is similar to the laser controller shown in FIG. 77, comprising laser μC 1181, communication interface 1182, clock 1183, non-volatile memory 1184, and volatile memory 1185. Protection functions include over-temperature protection 1131a with diode 1202 along with eye protection 1131b. The fault signals from over-temperature protection 1131a and eye protection 1131b and the PWM player output from laser μC 1181 are input into logical and gates 1228a and 1228b, then buffered by two series inverter pairs 1247 and 1246. The output is fed to the digital inputs of current sinks 1256 and 1257 in laser driver 1174. A dual output D/A converter 1245 is used to control the analog value of currents $I_{Laser1}$ and $I_{Laser2}$ when the current sinks 1256 and 1257 are conducting.

The controlled current sink 1256 is used to drive the string of lasers 1156a through 1156m with wavelength $\xi_1$. The controlled current sink 1257 is used to drive the string of lasers 1157a through 1157m with wavelength $\xi_2$ in laser array 1242. The laser strings 1156a-1156m and 1157a-1157m are powered by a supply voltage $+V_{HV}$ output from a boost-type switching regulator 1241 comprising an input capacitor 1265, a PWM controller 1260, a low-side power DMOSFET 1262, an inductor 1261, a Schottky rectifier 1263, and an output capacitor 1264 with voltage feedback to PWM controller 1260. The input to laser power supply 1241 is supplied by Li-Ion battery 1172 and battery charger 1171 from USB power input. A 2.5-V voltage-regulated output is also delivered from battery charger 1171 and filter capacitor 1266 to power the components of the laser PBT control circuit 1240. If a higher voltage is required, the $+V_{HV}$ power supply output used to drive the laser array may also be used to supply the laser PBT control after the boost converter is operating.

Autonomous LED Pads for Photobiomodulation Therapy—Another peripheral compatible with the distributed PBT system is autonomous LED pads to be used in applications when a PBT controller or cell phone is unavailable or inconvenient by which to administer emergency treatments, e.g. in a battle field or in a plane crash in a mountainous location. In operation, a single button located on the autonomous LED pad is used to select the treatment. In general, no UX display is available for information. And although autonomous LED pads operate "autonomously" (i.e. by themselves) during therapy treatments, during manufacturing they are connected to part of a distributed PBT system to load their applicable programs and to confirm their successful operation.

The PBT software programs loaded into the autonomous LED pads are determined by the markets and applications for which they are intended. For example, the treatment programs loaded into the LED pads in a ski resort might comprise treatments for concussion (a common ski injury) while those used by paramedics might focus on treating wounds such as lacerations or burns. In sports facilities and tennis clubs, autonomous LED pads for muscle and join pain may be more common. In military applications, the major field application is to slow or prevent the spread of infection in a bullet or shrapnel wound.

The electrical design of the intelligent LED 337 of FIG. 14 is equally applicable autonomous LED operation except for the addition of a push button to control on/off and program selection. During programming, the entire PBT system is present including power supply brick 132, PBT controller 131, USB cable 136, and autonomous intelligent LED pad 337. In programming, the PBT controller configures the LED pad by loading manufacturing data, and downloading a PBT player and the pre-loading LED playback files as required. A portable programming system may also be used to reprogram pads once sold or deployed into the field, allowing a client to repurpose their inventory to adapt to various types of disasters, e.g. frostbite in the winter, anti-viral treatments in a disease outbreak or pandemic, lung damage from a terrorist's nerve-agent release etc.

The important factor in a autonomous LED pad is the cost should be controlled by utilizing a standard design, i.e. using one common manufacturing flow and product BOM (build of materials) for all applications and markets, then to use software downloads to customize the generic product into an application specific version. FIG. 81A illustrates a general purpose self contained pre-programmed autonomous LED pad with a top view 1281, an underside view 1284, and side views, including a single USB socket 1198. As shown in the cross-sectional view 1280, the autonomous LED pad includes a rigid PCB 1288; a flexible PCB 1289, LEDs 1291 and 1292, a sensor 1290 and control switch 1293. A polymeric pad cover 1281 includes openings 1295 and a cavity 1296, a thin portion 1282 for switch 1293 and protective clear plastic 1287. Polymeric pad cover 1281 comprises a protrusion 1283, and a bottom flexible polymer comprises a protrusion 1285.

As described, autonomous LED pads do not utilize a display, a radio link, or a remote control and therefore offer a limited number of preloaded treatment programs, generally from one to five choices as illustrated in FIG. 81B. As shown, an autonomous LED pad is in its off state 1297*a*. It will change to its on state when the button 1293 is pressed once. After selecting this state, after a short time treatment will commence using the program "Treatment 1." Pressing the button 1293 a second time will advance the program to state 1297C and commence "Treatment 2." In a similar manner, each time the button 1293 is pressed, the program advances to the next treatment, 3, 4, and 5 shown as corresponding states 1297*d*, 1297*e*, and 1297*f*. Depressing button 1293 a sixth time returns the autonomous LED pad back to off state 1297*a*.

Pulsed LED Thermotherapy—In a manner similar to visible and near infrared light in photobiomodulation therapy, thermotherapy is the application of far infrared, typically comprising wavelengths of 1 µm to 100 µm. Thermotherapy includes spas, heating pads, and heater body wraps. According to Wikipedia, the therapeutic effects of heat include "increasing the extensibility of collagen tissues; decreasing joint stiffness; reducing pain; relieving muscle spasms; reducing inflammation, edema, and aids in the post acute phase of healing; and increasing blood flow. The increased blood flow to the affected area provides proteins, nutrients, and oxygen for better healing." It also expedites the delivery of metabolic waste and carbon dioxide. Heat therapy is also useful for ameliorating muscle spasms, myalgia, fibromyalgia, contracture, bursitis, While the therapeutic claims overlap those offered by PBT, the physical mechanism of thermotherapy is considerably different. Unlike PBT, which imparts photons absorbed by molecules to stimulate chemical reactions that otherwise would not occur, i.e. photobiomodulation, in thermotherapy heat absorbed by tissue and water accelerates molecular vibration rates to expedite ongoing chemical reactions. Since, however, in accordance with Einstein relation $E=h\,c/\xi$, the energy of a photon is inversely proportional to its wavelength, the energy of 3 µm far infrared radiation is only 20% to 20% that of red and NIR PBT. This energy difference is significant, as the lower energy is insufficient to break chemical bonds or transform molecular structure. As a result, thermotherapy is generally considered as symptomatic relief without the associated accelerated healing manifest in PBT. Penetration depths for far infrared sources shorter than 3 µm (i.e. IR type B) exhibit greater penetration depths than longer wavelengths and are therefore preferred over long wavelength sources.

The aforementioned PBT system can be adapted for thermotherapy by replacing the visible light and NIR LEDs with LEDs in the far IR spectrum. LEDs are generally limited to 12 µm wavelengths or shorter as described in "Far infrared radiation (FIR): its biological effects and medical applications", *Photonics Lasers Med.*, vol. 1, no. 4, Nov. 2012, pp. 255-266: https://www.ncbi.nlm.nih.gov/pmc/articles/PMC3699878/by F. Vatansever and M. R. Hamblin. By adjusting the crystalline structure of III-V compound superlattice compound semiconductors for smaller bandwidths, LEDs operating in far IR spectrum have been achieved to wavelengths up to 8.6 µm (see "Superlattice InAs/GaSb light-emitting diode with peak emission at a wavelength of 8.6 µm," IEEE J. Quant. Elect., vol. 47, no. 1, January 2011, pp. 5-54). The PBT system used for driving NIR LEDs disclosed herein can therefore easily be retrofitted to accommodate FIR LEDs simply by swapping the NIR LEDs for their longer wavelength counterparts. The drive circuitry can be used in an identical manner, using pulsed or sinusoidal waveforms. Because of the long wavelengths, drive frequencies below 100-Hz are more suitable to insure uniform delivery far infrared radiation. At even lower frequencies, e.g. below 10 Hz, the FIR LEDs in a pad can be scanned row by row to produce a massage like wave rippling across each pad, successively stimulating vasodilation in a systematic pattern across treated tissue. Optionally, near infrared LEDs for PBT and far infrared LED for thermotherapy can be combined into one intelligent pad, and driven either concurrently or alternating in time.

Magnetotherapy—Magnetotherapy (MT) is an alternative medicine therapy where injured tissue is subjected to magnetic fields. The influence of fixed magnetic fields on tissue is dubious and is generally considered pseudo-medicine, fringe medicine and even quackery. Some studies have concluded medical claims for permanent magnet magnetotherapy are wholly unsupported by the results of scientific and clinical studies, and prohibit marketing any magnet therapy product using medical claims (https://en.wikipedia.org/wiki/Magnet_therapy). Conflicting claims suggest that pulsed magnetic fields exhibit a therapeutic effect because the living tissue contains a large number of free ions and even electrically balanced molecules (such as water), which act as dipoles because of the direction of their charges. When subjected to an oscillating magnetic field, molecules are repelled and attracted according to their electric charge in a manner similar to imaging performed by magneto-resonant imaging (MRI), except that the excitation occurs at lower frequencies. This type of magnetic therapy is commonly referred to as pulsed magnetotherapy or PMT.

Reported effects of PMT are largely analgesic, including muscle relaxation, improved local blood circulation and vasodilation; anti-inflammatory effects; pain relief through the local release of endorphins; and beneficial effects on cellular membrane action potentials. The action mechanism is primarily believed to be electrochemical rather than thermal, in essence acting in a catalytic manner by accelerating ongoing chemical reaction rates. Reported PMT pulse frequencies range across the audio and infrasound spectrum from 20-kHz down to below 1-Hz. From the published literature it is impossible to determine the accuracy of these reported claims or to ascertain treatment efficacy of pulsed magnetotherapy. Moreover, PMT carries certain risks. In particular PMT is contraindicated in the case of tumors and has a safety risk of affecting pacemaker operation.

In accordance with this invention, a pulsed magnetotherapy system can be realized by repurposing the disclosed PBT system by replacing optical components with electromagnets and adapting the drive circuit contained in the intelligent pad or wand. Optionally, LEDs for PBT can be driven in combination with magnetic emitters, either concurrently or alternating in time. In the case of driving an array of electromagnets, the electromagnet array should be mounted on a three dimensionally bendable printed circuit board (or 3D PCB) similar to that described herein for LED arrays and disclosed in U.S. application Ser. No. 14/919,594, now U.S. Pat. No. 10,064,276, entitled "3D Bendable Printed Circuit Board with Redundant Interconnections," incorporated herein by reference. The rigid-flex PCB is necessary to adjust the orientation of numerous electromagnets to a 90° angle (i.e. a right angle) to the patient's tissue being treated without mechanically damaging the solder joints between the flexing PCB and the rigid electromagnets. The rigid flex PCB provides a perfect solution for achieving reliable 3D bendability.

Figure 82:
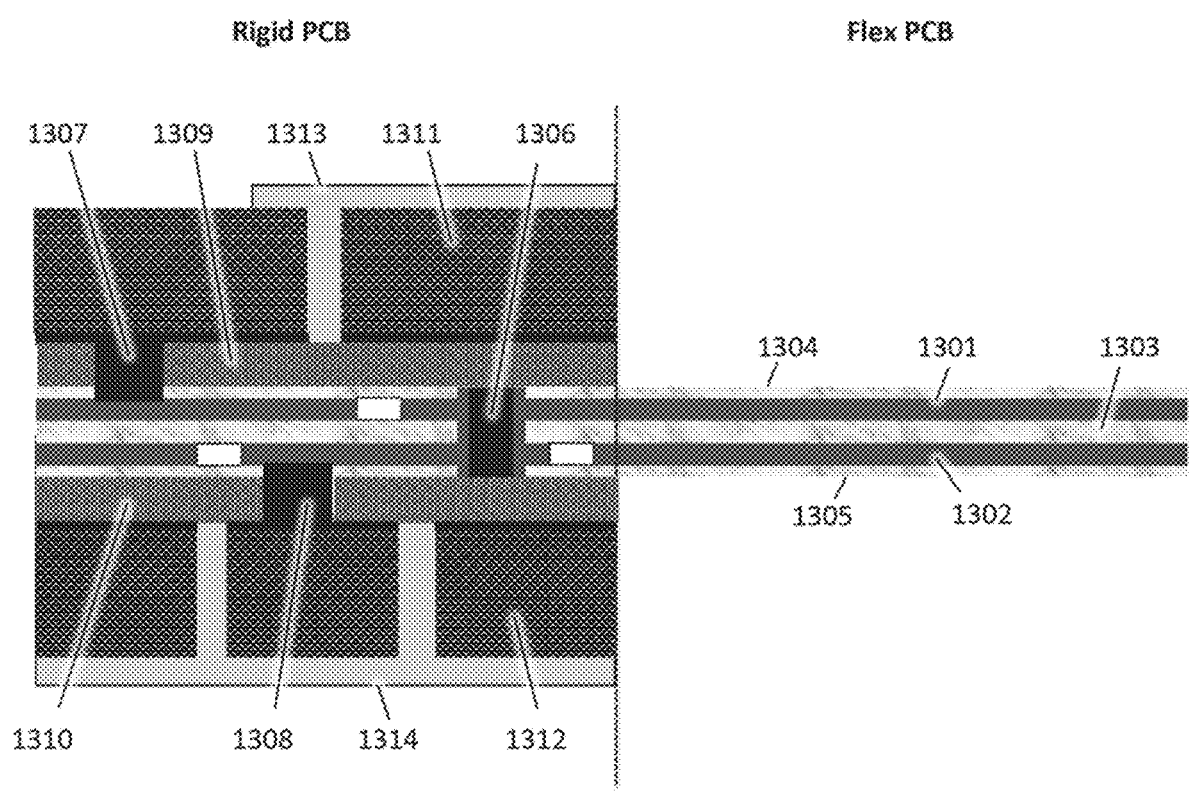
FIG. 82 is cross section of a rigid flex PCB.

FIG. 82 illustrates a cross-sectional view of a rigid-flex PCB with unprotected copper interconnections. As shown, the flex PCB comprises an insulating layer 1303 sandwiched between metal layers 1301 and 1302, typically comprising patterned copper. In some portions of the cross section shown and in other portions (not shown in FIG. 82), this flex PCB is sandwiched into the middle of a rigid PCB comprising insulating layers 1304 and 1305 and laminated with patterned metal layers 1311 and 1312. In general, flex PCB metal layers 1301 and 1302 are thinner than the metal layers 1311 and 1312 in the rigid PCB. The cross-sectional view of FIG. 82 is for illustrative purposes. The exact pattern of each layer shown depends on location and the circuit being implemented. As shown, a metal via 1307 is used to connect metal layers 1301 and 1311 and a via 1308 is used to connect metal layers 1302 and 1312. A fully buried via 1306 is used to connect flex metal layers 1301 and 1302.

Protective layers comprising a coating of polyimide, silicon, or other scratch protection material is used to seal both the rigid and flex portions of the PCB. As shown, an insulator 1304 protects metal layer 1301 and an insulator 1305 protects metal layer 1302, completely sealing the flex PCB from moisture and the risk of mechanically induced scratches. In the rigid portion of the PCB, a patterned insulating layer 1313 protects a portion of metal layer 1311 and an un-patterned insulating layer 1314 entirely protects metal layer 1312. Some portions of metal layer 1311 remain unprotected for the purpose of soldering components onto the rigid PCB.

As shown, the electrical interconnection of the various metal layers within a given rigid PCB, between rigid PCBs, and within flex PCB's can be accomplished without the need for wires, connectors or solder joints, using conductive vias 1306, 1307, and 1308. These conductive vias comprise conductive columns of metal or other low resistance materials formed perpendicular to the various metal layers and may penetrate two or more metal layers to facilitate multi-level connectivity and non-planar electrical topologies, i.e. circuits where conductors must cross one other without becoming electrically shorted.

Figure 83:
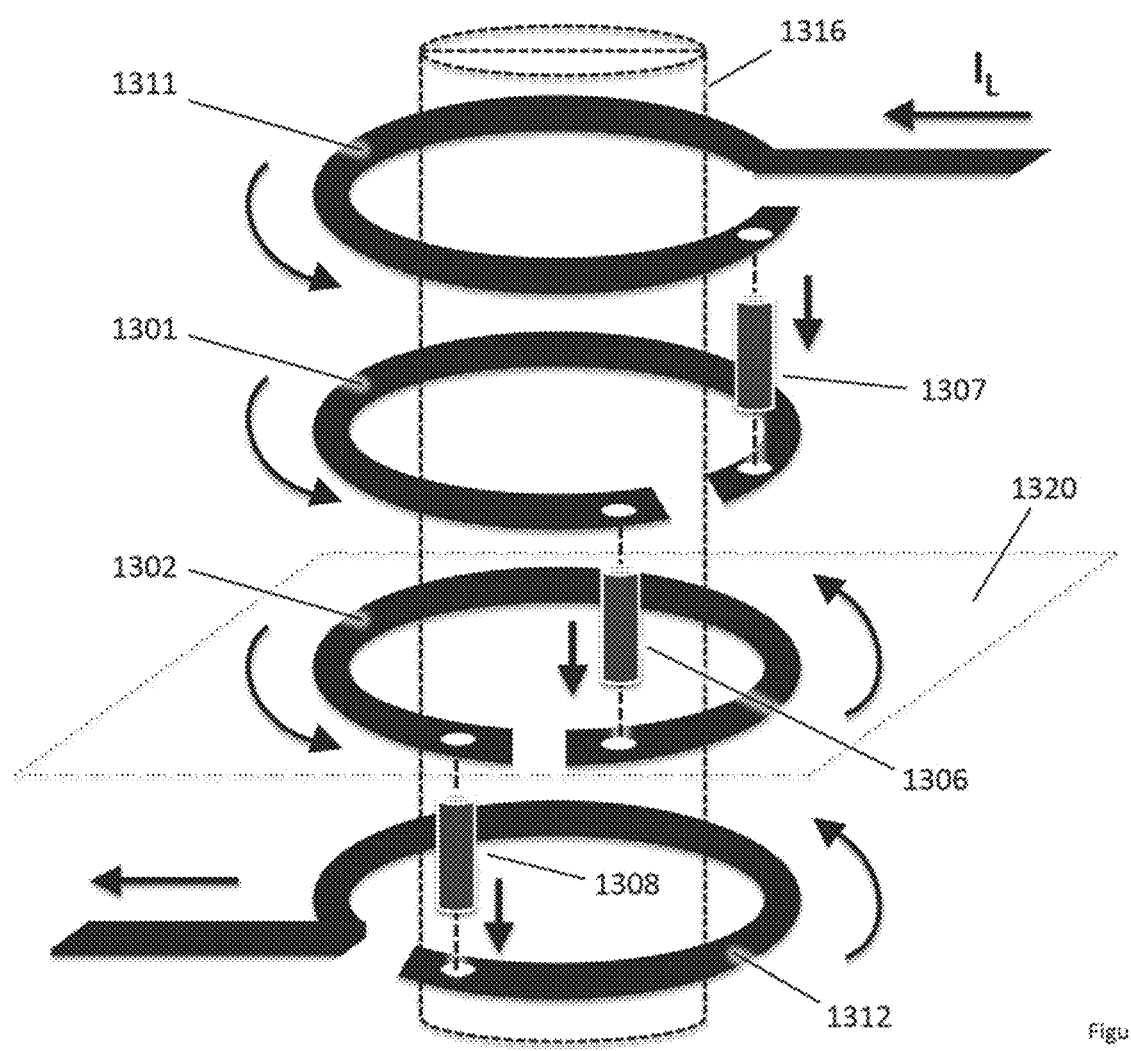
Figure 84:
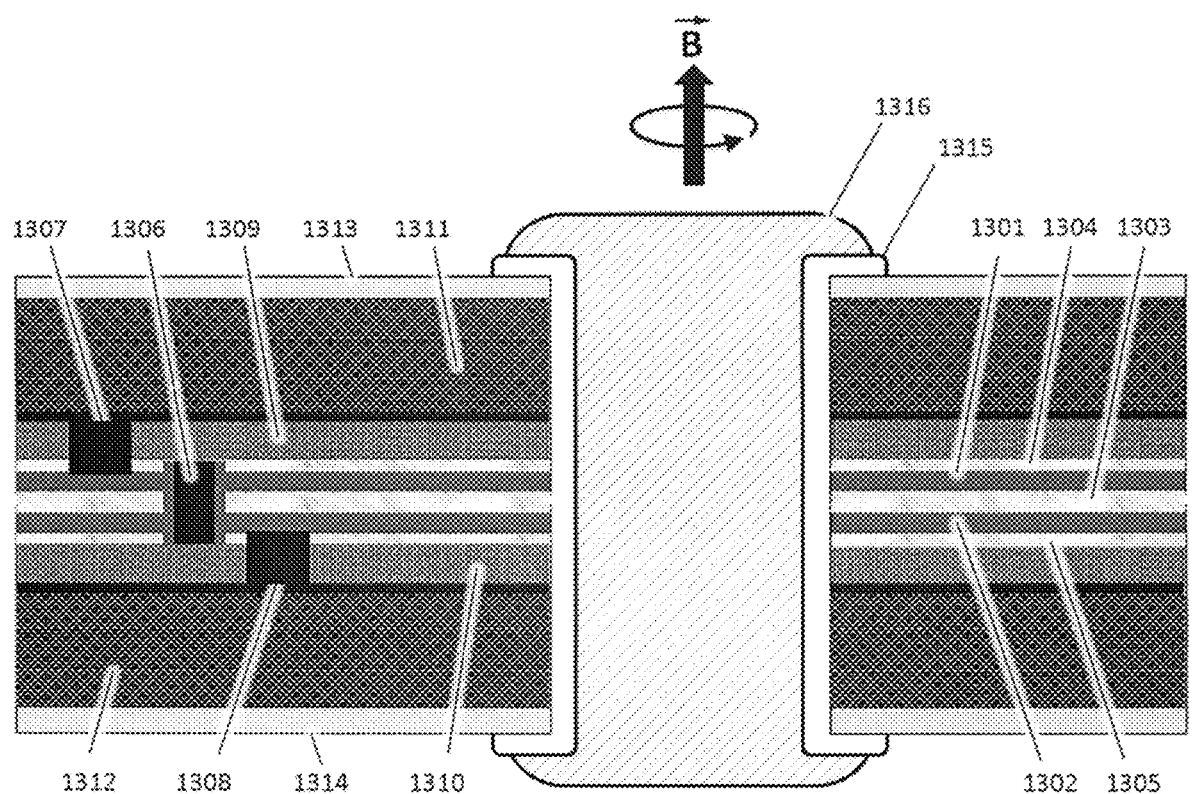
Figure 85:
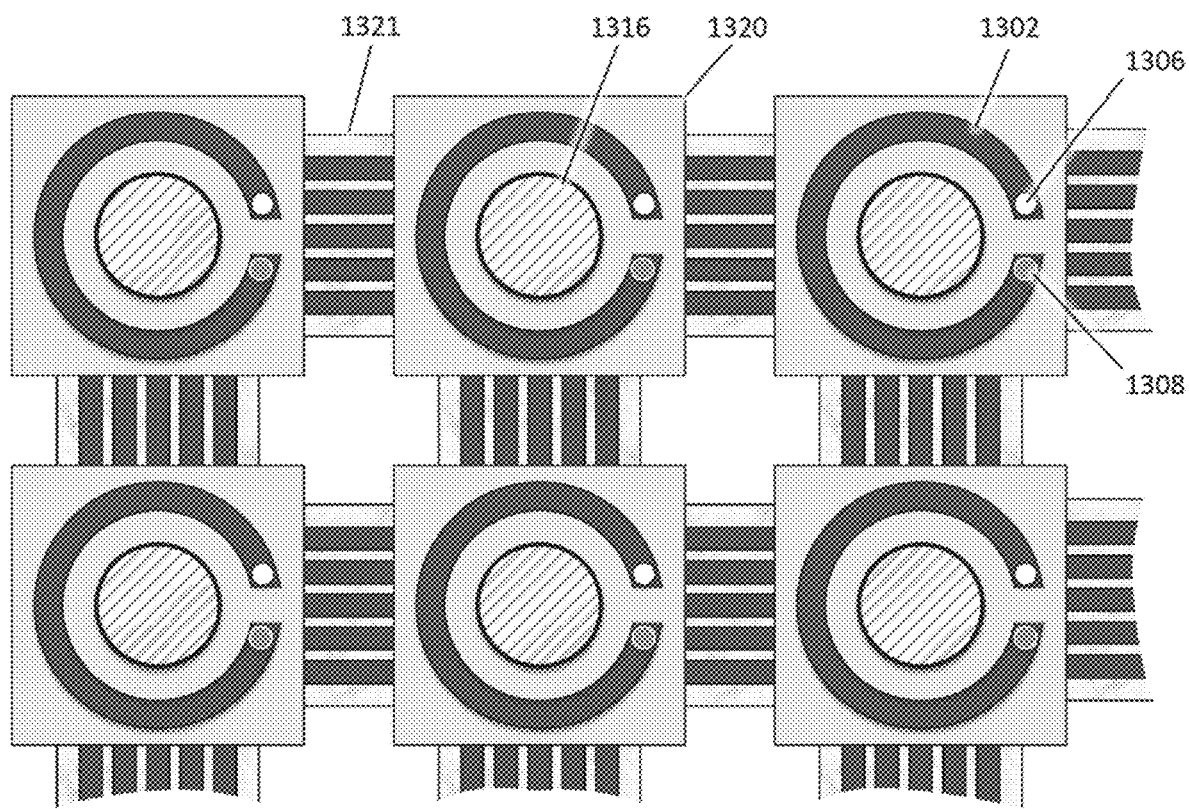

In PMT pads, the role of the rigid portion of the disclosed rigid-flex PCB may be used in various ways. In one case, discrete electromagnetic, permanent magnets, and permanent magnet/electromagnet stacks can be mounted onto the rigid portion of the rigid-flex PCB. Alternatively, the PCB interconnections can be used to form a toroid that when combined with through-hole magnetic material forms a planar magnetic structure. One exemplary layout of a planar magnetic toroid is illustrated in the exploded diagram of FIG. 83, wherein metal layers 1311, 1301, 1302, and 1312 form a circular toroid surrounding a magnetic core 1316. Each circular conductor on a given layer is rotated in comparison to the metal layer below it so that metal vias 1307, 1306, and 1308 are able to interconnect the layers in a manner where the current flows counterclockwise on every layer located on each plane of the PCB, e.g. on the plane of intersecting rigid PCB 1320. This structure is further detailed in FIG. 84, wherein the rigid-flex PCB forms the layers of the toroid surrounding magnetic core 1316. To prevent shorts between the conductive layers and the iron magnetic core, magnetic core 1316 may be insulated from metal layers 1311, 1301, 1302, and 1312 by an insulator 1315. FIG. 85 is a cross-sectional view of the structure taken from above through rigid PCB 1320 and interconnecting flex PCB 1321. As illustrated, circular shaped conductor 1302 surrounds magnetic core 1316 while connecting to an overlying conductive layer through via 1306 and also connecting to an underlying conductive layer through via 1308.

Figure 86:
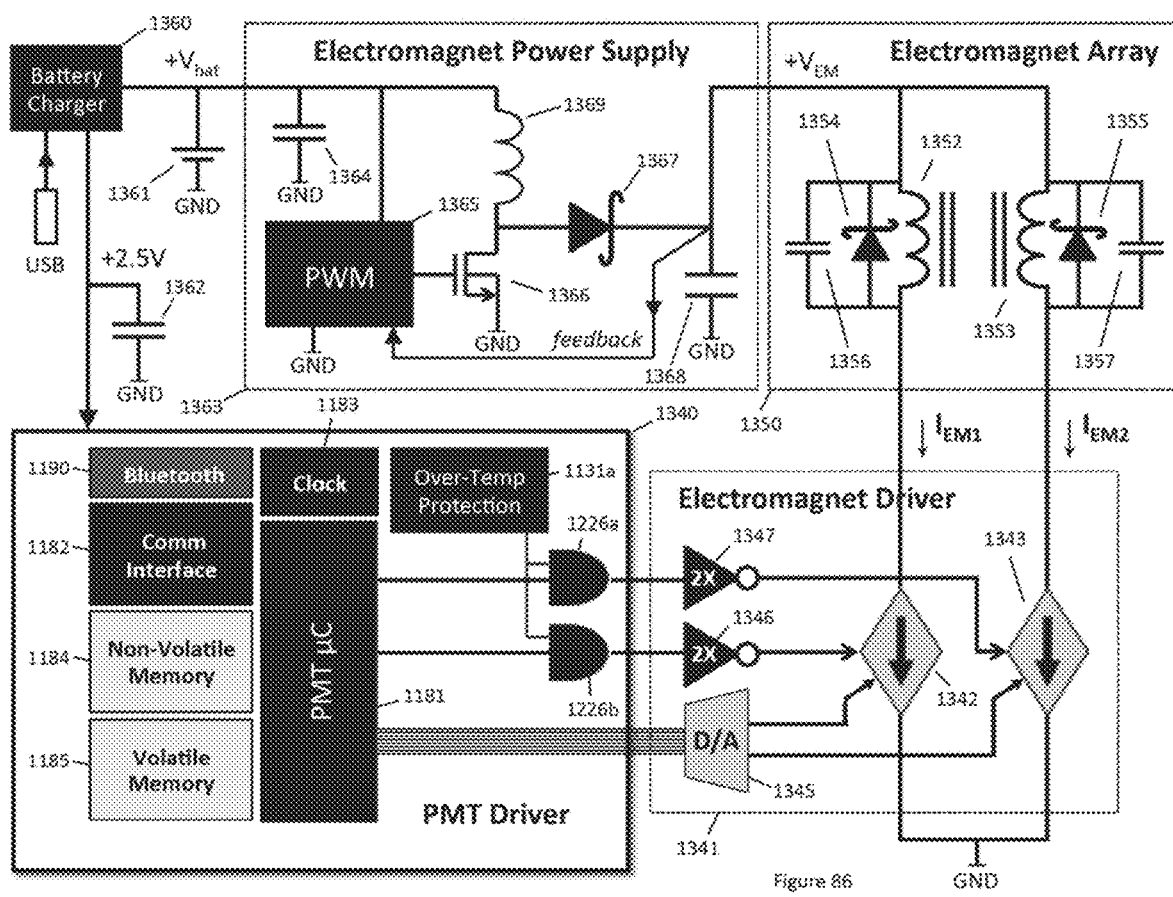

An exemplary circuit used to drive the PMT, illustrated in FIG. 86, comprises a PMT driver 1340; an electromagnet driver 1341; an electromagnet power supply 1363; and an electromagnet array 1350, along with a battery charger 1360, a Li-Ion battery 1361, and a USB connector connected to battery charger 1360. Similar to an intelligent LED pad or a laser wand circuit, PMT driver 1340 includes a PMT μC 1181, a clock 1183, a non-volatile memory 1184, a volatile memory 1185, a communication interface 1182 and Bluetooth or WiFi radio link 1190. Digital pulse outputs of PMT μC 1181 are gated by logical AND gates 1226a, 1226b, and optionally others (not shown) to facilitate over-temperature protection 1131a. The outputs of the AND gates 1226b and 1226a are then buffered by dual inverter strings 1346 and 1347 to drive the digital input of programmable current sinks 1342 and 1343, respectively. Controlled current sinks 1342 and 1343 control the magnitude and waveform of electromagnet currents $I_{EM1}$ and $I_{EM2}$ flowing through electromagnets 1352 and 1353 in response to their digital inputs from inverters 1346 and 1347 and also in response to analog reference currents derived from the outputs of D/A converter 1345.

Freewheeling diodes 1354 and 1355 are included to prevent high voltage spikes whenever the current sinks 1342 and 1343 are rapidly switched off by recirculating inductor current, until either the energy $E_L=0.5LI^2$ stored in electromagnets 1352 and 1353 is consumed or until the current sink once again conducts current. Capacitors 1356 and 1357 are used to filter switching noise or optionally to intentionally to form a tank circuit with the inductance represented by the coils with electromagnets 1352 and 1353 and oscillate at a resonant frequency of $f_{LC}=1/(2\pi SQRT(LC))$. A voltage $+V_{EM}$ for driving the electromagnets 1352 and 1353 is derived from a switching power supply 1363, which is shown as a boost converter but may be either a boost converter to step up the voltage or a Buck converter to step it down. Alternatively, since current sinks 1343 and 1343 control inductor current anyway the voltage regulator can be eliminated.

Although the operation of a switching power supplies is well known in the art, the circuitry of the boost converter within switching power supply 1363 is shown in FIG. 86 for illustrative purposes. In operation, a PWM controller 1365 turns on a power MOSFET 1366, allowing current in a boost inductor 1369 to ramp up for a fixed fraction of a switching period, after which power MOSFET 1366 is switched off. Interrupting conduction in the MOSFET 1366 instantly causes the voltage at the drain terminal of power MOSFET 1366 to fly up, forward biasing a Schottky diode 1367 and charging a capacitor 1368 to a voltage $+V_{EM}$. A voltage feedback signal from the capacitor 1368 is then "fed back" to the PWM controller 1365 allowing the PWM controller 1365 to determine if the voltage at capacitor 1368 is below or above a target voltage.

If the voltage at capacitor 1368 is below target, the width (on-time) of the pulses generated by PWM controller 1365 is increased to be a larger percentage $D=t_{on}/(t_{on}+t_{off})=(t_{on}/T_{PWM})$ of the next clock period $T_{PWM}$, i.e. the duty factor D increases, allowing the average current in the inductor 1369 to increase and driving the output voltage $+V_{EM}$ higher. If, on the other hand, the voltage at capacitor 1368 is too high, the duty factor D, i.e. the on-time for MOSFET 1366 will be reduced, allowing the current in inductor 1369 to gradually decrease over several switching cycles and thereby allow the output voltage $+V_{EM}$ to decline. By continuously adjusting the pulse width and consequent duty factor D (the on-time of power MOSFET 1366) the output voltage $+V_{EM}$ is regulated to a constant value by virtue of voltage feedback. The regulation process of switching power supply 1363,r operating at a switch frequency and period $T_{PWM}$, is therefore referred to a PWM, meaning pulse width modulation. The role of output capacitor 1368 is to filter the output voltage $+V_{EM}$, while input capacitor 1364 is used to prevent back injection of noise into the power source and to stabilize the power network. As shown, the output voltage $+V_{EM}$ of the switching converter and regulator is higher than its input, i.e. $+V_{EM} > V_{bat}$, so the converter within switching power supply 1363 is referred to as a boost converter. If however, the desired output voltage $+V_{EM}$ is lower than the battery voltage, i.e., $+V_{EM} < V_{bat}$, then a step-down or Buck converter is required. Topologically, realizing a Buck converter requires only a minor modification to the circuit shown for switching power supply 1363 in FIG. 86 by rearranging the same components by rotating the three components attached to the common node between inductor 1369 and power MOSFET 1366 to the right, i.e. replacing Schottky diode 1367 with inductor 1369, replacing power MOSFET 1366 with Schottky diode 1367, and replacing inductor 1369 with power MOSFET 1366.

Figure 87:
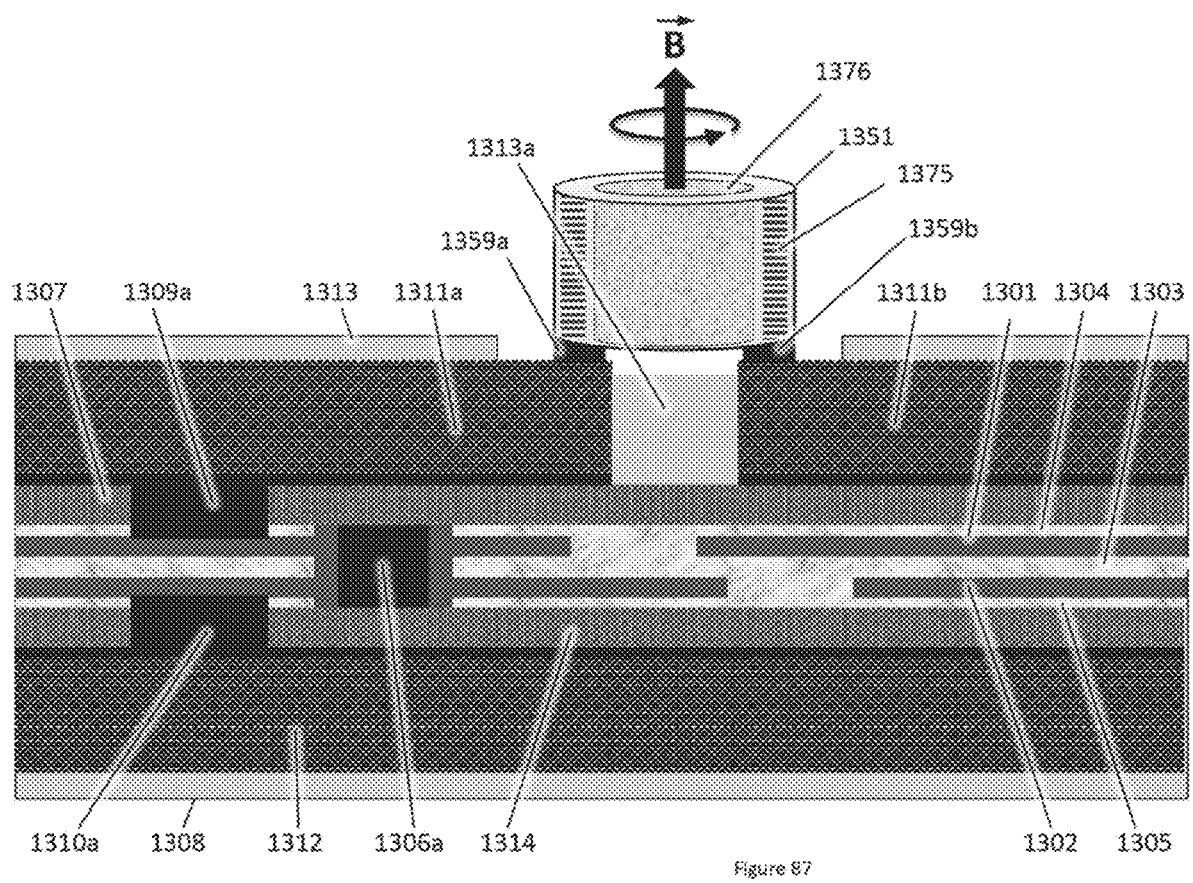
Figure 88A:
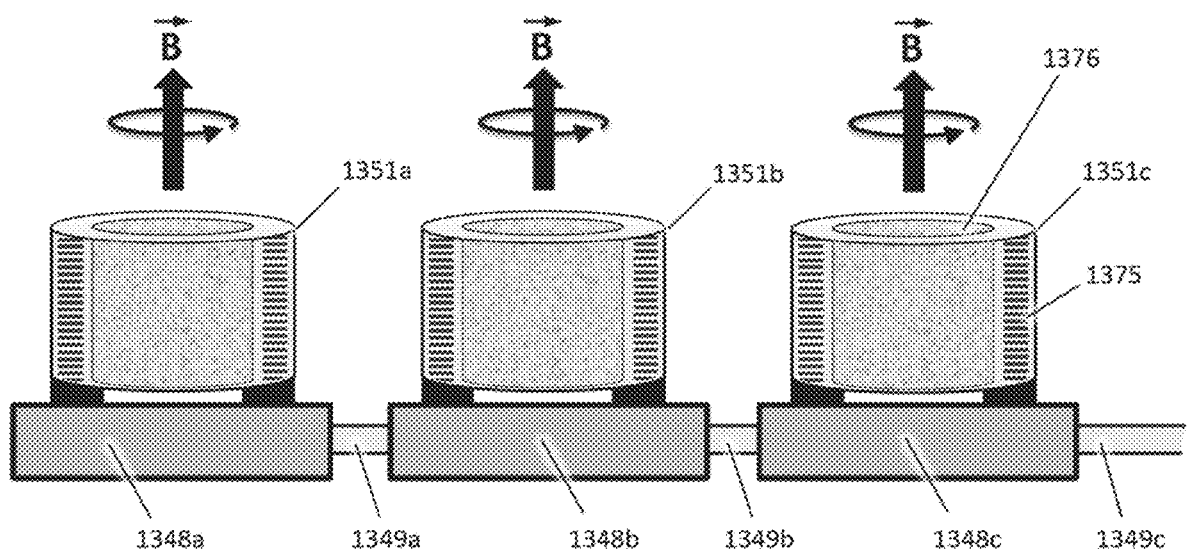

Alternatively, instead of employing planar magnetics to realize the electromagnet, a pre-assembled or discrete electromagnet module may be employed. As shown in FIG. 87, a discrete surface mount electromagnet 1351, including a magnetic core 1376 and a wire wound coil 1375, is attached as a surface mounted component to the rigid portion of a rigid-flex PCB by soldering metal feet 1359a and 1359b to two separate and electrically isolated conductive segments 1311a and 1311b of the metal 1311. As illustrated isolated conductive segment 1311a is connected to bottom conductive layer 1312 through patterned vias 1309a, 1306a, and 1310a. Metal foot 1359a is thus connected to metal layer 1312 while metal foot 1359b is connected to conductive segment 1311b. In this manner a separate discrete electromagnet can be positioned atop each rigid PCB to form an array such as shown in the cross section of FIG. 88A, wherein a discrete electromagnet 1351a is mounted to a rigid PCB 1348a, which in connected to a rigid PCB 1348b through a flex PCB portion 1349a; a discrete electromagnet 1351b is mounted to rigid PCB 1348b, which is connected to a rigid PCB 1348c through a flex PCB portion 1349b; and a discrete electromagnet 1351c is mounted to a rigid PCB 1348c, which is connected to other rigid PCBs (not shown) through a flex PCB portion 1349c.

In such a design every magnet 1351a, 1351b, 1351c, etc. in the array is an electromagnet and can be electronically controlled to vary its magnet field in accordance with the PMT circuit shown in FIG. 86 in response to drive signals generated by the PMT driver 1340. Such drive signals may produce continuous, pulsed or sinusoidal variations in the magnetic field of all the electromagnets in the array or alternatively may involve driving the electromagnets individually and in some sequence to form a special pattern or magnet wave across the PMT pad, e.g. generating an undulating magnet field wave row by row across the pad or along the length of a series of pads. In other cases some electromagnets may be biased on to produce a constant magnetic field while others are modulated to produce a time varying magnetic field.

Figure 88B:
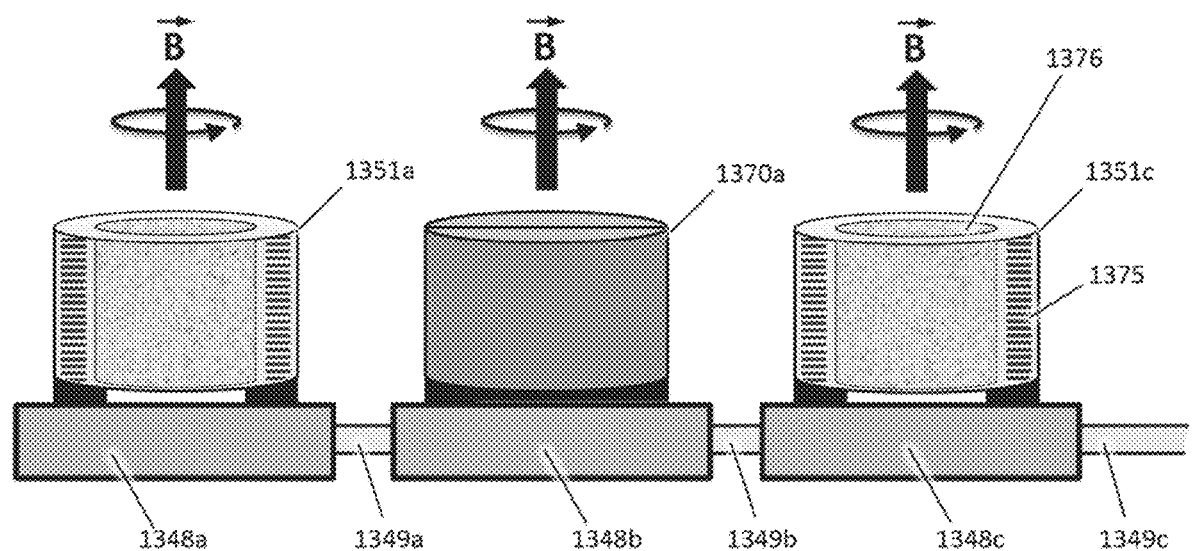
Figure 88C:
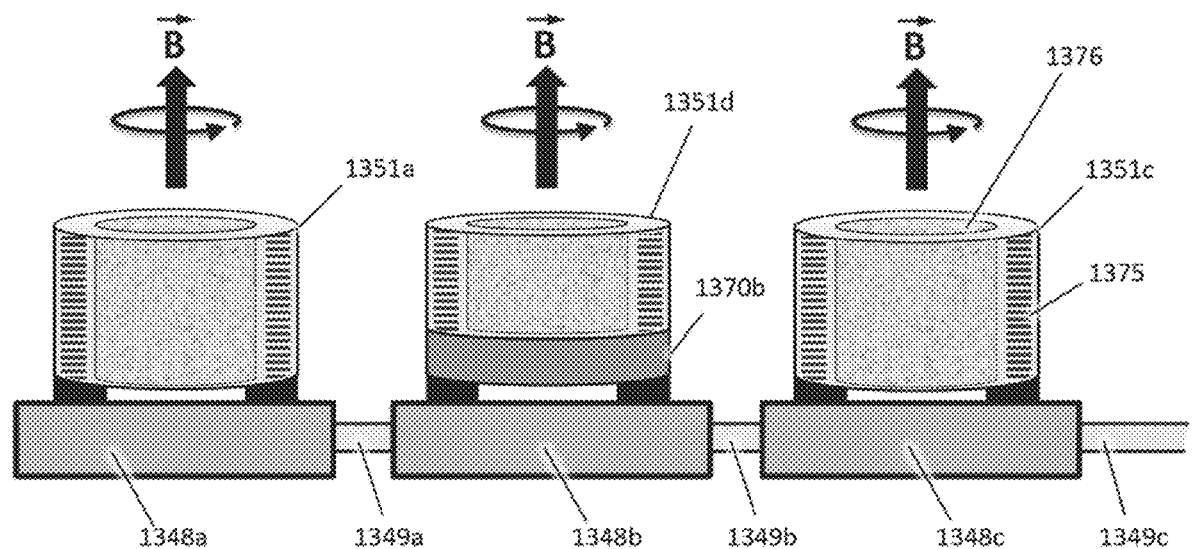
Figure 88D:
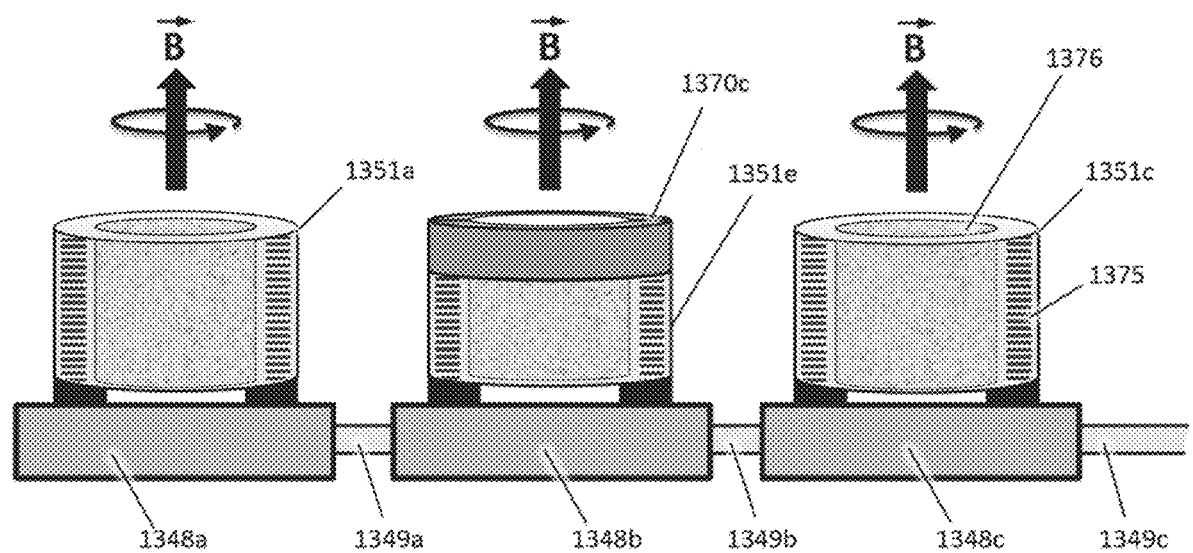

In an alternative embodiment, some electromagnets may be replaced by permanent magnets to combine a mix of constant and time varying magnetic fields. For example in FIG. 88B, electromagnet 1351b (shown in FIG. 88A) is replaced by a permanent magnet 1370a attached to rigid PCB 1348b while electromagnets 1351a and 1351c remain unchanged. In FIG. 88C, rigid PCB 1348b drives a stack including an electromagnet 1351d and an underlying permanent magnet 1370b or alternatively in FIG. 88D, rigid PCB 1348b drives a stack including an electromagnet 1351e and an overlying permanent magnet 1370c. In such cases operation of the electromagnet enhances (or alternatively reduces the magnetic field produced by the stacked permanent magnet.

Figure 89:
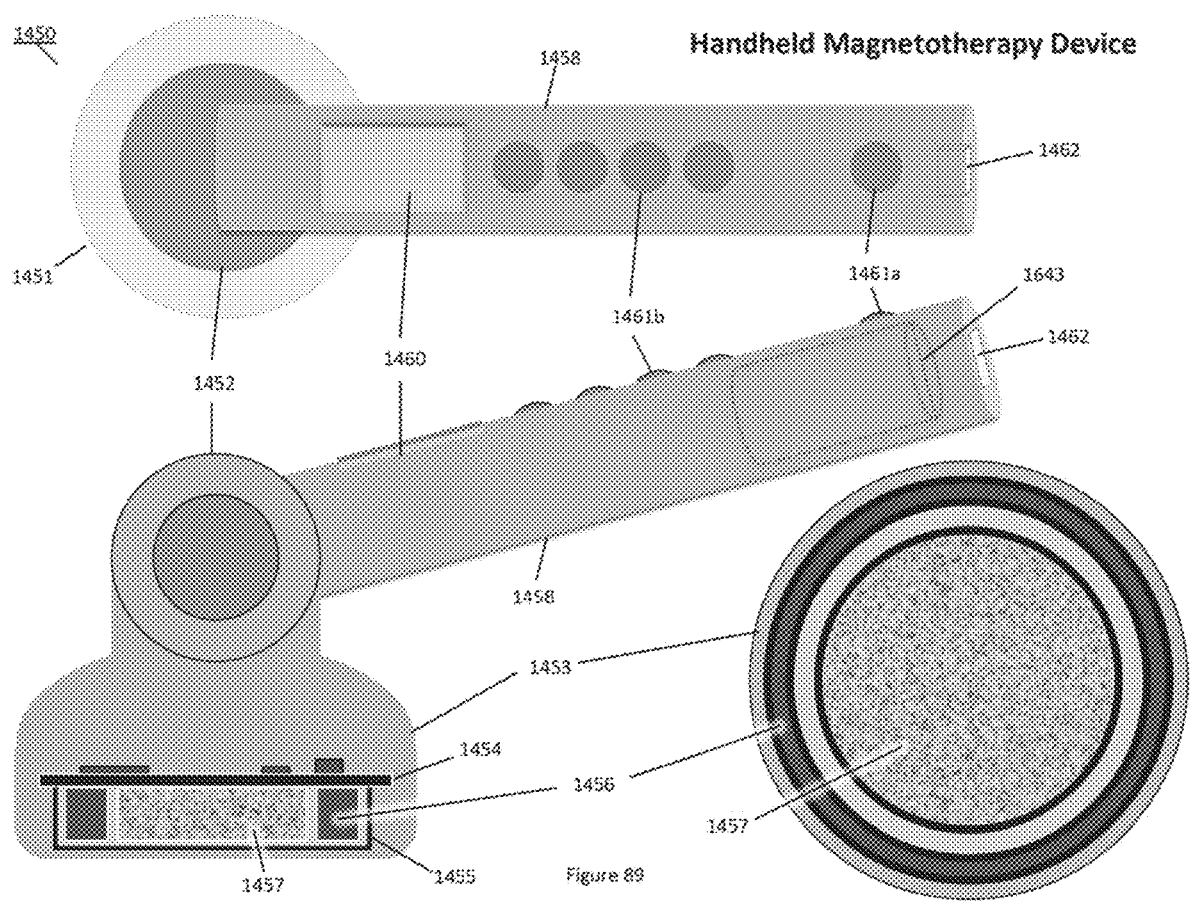

The PMT apparatus can also be adapted for use as a handheld magnetotherapy device or wand 1450 as shown in FIG. 89. Wand 1450 comprises a cylindrical handle 1458 with a UX display 1460, pushbuttons 1461b to control operation and program selection, an on/off button 1461a, a battery 1643, and a USB connector 1462. Cylindrical handle 1458 connects to a magnetic head unit 1453 through a movable gimbal 1452. Magnetic head unit 1453 includes an electromagnet 1455 comprising a ferrite core 1457 and a coil 1556 mounted onto a PCB 1454 along with control circuitry. If operated as part of a distributed system, the communication link of handheld magnetotherapy wand 1450 to a PBT controller may be performed through USB, WiFi, or possibly Bluetooth. If operated as an autonomous device, USB connector 1462 is used to program the magnetotherapy wand 1450 during manufacturing by connecting it to a PBT controller.

Periodontal PBT LED Mouthpiece—Although PBT can be performed through the cheeks to treat gum disease, another option is to inject light directly into the patient's mouth using lasers or LEDs in the near-infrared, infrared, and blue spectrum. Such as device must be small and must comfortably fit into the patient's mouth. As an autonomous therapy device, the device must use a lightweight software client capable of executing only a few pre-programmed algorithms. Alternatively, the device may employ data streaming from a user control module using a wired connection, Bluetooth, or low power WiFi 802.11ah. The user control module communicates with a PBT controller in the same manner as the controller of an intelligent LED pad except that its output does not drive LEDs within a pad but instead is streamed to the LED mouthpiece as a passive electrical signal so that no processing is performed within the mouthpiece.

Figure 90:
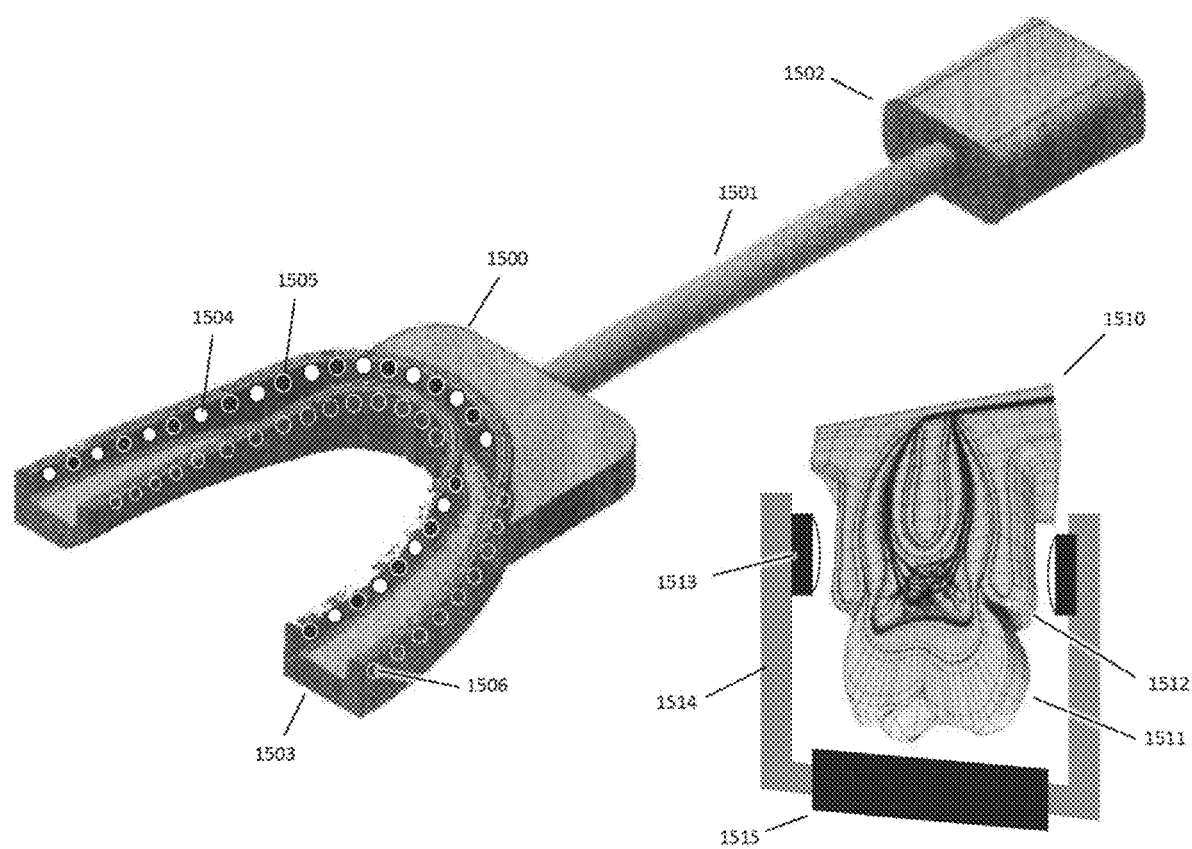

An example of such a periodontal PBT apparatus is shown in the three-dimensional perspective drawing of FIG. 90. The apparatus comprises a molded mouthpiece 1500, including a horseshoe shaped portion 1503 for covering the teeth and gums, LEDs 1504 and 1505 for emitting two different wavelengths of light lining the horseshoe shaped portion 1503 (where locations 1506 identify the locations of LEDs not visible in the 3D perspective drawing), an electrical cable 1501 and a control unit 1502 including a connector for power or optionally for bus communication. FIG. 90 also contains a cross-sectional view of the portion 1503 showing a U-shaped assembly surrounding a tooth 1510, comprising a rigid-flex PCB assembly with a flex PCB 1514, a rigid PCB 1515, and LEDs 1513. The mouthpiece 1500 is designed to position the LEDs 1513 near the gums 1512 adjacent to tooth 1511. The LEDs 1513 may comprise red, infrared, blue or purple LEDs to combat inflammation and periodontal disease. The U-shaped assembly shown in the cross-sectional view is contained within a thin silicone mouthpiece (not shown) that is molded around the rigid-flex PCB.

Figure 91:
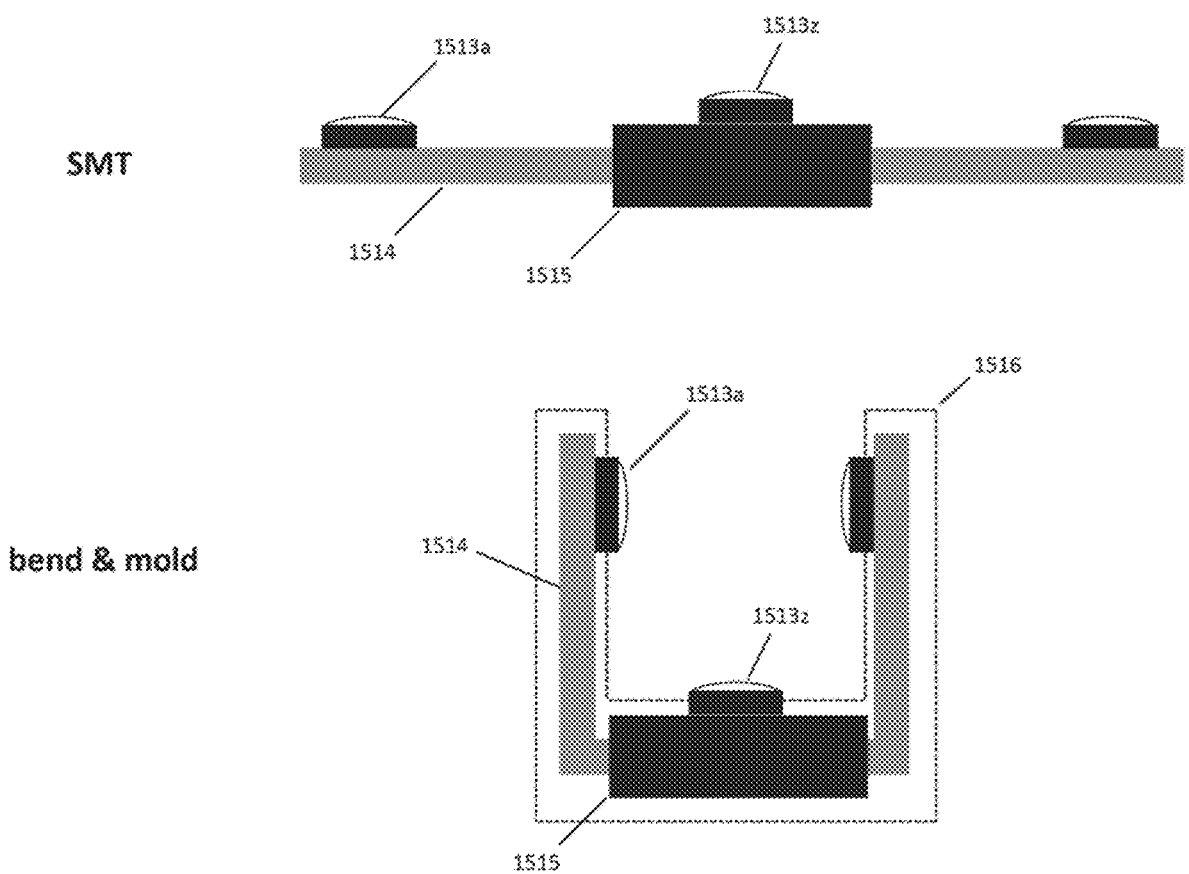

FIG. 91 shows two stages in the manufacture of the U-shaped assembly in mouthpiece 1500, designed for covering and treating a single jaw (either the upper or lower jaw but not both). As shown in FIG. 90, the U-shaped assembly comprises rigid PCB 1515, which serves as a base, and flex PCB 1514, which form "wings" on both sides of rigid PCB 1515. As shown, immediately after surface mount technology (SMT) manufacturing, LEDs 1513a are mounted on flex PCB 1514 and optionally an LED 1513z is mounted on rigid PCB 1515. During SMT assembly, the rigid-flex PCB comprising rigid PCB 1515 and flex PCB 1514 is situated so as to accommodate a high-volume automated assembly process, requiring component pick and place and uniform solder temperature profiles during reflow. It is important for the rigid-flex PCB to held firmly flat during the SMT assembly. Although the rigid and flex portions of the rigid-flex PCB are secured in the same plane during pick and place, the rigid-flex PCB need not be linear but instead can be laid-out in a horse-shoe shaped design, so that no unnecessary flexing of the flex PCB 1514 occurs or adds stress that may later cause $breaI_{ref}$ ge. After surface mount assembly, the wings formed by flex PCB 1514 are bent perpendicular to the base, rigid PCB 1515, forming a U-shape, and then molded into a transparent silicone mouthpiece 1516 covering the rigid-flex PCB.

The same process can be adapted into manufacturing a H-shaped mouthpiece useful in using PBT to treat both upper and lower jaws concurrently. The method shown in FIG. 92A utilizes the same manufacturing process as described for the aforementioned U-shaped mouthpiece except that after PCB assembly, two separate pieces are electrically and physically bonded to produce the H-shaped mouthpiece. As shown, two rigid-flex PCBs, one comprising a rigid PCB 1515a, a flex PCB 1514a, LEDs 1513a, and optional LEDs 1513z, and a second one comprising a rigid PCB 1515b, a flex PCB 1514b, LEDs 1513b, and optional LEDs 1513y, are bonded together. In the bonding process rigid PCBs 1515a and 1515b are soldered together to electrically and mechanically form a single multilayer PCB 1517, as shown in FIG. 92B. As such, the mouthpiece can treat both the upper and lower gums simultaneously.

The bonding of the rigid PCBs 1515a and 1515b is shown in FIG. 93. Conductive surfaces 1518b and 1518d atop rigid PCB 1515b are soldered to corresponding conductive surfaces 1518a and 1518c beneath rigid PCB 1515a to establish electrical connectivity between the top and bottom PCBs and to provide mechanical support and rigidity to the mouthpiece. Optionally through-hole vias 1519a and 1519b filled with silver solder paste can be melted to form a continuous through-hole via extending through both top rigid PCB 1515a and bottom rigid PCB 1515b.

Voltage supply and control circuitry for the periodontal PBT mouthpiece 1523 is shown in FIG. 94. Since high voltages are not allowed in a patient's mouth the input voltage $+V_{IN}$ should be stepped down are regulated to a lower voltage $+V_{LED}$ by low dropout (LDO) linear regulator 1520. Filter capacitors 1521 and 1522 are included to stabilize the regulator 1520 and to filter input and output transients respectively. A microcontroller 1535, executing programs stored in a volatile memory 1536a and a non-volatile memory 1536b in accordance with a clock 1534 and a time reference 1531, generates control signals 1537a and 1537b that are used to independently drive programmable current sources 1524a and 1524b.

The control signals 1537a and 1537b may be used to digitally strobe the LEDs 1504a-1504d and 1505a-1505d on and off, or alternatively to program the conducted current or synthesize a periodic waveform such as a sine wave. Current from current source 1524a is mirrored by NPN bipolar transistor 1525a to control the current in NPN bipolar transistor 1526a and therefore the current in LEDs 1504a and 1504b and to control the current in NPN bipolar transistor 1526b and therefore the current in LEDs 1504c and 1504d, all in accordance with the program executed by microcontroller 1535. Similarly, current from current source 1524b is mirrored by NPN bipolar transistor 1525b to control the current in NPN bipolar transistor 1527b and therefore the current in LEDs 1505a and 1505b to control the current in NPN bipolar transistor and therefore the current in LEDs 1505c and 1505d, also in accordance with the program executed by microcontroller 1535. In this manner LED current can be controlled using a minimal number of components to save space. The voltage supply and control circuitry shown in FIG. 94 can be housed in the enclosure for the control unit 1502 shown in FIG. 90.

Ultrasound Therapy—The distributed PBT system disclosed herein is also applicable of driving piezoelectric transducers to produce ultrasound in the frequency range from range from 100 kHz to 4 MHz. The dominant therapeutic action mechanism for ultrasound therapy is vibrational, effective for breaking up scar tissue and causing heating with good depth penetration. Driving algorithms can be similar to those used in sinusoidal drive of LEDs disclosed herein including both digital (pulsed) and sinusoidal drive. The disclosed distributed ultrasound therapy system is capable of performing ultrasonic therapy independently or in combination with PBT. Using the disclosed system, ultrasound transducers can also be combined with LED arrays to break up scar tissue using ultrasound, and to carry it away using PBT accelerated phagocytosis.

One implementation of a combined ultrasound PBT therapy system or USPBT pad is shown in FIG. 95. A microcontroller 1557 executes programs stored in a volatile memory 1558a and a non-volatile memory 1558b in accordance with a clock 1556 and a time reference 1553. Signals from the microcontroller 1557 are used to independently drive an H-bridge comprising low-side N-channel MOSFETs 1563a and 1563b and high-side P-channel MOSFETs 1564a and 1564b, which in turn drive a piezoelectric ultrasound transducer 1562. The H-bridge is powered by a regulated supply voltage $+V_{PZ}$, generated by a DC/DC converter 1550 with an input capacitor 1551, an output capacitor 1552, and optionally an inductor (not shown).

High side MOSFETs 1564a and 1564b are driven by level shifting driver-circuits 1566a and 1566b, respectively. Similarly, low-side MOSFETs 1563a and 1563b are driven by low side buffers 1565a and 1565b, respectively. In operation, the half-bridge formed by low-side N-channel MOSFET 1563a and high-side P-channel 1564a is driven out of phase with the half-bridge formed by low-side N-channel MOSFET 1563b and high-side P-channel 1564b. Whenever high-side P-channel MOSFET 1564a is on and conducting, then low-side N-channel 1563a is off and $V_x = +V_{PZ}$. Concurrently, high-side P-channel MOSFET 1564b is off and low-side N-channel MOSFET 1563b is on and conducting whereby $V_y = 0$, causing current to flow through the piezoelectric transducer 1562 from $V_x$ to $V_y$. In the next half cycle, current flow through the piezoelectric transducer 1562 reverses from $V_y$ to $V_x$. In operation, the two half-bridges are driven out of phase by an inverter 1567 in response to the output of pad μC 1557. The output of the half-bridge is bidirectional, having an absolute magnitude $\pm V_{PZ}$. The output of pad μC 1557 is also used to drive an LED array 1561 through an LED driver 1560, which is similar to the LED driver 335 shown in FIGS. 17 and 18.

In an alternative embodiment shown in FIG. 96, a programmable array of current sinks replaces the half bridge in driving multiple piezoelectric transducers. As shown pad μC 1557 outputs a digital magnitude to a D/A converter 1573 used to control the current conducted by current sinks 1575 and 1576 through corresponding piezoelectric transducers 1562a and 1562b respectively. The piezoelectric currents $I_{PZ1}$ and $P_{Z2}$ are digitally pulsed by inverters 1571 and 1572 to control the generated ultrasound frequency.

A pad for the combined application of ultrasonic and photobiomodulation therapy (referred to herein as USPBT) is shown in FIG. 97, the USPBT pad comprising an intelligent LED pad shown with top view 1581, underside view 1584, and side-view, including a single USB socket 1598. The cross-sectional view 1580 shows a rigid PCB 1588; a flex PCB 1589, LEDs 1591, a sensor 1590 and piezoelectric transducers 1592a and 1592b. A top flexible LED polymeric pad cover 1581 includes a protrusion 1583 and a cavity 1596. A bottom flexible polymeric cover 1584 includes openings 1595 and a protrusion 1583. A protective clear plastic 1587 covers the openings 1595.

Optionally, LEDs for PBT can be driven in combination with the ultrasonic piezoelectric emitters, either concurrently or alternating in time. The combined application of ultrasonic and photobiomodulation therapy is useful in breaking up scar tissue using ultrasound and using PBT to accelerate removal of the dead cells.

Infrasound Therapy—Infrasound therapy is analogous to tissue massage except that it occurs at very low frequencies below the audio spectrum, typically from 20-Hz down to 1-Hz or lower. The actuator for creating low frequencies must be relatively large, e.g. 10 cm in diameter and therefore is well suited for inclusion in wand similar to that shown in FIG. 89 except that the electromagnet 1455 is replaced by a voice coil driver similar to a speaker except that the movable portion attaches to a plunger or membrane that pushes on the treated tissue at very lower frequencies. The disclosed PBT system is therefore directly compatible to support ultrasound peripherals. Infrasound provides deep massage to tissue and low frequencies useful for improving range of motion and muscle elasticity. Optionally, LEDs for PBT can be driven in combination with the infrasound voice coil actuator, either concurrently or alternating in time.

PBT LED Buds for Nose/Ears—Although PBT can be performed transcranially, another option is to inject light directly into the nose or ears using lasers or LEDs in the near, infrared, and blue spectrum. Such as device is small. As an autonomous therapy device, the device must use a lightweight software client capable of executing only a few pre-programmed algorithms. Alternatively, the device may employ data streaming from a user control module using a wired connection, Bluetooth, or low power WiFi 802.11ah. The user control module communicates with the PBT controller and operates in the same manner as the controller of an intelligent LED pad except that its output does not drive LEDs within a pad but instead is streamed to the LED buds as a passive electrical signal so that no processing is performed within the buds. The disclosed PBT system is therefore directly compatible to support PBT LED buds for nose and ear treatments. Another benefit of intranasal and intra-aural (i.e. in the ear) PBT is its ability to kill pathogens and bacteria infecting the sinus cavities.

PBT LED Spots for Acupuncture—Another small sized LED source is a small LED or laser "spot", a coin sized pad attached to the body over acupuncture points. Such as device is small and has no room for battery power. The device may employ data streaming from a user control module using a wired connection, Bluetooth, or low power WiFi 802.11ah. The user control module communicates with the PBT controller and operates in the same manner as the controller of an intelligent LED pad except that its output does not drive LEDs within a pad but instead is streamed to the LED/laser spots as a passive electrical signal so that no processing is performed within the spots. The disclosed PBT system is therefore directly compatible to support PBT LED buds for acupuncture LED spots.

Bluetooth Headphones—Although not medically therapeutic, in relaxation applications music may be broadcast to headphones over Bluetooth synchronized to PBT treatment waveforms. Given the waveform synthesis capability of the disclosed PBT system, it is capable to support synchronized music and PBT treatments.

The invention claimed is:

1. A distributed photobiomodulation therapy (PBT) system comprising:
   a PBT controller, the PBT controller comprising a main microcontroller, a communication interface, and a digital clock;
   a light-emitting diode (LED) pad, the LED pad comprising:
      a pad microcontroller,
      a memory, the memory comprising a non-volatile memory,
      an array of light-emitting diodes (LEDs), the array of LEDs comprising one or more LED strings, the LEDs in each of the LED strings being connected in series,
      one or more LED drivers, each of the one or more LED drivers being linked to the pad microcontroller and also being connected to and for controlling a current in one of the LED strings, such that the pad microcontroller is capable of controlling a current in each LED string in the one or more LED strings, and
      a pad identity data register, the pad identity data register being stored in the non-volatile memory and comprising data for use by the PBT controller for authenticating the identity of the LED pad; and
   a communication link for carrying digital data between the PBT controller and the LED pad for controlling the current in and illumination of the one or more LED strings,
   wherein each of the one or more LED drivers comprises a MOSFET and a current sense and control element, each of the MOSFET and the current sense and control unit being connected in series with the LEDs in the LED string to which the LED driver is connected, the current sense and control unit being connected to a source of enable pulses for turning the MOSFET on and off and to a source of a reference current for controlling a level of the current in the MOSFET when the MOSFET is turned on.

2. A distributed photobiomodulation therapy (PBT) system comprising:
   a PBT controller, the PBT controller comprising a main microcontroller, a communication interface, and a digital clock;

a light-emitting diode (LED) pad, the LED pad comprising:
a pad microcontroller,
a memory, the memory comprising a non-volatile memory,
an array of light-emitting diodes (LEDs), the array of LEDs comprising one or more LED strings, the LEDs in each of the LED strings being connected in series,
one or more LED drivers, each of the one or more LED drivers being linked to the pad microcontroller and also being connected to and for controlling a current in one of the LED strings, such that the pad microcontroller is capable of controlling a current in each LED string in the one or more LED strings, and
a pad identity data register, the pad identity data register being stored in the non-volatile memory and comprising data for use by the PBT controller for authenticating the identity of the LED pad; and
a communication link for carrying digital data between the PBT controller and the LED pad for controlling the current in and illumination of the one or more LED strings,
wherein the array of LEDs comprises a first LED string and a second LED string and wherein a source of a reference current for the first LED string comprises a first reference MOSFET and a source of a reference current for the second LED string comprises a second reference MOSFET, each of the first and second reference MOSFETs being connected in a current mirror arrangement with a third threshold-connected MOSFET.

3. The distributed PBT system of claim 2 further comprising a trim network connected to the third threshold-connected MOSFET.

4. The distributed PBT system of claim 2 further comprising a digital-to-analog (D/A) converter, an output of the D/A converter controlling the magnitude of a current in the third threshold-connected MOSFET.

5. A method of performing photobiomodulation therapy (PBT) using a PBT system, the PBT system comprising:
a PBT controller, the PBT controller comprising a main microcontroller, a communication interface, and a digital clock;
a light-emitting diode (LED) pad, the LED pad comprising:
a pad microcontroller,
a memory, the memory comprising a non-volatile memory,
an array of light-emitting diodes (LEDs), the array of LEDs comprising one or more LED strings, the LEDs in each of the LED strings being connected in series,
one or more LED drivers, each of the one or more LED drivers being connected to and for controlling a current in one of the LED strings, and
a pad identity data register, the pad identity data register being stored in the non-volatile memory and comprising data for use by the PBT controller for authenticating the identity of the LED pad; and
a communication link for carrying digital data between the PBT controller and the LED pad for controlling the current in and illumination of the one or more LED strings;
the method comprising transferring a file containing executable code from the PBT controller to the LED pad, the executable code comprising instructions for the pad microcontroller to execute and complete a PBT treatment without further instruction from the PBT controller, wherein the file containing executable code transferred from the PBT controller to the LED pad is compressed and/or encrypted, the method further comprising decompressing and/or decrypting the file in the LED pad.

6. The method of claim 5 comprising decrypting the file in its entirety in the LED pad and then executing the PBT treatment.

7. The method of claim 5 comprising:
decrypting a first portion of the file in the LED pad and executing a first portion of the treatment; and
decrypting a second portion of the file in the LED pad and executing a second portion of the treatment.

8. A method of performing photobiomodulation therapy (PBT) using a PBT system, the PBT system comprising:
a PBT controller, the PBT controller comprising a main microcontroller, a communication interface, and a digital clock;
a light-emitting diode (LED) pad, the LED pad comprising:
a pad microcontroller,
a memory, the memory comprising a non-volatile memory,
an array of light-emitting diodes (LEDs), the array of LEDs comprising one or more LED strings, the LEDs in each of the LED strings being connected in series,
one or more LED drivers, each of the one or more LED drivers being connected to and for controlling a current in one of the LED strings, and
a pad identity data register, the pad identity data register being stored in the non-volatile memory and comprising data for use by the PBT controller for authenticating the identity of the LED pad; and
a communication link for carrying digital data between the PBT controller and the LED pad for controlling the current in and illumination of the one or more LED strings;
the method comprising transferring a file comprising an LED player from the PBT controller to the LED pad, the LED player comprising an LED driver file.

9. The method of claim 8 wherein the file comprising the LED player is encrypted and/or compressed, the method further comprising decrypting and/or decompressing the file in the LED pad and then storing the file in the volatile memory in the LED pad.

10. The method of claim 8 wherein the LED player comprises a waveform synthesizer and a pulse width modulation (PWM) player.

11. The method of claim 10 comprising delivering waveform primitives and waveform parametrics of a waveform to the waveform synthesizer, the waveform synthesizer processing the waveform primitives and the waveform parametrics to generate a PWM function representative of the waveform.

12. The method of claim 11 wherein the waveform primitives identify the waveform as a sine wave and the waveform parametrics specify a frequency and amplitude of the sine wave.

13. The method of claim 10 comprising delivering a mathematical function expressing the waveform to the waveform synthesizer, the waveform synthesizer processing the mathematical function to generate a PWM function representative of the waveform.

14. The method of claim 11 wherein the PWM player receives an output signal of the waveform synthesizer and generates a pulse train, each pulse in the pulse train comprising at least a portion of the PWM function representative of the waveform, the pulses in the pulse train having a frequency less than pulses in the PWM function.

15. The method of claim 14 wherein the LED driver receives an output signal of the PWM player and generates an analog signal representative of the waveform, the LED driver determining a maximum value of the analog signal by controlling a maximum value of a current in each of the one or more LED strings.

16. The method of claim 8 comprising transferring an LED playback file to the volatile memory, the LED playback file defining a sequence of a PBT treatment.

\* \* \* \* \*